US012712326B2

(12) United States Patent
Aldridge et al.

(10) Patent No.: US 12,712,326 B2
(45) Date of Patent: Aug. 18, 2026

(54) ULTRASONIC AND ELECTROSURGICAL DEVICES

(71) Applicant: Cilag GmbH International, Zug (CH)

(72) Inventors: Jeffrey L. Aldridge, Lebanon, OH (US); Craig N. Faller, Batavia, OH (US); Kevin D. Felder, Cincinnati, OH (US); Jacob S. Gee, Cincinnati, OH (US); William D. Kelly, Los Altos, CA (US); Robert J. Laird, Morrow, OH (US); Amy L. Marcotte, Mason, OH (US); Jeffrey D. Messerly, Cincinnati, OH (US); Emily H. Monroe, George's Mills, NH (US); Scott A. Nield, Morrow, OH (US); Daniel W. Price, Loveland, OH (US); Patrick J. Scoggins, Loveland, OH (US); John B. Schulte, West Chester, OH (US); Geoffrey S. Strobl, Williamsburg, OH (US); James W. Voegele, Cincinnati, OH (US); John A. Weed, III, Monroe, OH (US); William B. Weisenburgh, II, Maineville, OH (US); Patrick A. Weizman, Liberty Township, OH (US); John W. Willis, Batavia, OH (US)

(73) Assignee: Cilag GbmH International, Zug (CH)

( * ) Notice: Subject to any disclaimer, the term of this patent is extended or adjusted under 35 U.S.C. 154(b) by 571 days.

(21) Appl. No.: 17/545,653

(22) Filed: Dec. 8, 2021

(65) Prior Publication Data

US 2022/0168005 A1 Jun. 2, 2022

Related U.S. Application Data

(60) Continuation of application No. 14/627,792, filed on Feb. 20, 2015, now Pat. No. 11,324,527, which is a
(Continued)

(51) Int. Cl.
*A61B 17/32* (2006.01)
*A61B 18/12* (2006.01)
(Continued)

(52) U.S. Cl.
CPC ..... *H01R 29/00* (2013.01); *A61B 17/320092* (2013.01); *A61B 18/1206* (2013.01);
(Continued)

(58) Field of Classification Search
CPC .... A61B 2017/2936; A61B 2017/2939; A61B 2017/320093; A61B 2017/320094;
(Continued)

(56) References Cited

U.S. PATENT DOCUMENTS

| | | |
|---|---|---|
| 969,528 A | 9/1910 | Disbrow |
| 1,570,025 A | 1/1926 | Young |

(Continued)

FOREIGN PATENT DOCUMENTS

| | | |
|---|---|---|
| CA | 2535467 A1 | 4/1993 |
| CN | 2460047 Y | 11/2001 |

(Continued)

OTHER PUBLICATIONS

AST Products, Inc., "Principles of Video Contact Angle Analysis," 20 pages, (2006).

(Continued)

*Primary Examiner* — Katherine H Schwiker
(74) *Attorney, Agent, or Firm* — Vorys, Sater, Seymour and Pease LLP

(57) ABSTRACT

Disclosed are ultrasonic and electrosurgical devices. The disclosed embodiments include a surgical instrument comprising a waveguide, and end effector and an electrical switch. The waveguide may comprise a proximal end and a distal end, wherein the proximal end is configured to couple to an ultrasonic transducer and one output of a radio fre-
(Continued)

quency (RF) generator. The end effector may comprise an ultrasonic blade and a clamp arm coupled. The ultrasonic blade may be mechanically coupled to the distal end of the waveguide and electrically coupled to the waveguide. The clamp arm may comprise a movable jaw member electrically coupled to another output of the RF generator such that an electrical current can pass through the movable jaw member and the ultrasonic blade through tissue located between the movable jaw member and the ultrasonic blade. The electrical switch may be configured to electrically couple to the RF generator and the movable jaw member, wherein the switch is operable to cause the surgical instrument to deliver electrical current from the RF generator to the movable jaw member for a first period, and to cause the surgical instrument to deliver ultrasonic energy to the ultrasonic blade for a second period.

9 Claims, 62 Drawing Sheets

Related U.S. Application Data division of application No. 13/843,295, filed on Mar. 15, 2013, now abandoned.

(60) Provisional application No. 61/726,890, filed on Nov. 15, 2012.

(51) Int. Cl.

| | |
|---|---|
| ***A61B 18/14*** | (2006.01) |
| ***F15D 1/00*** | (2006.01) |
| ***H01R 29/00*** | (2006.01) |
| *A61B 17/00* | (2006.01) |
| *A61B 17/29* | (2006.01) |
| *A61B 18/00* | (2006.01) |
| *A61B 90/00* | (2016.01) |

(52) U.S. Cl.

CPC ........ *A61B 18/1445* (2013.01); *F15D 1/0015* (2013.01); *A61B 2017/005* (2013.01); *A61B 17/29* (2013.01); *A61B 2017/2927* (2013.01); *A61B 2017/2929* (2013.01); *A61B 2017/2936* (2013.01); *A61B 2017/2939* (2013.01); *A61B 2017/320074* (2017.08); *A61B 2017/320078* (2017.08); *A61B 2017/320084* (2013.01); *A61B 2017/320088* (2013.01); *A61B 2017/320093* (2017.08); *A61B 2017/320094* (2017.08); *A61B 2017/320095* (2017.08); *A61B 2018/00023* (2013.01); *A61B 2018/00083* (2013.01); *A61B 2018/00101* (2013.01); *A61B 2018/00107* (2013.01); *A61B 2018/00178* (2013.01); *A61B 2018/00916* (2013.01); *A61B 2018/00922* (2013.01); *A61B 2018/00958* (2013.01); *A61B 2018/00994* (2013.01); *A61B 2090/035* (2016.02); *A61B 2090/0436* (2016.02); *A61B 2090/0472* (2016.02); *A61B 2090/0813* (2016.02); *A61B 2217/005* (2013.01); *Y10T 137/2087* (2015.04)

(58) Field of Classification Search

CPC ....... A61B 2017/320095; A61B 2017/320097; A61B 2017/320069; A61B 2017/32007; A61B 2017/320071; A61B 2017/320072; A61B 2017/320073; A61B 2017/320074; A61B 2017/320075; A61B 2017/320077; A61B 2017/320078; A61B 2017/32008; A61B 2017/320082; A61B 2017/320084; A61B 2017/320088; A61B 2017/320089; A61B 2017/32009; A61B 2017/320098; A61B 17/320092; A61B 17/320068

See application file for complete search history.

(56) References Cited

U.S. PATENT DOCUMENTS

| | | | |
|---|---|---|---|
| 1,813,902 | A | 7/1931 | Bovie |
| 2,188,497 | A | 1/1940 | Calva |
| 2,366,274 | A | 1/1945 | Luth et al. |
| 2,425,245 | A | 8/1947 | Johnson |
| 2,442,966 | A | 6/1948 | Wallace |
| 2,458,152 | A | 1/1949 | Eakins |
| 2,510,693 | A | 6/1950 | Green |
| 2,597,564 | A | 5/1952 | Bugg |
| 2,704,333 | A | 3/1955 | Calosi et al. |
| 2,736,960 | A | 3/1956 | Armstrong |
| 2,748,967 | A | 6/1956 | Roach |
| 2,845,072 | A | 7/1958 | Shafer |
| 2,849,788 | A | 9/1958 | Creek |
| 2,867,039 | A | 1/1959 | Zach |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,033,407 | A | 5/1962 | Alfons |
| 3,053,124 | A | 9/1962 | Balamuth et al. |
| 3,082,805 | A | 3/1963 | Royce |
| 3,166,971 | A | 1/1965 | Stoecker |
| 3,322,403 | A | 5/1967 | Murphy |
| 3,432,691 | A | 3/1969 | Shoh |
| 3,433,226 | A | 3/1969 | Boyd |
| 3,489,930 | A | 1/1970 | Shoh |
| 3,513,848 | A | 5/1970 | Winston et al. |
| 3,514,856 | A | 6/1970 | Camp et al. |
| 3,525,912 | A | 8/1970 | Wallin |
| 3,526,219 | A | 9/1970 | Balamuth |
| 3,554,198 | A | 1/1971 | Tatoian et al. |
| 3,580,841 | A | 5/1971 | Cadotte et al. |
| 3,606,682 | A | 9/1971 | Camp et al. |
| 3,614,484 | A | 10/1971 | Shoh |
| 3,616,375 | A | 10/1971 | Inoue |
| 3,629,726 | A | 12/1971 | Popescu |
| 3,636,943 | A | 1/1972 | Balamuth |
| 3,668,486 | A | 6/1972 | Silver |
| 3,702,948 | A | 11/1972 | Balamuth |
| 3,703,651 | A | 11/1972 | Blowers |
| 3,776,238 | A | 12/1973 | Peyman et al. |
| 3,777,760 | A | 12/1973 | Essner |
| 3,805,787 | A | 4/1974 | Banko |
| 3,809,977 | A | 5/1974 | Balamuth et al. |
| 3,830,098 | A | 8/1974 | Antonevich |
| 3,854,737 | A | 12/1974 | Gilliam, Sr. |
| 3,862,630 | A | 1/1975 | Balamuth |
| 3,875,945 | A | 4/1975 | Friedman |
| 3,885,438 | A | 5/1975 | Harris, Sr. et al. |
| 3,900,823 | A | 8/1975 | Sokal et al. |
| 3,918,442 | A | 11/1975 | Nikolaev et al. |
| 3,924,335 | A | 12/1975 | Balamuth et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 3,989,952 | A | 11/1976 | Hohmann |
| 4,005,714 | A | 2/1977 | Hiltebrandt |
| 4,012,647 | A | 3/1977 | Balamuth et al. |
| 4,034,762 | A | 7/1977 | Cosens et al. |
| 4,058,126 | A | 11/1977 | Leveen |
| 4,074,719 | A | 2/1978 | Semm |
| 4,156,187 | A | 5/1979 | Murry et al. |
| 4,167,944 | A | 9/1979 | Banko |
| 4,188,927 | A | 2/1980 | Harris |
| 4,200,106 | A | 4/1980 | Douvas et al. |
| 4,203,430 | A | 5/1980 | Takahashi |
| 4,203,444 | A | 5/1980 | Bonnell et al. |
| 4,220,154 | A | 9/1980 | Semm |
| 4,237,441 | A | 12/1980 | van Konynenburg et al. |

(56) References Cited

U.S. PATENT DOCUMENTS 4,244,371 A 1/1981 Farin
4,281,785 A 8/1981 Brooks
4,300,083 A 11/1981 Heiges
4,302,728 A 11/1981 Nakamura
4,304,987 A 12/1981 van Konynenburg
4,306,570 A 12/1981 Matthews
4,314,559 A 2/1982 Allen
4,353,371 A 10/1982 Cosman
4,409,981 A 10/1983 Lundberg
4,445,063 A 4/1984 Smith
4,461,304 A 7/1984 Kuperstein
4,463,759 A 8/1984 Garito et al.
4,491,132 A 1/1985 Aikins
4,492,231 A 1/1985 Auth
4,494,759 A 1/1985 Kieffer
4,504,264 A 3/1985 Kelman
4,512,344 A 4/1985 Barber
4,526,571 A 7/1985 Wuchinich
4,535,773 A 8/1985 Yoon
4,541,638 A 9/1985 Ogawa et al.
4,545,374 A 10/1985 Jacobson
4,545,926 A 10/1985 Fouts, Jr. et al.
4,549,147 A 10/1985 Kondo
4,550,870 A 11/1985 Krumme et al.
4,553,544 A 11/1985 Nomoto et al.
4,562,838 A 1/1986 Walker
4,574,615 A 3/1986 Bower et al.
4,582,236 A 4/1986 Hirose
4,593,691 A 6/1986 Lindstrom et al.
4,603,696 A 8/1986 Cross, Jr. et al.
4,608,981 A 9/1986 Rothfuss et al.
4,617,927 A 10/1986 Manes
4,633,119 A 12/1986 Thompson
4,633,874 A 1/1987 Chow et al.
4,634,420 A 1/1987 Spinosa et al.
4,640,279 A 2/1987 Beard
4,641,053 A 2/1987 Takeda
4,646,738 A 3/1987 Trott
4,646,756 A 3/1987 Watmough et al.
4,649,919 A 3/1987 Thimsen et al.
4,662,068 A 5/1987 Polonsky
4,674,502 A 6/1987 Imonti
4,694,835 A 9/1987 Strand
4,708,127 A 11/1987 Abdelghani
4,712,722 A 12/1987 Hood et al.
4,735,603 A 4/1988 Goodson et al.
4,761,871 A 8/1988 O'Connor et al.
4,808,154 A 2/1989 Freeman
4,819,635 A 4/1989 Shapiro
4,827,911 A 5/1989 Broadwin et al.
4,830,462 A 5/1989 Karny et al.
4,832,683 A 5/1989 Idemoto et al.
4,836,186 A 6/1989 Scholz
4,838,853 A 6/1989 Parisi
4,844,064 A 7/1989 Thimsen et al.
4,849,133 A 7/1989 Yoshida et al.
4,850,354 A 7/1989 McGurk-Burleson et al.
4,852,578 A 8/1989 Companion et al.
4,860,745 A 8/1989 Farin et al.
4,862,890 A 9/1989 Stasz et al.
4,865,159 A 9/1989 Jamison
4,867,157 A 9/1989 McGurk-Burleson et al.
4,878,493 A 11/1989 Pasternak et al.
4,880,015 A 11/1989 Nierman
4,881,550 A 11/1989 Kothe
4,896,009 A 1/1990 Pawlowski
4,903,696 A 2/1990 Stasz et al.
4,910,389 A 3/1990 Sherman et al.
4,915,643 A 4/1990 Samejima et al.
4,920,978 A 5/1990 Colvin
4,922,902 A 5/1990 Wuchinich et al.
4,926,860 A 5/1990 Stice
4,936,842 A 6/1990 D'Amelio et al.
4,954,960 A 9/1990 Lo et al.
4,965,532 A 10/1990 Sakurai
4,979,952 A 12/1990 Kubota et al.
4,981,756 A 1/1991 Rhandhawa
5,001,649 A 3/1991 Lo et al.
5,009,661 A 4/1991 Michelson
5,013,956 A 5/1991 Kurozumi et al.
5,015,227 A 5/1991 Broadwin et al.
5,020,514 A 6/1991 Heckele
5,026,370 A 6/1991 Lottick
5,026,387 A 6/1991 Thomas
5,035,695 A 7/1991 Weber, Jr. et al.
5,042,461 A 8/1991 Inoue et al.
5,042,707 A 8/1991 Taheri
5,052,145 A 10/1991 Wang
5,061,269 A 10/1991 Muller
5,075,839 A 12/1991 Fisher et al.
5,084,052 A 1/1992 Jacobs
5,099,840 A 3/1992 Goble et al.
5,104,025 A 4/1992 Main et al.
5,105,117 A 4/1992 Yamaguchi
5,106,538 A 4/1992 Barma et al.
5,108,383 A 4/1992 White
5,109,819 A 5/1992 Custer et al.
5,112,300 A 5/1992 Ureche
5,113,139 A 5/1992 Furukawa
5,123,903 A 6/1992 Quaid et al.
5,126,618 A 6/1992 Takahashi et al.
D327,872 S 7/1992 McMills et al.
5,152,762 A 10/1992 McElhenney
5,156,633 A 10/1992 Smith
5,160,334 A 11/1992 Billings et al.
5,162,044 A 11/1992 Gahn et al.
5,163,421 A 11/1992 Bernstein et al.
5,163,537 A 11/1992 Radev
5,163,945 A 11/1992 Ortiz et al.
5,167,619 A 12/1992 Wuchinich
5,167,725 A 12/1992 Clark et al.
5,172,344 A 12/1992 Ehrlich
5,174,276 A 12/1992 Crockard
D332,660 S 1/1993 Rawson et al.
5,176,677 A 1/1993 Wuchinich
5,176,695 A 1/1993 Dulebohn
5,184,605 A 2/1993 Grzeszykowski
5,188,102 A 2/1993 Idemoto et al.
D334,173 S 3/1993 Liu et al.
5,190,517 A 3/1993 Zieve et al.
5,190,518 A 3/1993 Takasu
5,190,541 A 3/1993 Abele et al.
5,196,007 A 3/1993 Ellman et al.
5,203,380 A 4/1993 Chikama
5,205,459 A 4/1993 Brinkerhoff et al.
5,205,817 A 4/1993 Idemoto et al.
5,209,719 A 5/1993 Baruch et al.
5,213,569 A 5/1993 Davis
5,214,339 A 5/1993 Naito
5,217,460 A 6/1993 Knoepfler
5,218,529 A 6/1993 Meyer et al.
5,221,282 A 6/1993 Wuchinich
5,222,937 A 6/1993 Kagawa
5,226,909 A 7/1993 Evans et al.
5,226,910 A 7/1993 Kajiyama et al.
5,231,989 A 8/1993 Middleman et al.
5,234,428 A 8/1993 Kaufman
5,241,236 A 8/1993 Sasaki et al.
5,241,968 A 9/1993 Slater
5,242,339 A 9/1993 Thornton
5,242,460 A 9/1993 Klein et al.
5,246,003 A 9/1993 DeLonzor
5,254,129 A 10/1993 Alexander
5,257,988 A 11/1993 L'Esperance, Jr.
5,258,004 A 11/1993 Bales et al.
5,258,006 A 11/1993 Rydell et al.
5,261,922 A 11/1993 Hood
5,263,957 A 11/1993 Davison
5,264,925 A 11/1993 Shipp et al.
5,269,297 A 12/1993 Weng et al.
5,275,166 A 1/1994 Vaitekunas et al.
5,275,607 A 1/1994 Lo et al.
5,275,609 A 1/1994 Pingleton et al.
5,282,800 A 2/1994 Foshee et al.

(56) References Cited

U.S. PATENT DOCUMENTS 5,282,817 A 2/1994 Hoogeboom et al.
5,285,795 A 2/1994 Ryan et al.
5,285,945 A 2/1994 Brinkerhoff et al.
5,290,286 A 3/1994 Parins
5,293,863 A 3/1994 Zhu et al.
5,300,068 A 4/1994 Rosar et al.
5,304,115 A 4/1994 Pflueger et al.
D347,474 S 5/1994 Olson
5,307,976 A 5/1994 Olson et al.
5,309,927 A 5/1994 Welch
5,312,023 A 5/1994 Green et al.
5,312,425 A 5/1994 Evans et al.
5,318,525 A 6/1994 West et al.
5,318,563 A 6/1994 Malis et al.
5,318,564 A 6/1994 Eggers
5,318,570 A 6/1994 Hood et al.
5,318,589 A 6/1994 Lichtman
5,322,055 A 6/1994 Davison et al.
5,324,299 A 6/1994 Davison et al.
5,326,013 A 7/1994 Green et al.
5,326,342 A 7/1994 Pflueger et al.
5,330,471 A 7/1994 Eggers
5,330,502 A 7/1994 Hassler et al.
5,334,183 A 8/1994 Wuchinich
5,339,723 A 8/1994 Huitema
5,342,356 A 8/1994 Ellman et al.
5,342,359 A 8/1994 Rydell
5,344,420 A 9/1994 Hilal et al.
5,345,937 A 9/1994 Middleman et al.
5,346,502 A 9/1994 Estabrook et al.
5,353,474 A 10/1994 Good et al.
5,357,164 A 10/1994 Imabayashi et al.
5,357,423 A 10/1994 Weaver et al.
5,359,994 A 11/1994 Krauter et al.
5,361,583 A 11/1994 Huitema
5,366,466 A 11/1994 Christian et al.
5,368,557 A 11/1994 Nita et al.
5,370,645 A 12/1994 Klicek et al.
5,371,429 A 12/1994 Manna
5,374,813 A 12/1994 Shipp
D354,564 S 1/1995 Medema
5,381,067 A 1/1995 Greenstein et al.
5,383,874 A 1/1995 Jackson et al.
5,383,917 A 1/1995 Desai et al.
5,387,207 A 2/1995 Dyer et al.
5,387,215 A 2/1995 Fisher
5,389,098 A 2/1995 Tsuruta et al.
5,394,187 A 2/1995 Shipp
5,395,033 A 3/1995 Byrne et al.
5,395,312 A 3/1995 Desai
5,395,363 A 3/1995 Billings et al.
5,395,364 A 3/1995 Anderhub et al.
5,396,266 A 3/1995 Brimhall
5,396,900 A 3/1995 Slater et al.
5,400,267 A 3/1995 Denen et al.
5,403,312 A 4/1995 Yates et al.
5,403,334 A 4/1995 Evans et al.
5,406,503 A 4/1995 Williams, Jr. et al.
5,408,268 A 4/1995 Shipp
D358,887 S 5/1995 Feinberg
5,411,481 A 5/1995 Allen et al.
5,417,709 A 5/1995 Slater
5,419,761 A 5/1995 Narayanan et al.
5,421,829 A 6/1995 Olichney et al.
5,423,844 A 6/1995 Miller
5,428,504 A 6/1995 Bhatla
5,429,131 A 7/1995 Scheinman et al.
5,438,997 A 8/1995 Sieben et al.
5,441,499 A 8/1995 Fritzsch
5,443,463 A 8/1995 Stern et al.
5,445,638 A 8/1995 Rydell et al.
5,445,639 A 8/1995 Kuslich et al.
5,447,509 A 9/1995 Mills et al.
5,449,370 A 9/1995 Vaitekunas
5,451,053 A 9/1995 Garrido
5,451,161 A 9/1995 Sharp
5,451,220 A 9/1995 Ciervo
5,451,227 A 9/1995 Michaelson
5,456,684 A 10/1995 Schmidt et al.
5,458,598 A 10/1995 Feinberg et al.
5,462,604 A 10/1995 Shibano et al.
5,465,895 A 11/1995 Knodel et al.
5,471,988 A 12/1995 Fujio et al.
5,472,443 A 12/1995 Cordis et al.
5,476,479 A 12/1995 Green et al.
5,478,003 A 12/1995 Green et al.
5,480,409 A 1/1996 Riza
5,483,501 A 1/1996 Park et al.
5,484,436 A 1/1996 Eggers et al.
5,486,162 A 1/1996 Brumbach
5,486,189 A 1/1996 Mudry et al.
5,490,860 A 2/1996 Middle et al.
5,496,317 A 3/1996 Goble et al.
5,499,992 A 3/1996 Meade et al.
5,500,216 A 3/1996 Julian et al.
5,501,654 A 3/1996 Failla et al.
5,504,650 A 4/1996 Katsui et al.
5,505,693 A 4/1996 Mackool
5,507,297 A 4/1996 Slater et al.
5,507,738 A 4/1996 Ciervo
5,509,922 A 4/1996 Aranyi et al.
5,511,556 A 4/1996 DeSantis
5,520,704 A 5/1996 Castro et al.
5,522,832 A 6/1996 Kugo et al.
5,522,839 A 6/1996 Pilling
5,527,331 A 6/1996 Kresch et al.
5,531,744 A 7/1996 Nardella et al.
5,540,681 A 7/1996 Strul et al.
5,540,693 A 7/1996 Fisher
5,542,916 A 8/1996 Hirsch et al.
5,548,286 A 8/1996 Craven
5,549,637 A 8/1996 Crainich
5,553,675 A 9/1996 Pitzen et al.
5,558,671 A 9/1996 Yates
5,562,609 A 10/1996 Brumbach
5,562,610 A 10/1996 Brumbach
5,562,659 A 10/1996 Morris
5,562,703 A 10/1996 Desai
5,563,179 A 10/1996 Stone et al.
5,569,164 A 10/1996 Lurz
5,571,121 A 11/1996 Heifetz
5,573,424 A 11/1996 Poppe
5,573,533 A 11/1996 Strul
5,573,534 A 11/1996 Stone
5,577,654 A 11/1996 Bishop
5,584,830 A 12/1996 Ladd et al.
5,591,187 A 1/1997 Dekel
5,593,414 A 1/1997 Shipp et al.
5,599,350 A 2/1997 Schulze et al.
5,600,526 A 2/1997 Russell et al.
5,601,601 A 2/1997 Tal et al.
5,603,773 A 2/1997 Campbell
5,607,436 A 3/1997 Pratt et al.
5,607,450 A 3/1997 Zvenyatsky et al.
5,609,573 A 3/1997 Sandock
5,611,813 A 3/1997 Lichtman
5,618,304 A 4/1997 Hart et al.
5,618,307 A 4/1997 Donlon et al.
5,618,492 A 4/1997 Auten et al.
5,620,447 A 4/1997 Smith et al.
5,624,452 A 4/1997 Yates
5,626,587 A 5/1997 Bishop et al.
5,626,595 A 5/1997 Sklar et al.
5,626,608 A 5/1997 Cuny et al.
5,628,760 A 5/1997 Knoepfler
5,630,420 A 5/1997 Vaitekunas
5,632,432 A 5/1997 Schulze et al.
5,632,717 A 5/1997 Yoon
5,640,741 A 6/1997 Yano
D381,077 S 7/1997 Hunt
5,647,871 A 7/1997 Levine et al.
5,649,937 A 7/1997 Bito et al.
5,649,955 A 7/1997 Hashimoto et al.
5,651,780 A 7/1997 Jackson et al.

(56) References Cited

U.S. PATENT DOCUMENTS 5,653,713 A 8/1997 Michelson
5,655,100 A 8/1997 Ebrahim et al.
5,658,281 A 8/1997 Heard
5,662,662 A 9/1997 Bishop et al.
5,662,667 A 9/1997 Knodel
5,665,085 A 9/1997 Nardella
5,665,100 A 9/1997 Yoon
5,669,922 A 9/1997 Hood
5,674,219 A 10/1997 Monson et al.
5,674,220 A 10/1997 Fox et al.
5,674,235 A 10/1997 Parisi
5,678,568 A 10/1997 Uchikubo et al.
5,688,270 A 11/1997 Yates et al.
5,690,269 A 11/1997 Bolanos et al.
5,693,042 A 12/1997 Boiarski et al.
5,693,051 A 12/1997 Schulze et al.
5,694,936 A 12/1997 Fujimoto et al.
5,695,510 A 12/1997 Hood
5,700,261 A 12/1997 Brinkerhoff
5,704,534 A 1/1998 Huitema et al.
5,704,791 A 1/1998 Gillio
5,707,369 A 1/1998 Vaitekunas et al.
5,709,680 A 1/1998 Yates et al.
5,711,472 A 1/1998 Bryan
5,713,896 A 2/1998 Nardella
5,715,817 A 2/1998 Stevens-Wright et al.
5,716,366 A 2/1998 Yates
5,717,306 A 2/1998 Shipp
5,720,742 A 2/1998 Zacharias
5,720,744 A 2/1998 Eggleston et al.
5,722,980 A 3/1998 Schulz et al.
5,723,970 A 3/1998 Bell
5,728,130 A 3/1998 Ishikawa et al.
5,730,752 A 3/1998 Alden et al.
5,733,074 A 3/1998 Stock et al.
5,735,848 A 4/1998 Yates et al.
5,741,226 A 4/1998 Strukel et al.
5,743,906 A 4/1998 Parins et al.
5,752,973 A 5/1998 Kieturakis
5,755,717 A 5/1998 Yates et al.
5,762,255 A 6/1998 Chrisman et al.
5,766,164 A 6/1998 Mueller et al.
5,772,659 A 6/1998 Becker et al.
5,776,130 A 7/1998 Buysse et al.
5,776,155 A 7/1998 Beaupre et al.
5,779,130 A 7/1998 Alesi et al.
5,779,701 A 7/1998 McBrayer et al.
5,782,834 A 7/1998 Lucey et al.
5,792,135 A 8/1998 Madhani et al.
5,792,138 A 8/1998 Shipp
5,792,165 A 8/1998 Klieman et al.
5,796,188 A 8/1998 Bays
5,797,941 A 8/1998 Schulze et al.
5,797,958 A 8/1998 Yoon
5,797,959 A 8/1998 Castro et al.
5,800,432 A 9/1998 Swanson
5,800,448 A 9/1998 Banko
5,800,449 A 9/1998 Wales
5,805,140 A 9/1998 Rosenberg et al.
5,807,393 A 9/1998 Williamson, IV et al.
5,808,396 A 9/1998 Boukhny
5,810,811 A 9/1998 Yates et al.
5,810,828 A 9/1998 Lightman et al.
5,810,859 A 9/1998 DiMatteo et al.
5,817,033 A 10/1998 DeSantis et al.
5,817,084 A 10/1998 Jensen
5,817,093 A 10/1998 Williamson, IV et al.
5,817,119 A 10/1998 Klieman et al.
5,823,197 A 10/1998 Edwards
5,827,271 A 10/1998 Buysse et al.
5,827,323 A 10/1998 Klieman et al.
5,828,160 A 10/1998 Sugishita
5,833,696 A 11/1998 Whitfield et al.
5,836,897 A 11/1998 Sakurai et al.
5,836,909 A 11/1998 Cosmescu
5,836,943 A 11/1998 Miller, III
5,836,957 A 11/1998 Schulz et al.
5,836,990 A 11/1998 Li
5,843,109 A 12/1998 Mehta et al.
5,851,212 A 12/1998 Zirps et al.
5,853,412 A 12/1998 Mayenberger
5,854,590 A 12/1998 Dalstein
5,858,018 A 1/1999 Shipp et al.
5,865,361 A 2/1999 Milliman et al.
5,873,873 A 2/1999 Smith et al.
5,873,882 A 2/1999 Straub et al.
5,876,401 A 3/1999 Schulze et al.
5,878,193 A 3/1999 Wang et al.
5,879,364 A 3/1999 Bromfield et al.
5,880,668 A 3/1999 Hall
5,883,615 A 3/1999 Fago et al.
5,891,142 A 4/1999 Eggers et al.
5,893,835 A 4/1999 Witt et al.
5,897,523 A 4/1999 Wright et al.
5,897,569 A 4/1999 Kellogg et al.
5,903,607 A 5/1999 Tailliet
5,904,681 A 5/1999 West, Jr.
5,906,625 A 5/1999 Bito et al.
5,906,627 A 5/1999 Spaulding
5,906,628 A 5/1999 Miyawaki et al.
5,910,129 A 6/1999 Koblish et al.
5,911,699 A 6/1999 Anis et al.
5,913,823 A 6/1999 Hedberg et al.
5,916,229 A 6/1999 Evans
5,921,956 A 7/1999 Grinberg et al.
5,929,846 A 7/1999 Rosenberg et al.
5,935,143 A 8/1999 Hood
5,935,144 A 8/1999 Estabrook
5,938,633 A 8/1999 Beaupre
5,944,718 A 8/1999 Austin et al.
5,944,737 A 8/1999 Tsonton et al.
5,947,984 A 9/1999 Whipple
5,954,717 A 9/1999 Behl et al.
5,954,736 A 9/1999 Bishop et al.
5,954,746 A 9/1999 Holthaus et al.
5,957,882 A 9/1999 Nita et al.
5,957,943 A 9/1999 Vaitekunas
5,968,007 A 10/1999 Simon et al.
5,968,060 A 10/1999 Kellogg
5,974,342 A 10/1999 Petrofsky
D416,089 S 11/1999 Barton et al.
5,980,510 A 11/1999 Tsonton et al.
5,980,546 A 11/1999 Hood
5,984,938 A 11/1999 Yoon
5,987,344 A 11/1999 West
5,989,274 A 11/1999 Davison et al.
5,989,275 A 11/1999 Estabrook et al.
5,993,465 A 11/1999 Shipp et al.
5,993,972 A 11/1999 Reich et al.
5,994,855 A 11/1999 Lundell et al.
6,003,517 A 12/1999 Sheffield et al.
6,004,335 A 12/1999 Vaitekunas et al.
6,013,052 A 1/2000 Durman et al.
6,024,741 A 2/2000 Williamson, IV et al.
6,024,744 A 2/2000 Kese et al.
6,024,750 A 2/2000 Mastri et al.
6,027,515 A 2/2000 Cimino
6,031,526 A 2/2000 Shipp
6,033,375 A 3/2000 Brumbach
6,033,399 A 3/2000 Gines
6,036,667 A * 3/2000 Manna ........... A61B 17/320092
606/205
6,036,707 A 3/2000 Spaulding
6,039,734 A 3/2000 Goble
6,048,224 A 4/2000 Kay
6,050,943 A 4/2000 Slayton et al.
6,050,996 A 4/2000 Schmaltz et al.
6,051,010 A 4/2000 DiMatteo et al.
6,056,735 A 5/2000 Okada et al.
6,063,098 A 5/2000 Houser et al.
6,066,132 A 5/2000 Chen et al.
6,066,151 A 5/2000 Miyawaki et al.
6,068,627 A 5/2000 Orszulak et al.
6,068,629 A 5/2000 Haissaguerre et al.

(56) References Cited

U.S. PATENT DOCUMENTS 6,068,647 A 5/2000 Witt et al.
6,074,389 A 6/2000 Levine et al.
6,077,285 A 6/2000 Boukhny
6,080,149 A 6/2000 Huang et al.
6,083,191 A 7/2000 Rose
6,086,584 A 7/2000 Miller
6,090,120 A 7/2000 Wright et al.
6,091,995 A 7/2000 Ingle et al.
6,096,033 A 8/2000 Tu et al.
6,099,483 A 8/2000 Palmer et al.
6,099,542 A 8/2000 Cohn et al.
6,099,550 A 8/2000 Yoon
6,109,500 A 8/2000 Alli et al.
6,110,127 A 8/2000 Suzuki
6,113,594 A 9/2000 Savage
6,113,598 A 9/2000 Baker
6,117,152 A 9/2000 Huitema
H1904 H 10/2000 Yates et al.
6,126,629 A 10/2000 Perkins
6,126,658 A 10/2000 Baker
6,129,735 A 10/2000 Okada et al.
6,129,740 A 10/2000 Michelson
6,132,368 A 10/2000 Cooper
6,132,427 A 10/2000 Jones et al.
6,132,429 A 10/2000 Baker
6,132,448 A 10/2000 Perez et al.
6,139,320 A 10/2000 Hahn
6,139,561 A 10/2000 Shibata et al.
6,142,615 A 11/2000 Qiu et al.
6,142,994 A 11/2000 Swanson et al.
6,144,402 A 11/2000 Norsworthy et al.
6,147,560 A 11/2000 Erhage et al.
6,152,902 A 11/2000 Christian et al.
6,152,923 A 11/2000 Ryan
6,154,198 A 11/2000 Rosenberg
6,156,029 A 12/2000 Mueller
6,159,160 A 12/2000 Hsei et al.
6,159,175 A 12/2000 Strukel et al.
6,162,194 A 12/2000 Shipp
6,162,208 A 12/2000 Hipps
6,165,150 A 12/2000 Banko
6,174,309 B1 1/2001 Wrublewski et al.
6,174,310 B1 1/2001 Kirwan, Jr.
6,176,857 B1 1/2001 Ashley
6,179,853 B1 1/2001 Sachse et al.
6,183,426 B1 2/2001 Akisada et al.
6,187,003 B1 2/2001 Buysse et al.
6,190,386 B1 2/2001 Rydell
6,193,709 B1 2/2001 Miyawaki et al.
6,204,592 B1 3/2001 Hur
6,205,383 B1 3/2001 Hermann
6,205,855 B1 3/2001 Pfeiffer
6,206,844 B1 3/2001 Reichel et al.
6,206,876 B1 3/2001 Levine et al.
6,210,337 B1 4/2001 Dunham et al.
6,210,402 B1 4/2001 Olsen et al.
6,210,403 B1 4/2001 Klicek
6,214,023 B1 4/2001 Whipple et al.
6,228,080 B1 5/2001 Gines
6,231,565 B1 5/2001 Tovey et al.
6,232,899 B1 5/2001 Craven
6,233,476 B1 5/2001 Strommer et al.
6,238,366 B1 5/2001 Savage et al.
6,241,724 B1 6/2001 Fleischman et al.
6,245,065 B1 6/2001 Panescu et al.
6,251,110 B1 6/2001 Wampler
6,252,110 B1 6/2001 Uemura et al.
D444,365 S 7/2001 Bass et al.
D445,092 S 7/2001 Lee
D445,764 S 7/2001 Lee
6,254,623 B1 7/2001 Haibel, Jr. et al.
6,257,241 B1 7/2001 Wampler
6,258,034 B1 7/2001 Hanafy
6,259,230 B1 7/2001 Chou
6,267,761 B1 7/2001 Ryan
6,270,831 B2 8/2001 Kumar et al.
6,273,852 B1 8/2001 Lehe et al.
6,274,963 B1 8/2001 Estabrook et al.
6,277,115 B1 8/2001 Saadat
6,277,117 B1 8/2001 Tetzlaff et al.
6,278,218 B1 8/2001 Madan et al.
6,280,407 B1 8/2001 Manna et al.
6,283,981 B1 9/2001 Beaupre
6,287,344 B1 9/2001 Wampler et al.
6,290,575 B1 9/2001 Shipp
6,292,700 B1 9/2001 Morrison et al.
6,299,591 B1 10/2001 Banko
6,299,601 B1 10/2001 Hjertman
6,306,131 B1 10/2001 Hareyama et al.
6,306,157 B1 10/2001 Shchervinsky
6,309,400 B2 10/2001 Beaupre
6,311,783 B1 11/2001 Harpell
6,319,221 B1 11/2001 Savage et al.
6,325,795 B1 12/2001 Lindemann et al.
6,325,799 B1 12/2001 Goble
6,325,811 B1 12/2001 Messerly
6,328,751 B1 12/2001 Beaupre
6,332,891 B1 12/2001 Himes
6,338,657 B1 1/2002 Harper et al.
6,340,352 B1 1/2002 Okada et al.
6,340,878 B1 1/2002 Oglesbee
6,350,269 B1 2/2002 Shipp et al.
6,352,532 B1 3/2002 Kramer et al.
6,356,224 B1 3/2002 Wohlfarth
6,358,246 B1 3/2002 Behl et al.
6,358,264 B2 3/2002 Banko
6,364,888 B1 4/2002 Niemeyer et al.
6,379,320 B1 4/2002 Lafon et al.
D457,958 S 5/2002 Dycus et al.
6,383,194 B1 5/2002 Pothula
6,384,690 B1 5/2002 Wilhelmsson et al.
6,387,094 B1 5/2002 Eitenmuller
6,387,109 B1 5/2002 Davison et al.
6,388,657 B1 5/2002 Natoli
6,390,973 B1 5/2002 Ouchi
6,391,026 B1 5/2002 Hung et al.
6,391,042 B1 5/2002 Cimino
6,398,779 B1 6/2002 Buysse et al.
6,402,743 B1 6/2002 Orszulak et al.
6,402,748 B1 6/2002 Schoenman et al.
6,405,184 B1 6/2002 Bohme et al.
6,405,733 B1 6/2002 Fogarty et al.
6,409,722 B1 6/2002 Hoey et al.
H2037 H 7/2002 Yates et al.
6,416,469 B1 7/2002 Phung et al.
6,416,486 B1 7/2002 Wampler
6,419,675 B1 7/2002 Gallo, Sr.
6,423,073 B2 7/2002 Bowman
6,423,082 B1 7/2002 Houser et al.
6,425,906 B1 7/2002 Young et al.
6,428,538 B1 8/2002 Blewett et al.
6,428,539 B1 8/2002 Baxter et al.
6,430,446 B1 8/2002 Knowlton
6,432,118 B1 8/2002 Messerly
6,436,114 B1 8/2002 Novak et al.
6,436,115 B1 8/2002 Beaupre
6,440,062 B1 8/2002 Ouchi
6,443,968 B1 9/2002 Holthaus et al.
6,443,969 B1 9/2002 Novak et al.
6,449,006 B1 9/2002 Shipp
6,454,781 B1 9/2002 Witt et al.
6,454,782 B1 9/2002 Schwemberger
6,458,128 B1 10/2002 Schulze
6,458,130 B1 10/2002 Frazier et al.
6,458,142 B1 10/2002 Faller et al.
6,459,363 B1 10/2002 Walker et al.
6,461,363 B1 10/2002 Gadberry et al.
6,464,689 B1 10/2002 Qin et al.
6,464,702 B2 10/2002 Schulze et al.
6,468,270 B1 10/2002 Hovda et al.
6,475,211 B2 11/2002 Chess et al.
6,475,215 B1 11/2002 Tanrisever
6,480,796 B2 11/2002 Wiener
6,485,490 B2 11/2002 Wampler et al.

(56) References Cited

U.S. PATENT DOCUMENTS 6,491,690 B1 12/2002 Goble et al.
6,491,701 B2 12/2002 Tierney et al.
6,491,708 B2 12/2002 Madan et al.
6,497,715 B2 12/2002 Satou
6,500,112 B1 12/2002 Khouri
6,500,176 B1 12/2002 Truckai et al.
6,500,188 B2 12/2002 Harper et al.
6,500,312 B2 12/2002 Wedekamp
6,503,248 B1 1/2003 Levine
6,506,208 B2 1/2003 Hunt et al.
6,511,478 B1 1/2003 Burnside et al.
6,511,480 B1 1/2003 Tetzlaff et al.
6,511,493 B1 1/2003 Moutafis et al.
6,514,252 B2 2/2003 Nezhat et al.
6,514,267 B2 2/2003 Jewett
6,517,565 B1 2/2003 Whitman et al.
6,524,251 B2 2/2003 Rabiner et al.
6,524,316 B1 2/2003 Nicholson et al.
6,527,736 B1 3/2003 Attinger et al.
6,531,846 B1 3/2003 Smith
6,533,784 B2 3/2003 Truckai et al.
6,537,272 B2 3/2003 Christopherson et al.
6,537,291 B2 3/2003 Friedman et al.
6,543,452 B1 4/2003 Lavigne
6,543,456 B1 4/2003 Freeman
6,544,260 B1 4/2003 Markel et al.
6,551,309 B1 4/2003 LePivert
6,554,829 B2 4/2003 Schulze et al.
6,558,376 B2 5/2003 Bishop
6,561,983 B2 5/2003 Cronin et al.
6,562,035 B1 5/2003 Levin
6,562,037 B2 5/2003 Paton et al.
6,565,558 B1 5/2003 Lindenmeier et al.
6,572,563 B2 6/2003 Ouchi
6,572,632 B2 6/2003 Zisterer et al.
6,572,639 B1 6/2003 Ingle et al.
6,575,969 B1 6/2003 Rittman, III et al.
6,582,427 B1 6/2003 Goble et al.
6,582,451 B1 6/2003 Marucci et al.
6,584,360 B2 6/2003 Francischelli et al.
D477,408 S 7/2003 Bromley
6,585,735 B1 7/2003 Frazier et al.
6,588,277 B2 7/2003 Giordano et al.
6,589,200 B1 7/2003 Schwemberger et al.
6,589,239 B2 7/2003 Khandkar et al.
6,590,733 B1 7/2003 Wilson et al.
6,599,288 B2 7/2003 Maguire et al.
6,602,252 B2 8/2003 Mollenauer
6,602,262 B2 8/2003 Griego et al.
6,607,540 B1 8/2003 Shipp
6,610,059 B1 8/2003 West, Jr.
6,610,060 B2 8/2003 Mulier et al.
6,611,793 B1 8/2003 Burnside et al.
6,616,450 B2 9/2003 Mossle et al.
6,619,529 B2 9/2003 Green et al.
6,620,161 B2 9/2003 Schulze et al.
6,622,731 B2 9/2003 Daniel et al.
6,623,482 B2 9/2003 Pendekanti et al.
6,623,500 B1 9/2003 Cook et al.
6,623,501 B2 9/2003 Heller et al.
6,626,848 B2 9/2003 Neuenfeldt
6,626,926 B2 9/2003 Friedman et al.
6,629,974 B2 10/2003 Penny et al.
6,632,221 B1 10/2003 Edwards et al.
6,633,234 B2 10/2003 Wiener et al.
6,635,057 B2 10/2003 Harano et al.
6,644,532 B2 11/2003 Green et al.
6,651,669 B1 11/2003 Burnside
6,652,513 B2 11/2003 Panescu et al.
6,652,539 B2 11/2003 Shipp et al.
6,652,545 B2 11/2003 Shipp et al.
6,656,132 B1 12/2003 Ouchi
6,656,177 B2 12/2003 Truckai et al.
6,656,198 B2 12/2003 Tsonton et al.
6,660,017 B2 12/2003 Beaupre
6,662,127 B2 12/2003 Wiener et al.
6,663,941 B2 12/2003 Brown et al.
6,666,860 B1 12/2003 Takahashi
6,666,875 B1 12/2003 Sakurai et al.
6,669,690 B1 12/2003 Okada et al.
6,669,710 B2 12/2003 Moutafis et al.
6,673,248 B2 1/2004 Chowdhury
6,676,660 B2 1/2004 Wampler et al.
6,678,621 B2 1/2004 Wiener et al.
6,678,899 B2 1/2004 Fiorini et al.
6,679,875 B2 1/2004 Honda et al.
6,679,882 B1 1/2004 Kornerup
6,679,899 B2 1/2004 Wiener et al.
6,682,501 B1 1/2004 Nelson et al.
6,682,544 B2 1/2004 Mastri et al.
6,685,700 B2 2/2004 Behl et al.
6,685,701 B2 2/2004 Orszulak et al.
6,685,703 B2 2/2004 Pearson et al.
6,689,145 B2 2/2004 Lee et al.
6,689,146 B1 2/2004 Himes
6,690,960 B2 2/2004 Chen et al.
6,695,840 B2 2/2004 Schulze
6,702,821 B2 3/2004 Bonutti
6,716,215 B1 4/2004 David et al.
6,719,692 B2 4/2004 Kleffner et al.
6,719,765 B2 4/2004 Bonutti
6,719,776 B2 4/2004 Baxter et al.
6,722,552 B2 4/2004 Fenton, Jr.
6,723,091 B2 4/2004 Goble et al.
D490,059 S 5/2004 Conway et al.
6,730,080 B2 5/2004 Harano et al.
6,731,047 B2 5/2004 Kauf et al.
6,733,498 B2 5/2004 Paton et al.
6,733,506 B1 5/2004 McDevitt et al.
6,736,813 B2 5/2004 Yamauchi et al.
6,739,872 B1 5/2004 Turri
6,740,079 B1 5/2004 Eggers et al.
D491,666 S 6/2004 Kimmell et al.
6,743,245 B2 6/2004 Lobdell
6,746,284 B1 6/2004 Spink, Jr.
6,746,443 B1 6/2004 Morley et al.
6,752,815 B2 6/2004 Beaupre
6,755,825 B2 6/2004 Shoenman et al.
6,761,698 B2 7/2004 Shibata et al.
6,762,535 B2 7/2004 Take et al.
6,766,202 B2 7/2004 Underwood et al.
6,770,072 B1 8/2004 Truckai et al.
6,773,409 B2 8/2004 Truckai et al.
6,773,434 B2 8/2004 Ciarrocca
6,773,435 B2 8/2004 Schulze et al.
6,773,443 B2 8/2004 Truwit et al.
6,773,444 B2 8/2004 Messerly
6,775,575 B2 8/2004 Bommannan et al.
6,778,023 B2 8/2004 Christensen
6,783,524 B2 8/2004 Anderson et al.
6,786,382 B1 9/2004 Hoffman
6,786,383 B2 9/2004 Stegelmann
6,789,939 B2 9/2004 Schrodinger et al.
6,790,173 B2 9/2004 Saadat et al.
6,790,216 B1 9/2004 Ishikawa
6,794,027 B1 9/2004 Araki et al.
6,796,981 B2 9/2004 Wham et al.
D496,997 S 10/2004 Dycus et al.
6,800,085 B2 10/2004 Selmon et al.
6,802,843 B2 10/2004 Truckai et al.
6,808,525 B2 10/2004 Latterell et al.
6,809,508 B2 10/2004 Donofrio
6,810,281 B2 10/2004 Brock et al.
6,811,842 B1 11/2004 Ehrnsperger et al.
6,814,731 B2 11/2004 Swanson
6,819,027 B2 11/2004 Saraf
6,821,273 B2 11/2004 Mollenauer
6,827,712 B2 12/2004 Tovey et al.
6,828,712 B2 12/2004 Battaglin et al.
6,835,082 B2 12/2004 Gonnering
6,835,199 B2 12/2004 McGuckin, Jr. et al.
6,840,938 B1 1/2005 Morley et al.
6,843,789 B2 1/2005 Goble
6,849,073 B2 2/2005 Hoey et al.

(56) References Cited

U.S. PATENT DOCUMENTS 6,860,878 B2 3/2005 Brock
6,860,880 B2 3/2005 Treat et al.
6,863,676 B2 3/2005 Lee et al.
6,866,671 B2 3/2005 Tierney et al.
6,869,439 B2 3/2005 White et al.
6,875,220 B2 4/2005 Du et al.
6,877,647 B2 4/2005 Green et al.
6,882,439 B2 4/2005 Ishijima
6,887,209 B2 5/2005 Kadziauskas et al.
6,887,252 B1 5/2005 Okada et al.
6,893,435 B2 5/2005 Goble
6,898,536 B2 5/2005 Wiener et al.
6,899,685 B2 5/2005 Kermode et al.
6,905,497 B2 6/2005 Truckai et al.
6,908,463 B2 6/2005 Treat et al.
6,908,472 B2 6/2005 Wiener et al.
6,913,579 B2 7/2005 Truckai et al.
6,915,623 B2 7/2005 Dey et al.
6,923,804 B2 8/2005 Eggers et al.
6,923,806 B2 8/2005 Hooven et al.
6,926,712 B2 8/2005 Phan
6,926,716 B2 8/2005 Baker et al.
6,926,717 B1 8/2005 Garito et al.
6,929,602 B2 8/2005 Hirakui et al.
6,929,622 B2 8/2005 Chian
6,929,632 B2 8/2005 Nita et al.
6,929,644 B2 8/2005 Truckai et al.
6,933,656 B2 8/2005 Matsushita et al.
D509,589 S 9/2005 Wells
6,942,660 B2 9/2005 Pantera et al.
6,942,677 B2 9/2005 Nita et al.
6,945,981 B2 9/2005 Donofrio et al.
6,946,779 B2 9/2005 Birgel
6,948,503 B2 9/2005 Refior et al.
6,953,461 B2 10/2005 McClurken et al.
6,958,070 B2 10/2005 Witt et al.
D511,145 S 11/2005 Donofrio et al.
6,974,450 B2 12/2005 Weber et al.
6,976,844 B2 12/2005 Hickok et al.
6,976,969 B2 12/2005 Messerly
6,977,495 B2 12/2005 Donofrio
6,979,332 B2 12/2005 Adams
6,981,628 B2 1/2006 Wales
6,984,220 B2 1/2006 Wuchinich
6,984,231 B2 1/2006 Goble et al.
6,988,295 B2 1/2006 Tillim
6,994,708 B2 2/2006 Manzo
6,994,709 B2 2/2006 Iida
7,000,818 B2 2/2006 Shelton, IV et al.
7,001,335 B2 2/2006 Adachi et al.
7,001,379 B2 2/2006 Behl et al.
7,001,382 B2 2/2006 Gallo, Sr.
7,004,951 B2 2/2006 Gibbens, III
7,011,657 B2 3/2006 Truckai et al.
7,014,638 B2 3/2006 Michelson
7,018,389 B2 3/2006 Camerlengo
7,025,732 B2 4/2006 Thompson et al.
7,033,356 B2 4/2006 Latterell et al.
7,033,357 B2 4/2006 Baxter et al.
7,037,306 B2 5/2006 Podany et al.
7,041,083 B2 5/2006 Chu et al.
7,041,088 B2 5/2006 Nawrocki et al.
7,041,102 B2 5/2006 Truckai et al.
7,044,949 B2 5/2006 Orszulak et al.
7,052,494 B2 5/2006 Goble et al.
7,052,496 B2 5/2006 Yamauchi
7,055,731 B2 6/2006 Shelton, IV et al.
7,063,699 B2 6/2006 Hess et al.
7,066,893 B2 6/2006 Hibner et al.
7,066,895 B2 6/2006 Podany
7,066,936 B2 6/2006 Ryan
7,070,597 B2 7/2006 Truckai et al.
7,074,218 B2 7/2006 Washington et al.
7,074,219 B2 7/2006 Levine et al.
7,077,039 B2 7/2006 Gass et al.
7,077,845 B2 7/2006 Hacker et al.
7,077,853 B2 7/2006 Kramer et al.
7,083,075 B2 8/2006 Swayze et al.
7,083,613 B2 8/2006 Treat
7,083,618 B2 8/2006 Couture et al.
7,083,619 B2 8/2006 Truckai et al.
7,087,054 B2 8/2006 Truckai et al.
7,090,637 B2 8/2006 Danitz et al.
7,090,672 B2 8/2006 Underwood et al.
7,094,235 B2 8/2006 Francischelli
7,101,371 B2 9/2006 Dycus et al.
7,101,372 B2 9/2006 Dycus et al.
7,101,373 B2 9/2006 Dycus et al.
7,101,378 B2 9/2006 Salameh et al.
7,104,834 B2 9/2006 Robinson et al.
7,108,695 B2 9/2006 Witt et al.
7,111,769 B2 9/2006 Wales et al.
7,112,201 B2 9/2006 Truckai et al.
7,113,831 B2 9/2006 Hooven
D531,311 S 10/2006 Guerra et al.
7,117,034 B2 10/2006 Kronberg
7,118,564 B2 10/2006 Ritchie et al.
7,118,570 B2 10/2006 Tetzlaff et al.
7,118,587 B2 10/2006 Dycus et al.
7,119,516 B2 10/2006 Denning
7,124,932 B2 10/2006 Isaacson et al.
7,125,409 B2 10/2006 Truckai et al.
7,128,720 B2 10/2006 Podany
7,131,860 B2 11/2006 Sartor et al.
7,131,970 B2 11/2006 Moses et al.
7,135,018 B2 11/2006 Ryan et al.
7,135,030 B2 11/2006 Schwemberger et al.
7,137,980 B2 11/2006 Buysse et al.
7,143,925 B2 12/2006 Shelton, IV et al.
7,144,403 B2 12/2006 Booth
7,147,138 B2 12/2006 Shelton, IV
7,153,315 B2 12/2006 Miller
D536,093 S 1/2007 Nakajima et al.
7,156,189 B1 1/2007 Bar-Cohen et al.
7,156,846 B2 1/2007 Dycus et al.
7,156,853 B2 1/2007 Muratsu
7,157,058 B2 1/2007 Marhasin et al.
7,159,750 B2 1/2007 Racenet et al.
7,160,259 B2 1/2007 Tardy et al.
7,160,296 B2 1/2007 Pearson et al.
7,160,298 B2 1/2007 Lawes et al.
7,160,299 B2 1/2007 Baily
7,163,548 B2 1/2007 Stulen et al.
7,166,103 B2 1/2007 Carmel et al.
7,169,144 B2 1/2007 Hoey et al.
7,169,146 B2 1/2007 Truckai et al.
7,169,156 B2 1/2007 Hart
7,179,254 B2 2/2007 Pendekanti et al.
7,179,271 B2 2/2007 Friedman et al.
7,186,253 B2 3/2007 Truckai et al.
7,189,233 B2 3/2007 Truckai et al.
7,195,631 B2 3/2007 Dumbauld
D541,418 S 4/2007 Schechter et al.
7,198,635 B2 4/2007 Danek et al.
7,204,820 B2 4/2007 Akahoshi
7,207,471 B2 4/2007 Heinrich et al.
7,207,997 B2 4/2007 Shipp et al.
7,208,005 B2 4/2007 Frecker et al.
7,210,881 B2 5/2007 Greenberg
7,211,079 B2 5/2007 Treat
7,217,128 B2 5/2007 Atkin et al.
7,217,269 B2 5/2007 El-Galley et al.
7,220,951 B2 5/2007 Truckai et al.
7,223,229 B2 5/2007 Inman et al.
7,225,964 B2 6/2007 Mastri et al.
7,226,447 B2 6/2007 Uchida et al.
7,226,448 B2 6/2007 Bertolero et al.
7,229,455 B2 6/2007 Sakurai et al.
7,232,440 B2 6/2007 Dumbauld et al.
7,235,071 B2 6/2007 Gonnering
7,235,073 B2 6/2007 Levine et al.
7,241,294 B2 7/2007 Reschke
7,244,262 B2 7/2007 Wiener et al.
7,251,531 B2 7/2007 Mosher et al.

(56) References Cited

U.S. PATENT DOCUMENTS 7,252,641 B2 8/2007 Thompson et al.
7,252,667 B2 8/2007 Moses et al.
7,258,688 B1 8/2007 Shah et al.
7,264,618 B2 9/2007 Murakami et al.
7,267,677 B2 9/2007 Johnson et al.
7,267,685 B2 9/2007 Butaric et al.
7,269,873 B2 9/2007 Brewer et al.
7,273,483 B2 9/2007 Wiener et al.
D552,241 S 10/2007 Bromley et al.
7,282,048 B2 10/2007 Goble et al.
7,285,895 B2 10/2007 Beaupre
7,287,682 B1 10/2007 Ezzat et al.
7,297,149 B2 11/2007 Vitali et al.
7,300,431 B2 11/2007 Dubrovsky
7,300,435 B2 11/2007 Wham et al.
7,300,446 B2 11/2007 Beaupre
7,300,450 B2 11/2007 Vleugels et al.
7,303,531 B2 12/2007 Lee et al.
7,303,557 B2 12/2007 Wham et al.
7,306,597 B2 12/2007 Manzo
7,307,313 B2 12/2007 Ohyanagi et al.
7,309,849 B2 12/2007 Truckai et al.
7,311,706 B2 12/2007 Schoenman et al.
7,311,709 B2 12/2007 Truckai et al.
7,317,955 B2 1/2008 McGreevy
7,318,831 B2 1/2008 Alvarez et al.
7,318,832 B2 1/2008 Young et al.
7,322,858 B1 1/2008 Rogers et al.
7,326,236 B2 2/2008 Andreas et al.
7,329,257 B2 2/2008 Kanehira et al.
7,331,410 B2 2/2008 Yong et al.
7,335,165 B2 2/2008 Truwit et al.
7,335,997 B2 2/2008 Wiener
7,337,010 B2 2/2008 Howard et al.
7,353,068 B2 4/2008 Tanaka et al.
7,354,440 B2 4/2008 Truckal et al.
7,357,287 B2 4/2008 Shelton, IV et al.
7,357,802 B2 4/2008 Palanker et al.
7,361,172 B2 4/2008 Cimino
7,364,577 B2 4/2008 Wham et al.
7,367,976 B2 5/2008 Lawes et al.
7,371,227 B2 5/2008 Zeiner
RE40,388 E 6/2008 Gines
7,380,695 B2 6/2008 Doll et al.
7,380,696 B2 6/2008 Shelton, IV et al.
7,381,209 B2 6/2008 Truckai et al.
7,384,420 B2 6/2008 Dycus et al.
7,390,317 B2 6/2008 Taylor et al.
7,396,356 B2 7/2008 Mollenauer
7,403,224 B2 7/2008 Fuller et al.
7,404,508 B2 7/2008 Smith et al.
7,407,077 B2 8/2008 Ortiz et al.
7,408,288 B2 8/2008 Hara
7,412,008 B2 8/2008 Lliev
7,416,101 B2 8/2008 Shelton, IV et al.
7,416,437 B2 8/2008 Sartor et al.
D576,725 S 9/2008 Shumer et al.
7,419,490 B2 9/2008 Falkenstein et al.
7,422,139 B2 9/2008 Shelton, IV et al.
7,422,463 B2 9/2008 Kuo
7,422,582 B2 9/2008 Malackowski et al.
D578,643 S 10/2008 Shumer et al.
D578,644 S 10/2008 Shumer et al.
D578,645 S 10/2008 Shumer et al.
7,431,694 B2 10/2008 Stefanchik et al.
7,431,704 B2 10/2008 Babaev
7,431,720 B2 10/2008 Pendekanti et al.
7,435,582 B2 10/2008 Zimmermann et al.
7,441,684 B2 10/2008 Shelton, IV et al.
7,442,193 B2 10/2008 Shields et al.
7,445,621 B2 11/2008 Dumbauld et al.
7,449,004 B2 11/2008 Yamada et al.
7,451,904 B2 11/2008 Shelton, IV
7,455,208 B2 11/2008 Wales et al.
7,455,641 B2 11/2008 Yamada et al.
7,462,181 B2 12/2008 Kraft et al.
7,464,846 B2 12/2008 Shelton, IV et al.
7,464,849 B2 12/2008 Shelton, IV et al.
7,472,815 B2 1/2009 Shelton, IV et al.
7,473,145 B2 1/2009 Ehr et al.
7,473,253 B2 1/2009 Dycus et al.
7,473,263 B2 1/2009 Johnston et al.
7,479,148 B2 1/2009 Beaupre
7,479,160 B2 1/2009 Branch et al.
7,481,775 B2 1/2009 Weikel, Jr. et al.
7,488,285 B2 2/2009 Honda et al.
7,488,319 B2 2/2009 Yates
7,491,201 B2 2/2009 Shields et al.
7,491,202 B2 2/2009 Odom et al.
7,494,468 B2 2/2009 Rabiner et al.
7,494,501 B2 2/2009 Ahlberg et al.
7,498,080 B2 3/2009 Tung et al.
7,502,234 B2 3/2009 Goliszek et al.
7,503,893 B2 3/2009 Kucklick
7,503,895 B2 3/2009 Rabiner et al.
7,506,790 B2 3/2009 Shelton, IV
7,506,791 B2 3/2009 Omaits et al.
7,507,239 B2 3/2009 Shadduck
7,510,107 B2 3/2009 Timm et al.
7,510,556 B2 3/2009 Nguyen et al.
7,513,025 B2 4/2009 Fischer
7,517,349 B2 4/2009 Truckai et al.
7,520,865 B2 4/2009 Radley Young et al.
7,524,320 B2 4/2009 Tierney et al.
7,525,309 B2 4/2009 Sherman et al.
7,530,986 B2 5/2009 Beaupre et al.
7,534,243 B1 5/2009 Chin et al.
7,535,233 B2 5/2009 Kojovic et al.
D594,983 S 6/2009 Price et al.
7,540,871 B2 6/2009 Gonnering
7,540,872 B2 6/2009 Schechter et al.
7,543,730 B1 6/2009 Marczyk
7,544,200 B2 6/2009 Houser
7,549,564 B2 6/2009 Boudreaux
7,550,216 B2 6/2009 Ofer et al.
7,553,309 B2 6/2009 Buysse et al.
7,554,343 B2 6/2009 Bromfield
7,559,450 B2 7/2009 Wales et al.
7,559,452 B2 7/2009 Wales et al.
7,563,259 B2 7/2009 Takahashi
7,566,318 B2 7/2009 Haefner
7,567,012 B2 7/2009 Namikawa
7,568,603 B2 8/2009 Shelton, IV et al.
7,569,057 B2 8/2009 Liu et al.
7,572,266 B2 8/2009 Young et al.
7,572,268 B2 8/2009 Babaev
7,578,820 B2 8/2009 Moore et al.
7,582,084 B2 9/2009 Swanson et al.
7,582,086 B2 9/2009 Privitera et al.
7,582,087 B2 9/2009 Tetzlaff et al.
7,582,095 B2 9/2009 Shipp et al.
7,585,181 B2 9/2009 Olsen
7,586,289 B2 9/2009 Andruk et al.
7,587,536 B2 9/2009 McLeod
7,588,176 B2 9/2009 Timm et al.
7,588,177 B2 9/2009 Racenet
7,594,925 B2 9/2009 Danek et al.
7,597,693 B2 10/2009 Garrison
7,601,119 B2 10/2009 Shahinian
7,601,136 B2 10/2009 Akahoshi
7,604,150 B2 10/2009 Boudreaux
7,607,557 B2 10/2009 Shelton, IV et al.
7,617,961 B2 11/2009 Viola
7,621,930 B2 11/2009 Houser
7,625,370 B2 12/2009 Hart et al.
7,628,791 B2 12/2009 Garrison et al.
7,628,792 B2 12/2009 Guerra
7,632,267 B2 12/2009 Dahla
7,632,269 B2 12/2009 Truckai et al.
7,637,410 B2 12/2009 Marczyk
7,641,480 B1 1/2010 Hossack et al.
7,641,653 B2 1/2010 Dalla Betta et al.
7,641,671 B2 1/2010 Crainich
7,644,848 B2 1/2010 Swayze et al.

(56) References Cited

U.S. PATENT DOCUMENTS 7,645,240 B2 1/2010 Thompson et al.
7,645,277 B2 1/2010 McClurken et al.
7,645,278 B2 1/2010 Ichihashi et al.
7,648,499 B2 1/2010 Orszulak et al.
7,649,410 B2 1/2010 Andersen et al.
7,654,431 B2 2/2010 Hueil et al.
7,655,003 B2 2/2010 Lorang et al.
7,658,311 B2 2/2010 Boudreaux
7,659,833 B2 2/2010 Warner et al.
7,662,151 B2 2/2010 Crompton, Jr. et al.
7,665,647 B2 2/2010 Shelton, IV et al.
7,666,206 B2 2/2010 Taniguchi et al.
7,667,592 B2 2/2010 Ohyama et al.
7,670,334 B2 3/2010 Hueil et al.
7,670,338 B2 3/2010 Albrecht et al.
7,674,263 B2 3/2010 Ryan
7,678,069 B1 3/2010 Baker et al.
7,678,105 B2 3/2010 McGreevy et al.
7,678,125 B2 3/2010 Shipp
7,682,366 B2 3/2010 Sakurai et al.
7,686,770 B2 3/2010 Cohen
7,686,826 B2 3/2010 Lee et al.
7,688,028 B2 3/2010 Phillips et al.
7,691,095 B2 4/2010 Bednarek et al.
7,691,098 B2 4/2010 Wallace et al.
7,696,441 B2 4/2010 Kataoka
7,699,846 B2 4/2010 Ryan
7,703,459 B2 4/2010 Saadat et al.
7,703,653 B2 4/2010 Shah et al.
7,708,735 B2 5/2010 Chapman et al.
7,708,751 B2 5/2010 Hughes et al.
7,708,758 B2 5/2010 Lee et al.
7,708,768 B2 5/2010 Danek et al.
7,713,202 B2 5/2010 Boukhny et al.
7,713,267 B2 5/2010 Pozzato
7,714,481 B2 5/2010 Sakai
7,717,312 B2 5/2010 Beetel
7,717,914 B2 5/2010 Kimura
7,717,915 B2 5/2010 Miyazawa
7,721,935 B2 5/2010 Racenet et al.
7,722,527 B2 5/2010 Bouchier et al.
7,722,607 B2 5/2010 Dumbauld et al.
D618,797 S 6/2010 Price et al.
7,726,537 B2 6/2010 Olson et al.
7,727,177 B2 6/2010 Bayat
7,731,717 B2 6/2010 Odom et al.
7,738,969 B2 6/2010 Bleich
7,740,594 B2 6/2010 Hibner
7,744,615 B2 6/2010 Couture
7,749,240 B2 7/2010 Takahashi et al.
7,751,115 B2 7/2010 Song
7,753,245 B2 7/2010 Boudreaux et al.
7,753,904 B2 7/2010 Shelton, IV et al.
7,753,908 B2 7/2010 Swanson
7,762,445 B2 7/2010 Heinrich et al.
D621,503 S 8/2010 Otten et al.
7,766,210 B2 8/2010 Shelton, IV et al.
7,766,693 B2 8/2010 Sartor et al.
7,766,910 B2 8/2010 Hixson et al.
7,768,510 B2 8/2010 Tsai et al.
7,770,774 B2 8/2010 Mastri et al.
7,770,775 B2 8/2010 Shelton, IV et al.
7,771,425 B2 8/2010 Dycus et al.
7,771,444 B2 8/2010 Patel et al.
7,775,972 B2 8/2010 Brock et al.
7,776,036 B2 8/2010 Schechter et al.
7,776,037 B2 8/2010 Odom
7,778,733 B2 8/2010 Nowlin et al.
7,780,054 B2 8/2010 Wales
7,780,593 B2 8/2010 Ueno et al.
7,780,651 B2 8/2010 Madhani et al.
7,780,659 B2 8/2010 Okada et al.
7,780,663 B2 8/2010 Yates et al.
7,784,662 B2 8/2010 Wales et al.
7,784,663 B2 8/2010 Shelton, IV
7,789,883 B2 9/2010 Takashino et al.
7,793,814 B2 9/2010 Racenet et al.
7,794,475 B2 9/2010 Hess et al.
7,796,969 B2 9/2010 Kelly et al.
7,798,386 B2 9/2010 Schall et al.
7,798,864 B2 9/2010 Barker et al.
7,799,020 B2 9/2010 Shores et al.
7,799,027 B2 9/2010 Hafner
7,799,045 B2 9/2010 Masuda
7,803,152 B2 9/2010 Honda et al.
7,803,156 B2 9/2010 Eder et al.
7,803,168 B2 9/2010 Gifford et al.
7,806,891 B2 10/2010 Nowlin et al.
7,810,693 B2 10/2010 Broehl et al.
7,811,283 B2 10/2010 Moses et al.
7,815,238 B2 10/2010 Cao
7,815,641 B2 10/2010 Dodde et al.
7,819,298 B2 10/2010 Hall et al.
7,819,299 B2 10/2010 Shelton, IV et al.
7,819,819 B2 10/2010 Quick et al.
7,819,872 B2 10/2010 Johnson et al.
7,821,143 B2 10/2010 Wiener
D627,066 S 11/2010 Romero
7,824,401 B2 11/2010 Manzo et al.
7,832,408 B2 11/2010 Shelton, IV et al.
7,832,611 B2 11/2010 Boyden et al.
7,832,612 B2 11/2010 Baxter, III et al.
7,834,484 B2 11/2010 Sartor
7,837,699 B2 11/2010 Yamada et al.
7,845,537 B2 12/2010 Shelton, IV et al.
7,846,155 B2 12/2010 Houser et al.
7,846,159 B2 12/2010 Morrison et al.
7,846,160 B2 12/2010 Payne et al.
7,846,161 B2 12/2010 Dumbauld et al.
7,854,735 B2 12/2010 Houser et al.
D631,155 S 1/2011 Peine et al.
7,861,906 B2 1/2011 Doll et al.
7,862,560 B2 1/2011 Marion
7,862,561 B2 1/2011 Swanson et al.
7,867,228 B2 1/2011 Nobis et al.
7,871,392 B2 1/2011 Sartor
7,871,423 B2 1/2011 Livneh
7,876,030 B2 1/2011 Taki et al.
D631,965 S 2/2011 Price et al.
7,877,852 B2 2/2011 Unger et al.
7,878,991 B2 2/2011 Babaev
7,879,029 B2 2/2011 Jimenez
7,879,033 B2 2/2011 Sartor et al.
7,879,035 B2 2/2011 Garrison et al.
7,879,070 B2 2/2011 Ortiz et al.
7,883,475 B2 2/2011 Dupont et al.
7,892,606 B2 2/2011 Thies et al.
7,896,875 B2 3/2011 Heim et al.
7,897,792 B2 3/2011 Iikura et al.
7,901,400 B2 3/2011 Wham et al.
7,901,423 B2 3/2011 Stulen et al.
7,905,881 B2 3/2011 Masuda et al.
7,909,220 B2 3/2011 Viola
7,909,820 B2 3/2011 Lipson et al.
7,909,824 B2 3/2011 Masuda et al.
7,918,848 B2 4/2011 Lau et al.
7,919,184 B2 4/2011 Mohapatra et al.
7,922,061 B2 4/2011 Shelton, IV et al.
7,922,651 B2 4/2011 Yamada et al.
7,931,611 B2 4/2011 Novak et al.
7,931,649 B2 4/2011 Couture et al.
D637,288 S 5/2011 Houghton
D638,540 S 5/2011 Ijiri et al.
7,935,114 B2 5/2011 Takashino et al.
7,936,203 B2 5/2011 Zimlich
7,951,095 B2 5/2011 Makin et al.
7,951,165 B2 5/2011 Golden et al.
7,955,331 B2 6/2011 Truckai et al.
7,956,620 B2 6/2011 Gilbert
7,959,050 B2 6/2011 Smith et al.
7,959,626 B2 6/2011 Hong et al.
7,963,963 B2 6/2011 Francischelli et al.
7,967,602 B2 6/2011 Lindquist
7,972,328 B2 7/2011 Wham et al.

(56) References Cited

U.S. PATENT DOCUMENTS 7,972,329 B2 7/2011 Refior et al.
7,975,895 B2 7/2011 Milliman
7,976,544 B2 7/2011 McClurken et al.
7,980,443 B2 7/2011 Scheib et al.
7,981,050 B2 7/2011 Ritchart et al.
7,981,113 B2 7/2011 Truckai et al.
7,997,278 B2 8/2011 Utley et al.
7,998,157 B2 8/2011 Culp et al.
8,002,732 B2 8/2011 Visconti
8,002,770 B2 8/2011 Swanson et al.
8,020,743 B2 9/2011 Shelton, IV
8,025,672 B2 9/2011 Novak et al.
8,028,885 B2 10/2011 Smith et al.
8,033,173 B2 10/2011 Ehlert et al.
8,034,049 B2 10/2011 Odom et al.
8,038,693 B2 10/2011 Allen
8,048,070 B2 11/2011 O'Brien et al.
8,052,672 B2 11/2011 Laufer et al.
8,055,208 B2 11/2011 Lilla et al.
8,056,720 B2 11/2011 Hawkes
8,056,787 B2 11/2011 Boudreaux et al.
8,057,468 B2 11/2011 Konesky
8,057,498 B2 11/2011 Robertson
8,058,771 B2 11/2011 Giordano et al.
8,061,014 B2 11/2011 Smith et al.
8,066,167 B2 11/2011 Measamer et al.
8,070,036 B1 12/2011 Knodel
8,070,711 B2 12/2011 Bassinger et al.
8,070,762 B2 12/2011 Escudero et al.
8,075,555 B2 12/2011 Truckai et al.
8,075,558 B2 12/2011 Truckai et al.
8,089,197 B2 1/2012 Rinner et al.
8,092,475 B2 1/2012 Cotter et al.
8,096,459 B2 1/2012 Ortiz et al.
8,097,012 B2 1/2012 Kagarise
8,100,894 B2 1/2012 Mucko et al.
8,105,230 B2 1/2012 Honda et al.
8,105,323 B2 1/2012 Buysse et al.
8,105,324 B2 1/2012 Palanker et al.
8,114,104 B2 2/2012 Young et al.
8,118,276 B2 2/2012 Sanders et al.
8,128,624 B2 3/2012 Couture et al.
8,133,218 B2 3/2012 Daw et al.
8,136,712 B2 3/2012 Zingman
8,141,762 B2 3/2012 Bedi et al.
8,142,421 B2 3/2012 Cooper et al.
8,142,461 B2 3/2012 Houser et al.
8,147,485 B2 4/2012 Wham et al.
8,147,488 B2 4/2012 Masuda
8,147,508 B2 4/2012 Madan et al.
8,152,801 B2 4/2012 Goldberg et al.
8,152,825 B2 4/2012 Madan et al.
8,157,145 B2 4/2012 Shelton, IV et al.
8,161,977 B2 4/2012 Shelton, IV et al.
8,162,966 B2 4/2012 Connor et al.
8,170,717 B2 5/2012 Sutherland et al.
8,172,846 B2 5/2012 Brunnett et al.
8,172,870 B2 5/2012 Shipp
8,177,800 B2 5/2012 Spitz et al.
8,182,502 B2 5/2012 Stulen et al.
8,186,560 B2 5/2012 Hess et al.
8,186,877 B2 5/2012 Klimovitch et al.
8,187,267 B2 5/2012 Pappone et al.
D661,801 S 6/2012 Price et al.
D661,802 S 6/2012 Price et al.
D661,803 S 6/2012 Price et al.
D661,804 S 6/2012 Price et al.
8,197,472 B2 6/2012 Lau et al.
8,197,479 B2 6/2012 Olson et al.
8,197,502 B2 6/2012 Smith et al.
8,207,651 B2 6/2012 Gilbert
8,210,411 B2 7/2012 Yates et al.
8,211,100 B2 7/2012 Podhajsky et al.
8,220,688 B2 7/2012 Laurent et al.
8,221,306 B2 7/2012 Okada et al.
8,221,415 B2 7/2012 Francischelli
8,221,418 B2 7/2012 Prakash et al.
8,226,580 B2 7/2012 Govari et al.
8,226,665 B2 7/2012 Cohen
8,226,675 B2 7/2012 Houser et al.
8,231,607 B2 7/2012 Takuma
8,235,917 B2 8/2012 Joseph et al.
8,236,018 B2 8/2012 Yoshimine et al.
8,236,019 B2 8/2012 Houser
8,236,020 B2 8/2012 Smith et al.
8,241,235 B2 8/2012 Kahler et al.
8,241,271 B2 8/2012 Millman et al.
8,241,282 B2 8/2012 Unger et al.
8,241,283 B2 8/2012 Guerra et al.
8,241,284 B2 8/2012 Dycus et al.
8,241,312 B2 8/2012 Messerly
8,246,575 B2 8/2012 Viola
8,246,615 B2 8/2012 Behnke
8,246,616 B2 8/2012 Amoah et al.
8,246,618 B2 8/2012 Bucciaglia et al.
8,246,642 B2 8/2012 Houser et al.
8,251,994 B2 8/2012 McKenna et al.
8,252,012 B2 8/2012 Stulen
8,253,303 B2 8/2012 Giordano et al.
8,257,377 B2 9/2012 Wiener et al.
8,257,387 B2 9/2012 Cunningham
8,262,563 B2 9/2012 Bakos et al.
8,267,300 B2 9/2012 Boudreaux
8,267,935 B2 9/2012 Couture et al.
8,273,028 B2 9/2012 Harshman et al.
8,273,087 B2 9/2012 Kimura et al.
D669,992 S 10/2012 Schafer et al.
D669,993 S 10/2012 Merchant et al.
8,277,446 B2 10/2012 Heard
8,277,447 B2 10/2012 Garrison et al.
8,277,471 B2 10/2012 Wiener et al.
8,282,581 B2 10/2012 Zhao et al.
8,282,669 B2 10/2012 Gerber et al.
8,286,846 B2 10/2012 Smith et al.
8,287,485 B2 10/2012 Kimura et al.
8,287,528 B2 10/2012 Wham et al.
8,287,532 B2 10/2012 Carroll et al.
8,292,886 B2 10/2012 Kerr et al.
8,292,888 B2 10/2012 Whitman
8,292,905 B2 10/2012 Taylor et al.
8,295,902 B2 10/2012 Salahieh et al.
8,298,223 B2 10/2012 Wham et al.
8,298,225 B2 10/2012 Gilbert
8,298,232 B2 10/2012 Unger
8,298,233 B2 10/2012 Mueller
8,303,576 B2 11/2012 Brock
8,303,579 B2 11/2012 Shibata
8,303,580 B2 11/2012 Wham et al.
8,303,583 B2 11/2012 Hosier et al.
8,303,613 B2 11/2012 Crandall et al.
8,306,629 B2 11/2012 Mioduski et al.
8,308,040 B2 11/2012 Huang et al.
8,313,336 B2 11/2012 Bondo et al.
8,319,400 B2 11/2012 Houser et al.
8,323,302 B2 12/2012 Robertson et al.
8,323,310 B2 12/2012 Kingsley
8,328,061 B2 12/2012 Kasvikis
8,328,761 B2 12/2012 Widenhouse et al.
8,328,802 B2 12/2012 Deville et al.
8,328,833 B2 12/2012 Cuny
8,328,834 B2 12/2012 Isaacs et al.
8,333,764 B2 12/2012 Francischelli et al.
8,333,778 B2 12/2012 Smith et al.
8,333,779 B2 12/2012 Smith et al.
8,334,468 B2 12/2012 Palmer et al.
8,334,635 B2 12/2012 Voegele et al.
8,337,407 B2 12/2012 Quistgaard et al.
8,338,726 B2 12/2012 Palmer et al.
8,343,146 B2 1/2013 Godara et al.
8,344,596 B2 1/2013 Nield et al.
8,348,880 B2 1/2013 Messerly et al.
8,348,947 B2 1/2013 Takashino et al.
8,348,967 B2 1/2013 Stulen
8,353,297 B2 1/2013 Dacquay et al.

(56) References Cited

U.S. PATENT DOCUMENTS 8,357,103 B2 1/2013 Mark et al.
8,357,144 B2 1/2013 Whitman et al.
8,357,149 B2 1/2013 Govari et al.
8,357,158 B2 1/2013 McKenna et al.
8,360,299 B2 1/2013 Zemlok et al.
8,361,066 B2 1/2013 Long et al.
8,361,072 B2 1/2013 Dumbauld et al.
8,361,569 B2 1/2013 Saito et al.
8,366,727 B2 2/2013 Witt et al.
8,372,064 B2 2/2013 Douglass et al.
8,372,099 B2 2/2013 Deville et al.
8,372,101 B2 2/2013 Smith et al.
8,372,102 B2 2/2013 Stulen et al.
8,374,670 B2 2/2013 Selkee
8,377,044 B2 2/2013 Coe et al.
8,377,059 B2 2/2013 Deville et al.
8,377,085 B2 2/2013 Smith et al.
8,382,748 B2 2/2013 Geisel
8,382,775 B1 2/2013 Bender et al.
8,382,782 B2 2/2013 Robertson et al.
8,382,792 B2 2/2013 Chojin
8,388,646 B2 3/2013 Chojin
8,388,647 B2 3/2013 Nau, Jr. et al.
8,393,514 B2 3/2013 Shelton, IV et al.
8,394,115 B2 3/2013 Houser et al.
8,397,971 B2 3/2013 Yates et al.
8,398,394 B2 3/2013 Sauter et al.
8,403,926 B2 3/2013 Nobis et al.
8,403,945 B2 3/2013 Whitfield et al.
8,403,948 B2 3/2013 Deville et al.
8,403,949 B2 3/2013 Palmer et al.
8,403,950 B2 3/2013 Palmer et al.
8,409,234 B2 4/2013 Stahler et al.
8,414,577 B2 4/2013 Boudreaux et al.
8,418,073 B2 4/2013 Mohr et al.
8,418,349 B2 4/2013 Smith et al.
8,419,757 B2 4/2013 Smith et al.
8,419,758 B2 4/2013 Smith et al.
8,419,759 B2 4/2013 Dietz
8,423,182 B2 4/2013 Robinson et al.
8,425,410 B2 4/2013 Murray et al.
8,425,545 B2 4/2013 Smith et al.
8,430,811 B2 4/2013 Hess et al.
8,430,874 B2 4/2013 Newton et al.
8,430,876 B2 4/2013 Kappus et al.
8,430,897 B2 4/2013 Novak et al.
8,430,898 B2 4/2013 Wiener et al.
8,435,257 B2 5/2013 Smith et al.
8,437,832 B2 5/2013 Govari et al.
8,439,912 B2 5/2013 Cunningham et al.
8,439,939 B2 5/2013 Deville et al.
8,444,036 B2 5/2013 Shelton, IV
8,444,637 B2 5/2013 Podmore et al.
8,444,662 B2 5/2013 Palmer et al.
8,444,663 B2 5/2013 Houser et al.
8,444,664 B2 5/2013 Balanev et al.
8,453,906 B2 6/2013 Huang et al.
8,454,599 B2 6/2013 Inagaki et al.
8,454,639 B2 6/2013 Du et al.
8,459,525 B2 6/2013 Yates et al.
8,460,284 B2 6/2013 Aronow et al.
8,460,288 B2 6/2013 Tamai et al.
8,460,292 B2 6/2013 Truckai et al.
8,461,744 B2 6/2013 Wiener et al.
8,469,981 B2 6/2013 Robertson et al.
8,471,685 B2 6/2013 Shingai
8,479,969 B2 7/2013 Shelton, IV
8,480,703 B2 7/2013 Nicholas et al.
8,484,833 B2 7/2013 Cunningham et al.
8,485,413 B2 7/2013 Scheib et al.
8,485,970 B2 7/2013 Widenhouse et al.
8,486,057 B2 7/2013 Behnke, II
8,486,096 B2 7/2013 Robertson et al.
8,491,578 B2 7/2013 Manwaring et al.
8,491,625 B2 7/2013 Horner
8,496,682 B2 7/2013 Guerra et al.
D687,549 S 8/2013 Johnson et al.
8,506,555 B2 8/2013 Ruiz Morales
8,509,318 B2 8/2013 Tailliet
8,512,336 B2 8/2013 Couture
8,512,337 B2 8/2013 Francischelli et al.
8,512,359 B2 8/2013 Whitman et al.
8,512,364 B2 8/2013 Kowalski et al.
8,512,365 B2 8/2013 Wiener et al.
8,518,067 B2 8/2013 Masuda et al.
8,521,331 B2 8/2013 Itkowitz
8,523,043 B2 9/2013 Ullrich et al.
8,523,882 B2 9/2013 Huitema et al.
8,523,889 B2 9/2013 Stulen et al.
8,528,563 B2 9/2013 Gruber
8,529,437 B2 9/2013 Taylor et al.
8,529,565 B2 9/2013 Masuda et al.
8,531,064 B2 9/2013 Robertson et al.
8,535,308 B2 9/2013 Govari et al.
8,535,311 B2 9/2013 Schall
8,535,340 B2 9/2013 Allen
8,535,341 B2 9/2013 Allen
8,540,128 B2 9/2013 Shelton, IV et al.
8,546,996 B2 10/2013 Messerly et al.
8,546,999 B2 10/2013 Houser et al.
8,551,077 B2 10/2013 Main et al.
8,551,086 B2 10/2013 Kimura et al.
8,556,929 B2 10/2013 Harper et al.
8,561,870 B2 10/2013 Baxter, III et al.
8,562,592 B2 10/2013 Conlon et al.
8,562,598 B2 10/2013 Falkenstein et al.
8,562,600 B2 10/2013 Kirkpatrick et al.
8,562,604 B2 10/2013 Nishimura
8,568,390 B2 10/2013 Mueller
8,568,397 B2 10/2013 Horner et al.
8,568,400 B2 10/2013 Gilbert
8,568,412 B2 10/2013 Brandt et al.
8,569,997 B2 10/2013 Lee
8,573,461 B2 11/2013 Shelton, IV et al.
8,573,465 B2 11/2013 Shelton, IV
8,574,231 B2 11/2013 Boudreaux et al.
8,574,253 B2 11/2013 Gruber et al.
8,579,176 B2 11/2013 Smith et al.
8,579,897 B2 11/2013 Vakharia et al.
8,579,928 B2 11/2013 Robertson et al.
8,579,937 B2 11/2013 Gresham
8,585,727 B2 11/2013 Polo
8,588,371 B2 11/2013 Ogawa et al.
8,591,459 B2 11/2013 Clymer et al.
8,591,506 B2 11/2013 Wham et al.
8,591,536 B2 11/2013 Robertson
D695,407 S 12/2013 Price et al.
D696,631 S 12/2013 Price et al.
8,596,513 B2 12/2013 Olson et al.
8,597,193 B2 12/2013 Grunwald et al.
8,597,287 B2 12/2013 Benamou et al.
8,602,031 B2 12/2013 Reis et al.
8,602,288 B2 12/2013 Shelton, IV et al.
8,603,085 B2 12/2013 Jimenez
8,603,089 B2 12/2013 Viola
8,608,044 B2 12/2013 Hueil et al.
8,608,045 B2 12/2013 Smith et al.
8,608,745 B2 12/2013 Guzman et al.
8,613,383 B2 12/2013 Beckman et al.
8,616,431 B2 12/2013 Timm et al.
8,617,152 B2 12/2013 Werneth et al.
8,617,194 B2 12/2013 Beaupre
8,622,274 B2 1/2014 Yates et al.
8,623,011 B2 1/2014 Spivey
8,623,016 B2 1/2014 Fischer
8,623,027 B2 1/2014 Price et al.
8,623,040 B2 1/2014 Artsyukhovich et al.
8,623,044 B2 1/2014 Timm et al.
8,628,529 B2 1/2014 Aldridge et al.
8,628,534 B2 1/2014 Jones et al.
8,632,461 B2 1/2014 Glossop
8,636,736 B2 1/2014 Yates et al.
8,638,428 B2 1/2014 Brown
8,640,788 B2 2/2014 Dachs, II et al.

(56) References Cited

U.S. PATENT DOCUMENTS 8,641,663 B2 2/2014 Kirschenman et al.
8,647,350 B2 2/2014 Mohan et al.
8,650,728 B2 2/2014 Wan et al.
8,652,120 B2 2/2014 Giordano et al.
8,652,132 B2 2/2014 Tsuchiya et al.
8,652,155 B2 2/2014 Houser et al.
8,657,489 B2 2/2014 Ladurner et al.
8,659,208 B1 2/2014 Rose et al.
8,663,214 B2 3/2014 Weinberg et al.
8,663,220 B2 3/2014 Wiener et al.
8,663,222 B2 3/2014 Anderson et al.
8,663,223 B2 3/2014 Masuda et al.
8,663,262 B2 3/2014 Smith et al.
8,668,691 B2 3/2014 Heard
8,668,710 B2 3/2014 Slipszenko et al.
8,684,253 B2 4/2014 Giordano et al.
8,685,016 B2 4/2014 Wham et al.
8,685,020 B2 4/2014 Weizman et al.
8,690,582 B2 4/2014 Rohrbach et al.
8,695,866 B2 4/2014 Leimbach et al.
8,696,366 B2 4/2014 Chen et al.
8,696,665 B2 4/2014 Hunt et al.
8,696,666 B2 4/2014 Sanai et al.
8,696,917 B2 4/2014 Petisce et al.
8,702,609 B2 4/2014 Hadjicostis
8,702,704 B2 4/2014 Shelton, IV et al.
8,704,425 B2 4/2014 Giordano et al.
8,708,213 B2 4/2014 Shelton, IV et al.
8,709,008 B2 4/2014 Willis et al.
8,709,031 B2 4/2014 Stulen
8,709,035 B2 4/2014 Johnson et al.
8,715,270 B2 5/2014 Weitzner et al.
8,715,277 B2 5/2014 Weizman
8,721,640 B2 5/2014 Taylor et al.
8,721,657 B2 5/2014 Kondoh et al.
8,733,613 B2 5/2014 Huitema et al.
8,733,614 B2 5/2014 Ross et al.
8,734,443 B2 5/2014 Hixson et al.
8,738,110 B2 5/2014 Tabada et al.
8,747,238 B2 6/2014 Shelton, IV et al.
8,747,351 B2 6/2014 Schultz
8,747,404 B2 6/2014 Boudreaux et al.
8,749,116 B2 6/2014 Messerly et al.
8,752,264 B2 6/2014 Ackley et al.
8,752,749 B2 6/2014 Moore et al.
8,753,338 B2 6/2014 Widenhouse et al.
8,754,570 B2 6/2014 Voegele et al.
8,758,342 B2 6/2014 Bales et al.
8,758,352 B2 6/2014 Cooper et al.
8,758,391 B2 6/2014 Swayze et al.
8,764,735 B2 7/2014 Coe et al.
8,764,747 B2 7/2014 Cummings et al.
8,767,970 B2 7/2014 Eppolito
8,770,459 B2 7/2014 Racenet et al.
8,771,269 B2 7/2014 Sherman et al.
8,771,270 B2 7/2014 Burbank
8,771,293 B2 7/2014 Surti et al.
8,773,001 B2 7/2014 Wiener et al.
8,777,944 B2 7/2014 Frankhouser et al.
8,777,945 B2 7/2014 Floume et al.
8,779,648 B2 7/2014 Giordano et al.
8,783,541 B2 7/2014 Shelton, IV et al.
8,784,415 B2 7/2014 Malackowski et al.
8,784,418 B2 7/2014 Romero
8,790,342 B2 7/2014 Stulen et al.
8,795,274 B2 8/2014 Hanna
8,795,275 B2 8/2014 Hafner
8,795,276 B2 8/2014 Dietz et al.
8,795,327 B2 8/2014 Dietz et al.
8,800,838 B2 8/2014 Shelton, IV
8,801,710 B2 8/2014 Ullrich et al.
8,801,752 B2 8/2014 Fortier et al.
8,808,204 B2 8/2014 Irisawa et al.
8,808,319 B2 8/2014 Houser et al.
8,814,856 B2 8/2014 Elmouelhi et al.
8,814,870 B2 8/2014 Paraschiv et al.
8,820,605 B2 9/2014 Shelton, IV
8,821,388 B2 9/2014 Naito et al.
8,827,992 B2 9/2014 Koss et al.
8,827,995 B2 9/2014 Schaller et al.
8,834,466 B2 9/2014 Cummings et al.
8,834,518 B2 9/2014 Faller et al.
8,844,789 B2 9/2014 Shelton, IV et al.
8,845,537 B2 9/2014 Tanaka et al.
8,845,630 B2 9/2014 Mehta et al.
8,848,808 B2 9/2014 Dress
8,851,354 B2 10/2014 Swensgard et al.
8,852,184 B2 10/2014 Kucklick
8,858,547 B2 10/2014 Brogna
8,862,955 B2 10/2014 Cesari
8,864,749 B2 10/2014 Okada
8,864,757 B2 10/2014 Klimovitch et al.
8,864,761 B2 10/2014 Johnson et al.
8,870,865 B2 10/2014 Frankhouser et al.
8,874,220 B2 10/2014 Draghici et al.
8,876,726 B2 11/2014 Amit et al.
8,876,858 B2 11/2014 Braun
8,882,766 B2 11/2014 Couture et al.
8,882,791 B2 11/2014 Stulen
8,888,776 B2 11/2014 Dietz et al.
8,888,783 B2 11/2014 Young
8,888,809 B2 11/2014 Davison et al.
8,899,462 B2 12/2014 Kostrzewski et al.
8,900,259 B2 12/2014 Houser et al.
8,906,016 B2 12/2014 Boudreaux et al.
8,906,017 B2 12/2014 Rioux et al.
8,911,438 B2 12/2014 Swoyer et al.
8,911,460 B2 12/2014 Neurohr et al.
8,920,412 B2 12/2014 Fritz et al.
8,920,414 B2 12/2014 Stone et al.
8,920,421 B2 12/2014 Rupp
8,926,607 B2 1/2015 Norvell et al.
8,926,608 B2 1/2015 Bacher et al.
8,926,620 B2 1/2015 Chasmawala et al.
8,931,682 B2 1/2015 Timm et al.
8,932,282 B2 1/2015 Gilbert
8,932,299 B2 1/2015 Bono et al.
8,936,614 B2 1/2015 Allen, IV
8,939,974 B2 1/2015 Boudreaux et al.
8,945,126 B2 2/2015 Garrison et al.
8,951,248 B2 2/2015 Messerly et al.
8,951,272 B2 2/2015 Robertson et al.
8,956,349 B2 2/2015 Aldridge et al.
8,960,520 B2 2/2015 McCuen
8,961,515 B2 2/2015 Twomey et al.
8,961,547 B2 2/2015 Dietz et al.
8,967,443 B2 3/2015 McCuen
8,968,283 B2 3/2015 Kharin
8,968,294 B2 3/2015 Maass et al.
8,968,296 B2 3/2015 McPherson
8,968,355 B2 3/2015 Malkowski et al.
8,974,447 B2 3/2015 Kimball et al.
8,974,477 B2 3/2015 Yamada
8,974,479 B2 3/2015 Ross et al.
8,974,932 B2 3/2015 McGahan et al.
8,979,843 B2 3/2015 Timm et al.
8,979,844 B2 3/2015 White et al.
8,979,890 B2 3/2015 Boudreaux
8,986,287 B2 3/2015 Park et al.
8,986,297 B2 3/2015 Daniel et al.
8,986,302 B2 3/2015 Aldridge et al.
8,989,855 B2 3/2015 Murphy et al.
8,989,903 B2 3/2015 Weir et al.
8,991,678 B2 3/2015 Wellman et al.
8,992,422 B2 3/2015 Spivey et al.
8,992,526 B2 3/2015 Brodbeck et al.
8,998,891 B2 4/2015 Garito et al.
9,005,199 B2 4/2015 Beckman et al.
9,011,437 B2 4/2015 Woodruff et al.
9,011,471 B2 4/2015 Timm et al.
9,017,326 B2 4/2015 DiNardo et al.
9,017,355 B2 4/2015 Smith et al.
9,017,372 B2 4/2015 Artale et al.
9,023,070 B2 5/2015 Levine et al.

(56) References Cited

U.S. PATENT DOCUMENTS 9,023,071 B2 5/2015 Miller et al.
9,028,397 B2 5/2015 Naito
9,028,476 B2 5/2015 Bonn
9,028,478 B2 5/2015 Mueller
9,028,481 B2 5/2015 Behnke, II
9,028,494 B2 5/2015 Shelton, IV et al.
9,028,519 B2 5/2015 Yates et al.
9,031,667 B2 5/2015 Williams
9,033,973 B2 5/2015 Krapohl et al.
9,035,741 B2 5/2015 Hamel et al.
9,037,259 B2 5/2015 Mathur
9,039,690 B2 5/2015 Kersten et al.
9,039,695 B2 5/2015 Giordano et al.
9,039,696 B2 5/2015 Assmus et al.
9,039,705 B2 5/2015 Takashino
9,039,731 B2 5/2015 Joseph
9,043,018 B2 5/2015 Mohr
9,044,227 B2 6/2015 Shelton, IV et al.
9,044,230 B2 6/2015 Morgan et al.
9,044,238 B2 6/2015 Orszulak
9,044,243 B2 6/2015 Johnson et al.
9,044,245 B2 6/2015 Condie et al.
9,044,256 B2 6/2015 Cadeddu et al.
9,044,261 B2 6/2015 Houser
9,050,093 B2 6/2015 Aldridge et al.
9,050,098 B2 6/2015 Deville et al.
9,050,123 B2 6/2015 Krause et al.
9,050,124 B2 6/2015 Houser
9,055,961 B2 6/2015 Manzo et al.
9,059,547 B2 6/2015 McLawhorn
9,060,770 B2 6/2015 Shelton, IV et al.
9,060,775 B2 6/2015 Wiener et al.
9,060,776 B2 6/2015 Yates et al.
9,060,778 B2 6/2015 Condie et al.
9,066,720 B2 6/2015 Ballakur et al.
9,066,723 B2 6/2015 Beller et al.
9,066,747 B2 6/2015 Robertson
9,072,523 B2 7/2015 Houser et al.
9,072,535 B2 7/2015 Shelton, IV et al.
9,072,536 B2 7/2015 Shelton, IV et al.
9,072,538 B2 7/2015 Suzuki et al.
9,072,539 B2 7/2015 Messerly et al.
9,084,624 B2 7/2015 Larkin et al.
9,089,327 B2 7/2015 Worrell et al.
9,089,360 B2 7/2015 Messerly et al.
9,095,362 B2 8/2015 Dachs, II et al.
9,095,367 B2 8/2015 Olson et al.
9,099,863 B2 8/2015 Smith et al.
9,101,358 B2 8/2015 Kerr et al.
9,101,385 B2 8/2015 Shelton, IV et al.
9,107,684 B2 8/2015 Ma
9,107,689 B2 8/2015 Robertson et al.
9,107,690 B2 8/2015 Bales, Jr. et al.
9,113,900 B2 8/2015 Buysse et al.
9,113,907 B2 8/2015 Allen, IV et al.
9,113,940 B2 8/2015 Twomey
9,119,657 B2 9/2015 Shelton, IV et al.
9,119,957 B2 9/2015 Gantz et al.
9,125,662 B2 9/2015 Shelton, IV
9,125,667 B2 9/2015 Stone et al.
9,144,453 B2 9/2015 Rencher et al.
9,147,965 B2 9/2015 Lee
9,149,324 B2 10/2015 Huang et al.
9,149,325 B2 10/2015 Worrell et al.
9,161,803 B2 10/2015 Yates et al.
9,165,114 B2 10/2015 Jain et al.
9,168,054 B2 10/2015 Turner et al.
9,168,085 B2 10/2015 Juzkiw et al.
9,168,089 B2 10/2015 Buysse et al.
9,173,656 B2 11/2015 Schurr et al.
9,179,912 B2 11/2015 Yates et al.
9,186,199 B2 11/2015 Strauss et al.
9,186,204 B2 11/2015 Nishimura et al.
9,186,796 B2 11/2015 Ogawa
9,192,380 B2 11/2015 Racenet et al.
9,192,421 B2 11/2015 Garrison
9,192,428 B2 11/2015 Houser et al.
9,192,431 B2 11/2015 Woodruff et al.
9,198,714 B2 12/2015 Worrell et al.
9,198,715 B2 12/2015 Livneh
9,198,718 B2 12/2015 Marczyk et al.
9,198,776 B2 12/2015 Young
9,204,879 B2 12/2015 Shelton, IV
9,204,891 B2 12/2015 Weitzman
9,204,918 B2 12/2015 Germain et al.
9,204,923 B2 12/2015 Manzo et al.
9,216,050 B2 12/2015 Condie et al.
9,216,051 B2 12/2015 Fischer et al.
9,216,062 B2 12/2015 Duque et al.
9,220,483 B2 12/2015 Frankhouser et al.
9,220,527 B2 12/2015 Houser et al.
9,220,559 B2 12/2015 Worrell et al.
9,226,750 B2 1/2016 Weir et al.
9,226,751 B2 1/2016 Shelton, IV et al.
9,226,766 B2 1/2016 Aldridge et al.
9,226,767 B2 1/2016 Stulen et al.
9,232,979 B2 1/2016 Parihar et al.
9,237,891 B2 1/2016 Shelton, IV
9,237,921 B2 1/2016 Messerly et al.
9,241,060 B1 1/2016 Fujisaki
9,241,692 B2 1/2016 Gunday et al.
9,241,728 B2 1/2016 Price et al.
9,241,730 B2 1/2016 Babaev
9,241,731 B2 1/2016 Boudreaux et al.
9,241,768 B2 1/2016 Sandhu et al.
9,247,953 B2 2/2016 Palmer et al.
9,254,165 B2 2/2016 Aronow et al.
9,259,234 B2 2/2016 Robertson et al.
9,259,265 B2 2/2016 Harris et al.
9,265,567 B2 2/2016 Orban, III et al.
9,265,926 B2 2/2016 Strobl et al.
9,265,973 B2 2/2016 Akagane
9,277,962 B2 3/2016 Koss et al.
9,282,974 B2 3/2016 Shelton, IV
9,283,027 B2 3/2016 Monson et al.
9,283,045 B2 3/2016 Rhee et al.
9,283,054 B2 3/2016 Morgan et al.
9,289,256 B2 3/2016 Shelton, IV et al.
9,295,514 B2 3/2016 Shelton, IV et al.
9,301,759 B2 4/2016 Spivey et al.
9,305,497 B2 4/2016 Seo et al.
9,307,388 B2 4/2016 Liang et al.
9,307,986 B2 4/2016 Hall et al.
9,308,009 B2 4/2016 Madan et al.
9,308,014 B2 4/2016 Fischer
9,314,261 B2 4/2016 Bales, Jr. et al.
9,314,292 B2 4/2016 Trees et al.
9,314,301 B2 4/2016 Ben-Haim et al.
9,326,754 B2 5/2016 Polster
9,326,787 B2 5/2016 Sanai et al.
9,326,788 B2 5/2016 Batross et al.
9,333,025 B2 5/2016 Monson et al.
9,333,034 B2 5/2016 Hancock
9,339,289 B2 5/2016 Robertson
9,339,323 B2 5/2016 Eder et al.
9,339,326 B2 5/2016 McCullagh et al.
9,345,481 B2 5/2016 Hall et al.
9,345,534 B2 5/2016 Artale et al.
9,345,900 B2 5/2016 Wu et al.
9,351,642 B2 5/2016 Nadkarni et al.
9,351,726 B2 5/2016 Leimbach et al.
9,351,754 B2 5/2016 Vakharia et al.
9,352,173 B2 5/2016 Yamada et al.
9,358,065 B2 6/2016 Ladtkow et al.
9,364,171 B2 6/2016 Harris et al.
9,364,230 B2 6/2016 Shelton, IV et al.
9,364,279 B2 6/2016 Houser et al.
9,370,364 B2 6/2016 Smith et al.
9,370,400 B2 6/2016 Parihar
9,370,611 B2 6/2016 Ross et al.
9,375,230 B2 6/2016 Ross et al.
9,375,232 B2 6/2016 Hunt et al.
9,375,256 B2 6/2016 Cunningham et al.
9,375,264 B2 6/2016 Horner et al.

(56) References Cited

U.S. PATENT DOCUMENTS 9,375,267 B2 6/2016 Kerr et al.
9,385,831 B2 7/2016 Marr et al.
9,386,983 B2 7/2016 Swensgard et al.
9,393,037 B2 7/2016 Olson et al.
9,393,070 B2 7/2016 Gelfand et al.
9,398,911 B2 7/2016 Auld
9,402,680 B2 8/2016 Ginnebaugh et al.
9,402,682 B2 8/2016 Worrell et al.
9,408,606 B2 8/2016 Shelton, IV
9,408,622 B2 8/2016 Stulen et al.
9,408,660 B2 8/2016 Strobl et al.
9,414,853 B2 8/2016 Stulen et al.
9,414,880 B2 8/2016 Monson et al.
9,421,014 B2 8/2016 Ingmanson et al.
9,421,060 B2 8/2016 Monson et al.
9,427,249 B2 8/2016 Robertson et al.
9,427,279 B2 8/2016 Muniz-Medina et al.
9,439,668 B2 9/2016 Timm et al.
9,439,669 B2 9/2016 Wiener et al.
9,439,671 B2 9/2016 Akagane
9,442,288 B2 9/2016 Tanimura
9,445,784 B2 9/2016 O'Keeffe
9,445,832 B2 9/2016 Wiener et al.
9,451,967 B2 9/2016 Jordan et al.
9,456,863 B2 10/2016 Moua
9,456,864 B2 10/2016 Witt et al.
9,468,498 B2 10/2016 Sigmon, Jr.
9,474,542 B2 10/2016 Slipszenko et al.
9,474,568 B2 10/2016 Akagane
9,486,236 B2 11/2016 Price et al.
9,492,146 B2 11/2016 Kostrzewski et al.
9,492,224 B2 11/2016 Boudreaux et al.
9,498,245 B2 11/2016 Voegele et al.
9,498,275 B2 11/2016 Wham et al.
9,504,483 B2 11/2016 Houser et al.
9,504,520 B2 11/2016 Worrell et al.
9,504,524 B2 11/2016 Behnke, II
9,504,855 B2 11/2016 Messerly et al.
9,510,850 B2 12/2016 Robertson et al.
9,510,906 B2 12/2016 Boudreaux et al.
9,522,029 B2 12/2016 Yates et al.
9,522,032 B2 12/2016 Behnke
9,526,564 B2 12/2016 Rusin
9,526,565 B2 12/2016 Strobl
9,545,253 B2 1/2017 Worrell et al.
9,545,497 B2 1/2017 Wenderow et al.
9,554,846 B2 1/2017 Boudreaux
9,554,854 B2 1/2017 Yates et al.
9,560,995 B2 2/2017 Addison et al.
9,561,038 B2 2/2017 Shelton, IV et al.
9,572,592 B2 2/2017 Price et al.
9,574,644 B2 2/2017 Parihar
9,585,714 B2 3/2017 Livneh
9,592,056 B2 3/2017 Mozdzierz
9,592,072 B2 3/2017 Akagane
9,597,143 B2 3/2017 Madan et al.
9,603,669 B2 3/2017 Govari et al.
9,610,091 B2 4/2017 Johnson et al.
9,610,114 B2 4/2017 Baxter, III et al.
9,615,877 B2 4/2017 Tyrrell et al.
9,623,237 B2 4/2017 Turner et al.
9,629,629 B2 4/2017 Leimbach et al.
9,636,135 B2 5/2017 Stulen
9,636,165 B2 5/2017 Larson et al.
9,636,167 B2 5/2017 Gregg
9,638,770 B2 5/2017 Dietz et al.
9,642,644 B2 5/2017 Houser et al.
9,642,669 B2 5/2017 Takashino et al.
9,643,052 B2 5/2017 Tchao et al.
9,649,110 B2 5/2017 Parihar et al.
9,649,111 B2 5/2017 Shelton, IV et al.
9,649,126 B2 5/2017 Robertson et al.
9,649,173 B2 5/2017 Choi et al.
9,655,670 B2 5/2017 Larson et al.
9,662,131 B2 5/2017 Omori et al.
9,668,806 B2 6/2017 Unger et al.
9,671,860 B2 6/2017 Ogawa et al.
9,674,949 B1 6/2017 Liu et al.
9,675,374 B2 6/2017 Stulen et al.
9,675,375 B2 6/2017 Houser et al.
9,681,884 B2 6/2017 Clem et al.
9,687,290 B2 6/2017 Keller
9,690,362 B2 6/2017 Leimbach et al.
9,693,817 B2 7/2017 Mehta et al.
9,700,309 B2 7/2017 Jaworek et al.
9,700,339 B2 7/2017 Nield
9,700,343 B2 7/2017 Messerly et al.
9,705,456 B2 7/2017 Gilbert
9,707,004 B2 7/2017 Houser et al.
9,707,027 B2 7/2017 Ruddenklau et al.
9,707,030 B2 7/2017 Davison et al.
9,713,507 B2 7/2017 Stulen et al.
9,717,548 B2 8/2017 Couture
9,717,552 B2 8/2017 Cosman et al.
9,724,118 B2 8/2017 Schulte et al.
9,724,120 B2 8/2017 Faller et al.
9,724,152 B2 8/2017 Horlle et al.
9,730,695 B2 8/2017 Leimbach et al.
9,737,326 B2 8/2017 Worrell et al.
9,737,355 B2 8/2017 Yates et al.
9,737,358 B2 8/2017 Beckman et al.
9,743,929 B2 8/2017 Leimbach et al.
9,743,946 B2 8/2017 Faller et al.
9,743,947 B2 8/2017 Price et al.
9,757,142 B2 9/2017 Shimizu
9,757,150 B2 9/2017 Alexander et al.
9,757,186 B2 9/2017 Boudreaux et al.
9,764,164 B2 9/2017 Wiener et al.
9,770,285 B2 9/2017 Zoran et al.
9,782,214 B2 10/2017 Houser et al.
9,788,851 B2 10/2017 Dannaher et al.
9,795,405 B2 10/2017 Price et al.
9,795,436 B2 10/2017 Yates et al.
9,795,808 B2 10/2017 Messerly et al.
9,801,626 B2 10/2017 Parihar et al.
9,801,648 B2 10/2017 Houser et al.
9,802,033 B2 10/2017 Hibner et al.
9,808,246 B2 11/2017 Shelton, IV et al.
9,808,308 B2 11/2017 Faller et al.
9,814,460 B2 11/2017 Kimsey et al.
9,814,514 B2 11/2017 Shelton, IV et al.
9,815,211 B2 11/2017 Cao et al.
9,820,738 B2 11/2017 Lytle, IV et al.
9,820,768 B2 11/2017 Gee et al.
9,820,771 B2 11/2017 Norton et al.
9,820,806 B2 11/2017 Lee et al.
9,826,976 B2 11/2017 Parihar et al.
9,839,443 B2 12/2017 Brockman et al.
9,844,368 B2 12/2017 Boudreaux et al.
9,844,374 B2 12/2017 Lytle, IV et al.
9,844,375 B2 12/2017 Overmyer et al.
9,848,901 B2 12/2017 Robertson et al.
9,848,902 B2 12/2017 Price et al.
9,848,937 B2 12/2017 Trees et al.
9,861,381 B2 1/2018 Johnson
9,861,428 B2 1/2018 Trees et al.
9,867,612 B2 1/2018 Parihar et al.
9,867,651 B2 1/2018 Wham
9,867,670 B2 1/2018 Brannan et al.
9,872,722 B2 1/2018 Lech
9,872,725 B2 1/2018 Worrell et al.
9,872,726 B2 1/2018 Morisaki
9,877,720 B2 1/2018 Worrell et al.
9,877,776 B2 1/2018 Boudreaux
9,878,184 B2 1/2018 Beaupre
9,883,884 B2 2/2018 Neurohr et al.
9,888,919 B2 2/2018 Leimbach et al.
9,888,958 B2 2/2018 Evans et al.
9,895,148 B2 2/2018 Shelton, IV et al.
9,901,321 B2 2/2018 Harks et al.
9,901,342 B2 2/2018 Shelton, IV et al.
9,901,383 B2 2/2018 Hassler, Jr.
9,901,754 B2 2/2018 Yamada
9,907,563 B2 3/2018 Germain et al.

(56) References Cited

U.S. PATENT DOCUMENTS 9,913,642 B2 3/2018 Leimbach et al.
9,913,656 B2 3/2018 Stulen
9,913,680 B2 3/2018 Voegele et al.
9,918,730 B2 3/2018 Trees et al.
9,924,961 B2 3/2018 Shelton, IV et al.
9,925,003 B2 3/2018 Parihar et al.
9,931,118 B2 4/2018 Shelton, IV et al.
9,943,309 B2 4/2018 Shelton, IV et al.
9,949,785 B2 4/2018 Price et al.
9,949,788 B2 4/2018 Boudreaux
9,962,182 B2 5/2018 Dietz et al.
9,968,355 B2 5/2018 Shelton, IV et al.
9,974,539 B2 5/2018 Yates et al.
9,987,000 B2 6/2018 Shelton, IV et al.
9,987,033 B2 6/2018 Neurohr et al.
9,993,248 B2 6/2018 Shelton, IV et al.
9,993,258 B2 6/2018 Shelton, IV et al.
10,004,497 B2 6/2018 Overmyer et al.
10,004,501 B2 6/2018 Shelton, IV et al.
10,004,526 B2 6/2018 Dycus et al.
10,004,527 B2 6/2018 Gee et al.
D822,206 S 7/2018 Shelton, IV et al.
10,010,339 B2 7/2018 Witt et al.
10,010,341 B2 7/2018 Houser et al.
10,016,207 B2 7/2018 Suzuki et al.
10,022,142 B2 7/2018 Aranyi et al.
10,022,567 B2 7/2018 Messerly et al.
10,022,568 B2 7/2018 Messerly et al.
10,028,761 B2 7/2018 Leimbach et al.
10,028,786 B2 7/2018 Mucilli et al.
10,034,684 B2 7/2018 Weisenburgh, II et al.
10,034,704 B2 7/2018 Asher et al.
D826,405 S 8/2018 Shelton, IV et al.
10,039,588 B2 8/2018 Harper et al.
10,045,776 B2 8/2018 Shelton, IV et al.
10,045,779 B2 8/2018 Savage et al.
10,045,794 B2 8/2018 Witt et al.
10,045,810 B2 8/2018 Schall et al.
10,045,819 B2 8/2018 Jensen et al.
10,052,044 B2 8/2018 Shelton, IV et al.
10,052,102 B2 8/2018 Baxter, III et al.
10,070,916 B2 9/2018 Artale
10,080,609 B2 9/2018 Hancock et al.
10,085,748 B2 10/2018 Morgan et al.
10,085,762 B2 10/2018 Timm et al.
10,085,792 B2 10/2018 Johnson et al.
10,092,310 B2 10/2018 Boudreaux et al.
10,092,344 B2 10/2018 Mohr et al.
10,092,348 B2 10/2018 Boudreaux
10,092,350 B2 10/2018 Rothweiler et al.
10,105,140 B2 10/2018 Malinouskas et al.
10,111,699 B2 10/2018 Boudreaux
10,111,703 B2 10/2018 Cosman, Jr. et al.
10,117,649 B2 11/2018 Baxter, III et al.
10,117,667 B2 11/2018 Robertson et al.
10,117,702 B2 11/2018 Danziger et al.
10,123,835 B2 11/2018 Keller et al.
10,130,367 B2 11/2018 Cappola et al.
10,130,410 B2 11/2018 Strobl et al.
10,130,412 B2 11/2018 Wham
10,136,887 B2 11/2018 Shelton, IV et al.
10,149,680 B2 12/2018 Parihar et al.
10,154,848 B2 12/2018 Chernov et al.
10,154,852 B2 12/2018 Conlon et al.
10,159,483 B2 12/2018 Beckman et al.
10,159,524 B2 12/2018 Yates et al.
10,166,060 B2 1/2019 Johnson et al.
10,172,665 B2 1/2019 Heckel et al.
10,172,669 B2 1/2019 Felder et al.
10,178,992 B2 1/2019 Wise et al.
10,179,022 B2 1/2019 Yates et al.
10,180,463 B2 1/2019 Beckman et al.
10,182,816 B2 1/2019 Shelton, IV et al.
10,182,818 B2 1/2019 Hensel et al.
10,188,385 B2 1/2019 Kerr et al.
10,188,455 B2 1/2019 Hancock et al.
10,194,907 B2 2/2019 Marczyk et al.
10,194,972 B2 2/2019 Yates et al.
10,194,973 B2 2/2019 Wiener et al.
10,194,976 B2 2/2019 Boudreaux
10,194,977 B2 2/2019 Yang
10,194,999 B2 2/2019 Bacher et al.
10,201,364 B2 2/2019 Leimbach et al.
10,201,365 B2 2/2019 Boudreaux et al.
10,201,382 B2 2/2019 Wiener et al.
10,226,250 B2 3/2019 Beckman et al.
10,226,273 B2 3/2019 Messerly et al.
10,231,747 B2 3/2019 Stulen et al.
10,238,385 B2 3/2019 Yates et al.
10,238,391 B2 3/2019 Leimbach et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,033 B2 4/2019 Overmyer et al.
10,245,095 B2 4/2019 Boudreaux
10,245,104 B2 4/2019 McKenna et al.
10,251,664 B2 4/2019 Shelton, IV et al.
10,258,331 B2 4/2019 Shelton, IV et al.
10,258,505 B2 4/2019 Ovchinnikov
10,263,171 B2 4/2019 Wiener et al.
10,265,068 B2 4/2019 Harris et al.
10,265,117 B2 4/2019 Wiener et al.
10,265,118 B2 4/2019 Gerhardt
10,271,840 B2 4/2019 Sapre
10,271,851 B2 4/2019 Shelton, IV et al.
D847,989 S 5/2019 Shelton, IV et al.
10,278,721 B2 5/2019 Dietz et al.
10,285,705 B2 5/2019 Shelton, IV et al.
10,285,724 B2 5/2019 Faller et al.
10,285,750 B2 5/2019 Coulson et al.
10,292,704 B2 5/2019 Harris et al.
10,299,810 B2 5/2019 Robertson et al.
10,299,821 B2 5/2019 Shelton, IV et al.
D850,617 S 6/2019 Shelton, IV et al.
D851,762 S 6/2019 Shelton, IV
10,307,159 B2 6/2019 Harris et al.
10,314,579 B2 6/2019 Chowaniec et al.
10,314,582 B2 6/2019 Shelton, IV et al.
10,314,638 B2 6/2019 Gee et al.
10,321,907 B2 6/2019 Shelton, IV et al.
10,321,950 B2 6/2019 Yates et al.
D854,151 S 7/2019 Shelton, IV
10,335,149 B2 7/2019 Baxter, III et al.
10,335,182 B2 7/2019 Stulen et al.
10,335,183 B2 7/2019 Worrell et al.
10,335,614 B2 7/2019 Messerly et al.
10,342,543 B2 7/2019 Shelton, IV et al.
10,342,602 B2 7/2019 Strobl et al.
10,342,606 B2 7/2019 Cosman et al.
10,342,623 B2 7/2019 Huelman et al.
10,348,941 B2 7/2019 Elliot, Jr. et al.
10,349,999 B2 7/2019 Yates et al.
10,350,016 B2 7/2019 Burbank et al.
10,350,025 B1 7/2019 Loyd et al.
10,357,246 B2 7/2019 Shelton, IV et al.
10,357,247 B2 7/2019 Shelton, IV et al.
10,357,303 B2 7/2019 Conlon et al.
10,363,084 B2 7/2019 Friedrichs
10,368,861 B2 8/2019 Baxter, III et al.
10,368,865 B2 8/2019 Harris et al.
10,376,263 B2 8/2019 Morgan et al.
10,376,305 B2 8/2019 Yates et al.
10,390,841 B2 8/2019 Shelton, IV
10,398,439 B2 9/2019 Cabrera et al.
10,398,466 B2 9/2019 Stulen et al.
10,398,497 B2 9/2019 Batross et al.
10,405,857 B2 9/2019 Shelton, IV et al.
10,405,863 B2 9/2019 Wise et al.
10,413,291 B2 9/2019 Worthington et al.
10,413,293 B2 9/2019 Shelton, IV et al.
10,413,297 B2 9/2019 Harris et al.
10,413,352 B2 9/2019 Thomas et al.
10,413,353 B2 9/2019 Kerr et al.

(56) References Cited

U.S. PATENT DOCUMENTS 10,420,552 B2 9/2019 Shelton, IV et al.
10,420,579 B2 9/2019 Wiener et al.
10,420,607 B2 9/2019 Woloszko et al.
D865,175 S 10/2019 Widenhouse et al.
10,426,471 B2 10/2019 Shelton, IV et al.
10,426,507 B2 10/2019 Wiener et al.
10,426,978 B2 10/2019 Akagane
10,433,837 B2 10/2019 Worthington et al.
10,433,849 B2 10/2019 Shelton, IV et al.
10,433,865 B2 10/2019 Witt et al.
10,433,866 B2 10/2019 Witt et al.
10,433,900 B2 10/2019 Harris et al.
10,441,279 B2 10/2019 Shelton, IV et al.
10,441,308 B2 10/2019 Robertson
10,441,310 B2 10/2019 Olson et al.
10,441,345 B2 10/2019 Aldridge et al.
10,448,948 B2 10/2019 Shelton, IV et al.
10,448,950 B2 10/2019 Shelton, IV et al.
10,448,986 B2 10/2019 Zikorus et al.
10,456,140 B2 10/2019 Shelton, IV et al.
10,456,193 B2 10/2019 Yates et al.
10,463,421 B2 11/2019 Boudreaux et al.
10,463,887 B2 11/2019 Witt et al.
10,470,764 B2 11/2019 Baxter, III et al.
10,478,182 B2 11/2019 Taylor
10,478,190 B2 11/2019 Miller et al.
10,485,542 B2 11/2019 Shelton, IV et al.
10,485,543 B2 11/2019 Shelton, IV et al.
10,485,607 B2 11/2019 Strobl et al.
D869,655 S 12/2019 Shelton, IV
10,492,785 B2 12/2019 Overmyer et al.
10,492,849 B2 12/2019 Juergens et al.
10,499,914 B2 12/2019 Huang et al.
10,507,033 B2 12/2019 Dickerson et al.
10,512,795 B2 12/2019 Voegele et al.
10,517,595 B2 12/2019 Hunter et al.
10,517,596 B2 12/2019 Hunter et al.
10,517,627 B2 12/2019 Timm et al.
10,524,787 B2 1/2020 Shelton, IV et al.
10,524,789 B2 1/2020 Swayze et al.
10,524,854 B2 1/2020 Woodruff et al.
10,524,872 B2 1/2020 Stewart et al.
10,531,874 B2 1/2020 Morgan et al.
10,537,324 B2 1/2020 Shelton, IV et al.
10,537,325 B2 1/2020 Bakos et al.
10,537,351 B2 1/2020 Shelton, IV et al.
10,542,979 B2 1/2020 Shelton, IV et al.
10,542,982 B2 1/2020 Beckman et al.
10,542,991 B2 1/2020 Shelton, IV et al.
10,543,008 B2 1/2020 Vakharia et al.
10,548,504 B2 2/2020 Shelton, IV et al.
10,548,655 B2 2/2020 Scheib et al.
10,555,769 B2 2/2020 Worrell et al.
10,561,560 B2 2/2020 Boutoussov et al.
10,568,624 B2 2/2020 Shelton, IV et al.
10,568,625 B2 2/2020 Harris et al.
10,568,626 B2 2/2020 Shelton, IV et al.
10,568,632 B2 2/2020 Miller et al.
10,575,892 B2 3/2020 Danziger et al.
10,582,928 B2 3/2020 Hunter et al.
10,588,625 B2 3/2020 Weaner et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV
10,595,929 B2 3/2020 Boudreaux et al.
10,595,930 B2 3/2020 Scheib et al.
10,603,036 B2 3/2020 Hunter et al.
10,610,224 B2 4/2020 Shelton, IV et al.
10,610,286 B2 4/2020 Wiener et al.
10,610,313 B2 4/2020 Bailey et al.
10,617,412 B2 4/2020 Shelton, IV et al.
10,617,420 B2 4/2020 Shelton, IV et al.
10,617,464 B2 4/2020 Duppuis
10,624,635 B2 4/2020 Harris et al.
10,624,691 B2 4/2020 Wiener et al.
10,631,858 B2 4/2020 Burbank
10,631,859 B2 4/2020 Shelton, IV
10,632,630 B2 4/2020 Cao et al.
RE47,996 E 5/2020 Turner et al.
10,639,034 B2 5/2020 Harris et al.
10,639,035 B2 5/2020 Shelton, IV et al.
10,639,037 B2 5/2020 Shelton, IV
10,639,092 B2 5/2020 Corbett et al.
10,639,098 B2 5/2020 Cosman et al.
10,646,269 B2 5/2020 Worrell et al.
10,653,413 B2 5/2020 Worthington et al.
10,667,809 B2 6/2020 Bakos et al.
10,667,810 B2 6/2020 Shelton, IV et al.
10,667,811 B2 6/2020 Harris et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,677,764 B2 6/2020 Ross et al.
10,682,136 B2 6/2020 Harris et al.
10,682,138 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,884 B2 6/2020 Wiener et al.
10,688,321 B2 6/2020 Wiener et al.
10,695,055 B2 6/2020 Shelton, IV et al.
10,695,057 B2 6/2020 Shelton, IV
10,695,058 B2 6/2020 Lytle, IV
10,695,119 B2 6/2020 Smith
10,702,270 B2 7/2020 Shelton, IV et al.
10,702,329 B2 7/2020 Strobl et al.
10,709,446 B2 7/2020 Harris et al.
10,709,469 B2 7/2020 Shelton, IV et al.
10,709,906 B2 7/2020 Nield
10,716,615 B2 7/2020 Shelton, IV et al.
10,722,233 B2 7/2020 Wellman
D893,717 S 8/2020 Messerly et al.
10,729,458 B2 8/2020 Stoddard et al.
10,729,494 B2 8/2020 Parihar et al.
10,736,629 B2 8/2020 Shelton, IV et al.
10,736,685 B2 8/2020 Wiener et al.
10,751,108 B2 8/2020 Yates et al.
10,758,229 B2 9/2020 Shelton, IV et al.
10,758,230 B2 9/2020 Shelton, IV et al.
10,758,232 B2 9/2020 Shelton, IV et al.
10,758,294 B2 9/2020 Jones
10,765,427 B2 9/2020 Shelton, IV et al.
10,765,470 B2 9/2020 Yates et al.
10,772,629 B2 9/2020 Shelton, IV
10,772,630 B2 9/2020 Wixey
10,779,821 B2 9/2020 Harris et al.
10,779,823 B2 9/2020 Shelton, IV et al.
10,779,824 B2 9/2020 Shelton, IV
10,779,825 B2 9/2020 Shelton, IV
10,779,845 B2 9/2020 Timm et al.
10,779,849 B2 9/2020 Shelton, IV et al.
10,779,879 B2 9/2020 Yates et al.
10,786,253 B2 9/2020 Shelton, IV
10,806,454 B2 10/2020 Kopp
10,813,638 B2 10/2020 Shelton, IV et al.
10,820,938 B2 11/2020 Fischer et al.
10,828,058 B2 11/2020 Shelton, IV et al.
10,835,245 B2 11/2020 Swayze et al.
10,835,246 B2 11/2020 Shelton, IV et al.
10,835,247 B2 11/2020 Shelton, IV et al.
10,835,307 B2 11/2020 Shelton, IV et al.
10,842,492 B2 11/2020 Shelton, IV et al.
10,842,523 B2 11/2020 Shelton, IV et al.
10,842,563 B2 11/2020 Gilbert et al.
D906,355 S 12/2020 Messerly
10,856,867 B2 12/2020 Shelton, IV et al.
10,856,868 B2 12/2020 Shelton, IV et al.
10,856,869 B2 12/2020 Shelton, IV
10,856,870 B2 12/2020 Harris et al.
10,856,896 B2 12/2020 Eichmann et al.
10,856,929 B2 12/2020 Yates et al.
10,856,934 B2 12/2020 Trees et al.

(56) References Cited

U.S. PATENT DOCUMENTS 10,874,465 B2 12/2020 Weir et al.
D908,216 S 1/2021 Messerly
10,881,399 B2 1/2021 Shelton, IV et al.
10,881,401 B2 1/2021 Baber et al.
10,881,409 B2 1/2021 Cabrera
10,881,449 B2 1/2021 Boudreaux et al.
10,888,322 B2 1/2021 Morgan et al.
10,888,347 B2 1/2021 Witt et al.
10,893,863 B2 1/2021 Shelton, IV et al.
10,893,864 B2 1/2021 Harris et al.
10,893,883 B2 1/2021 Dannaher
10,898,186 B2 1/2021 Bakos et al.
10,898,256 B2 1/2021 Yates et al.
10,912,559 B2 2/2021 Harris et al.
10,912,580 B2 2/2021 Green et al.
10,912,603 B2 2/2021 Boudreaux et al.
10,918,385 B2 2/2021 Overmyer et al.
10,925,659 B2 2/2021 Shelton, IV et al.
D914,878 S 3/2021 Shelton, IV et al.
10,932,766 B2 3/2021 Tesar et al.
10,932,847 B2 3/2021 Yates et al.
10,945,727 B2 3/2021 Shelton, IV et al.
10,952,788 B2 3/2021 Asher et al.
10,959,727 B2 3/2021 Hunter et al.
10,966,741 B2 4/2021 Illizaliturri-Sanchez et al.
10,966,747 B2 4/2021 Worrell et al.
10,973,516 B2 4/2021 Shelton, IV et al.
10,973,517 B2 4/2021 Wixey
10,973,520 B2 4/2021 Shelton, IV et al.
10,980,536 B2 4/2021 Weaner et al.
10,987,123 B2 4/2021 Weir et al.
10,987,156 B2 4/2021 Trees et al.
10,993,715 B2 5/2021 Shelton, IV et al.
10,993,716 B2 5/2021 Shelton, IV et al.
10,993,763 B2 5/2021 Batross et al.
11,000,278 B2 5/2021 Shelton, IV et al.
11,000,279 B2 5/2021 Shelton, IV
11,020,114 B2 6/2021 Shelton, IV
11,020,140 B2 6/2021 Gee et al.
11,033,322 B2 6/2021 Wiener et al.
11,039,834 B2 6/2021 Harris et al.
11,045,191 B2 6/2021 Shelton, IV et al.
11,045,192 B2 6/2021 Harris et al.
11,051,840 B2 7/2021 Shelton, IV et al.
11,051,873 B2 7/2021 Wiener et al.
11,058,424 B2 7/2021 Shelton, IV
11,058,447 B2 7/2021 Houser
11,058,448 B2 7/2021 Shelton, IV et al.
11,058,475 B2 7/2021 Wiener et al.
11,064,997 B2 7/2021 Shelton, IV et al.
11,065,048 B2 7/2021 Messerly et al.
11,083,455 B2 8/2021 Shelton, IV
11,083,458 B2 8/2021 Harris et al.
11,090,048 B2 8/2021 Fanelli et al.
11,090,049 B2 8/2021 Bakos
11,090,104 B2 8/2021 Wiener et al.
11,096,688 B2 8/2021 Shelton, IV et al.
11,096,752 B2 8/2021 Stulen et al.
11,109,866 B2 9/2021 Shelton, IV et al.
11,129,611 B2 9/2021 Fox et al.
11,129,666 B2 9/2021 Messerly
11,129,669 B2 9/2021 Stulen et al.
11,129,670 B2 9/2021 Shelton, IV et al.
11,134,942 B2 10/2021 Harris
11,134,978 B2 10/2021 Shelton, IV et al.
11,141,154 B2 10/2021 Shelton, IV
11,141,213 B2 10/2021 Yates et al.
11,147,551 B2 10/2021 Shelton, IV
11,147,553 B2 10/2021 Shelton, IV
11,160,551 B2 11/2021 Shelton, IV et al.
11,166,716 B2 11/2021 Shelton, IV et al.
11,172,929 B2 11/2021 Shelton, IV
11,179,155 B2 11/2021 Shelton, IV et al.
11,191,539 B2 12/2021 Overmyer et al.
11,191,540 B2 12/2021 Aronhalt et al.
11,197,668 B2 12/2021 Shelton, IV et al.
11,202,670 B2 12/2021 Worrell et al.
11,207,065 B2 12/2021 Harris et al.
11,207,067 B2 12/2021 Shelton, IV et al.
11,213,293 B2 1/2022 Worthington et al.
11,213,294 B2 1/2022 Shelton, IV et al.
11,219,453 B2 1/2022 Shelton, IV et al.
11,224,426 B2 1/2022 Shelton, IV
11,224,497 B2 1/2022 Shelton, IV
11,229,437 B2 1/2022 Shelton, IV et al.
11,229,450 B2 1/2022 Shelton, IV et al.
11,229,471 B2 1/2022 Shelton, IV et al.
11,229,472 B2 1/2022 Shelton, IV et al.
11,234,698 B2 2/2022 Shelton, IV et al.
11,241,235 B2 2/2022 Shelton, IV et al.
11,246,592 B2 2/2022 Shelton, IV
11,246,625 B2 2/2022 Kane et al.
11,246,678 B2 2/2022 Shelton, IV et al.
11,253,256 B2 2/2022 Harris et al.
11,259,803 B2 3/2022 Shelton, IV
11,259,805 B2 3/2022 Shelton, IV
11,259,806 B2 3/2022 Shelton, IV
11,259,807 B2 3/2022 Shelton, IV
11,266,405 B2 3/2022 Shelton, IV
11,272,931 B2 3/2022 Boudreaux et al.
11,278,280 B2 3/2022 Shelton, IV
11,284,890 B2 3/2022 Nalagatla et al.
11,291,440 B2 4/2022 Harris et al.
11,291,444 B2 4/2022 Boudreaux et al.
11,291,445 B2 4/2022 Shelton, IV et al.
11,291,447 B2 4/2022 Shelton, IV
11,291,451 B2 4/2022 Shelton, IV
11,298,127 B2 4/2022 Shelton, IV
11,298,129 B2 4/2022 Bakos et al.
11,298,130 B2 4/2022 Bakos et al.
11,304,695 B2 4/2022 Shelton, IV et al.
11,304,696 B2 4/2022 Shelton, IV
11,304,699 B2 4/2022 Shelton, IV et al.
11,311,306 B2 4/2022 Shelton, IV et al.
11,311,342 B2 4/2022 Parihar et al.
11,317,915 B2 5/2022 Boudreaux et al.
11,324,503 B2 5/2022 Shelton, IV
11,324,557 B2 5/2022 Shelton, IV
11,331,100 B2 5/2022 Boudreaux et al.
11,331,101 B2 5/2022 Harris et al.
11,350,938 B2 6/2022 Shelton, IV
11,357,503 B2 6/2022 Bakos et al.
11,361,176 B2 6/2022 Shelton, IV
2001/0025173 A1 9/2001 Ritchie et al.
2001/0025183 A1 9/2001 Shahidi
2001/0025184 A1 9/2001 Messerly
2001/0031950 A1 10/2001 Ryan
2001/0039419 A1 11/2001 Francischelli et al.
2002/0002377 A1 1/2002 Cimino
2002/0002380 A1 1/2002 Bishop
2002/0019649 A1 2/2002 Sikora et al.
2002/0022836 A1 2/2002 Goble et al.
2002/0029036 A1 3/2002 Goble et al.
2002/0029055 A1 3/2002 Bonutti
2002/0049551 A1 4/2002 Friedman et al.
2002/0052617 A1 5/2002 Anis et al.
2002/0077550 A1 6/2002 Rabiner et al.
2002/0107517 A1 8/2002 Witt et al.
2002/0156466 A1 10/2002 Sakurai et al.
2002/0156493 A1 10/2002 Houser et al.
2002/0165577 A1* 11/2002 Witt ............... A61B 17/320092
606/205
2002/0177862 A1 11/2002 Aranyi et al.
2003/0014053 A1 1/2003 Nguyen et al.
2003/0014087 A1 1/2003 Fang et al.
2003/0036705 A1 2/2003 Hare et al.
2003/0040758 A1 2/2003 Wang et al.
2003/0050572 A1 3/2003 Brautigam et al.
2003/0055443 A1 3/2003 Spotnitz
2003/0109778 A1 6/2003 Rashidi
2003/0109875 A1 6/2003 Tetzlaff et al.
2003/0114851 A1 6/2003 Truckai et al.
2003/0130693 A1 7/2003 Levin et al.
2003/0139741 A1 7/2003 Goble et al.

(56) References Cited

U.S. PATENT DOCUMENTS

2003/0144680 A1 7/2003 Kellogg et al.
2003/0158548 A1 8/2003 Phan et al.
2003/0171747 A1 9/2003 Kanehira et al.
2003/0181898 A1 9/2003 Bowers
2003/0199794 A1 10/2003 Sakurai et al.
2003/0204199 A1 10/2003 Novak et al.
2003/0208186 A1 11/2003 Moreyra
2003/0212332 A1 11/2003 Fenton et al.
2003/0212363 A1 11/2003 Shipp
2003/0212392 A1 11/2003 Fenton et al.
2003/0212422 A1 11/2003 Fenton et al.
2003/0225332 A1 12/2003 Okada et al.
2003/0229344 A1 12/2003 Dycus et al.
2004/0030254 A1 2/2004 Babaev
2004/0030330 A1 2/2004 Brassell et al.
2004/0047485 A1 3/2004 Sherrit et al.
2004/0054364 A1 3/2004 Aranyi et al.
2004/0064151 A1 4/2004 Mollenauer
2004/0087943 A1 5/2004 Dycus et al.
2004/0092921 A1 5/2004 Kadziauskas et al.
2004/0092992 A1 5/2004 Adams et al.
2004/0097911 A1 5/2004 Murakami et al.
2004/0097912 A1 5/2004 Gonnering
2004/0097919 A1 5/2004 Wellman et al.
2004/0097996 A1 5/2004 Rabiner et al.
2004/0116952 A1 6/2004 Sakurai et al.
2004/0122423 A1 6/2004 Dycus et al.
2004/0132383 A1 7/2004 Langford et al.
2004/0138621 A1 7/2004 Jahns et al.
2004/0142667 A1 7/2004 Lochhead et al.
2004/0147934 A1 7/2004 Kiester
2004/0147945 A1 7/2004 Fritzsch
2004/0158237 A1 8/2004 Abboud et al.
2004/0167508 A1 8/2004 Wham et al.
2004/0176686 A1 9/2004 Hare et al.
2004/0176751 A1 9/2004 Weitzner et al.
2004/0193150 A1 9/2004 Sharkey et al.
2004/0193153 A1 9/2004 Sartor et al.
2004/0199193 A1 10/2004 Hayashi et al.
2004/0215132 A1 10/2004 Yoon
2004/0243147 A1 12/2004 Lipow
2004/0249374 A1 12/2004 Tetzlaff et al.
2004/0260273 A1 12/2004 Wan
2004/0260300 A1 12/2004 Gorensek et al.
2004/0267311 A1 12/2004 Viola et al.
2005/0015125 A1 1/2005 Mioduski et al.
2005/0020967 A1 1/2005 Ono
2005/0021018 A1 1/2005 Anderson et al.
2005/0021065 A1 1/2005 Yamada et al.
2005/0021078 A1 1/2005 Vleugels et al.
2005/0033278 A1 2/2005 McClurken et al.
2005/0033337 A1 2/2005 Muir et al.
2005/0033358 A1* 2/2005 Suzuki .................. A61B 17/29 606/207
2005/0070800 A1 3/2005 Takahashi
2005/0080427 A1 4/2005 Govari et al.
2005/0088285 A1 4/2005 Jei
2005/0090817 A1 4/2005 Phan
2005/0096683 A1 5/2005 Ellins et al.
2005/0099824 A1 5/2005 Dowling et al.
2005/0107777 A1 5/2005 West et al.
2005/0131390 A1 6/2005 Heinrich et al.
2005/0143769 A1 6/2005 White et al.
2005/0149108 A1 7/2005 Cox
2005/0165429 A1 7/2005 Douglas et al.
2005/0171522 A1 8/2005 Christopherson
2005/0177184 A1 8/2005 Easley
2005/0182339 A1 8/2005 Lee et al.
2005/0188743 A1 9/2005 Land
2005/0192610 A1 9/2005 Houser et al.
2005/0192611 A1 9/2005 Houser
2005/0206583 A1 9/2005 Lemelson et al.
2005/0222598 A1 10/2005 Ho et al.
2005/0234484 A1 10/2005 Houser et al.
2005/0249667 A1 11/2005 Tuszynski et al.
2005/0256405 A1 11/2005 Makin et al.
2005/0261588 A1 11/2005 Makin et al.
2005/0262175 A1 11/2005 Iino et al.
2005/0267464 A1 12/2005 Truckai et al.
2005/0271807 A1 12/2005 Iljima et al.
2005/0273090 A1 12/2005 Nieman et al.
2005/0288659 A1 12/2005 Kimura et al.
2006/0025757 A1 2/2006 Heim
2006/0030797 A1 2/2006 Zhou et al.
2006/0030848 A1 2/2006 Craig et al.
2006/0058825 A1 3/2006 Ogura et al.
2006/0063130 A1 3/2006 Hayman et al.
2006/0064086 A1 3/2006 Odom
2006/0066181 A1 3/2006 Bromfield et al.
2006/0074442 A1 4/2006 Noriega et al.
2006/0079874 A1 4/2006 Faller et al.
2006/0079879 A1 4/2006 Faller et al.
2006/0095046 A1 5/2006 Trieu et al.
2006/0109061 A1 5/2006 Dobson et al.
2006/0159731 A1 7/2006 Shoshan
2006/0190034 A1 8/2006 Nishizawa et al.
2006/0206100 A1 9/2006 Eskridge et al.
2006/0206115 A1 9/2006 Schomer et al.
2006/0211943 A1 9/2006 Beaupre
2006/0217729 A1 9/2006 Eskridge et al.
2006/0224160 A1* 10/2006 Trieu ................ A61B 17/1608 606/83
2006/0247558 A1 11/2006 Yamada
2006/0253050 A1 11/2006 Yoshimine et al.
2006/0259026 A1 11/2006 Godara et al.
2006/0264809 A1 11/2006 Hansmann et al.
2006/0264995 A1 11/2006 Fanton et al.
2006/0265035 A1 11/2006 Yachi et al.
2006/0270916 A1 11/2006 Skwarek et al.
2006/0271030 A1 11/2006 Francis et al.
2006/0293656 A1 12/2006 Shadduck et al.
2007/0016235 A1 1/2007 Tanaka et al.
2007/0016236 A1 1/2007 Beaupre
2007/0021738 A1 1/2007 Hasser et al.
2007/0027468 A1 2/2007 Wales et al.
2007/0032704 A1 2/2007 Gandini et al.
2007/0055228 A1 3/2007 Berg et al.
2007/0056596 A1 3/2007 Fanney et al.
2007/0060935 A1 3/2007 Schwardt et al.
2007/0063618 A1 3/2007 Bromfield
2007/0066971 A1 3/2007 Podhajsky
2007/0067123 A1 3/2007 Jungerman
2007/0073185 A1 3/2007 Nakao
2007/0073341 A1 3/2007 Smith et al.
2007/0074584 A1 4/2007 Talarico et al.
2007/0106317 A1 5/2007 Shelton et al.
2007/0118115 A1 5/2007 Artale et al.
2007/0130771 A1 6/2007 Ehlert et al.
2007/0135803 A1 6/2007 Belson
2007/0149881 A1 6/2007 Rabin
2007/0156163 A1 7/2007 Davison et al.
2007/0166663 A1 7/2007 Telles et al.
2007/0173803 A1 7/2007 Wham et al.
2007/0173813 A1 7/2007 Odom
2007/0173872 A1 7/2007 Neuenfeldt
2007/0175955 A1 8/2007 Shelton et al.
2007/0185474 A1 8/2007 Nahen
2007/0191712 A1 8/2007 Messerly et al.
2007/0191713 A1 8/2007 Eichmann et al.
2007/0203483 A1 8/2007 Kim et al.
2007/0208336 A1 9/2007 Kim et al.
2007/0208340 A1 9/2007 Ganz et al.
2007/0219481 A1 9/2007 Babaev
2007/0232926 A1 10/2007 Stulen et al.
2007/0232928 A1 10/2007 Wiener et al.
2007/0236213 A1 10/2007 Paden et al.
2007/0239101 A1 10/2007 Kellogg
2007/0249941 A1 10/2007 Salehi et al.
2007/0260242 A1 11/2007 Dycus et al.
2007/0265560 A1 11/2007 Soltani et al.
2007/0265613 A1 11/2007 Edelstein et al.
2007/0265616 A1 11/2007 Couture et al.
2007/0265620 A1 11/2007 Kraas et al.
2007/0275348 A1 11/2007 Lemon

(56) References Cited

U.S. PATENT DOCUMENTS

2007/0287933 A1 12/2007 Phan et al.
2007/0288055 A1 12/2007 Lee
2007/0299895 A1 12/2007 Johnson et al.
2008/0005213 A1 1/2008 Holtzman
2008/0013809 A1 1/2008 Zhu et al.
2008/0015575 A1 1/2008 Odom et al.
2008/0033465 A1 2/2008 Schmitz et al.
2008/0039746 A1 2/2008 Hissong et al.
2008/0051812 A1 2/2008 Schmitz et al.
2008/0058775 A1 3/2008 Darian et al.
2008/0058845 A1 3/2008 Shimizu et al.
2008/0071269 A1 3/2008 Hilario et al.
2008/0077145 A1 3/2008 Boyden et al.
2008/0082039 A1 4/2008 Babaev
2008/0082098 A1 4/2008 Tanaka et al.
2008/0097501 A1 4/2008 Blier
2008/0114355 A1 5/2008 Whayne et al.
2008/0114364 A1 5/2008 Goldin et al.
2008/0122496 A1 5/2008 Wagner
2008/0125768 A1 5/2008 Tahara et al.
2008/0147058 A1 6/2008 Horrell et al.
2008/0147062 A1 6/2008 Truckai et al.
2008/0147092 A1 6/2008 Rogge et al.
2008/0171938 A1 7/2008 Masuda et al.
2008/0177268 A1 7/2008 Daum et al.
2008/0188755 A1 8/2008 Hart
2008/0200940 A1 8/2008 Eichmann et al.
2008/0208108 A1 8/2008 Kimura
2008/0208231 A1 8/2008 Ota et al.
2008/0214967 A1 9/2008 Aranyi et al.
2008/0234709 A1 9/2008 Houser
2008/0243162 A1 10/2008 Shibata et al.
2008/0255413 A1 10/2008 Zemlok et al.
2008/0275440 A1 11/2008 Kratoska et al.
2008/0281200 A1 11/2008 Voic et al.
2008/0281315 A1 11/2008 Gines
2008/0287944 A1 11/2008 Pearson et al.
2008/0287948 A1 11/2008 Newton et al.
2008/0296346 A1 12/2008 Shelton, IV et al.
2008/0300588 A1 12/2008 Groth et al.
2009/0012516 A1 1/2009 Curtis et al.
2009/0023985 A1 1/2009 Ewers
2009/0043293 A1 2/2009 Pankratov et al.
2009/0048537 A1 2/2009 Lydon et al.
2009/0048589 A1 2/2009 Takashino et al.
2009/0054886 A1 2/2009 Yachi et al.
2009/0054889 A1 2/2009 Newton et al.
2009/0054894 A1 2/2009 Yachi
2009/0055750 A1 2/2009 Oshima et al.
2009/0065565 A1 3/2009 Cao
2009/0076506 A1 3/2009 Baker
2009/0082716 A1 3/2009 Akahoshi
2009/0082766 A1 3/2009 Unger et al.
2009/0088785 A1 4/2009 Masuda
2009/0090763 A1 4/2009 Zemlok et al.
2009/0101692 A1 4/2009 Whitman et al.
2009/0118751 A1 5/2009 Wiener et al.
2009/0131885 A1 5/2009 Akahoshi
2009/0143678 A1 6/2009 Keast et al.
2009/0143799 A1 6/2009 Smith et al.
2009/0143800 A1 6/2009 Deville et al.
2009/0157064 A1 6/2009 Hodel
2009/0163807 A1 6/2009 Sliwa
2009/0177119 A1 7/2009 Heidner et al.
2009/0179923 A1 7/2009 Amundson et al.
2009/0182322 A1 7/2009 D'Amelio et al.
2009/0182331 A1 7/2009 D'Amelio et al.
2009/0182332 A1 7/2009 Long et al.
2009/0192441 A1 7/2009 Gelbart et al.
2009/0198272 A1 8/2009 Kerver et al.
2009/0204114 A1 8/2009 Odom
2009/0216157 A1 8/2009 Yamada
2009/0223033 A1 9/2009 Houser
2009/0240244 A1 9/2009 Malis et al.
2009/0248021 A1 10/2009 McKenna
2009/0254077 A1 10/2009 Craig
2009/0254080 A1 10/2009 Honda
2009/0259149 A1 10/2009 Tahara et al.
2009/0264909 A1 10/2009 Beaupre
2009/0270771 A1 10/2009 Takahashi
2009/0270812 A1 10/2009 Litscher et al.
2009/0270853 A1 10/2009 Yachi et al.
2009/0270891 A1 10/2009 Beaupre
2009/0270899 A1 10/2009 Carusillo et al.
2009/0287205 A1 11/2009 Ingle
2009/0292283 A1 11/2009 Odom
2009/0299141 A1 12/2009 Downey et al.
2009/0306639 A1 12/2009 Nevo et al.
2009/0327715 A1 12/2009 Smith et al.
2010/0004508 A1 1/2010 Naito et al.
2010/0022825 A1 1/2010 Yoshie
2010/0030233 A1 2/2010 Whitman et al.
2010/0034605 A1 2/2010 Huckins et al.
2010/0036370 A1 2/2010 Mirel et al.
2010/0042093 A9 2/2010 Wham et al.
2010/0049180 A1 2/2010 Wells et al.
2010/0057118 A1 3/2010 Dietz et al.
2010/0063437 A1 3/2010 Nelson et al.
2010/0063525 A1 3/2010 Beaupre et al.
2010/0063528 A1* 3/2010 Beaupre ......... A61B 17/320092
606/169
2010/0081863 A1 4/2010 Hess et al.
2010/0081864 A1 4/2010 Hess et al.
2010/0081883 A1 4/2010 Murray et al.
2010/0094323 A1 4/2010 Isaacs et al.
2010/0106173 A1 4/2010 Yoshimine
2010/0109480 A1 5/2010 Forslund et al.
2010/0158307 A1 6/2010 Kubota et al.
2010/0168741 A1 7/2010 Sanai et al.
2010/0181966 A1 7/2010 Sakakibara
2010/0187283 A1 7/2010 Crainich et al.
2010/0204721 A1 8/2010 Young et al.
2010/0222714 A1 9/2010 Muir et al.
2010/0222752 A1 9/2010 Collins, Jr. et al.
2010/0228250 A1 9/2010 Brogna
2010/0234906 A1 9/2010 Koh
2010/0274160 A1 10/2010 Yachi et al.
2010/0274278 A1 10/2010 Fleenor et al.
2010/0280368 A1 11/2010 Can et al.
2010/0298743 A1 11/2010 Nield et al.
2010/0331742 A1 12/2010 Masuda
2011/0004233 A1 1/2011 Muir et al.
2011/0015650 A1 1/2011 Choi et al.
2011/0028964 A1 2/2011 Edwards
2011/0071523 A1 3/2011 Dickhans
2011/0106141 A1 5/2011 Nakamura
2011/0112400 A1 5/2011 Emery et al.
2011/0125149 A1 5/2011 El-Galley et al.
2011/0125151 A1 5/2011 Strauss et al.
2011/0144640 A1 6/2011 Heinrich et al.
2011/0160725 A1 6/2011 Kabaya et al.
2011/0238010 A1 9/2011 Kirschenman et al.
2011/0273465 A1 11/2011 Konishi et al.
2011/0278343 A1 11/2011 Knodel et al.
2011/0279268 A1 11/2011 Konishi et al.
2011/0284014 A1 11/2011 Cadeddu et al.
2011/0290856 A1 12/2011 Shelton, IV et al.
2011/0295295 A1 12/2011 Shelton, IV et al.
2011/0306967 A1 12/2011 Payne et al.
2011/0313415 A1 12/2011 Fernandez et al.
2012/0004655 A1 1/2012 Kim et al.
2012/0016413 A1 1/2012 Timm et al.
2012/0022519 A1 1/2012 Huang et al.
2012/0022526 A1 1/2012 Aldridge et al.
2012/0022583 A1 1/2012 Sugalski et al.
2012/0041358 A1 2/2012 Mann et al.
2012/0053597 A1 3/2012 Anvari et al.
2012/0059286 A1 3/2012 Hastings et al.
2012/0059289 A1 3/2012 Nield et al.
2012/0071863 A1 3/2012 Lee et al.
2012/0078244 A1 3/2012 Worrell et al.
2012/0080344 A1 4/2012 Shelton, IV
2012/0101495 A1 4/2012 Young et al.
2012/0109186 A1 5/2012 Parrott et al.

(56) References Cited

U.S. PATENT DOCUMENTS

2012/0116222 A1 5/2012 Sawada et al.
2012/0116265 A1 5/2012 Houser et al.
2012/0116266 A1 5/2012 Houser et al.
2012/0116381 A1 5/2012 Houser et al.
2012/0136279 A1 5/2012 Tanaka et al.
2012/0136347 A1 5/2012 Brustad et al.
2012/0136386 A1 5/2012 Kishida et al.
2012/0143211 A1 6/2012 Kishi
2012/0150049 A1 6/2012 Zielinski et al.
2012/0150169 A1 6/2012 Zielinksi et al.
2012/0172904 A1 7/2012 Muir et al.
2012/0191091 A1 7/2012 Allen
2012/0193396 A1 8/2012 Zemlok et al.
2012/0211542 A1 8/2012 Racenet
2012/0253328 A1 10/2012 Cunningham et al.
2012/0264316 A1 10/2012 Cameron
2012/0265241 A1 10/2012 Hart et al.
2012/0296325 A1 11/2012 Takashino
2012/0296371 A1 11/2012 Kappus et al.
2013/0023925 A1 1/2013 Mueller
2013/0085510 A1 4/2013 Stefanchik et al.
2013/0123776 A1 5/2013 Monson et al.
2013/0158659 A1 6/2013 Bergs et al.
2013/0158660 A1 6/2013 Bergs et al.
2013/0165929 A1 6/2013 Muir et al.
2013/0214025 A1 8/2013 Zemlok et al.
2013/0253256 A1 9/2013 Griffith et al.
2013/0253480 A1 9/2013 Kimball et al.
2013/0277410 A1 10/2013 Fernandez et al.
2013/0296843 A1 11/2013 Boudreaux et al.
2013/0334989 A1 12/2013 Kataoka
2013/0345701 A1 12/2013 Allen, IV et al.
2014/0001231 A1 1/2014 Shelton, IV et al.
2014/0001234 A1 1/2014 Shelton, IV et al.
2014/0005640 A1 1/2014 Shelton, IV et al.
2014/0005678 A1 1/2014 Shelton, IV et al.
2014/0005702 A1 1/2014 Timm et al.
2014/0005705 A1 1/2014 Weir et al.
2014/0005718 A1 1/2014 Shelton, IV et al.
2014/0014544 A1 1/2014 Bugnard et al.
2014/0121569 A1 5/2014 Schafer et al.
2014/0135804 A1 5/2014 Weisenburgh, II et al.
2014/0180274 A1 6/2014 Kabaya et al.
2014/0194868 A1 7/2014 Sanai et al.
2014/0194874 A1 7/2014 Dietz et al.
2014/0194875 A1 7/2014 Reschke et al.
2014/0207124 A1 7/2014 Aldridge
2014/0207135 A1 7/2014 Winter
2014/0246475 A1 9/2014 Hall et al.
2014/0263541 A1 9/2014 Leimbach et al.
2014/0263552 A1 9/2014 Hall et al.
2014/0276797 A1 9/2014 Batchelor et al.
2014/0373003 A1 12/2014 Grez
2015/0014392 A1 1/2015 Williams et al.
2015/0032150 A1 1/2015 Ishida et al.
2015/0048140 A1 2/2015 Penna et al.
2015/0080876 A1 3/2015 Worrell et al.
2015/0080887 A1 3/2015 Sobajima et al.
2015/0088122 A1 3/2015 Jensen
2015/0112335 A1 4/2015 Boudreaux et al.
2015/0157356 A1 6/2015 Gee
2015/0164533 A1 6/2015 Felder et al.
2015/0164534 A1 6/2015 Felder et al.
2015/0164535 A1 6/2015 Felder et al.
2015/0164536 A1 6/2015 Czarnecki et al.
2015/0164537 A1 6/2015 Cagle et al.
2015/0164538 A1 6/2015 Aldridge et al.
2015/0238260 A1 8/2015 Nau, Jr.
2015/0272557 A1 10/2015 Overmyer et al.
2015/0272581 A1 10/2015 Leimbach et al.
2015/0272659 A1 10/2015 Boudreaux et al.
2015/0282879 A1 10/2015 Ruelas
2015/0289364 A1 10/2015 Ilkko et al.
2015/0313667 A1 11/2015 Allen, IV
2015/0317899 A1 11/2015 Dumbauld et al.
2015/0351765 A1 12/2015 Valentine et al.
2015/0374430 A1 12/2015 Weiler et al.
2016/0044841 A1 2/2016 Chamberlain
2016/0045248 A1 2/2016 Unger et al.
2016/0051316 A1 2/2016 Boudreaux
2016/0066909 A1 3/2016 Swayze et al.
2016/0175025 A1 6/2016 Strobl
2016/0175029 A1 6/2016 Witt et al.
2016/0206342 A1 7/2016 Robertson et al.
2016/0249910 A1 9/2016 Shelton, IV et al.
2016/0262786 A1 9/2016 Madan et al.
2016/0270842 A1 9/2016 Strobl et al.
2016/0296251 A1 10/2016 Olson et al.
2016/0296252 A1 10/2016 Olson et al.
2016/0296270 A1 10/2016 Strobl et al.
2016/0358849 A1 12/2016 Jur et al.
2017/0086909 A1 3/2017 Yates et al.
2017/0119426 A1 5/2017 Akagane
2017/0135751 A1 5/2017 Rothweiler et al.
2017/0164997 A1 6/2017 Johnson et al.
2017/0189095 A1 7/2017 Danziger et al.
2017/0202595 A1 7/2017 Shelton, IV
2017/0224332 A1 8/2017 Hunter et al.
2017/0231628 A1 8/2017 Shelton, IV et al.
2017/0281186 A1 10/2017 Shelton, IV et al.
2017/0296177 A1 10/2017 Harris et al.
2017/0296180 A1 10/2017 Harris et al.
2017/0312018 A1 11/2017 Trees et al.
2017/0325874 A1 11/2017 Noack et al.
2018/0014872 A1 1/2018 Dickerson
2018/0098785 A1 4/2018 Price et al.
2018/0132850 A1 5/2018 Leimbach
2018/0146976 A1 5/2018 Clauda et al.
2018/0168575 A1 6/2018 Simms et al.
2018/0168577 A1 6/2018 Aronhalt et al.
2018/0168579 A1 6/2018 Aronhalt et al.
2018/0168592 A1 6/2018 Overmyer et al.
2018/0168598 A1 6/2018 Shelton, IV et al.
2018/0168608 A1 6/2018 Shelton, IV et al.
2018/0168609 A1 6/2018 Fanelli et al.
2018/0168610 A1 6/2018 Shelton, IV et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0188125 A1 7/2018 Park et al.
2018/0235691 A1 8/2018 Voegele et al.
2018/0289432 A1 10/2018 Kostrzewski
2018/0325517 A1 11/2018 Wingardner et al.
2018/0368844 A1 12/2018 Bakos
2019/0000459 A1 1/2019 Shelton, IV
2019/0000461 A1 1/2019 Shelton, IV
2019/0000462 A1 1/2019 Shelton, IV et al.
2019/0000474 A1 1/2019 Shelton, IV et al.
2019/0000475 A1 1/2019 Shelton, IV et al.
2019/0000476 A1 1/2019 Shelton, IV et al.
2019/0000477 A1 1/2019 Shelton, IV et al.
2019/0038282 A1 2/2019 Shelton, IV et al.
2019/0038283 A1 2/2019 Shelton, IV et al.
2019/0104919 A1 4/2019 Shelton, IV et al.
2019/0105067 A1 4/2019 Boudreaux et al.
2019/0125390 A1 5/2019 Shelton, IV et al.
2019/0130183 A1 5/2019 Yoshida et al.
2019/0183504 A1 6/2019 Shelton, IV et al.
2019/0200844 A1 7/2019 Shelton, IV et al.
2019/0200977 A1 7/2019 Shelton, IV et al.
2019/0200981 A1 7/2019 Harris et al.
2019/0201030 A1 7/2019 Shelton, IV et al.
2019/0201045 A1 7/2019 Yates et al.
2019/0201046 A1 7/2019 Shelton, IV et al.
2019/0201047 A1 7/2019 Yates et al.
2019/0201048 A1 7/2019 Stulen et al.
2019/0201104 A1 7/2019 Shelton, IV et al.
2019/0201136 A1 7/2019 Shelton, IV et al.

(56) References Cited

U.S. PATENT DOCUMENTS

| | | | |
|---|---|---|---|
| 2019/0201137 | A1 | 7/2019 | Shelton, IV et al. |
| 2019/0201594 | A1 | 7/2019 | Shelton, IV et al. |
| 2019/0206562 | A1 | 7/2019 | Shelton, IV et al. |
| 2019/0206564 | A1 | 7/2019 | Shelton, IV et al. |
| 2019/0206565 | A1 | 7/2019 | Shelton, IV |
| 2019/0206569 | A1 | 7/2019 | Shelton, IV et al. |
| 2019/0208641 | A1 | 7/2019 | Yates et al. |
| 2019/0209201 | A1 | 7/2019 | Boudreaux et al. |
| 2019/0262030 | A1 | 8/2019 | Faller et al. |
| 2019/0274700 | A1 | 9/2019 | Robertson et al. |
| 2019/0282288 | A1 | 9/2019 | Boudreaux |
| 2019/0290265 | A1 | 9/2019 | Shelton, IV et al. |
| 2019/0298340 | A1 | 10/2019 | Shelton, IV et al. |
| 2019/0298350 | A1 | 10/2019 | Shelton, IV et al. |
| 2019/0298352 | A1 | 10/2019 | Shelton, IV et al. |
| 2019/0298353 | A1 | 10/2019 | Shelton, IV et al. |
| 2019/0366562 | A1 | 12/2019 | Zhang et al. |
| 2019/0388091 | A1 | 12/2019 | Eschbach et al. |
| 2020/0030021 | A1 | 1/2020 | Yates et al. |
| 2020/0054321 | A1 | 2/2020 | Harris et al. |
| 2020/0054382 | A1 | 2/2020 | Yates et al. |
| 2020/0078076 | A1 | 3/2020 | Henderson et al. |
| 2020/0078085 | A1 | 3/2020 | Yates et al. |
| 2020/0078106 | A1 | 3/2020 | Henderson et al. |
| 2020/0078609 | A1 | 3/2020 | Messerly et al. |
| 2020/0085465 | A1 | 3/2020 | Timm et al. |
| 2020/0100825 | A1 | 4/2020 | Henderson et al. |
| 2020/0100830 | A1 | 4/2020 | Henderson et al. |
| 2020/0129261 | A1 | 4/2020 | Eschbach |
| 2020/0138473 | A1 | 5/2020 | Shelton, IV et al. |
| 2020/0188047 | A1 | 6/2020 | Itkowitz et al. |
| 2020/0229833 | A1 | 7/2020 | Vakharia et al. |
| 2020/0229834 | A1 | 7/2020 | Olson et al. |
| 2020/0237434 | A1 | 7/2020 | Scheib et al. |
| 2020/0261078 | A1 | 8/2020 | Bakos et al. |
| 2020/0261081 | A1 | 8/2020 | Boudreaux et al. |
| 2020/0261086 | A1 | 8/2020 | Zeiner et al. |
| 2020/0261087 | A1 | 8/2020 | Timm |
| 2020/0261141 | A1 | 8/2020 | Wiener et al. |
| 2020/0268433 | A1 | 8/2020 | Wiener et al. |
| 2020/0305870 | A1 | 10/2020 | Shelton, IV |
| 2020/0315623 | A1 | 10/2020 | Eisinger |
| 2020/0315712 | A1 | 10/2020 | Jasperson et al. |
| 2020/0405296 | A1 | 12/2020 | Shelton, IV |
| 2020/0405302 | A1 | 12/2020 | Shelton, IV et al. |
| 2020/0405312 | A1 | 12/2020 | Shelton, IV et al. |
| 2020/0405314 | A1 | 12/2020 | Shelton, IV et al. |
| 2020/0405316 | A1 | 12/2020 | Shelton, IV et al. |
| 2020/0405409 | A1 | 12/2020 | Shelton, IV et al. |
| 2020/0405410 | A1 | 12/2020 | Shelton, IV |
| 2020/0405436 | A1 | 12/2020 | Shelton, IV et al. |
| 2020/0405437 | A1 | 12/2020 | Shelton, IV et al. |
| 2020/0405439 | A1 | 12/2020 | Shelton, IV et al. |
| 2020/0410177 | A1 | 12/2020 | Shelton, IV |
| 2021/0052313 | A1 | 2/2021 | Shelton, IV et al. |
| 2021/0100578 | A1 | 4/2021 | Weir et al. |
| 2021/0100579 | A1 | 4/2021 | Shelton, IV et al. |
| 2021/0177481 | A1 | 6/2021 | Shelton, IV et al. |
| 2021/0177496 | A1 | 6/2021 | Shelton, IV et al. |
| 2021/0186492 | A1 | 6/2021 | Shelton, IV |
| 2021/0186493 | A1 | 6/2021 | Shelton, IV et al. |
| 2021/0186494 | A1 | 6/2021 | Shelton, IV et al. |
| 2021/0186495 | A1 | 6/2021 | Shelton, IV et al. |
| 2021/0186497 | A1 | 6/2021 | Shelton, IV |
| 2021/0186498 | A1 | 6/2021 | Boudreaux et al. |
| 2021/0186499 | A1 | 6/2021 | Shelton, IV |
| 2021/0186500 | A1 | 6/2021 | Shelton, IV et al. |
| 2021/0186501 | A1 | 6/2021 | Shelton, IV |
| 2021/0186502 | A1 | 6/2021 | Shelton, IV et al. |
| 2021/0186504 | A1 | 6/2021 | Shelton, IV et al. |
| 2021/0186505 | A1 | 6/2021 | Shelton, IV et al. |
| 2021/0186507 | A1 | 6/2021 | Shelton, IV et al. |
| 2021/0186553 | A1 | 6/2021 | Green et al. |
| 2021/0186554 | A1 | 6/2021 | Green et al. |
| 2021/0196263 | A1 | 7/2021 | Shelton, IV et al. |
| 2021/0196265 | A1 | 7/2021 | Shelton, IV et al. |
| 2021/0196266 | A1 | 7/2021 | Shelton, IV et al. |
| 2021/0196267 | A1 | 7/2021 | Shelton, IV et al. |
| 2021/0196268 | A1 | 7/2021 | Shelton, IV et al. |
| 2021/0196269 | A1 | 7/2021 | Shelton, IV et al. |
| 2021/0196270 | A1 | 7/2021 | Shelton, IV et al. |
| 2021/0196271 | A1 | 7/2021 | Shelton, IV et al. |
| 2021/0196301 | A1 | 7/2021 | Shelton, IV et al. |
| 2021/0196302 | A1 | 7/2021 | Shelton, IV et al. |
| 2021/0196305 | A1 | 7/2021 | Strobl |
| 2021/0196306 | A1 | 7/2021 | Estera et al. |
| 2021/0196307 | A1 | 7/2021 | Shelton, IV |
| 2021/0196334 | A1 | 7/2021 | Sarley et al. |
| 2021/0196335 | A1 | 7/2021 | Messerly et al. |
| 2021/0196336 | A1 | 7/2021 | Faller et al. |
| 2021/0196343 | A1 | 7/2021 | Shelton, IV et al. |
| 2021/0196344 | A1 | 7/2021 | Shelton, IV et al. |
| 2021/0196345 | A1 | 7/2021 | Messerly et al. |
| 2021/0196346 | A1 | 7/2021 | Leuck et al. |
| 2021/0196349 | A1 | 7/2021 | Fiebig et al. |
| 2021/0196350 | A1 | 7/2021 | Fiebig et al. |
| 2021/0196351 | A1 | 7/2021 | Sarley et al. |
| 2021/0196352 | A1 | 7/2021 | Messerly et al. |
| 2021/0196353 | A1 | 7/2021 | Gee et al. |
| 2021/0196354 | A1 | 7/2021 | Shelton, IV et al. |
| 2021/0196355 | A1 | 7/2021 | Shelton, IV et al. |
| 2021/0196356 | A1 | 7/2021 | Shelton, IV et al. |
| 2021/0196357 | A1 | 7/2021 | Shelton, IV et al. |
| 2021/0196358 | A1 | 7/2021 | Shelton, IV et al. |
| 2021/0196359 | A1 | 7/2021 | Shelton, IV et al. |
| 2021/0196360 | A1 | 7/2021 | Shelton, IV et al. |
| 2021/0196361 | A1 | 7/2021 | Shelton, IV et al. |
| 2021/0196362 | A1 | 7/2021 | Shelton, IV et al. |
| 2021/0196363 | A1 | 7/2021 | Shelton, IV et al. |
| 2021/0196364 | A1 | 7/2021 | Shelton, IV et al. |
| 2021/0196365 | A1 | 7/2021 | Shelton, IV et al. |
| 2021/0196366 | A1 | 7/2021 | Shelton, IV et al. |
| 2021/0196367 | A1 | 7/2021 | Salguero et al. |
| 2021/0212744 | A1 | 7/2021 | Shelton, IV et al. |
| 2021/0220036 | A1 | 7/2021 | Shelton, IV et al. |
| 2021/0236195 | A1 | 8/2021 | Asher et al. |
| 2021/0282804 | A1 | 9/2021 | Worrell et al. |
| 2021/0393288 | A1 | 12/2021 | Shelton, IV et al. |
| 2021/0393314 | A1 | 12/2021 | Wiener et al. |
| 2021/0393319 | A1 | 12/2021 | Shelton, IV et al. |

FOREIGN PATENT DOCUMENTS

| | | | |
|---|---|---|---|
| CN | 1634601 | A | 7/2005 |
| CN | 1775323 | A | 5/2006 |
| CN | 1922563 | A | 2/2007 |
| CN | 2868227 | Y | 2/2007 |
| CN | 201029899 | Y | 3/2008 |
| CN | 101474081 | A | 7/2009 |
| CN | 101516285 | A | 8/2009 |
| CN | 101522112 | A | 9/2009 |
| CN | 102100582 | A | 6/2011 |
| CN | 102149312 | A | 8/2011 |
| CN | 202027624 | U | 11/2011 |
| CN | 102792181 | A | 11/2012 |
| CN | 103281982 | A | 9/2013 |
| CN | 103379853 | A | 10/2013 |
| CN | 203468630 | U | 3/2014 |
| CN | 104001276 | A | 8/2014 |
| CN | 104013444 | A | 9/2014 |
| CN | 104434298 | A | 3/2015 |
| CN | 107374752 | A | 11/2017 |
| CN | 109011149 | A | 12/2018 |
| DE | 3904558 | A1 | 8/1990 |
| DE | 9210327 | U1 | 11/1992 |
| DE | 4300307 | A1 | 7/1994 |
| DE | 29623113 | U1 | 10/1997 |
| DE | 20004812 | U1 | 9/2000 |
| DE | 20021619 | U1 | 3/2001 |
| DE | 10042606 | A1 | 8/2001 |
| DE | 10201569 | A1 | 7/2003 |
| DE | 102012109037 | A1 | 4/2014 |
| EP | 0171967 | A2 | 2/1986 |
| EP | 0336742 | A2 | 10/1989 |

(56) References Cited

FOREIGN PATENT DOCUMENTS

| | | | |
|---|---|---|---|
| EP | 0136855 | B1 | 11/1989 |
| EP | 0705571 | A1 | 4/1996 |
| EP | 1698289 | A2 | 9/2006 |
| EP | 1862133 | A1 | 12/2007 |
| EP | 1972264 | A1 | 9/2008 |
| EP | 2060238 | A1 | 5/2009 |
| EP | 1747761 | B1 | 10/2009 |
| EP | 2131760 | A1 | 12/2009 |
| EP | 1214913 | B1 | 7/2010 |
| EP | 1946708 | B1 | 6/2011 |
| EP | 1767164 | B1 | 1/2013 |
| EP | 2578172 | A2 | 4/2013 |
| EP | 2668922 | A1 | 12/2013 |
| EP | 2700365 | A1 | 2/2014 |
| EP | 2754383 | A2 | 7/2014 |
| EP | 2076195 | B1 | 12/2015 |
| EP | 2510891 | B1 | 6/2016 |
| EP | 3367387 | A1 | 8/2018 |
| EP | 3476302 | A2 | 5/2019 |
| EP | 3476331 | A1 | 5/2019 |
| EP | 3694298 | A1 | 8/2020 |
| GB | 2032221 | A | 4/1980 |
| GB | 2317566 | A | 4/1998 |
| JP | S50100891 | A | 8/1975 |
| JP | S5968513 | A | 4/1984 |
| JP | S5968513 | U | 5/1984 |
| JP | S59141938 | A | 8/1984 |
| JP | S62221343 | A | 9/1987 |
| JP | S62227343 | A | 10/1987 |
| JP | S62292153 | A | 12/1987 |
| JP | S62292154 | A | 12/1987 |
| JP | S63109386 | A | 5/1988 |
| JP | S63315049 | A | 12/1988 |
| JP | H01151452 | A | 6/1989 |
| JP | H01198540 | A | 8/1989 |
| JP | H0271510 | U | 5/1990 |
| JP | H02286149 | A | 11/1990 |
| JP | H02292193 | A | 12/1990 |
| JP | H0337061 | A | 2/1991 |
| JP | H0425707 | U | 2/1992 |
| JP | H0464351 | A | 2/1992 |
| JP | H0430508 | U | 3/1992 |
| JP | H04152942 | A | 5/1992 |
| JP | H 0541716 | A | 2/1993 |
| JP | H0595955 | A | 4/1993 |
| JP | H05115490 | A | 5/1993 |
| JP | H0670938 | A | 3/1994 |
| JP | H06104503 | A | 4/1994 |
| JP | H0824266 | A | 1/1996 |
| JP | H08229050 | A | 9/1996 |
| JP | H08275951 | A | 10/1996 |
| JP | H08299351 | A | 11/1996 |
| JP | H08336545 | A | 12/1996 |
| JP | H09130655 | A | 5/1997 |
| JP | H09135553 | A | 5/1997 |
| JP | H09140722 | A | 6/1997 |
| JP | H105237 | A | 1/1998 |
| JP | 10127654 | A | 5/1998 |
| JP | H10295700 | A | 11/1998 |
| JP | H11128238 | A | 5/1999 |
| JP | 2000210299 | A | 8/2000 |
| JP | 2000271142 | A | 10/2000 |
| JP | 2000271145 | A | 10/2000 |
| JP | 2000287987 | A | 10/2000 |
| JP | 2001029353 | A | 2/2001 |
| JP | 2002059380 | A | 2/2002 |
| JP | 2002186901 | A | 7/2002 |
| JP | 2002263579 | A | 9/2002 |
| JP | 2002330977 | A | 11/2002 |
| JP | 2003000612 | A | 1/2003 |
| JP | 2003010201 | A | 1/2003 |
| JP | 2003116870 | A | 4/2003 |
| JP | 2003126104 | A | 5/2003 |
| JP | 2003126110 | A | 5/2003 |
| JP | 2003153919 | A | 5/2003 |
| JP | 2003339730 | A | 12/2003 |
| JP | 2004129871 | A | 4/2004 |
| JP | 2004147701 | A | 5/2004 |
| JP | 2005003496 | A | 1/2005 |
| JP | 2005027026 | A | 1/2005 |
| JP | 2005074088 | A | 3/2005 |
| JP | 2005337119 | A | 12/2005 |
| JP | 2006068396 | A | 3/2006 |
| JP | 2006081664 | A | 3/2006 |
| JP | 2006114072 | A | 4/2006 |
| JP | 2006217716 | A | 8/2006 |
| JP | 2006288431 | A | 10/2006 |
| JP | 2007037568 | A | 2/2007 |
| JP | 200801876 | A | 1/2008 |
| JP | 200833644 | A | 2/2008 |
| JP | 2008188160 | A | 8/2008 |
| JP | D1339835 | S | 8/2008 |
| JP | 2009236177 | A | 10/2009 |
| JP | 2010009686 | A | 1/2010 |
| JP | 2010121865 | A | 6/2010 |
| JP | 2012071186 | A | 4/2012 |
| JP | 2012235658 | A | 11/2012 |
| KR | 100789356 | B1 | 12/2007 |
| RU | 2154437 | C1 | 8/2000 |
| RU | 22035 | U1 | 3/2002 |
| RU | 2201169 | C2 | 3/2003 |
| RU | 2405603 | C1 | 12/2010 |
| RU | 2013119977 | A | 11/2014 |
| SU | 850068 | A1 | 7/1981 |
| WO | WO-8103272 | A1 | 11/1981 |
| WO | WO-9308757 | A1 | 5/1993 |
| WO | WO-9314708 | A1 | 8/1993 |
| WO | WO-9421183 | A1 | 9/1994 |
| WO | WO-9424949 | A1 | 11/1994 |
| WO | WO-9639086 | A1 | 12/1996 |
| WO | WO-9800069 | A1 | 1/1998 |
| WO | WO-9840015 | A2 | 9/1998 |
| WO | WO-9920213 | A1 | 4/1999 |
| WO | WO-9923960 | A1 | 5/1999 |
| WO | WO-0024330 | A1 | 5/2000 |
| WO | WO-0064358 | A2 | 11/2000 |
| WO | 0074585 | A2 | 12/2000 |
| WO | WO-0128444 | A1 | 4/2001 |
| WO | WO-0167970 | A1 | 9/2001 |
| WO | WO-0172251 | A1 | 10/2001 |
| WO | WO-0195810 | A2 | 12/2001 |
| WO | WO-03095028 | A1 | 11/2003 |
| WO | WO-2004037095 | A2 | 5/2004 |
| WO | WO-2004078051 | A2 | 9/2004 |
| WO | WO-2004098426 | A1 | 11/2004 |
| WO | 2006091494 | A1 | 8/2006 |
| WO | WO-2007008710 | A2 | 1/2007 |
| WO | WO-2008118709 | A1 | 10/2008 |
| WO | WO-2008130793 | A1 | 10/2008 |
| WO | WO-2010027109 | A1 | 3/2010 |
| WO | WO-2010104755 | A1 | 9/2010 |
| WO | WO-2011008672 | A2 | 1/2011 |
| WO | WO-2011044343 | A2 | 4/2011 |
| WO | WO-2011052939 | A2 | 5/2011 |
| WO | WO-2011060031 | A1 | 5/2011 |
| WO | WO-2012044606 | A2 | 4/2012 |
| WO | WO-2012088535 | A1 | 6/2012 |
| WO | WO-2012150567 | A1 | 11/2012 |
| WO | 2016130844 | A1 | 8/2016 |
| WO | 2017042171 | A1 | 3/2017 |
| WO | 2019130090 | A1 | 7/2019 |
| WO | 2019130113 | A1 | 7/2019 |

OTHER PUBLICATIONS

Lim et al., "A Review of Mechanism Used in Laparoscopic Surgical Instruments," Mechanism and Machine Theory, vol. 38, pp. 1133-1147, (2003).

F. A. Duck, "Optical Properties of Tissue Including Ultraviolet and Infrared Radiation," pp. 43-71 in Physical Properties of Tissue (1990).

Makarov, S. N., Ochmann, M., Desinger, K., "The longitudinal vibration response of a curved fiber used for laser ultrasound

(56) References Cited

OTHER PUBLICATIONS surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
http://www.apicalinstr.com/generators.htm.
http://www.medicalexpo.com/medical-manufacturer/electrosurgical-generator-6951.html.
http://www.valleylab.com/product/es/generators/index.html.
Covidien 501 (k) Summary Sonicision, dated Feb. 24, 2011 (7 pages).
Gerhard, Glen C., "Surgical Electrotechnology: Quo Vadis?," IEEE Transactions on Biomedical Engineering, vol. BME-31, No. 12, pp. 787-792, Dec. 1984.
http://www.dotmed.com/listing/electrosurical-unit/ethicon/ultracision-g110-/1466724.
http:/www.ethicon.com/gb-en/healthcare-professionals/products/energy-devices/capital//ge . . . .
http://www.megadyne.com/es_generator.php.
Sullivan, "Optimal Choice for Number of Strands in a Litz-Wire Transformer Winding," IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-17(1), 1-6 (1970).
Incropera et al., Fundamentals of Heat and Mass Transfer, Wiley, New York (1990). (Book—not attached).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in Medical Infrared Imaging, N. A. Diakides and J. D. Bronzino, Eds. (2008).
http://www.4-traders.com/JOHNSON-JOHNSON-4832/news/Johnson-Johnson-Ethicon-E . . . .
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe, Integrated Circuit Engineering, Addison-Wesley Publishing, Reading, MA (1979). (book—not attached).

(56) References Cited

OTHER PUBLICATIONS

Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 Erbe En VIO 200 S D027541.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.
"ATM-MPLS Network Interworking Version 2.0, af-aic-0178.001", ATM Standard, The ATM Forum Technical Committee, 34 pages, Aug. 2003.
"IEEE Std 802.3-2012 (Revision of IEEE Std 802.3-2008)" IEEE Standard Association, 634 pages, Dec. 28, 2012.
Missinne et al., "Stretchable Optical Waveguides", Optics Express, vol. 22, No. 04, pp. 4168-4179, Feb. 18, 2014.
U.S. Appl. No. 13/751,680, filed Jan. 28, 2013, 27 pages.
Invitation to Pay Additional Fees received for PCT Application No. PCT/US2013/070120, mailed on Apr. 25, 2014, 8 pages.
International Search Report and Written Opinion received for PCT Application No. PCT/US2013/070120, mailed on Sep. 17, 2014, 35 pages.
International Preliminary Report on Patentability received for PCT Application No. PCT/US2013/070120 mailed on May 19, 2015, 22 pages.
"Open Technique for Low Anterior Resection", Abdominal Key, Fastest Abdominal Insight Engine, Retrieved from https://abdominalkey.com/open-technique-for-low-anterior-resection/, Jun. 28, 2016, 6 pages.
"Thyroid Fine Needle Aspiration (FNA) Biopsy", Fairview, Retrieved from https://www.fairview.org/patient-education/90246, Feb. 4, 2020, 3 pages.
"X12C4 Robotic Drop-In", BK Ultrasound, Retrieved from https://bkmedical.com/transducers/x12c4-robotic-drop-in/, Feb. 13, 2020, 2 pages.
Brecht et al., "Whole-body Three-dimensional Optoacoustic Tomography System for Small Animals", Journal of Biomedical Optics, vol. 14, No. 6, Nov./Dec. 2009, pp. 064007-1-064007-7.
Elhaj et al., "Sleeve Gastrectomy Surgical Assistive Instrument for Accurate Remnant Stomach Volume", Journal of Medical Devices, vol. 4, No. 2, Jun. 2010, pp. 025001-1-025001-10.
Ge et al., "Landmark-Guided Deformable Image Registration for Supervised Autonomous Robotic Tumor Resection", Medical Image Computing and Computer Assisted Intervention, vol. 11764, Oct. 10, 2019, pp. 320-328.
Kurata et al., "Time-of-flight Near-infrared Spectroscopy for Nondestructive Measurement of Internal Quality in Grapefruit", Journal of the American Society for Horticultural Science, vol. 138, No. 3, May 1, 2013, pp. 225-228.
Lacy, "Main Steps to Perform a Sleeve Gastrectomy", AiS Channel, Retrieved from https://aischannel.com/society/main-step-to-perform-a-sleeve-gastrectomy/, Jun. 11, 2015, 7 pages.
Sukumar et al., "Robotic Partial Nephrectomy Using Robotic Bulldog Clamps", Journal of the Society of Laparoendoscopic Surgeons, vol. 15, No. 4, 2011, pp. 520-526.

* cited by examiner

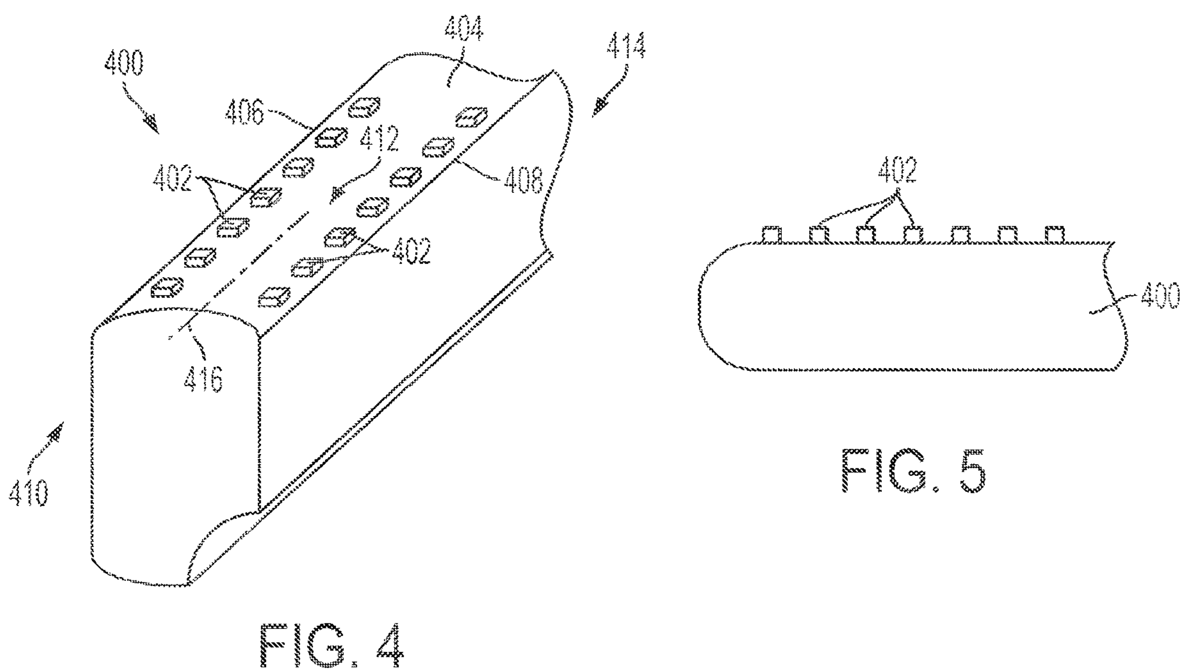
FIG. 4
FIG. 5
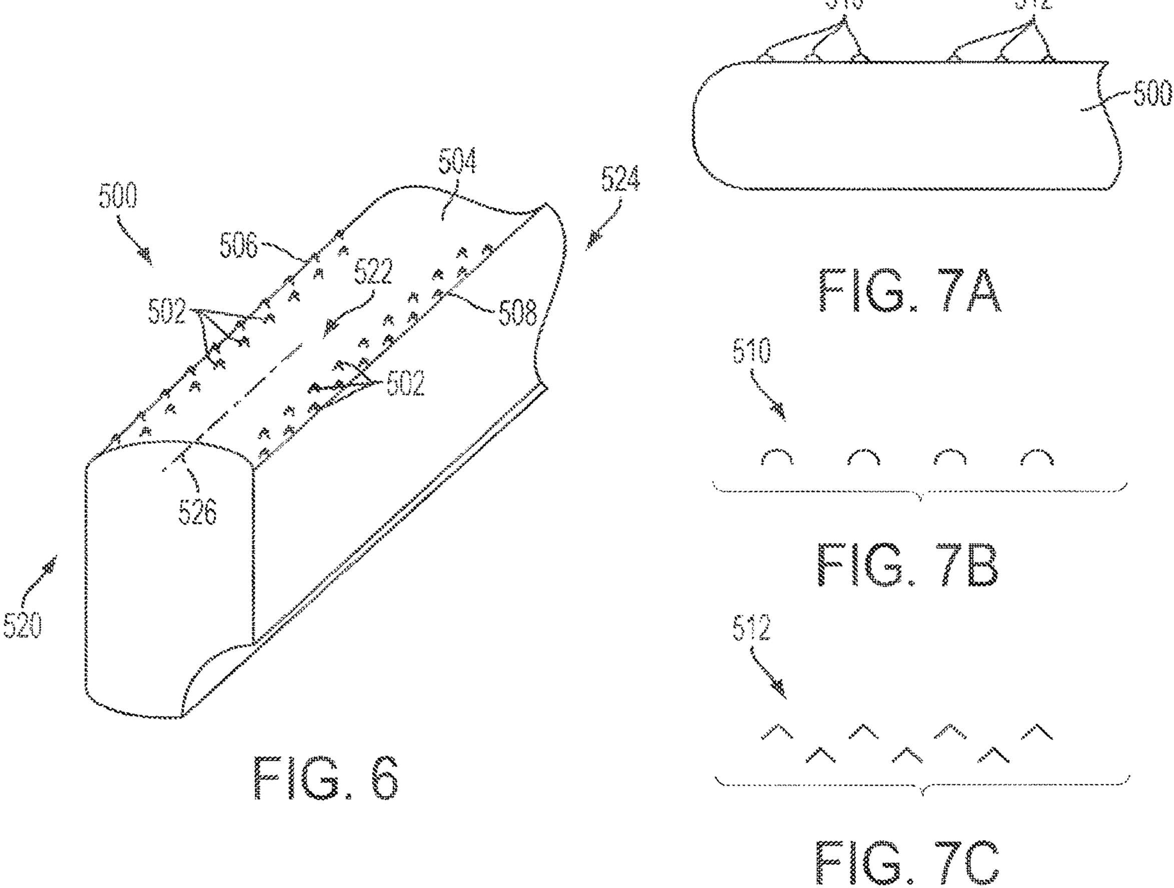
FIG. 7A
FIG. 6
FIG. 7B
FIG. 7C

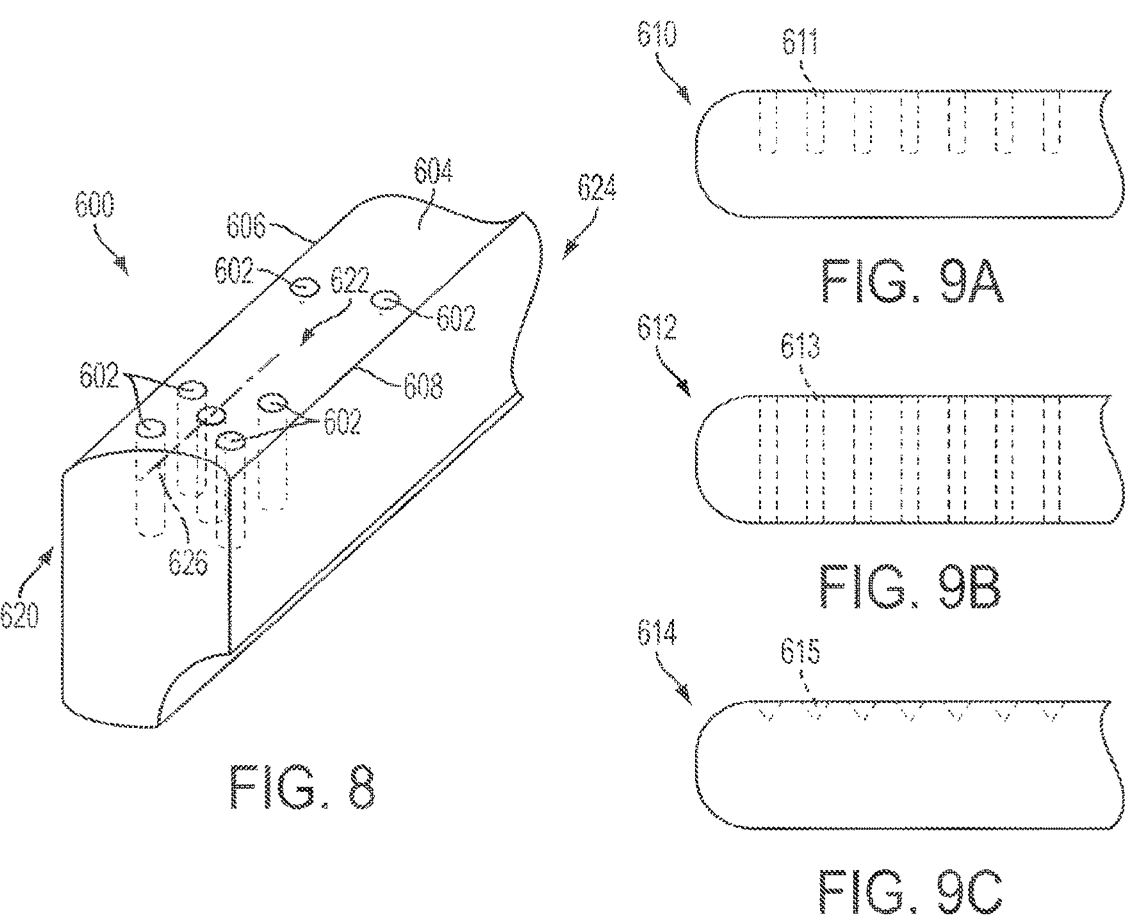
FIG. 8
FIG. 9A
FIG. 9B
FIG. 9C
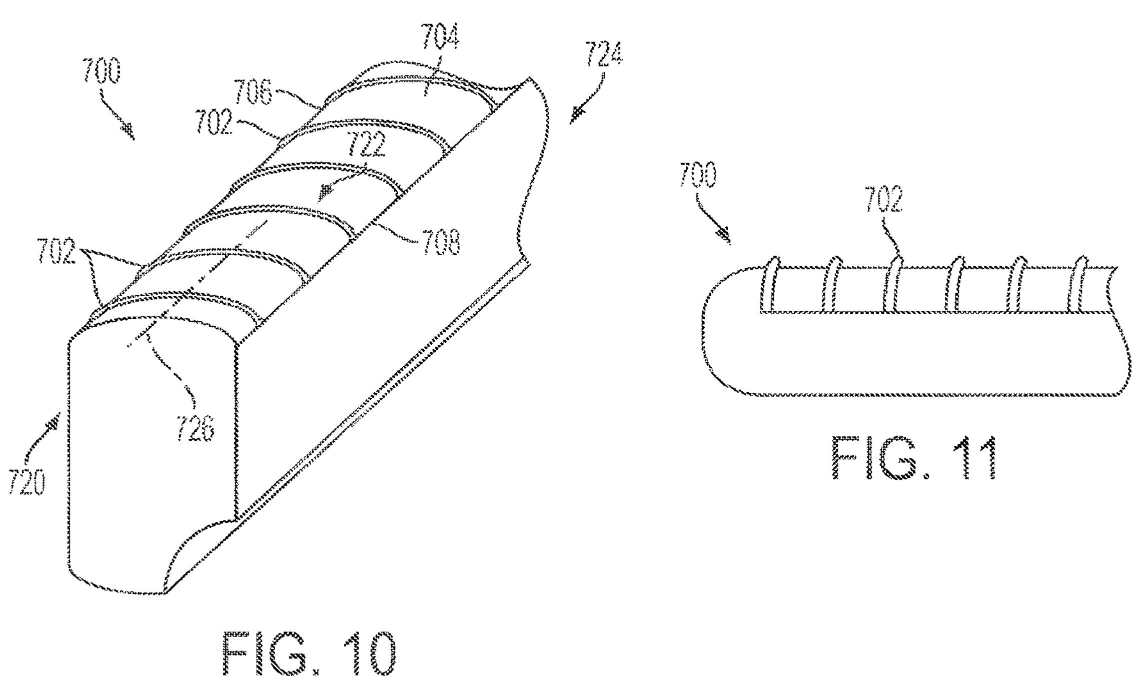
FIG. 10
FIG. 11

800
802
804
b
c
d

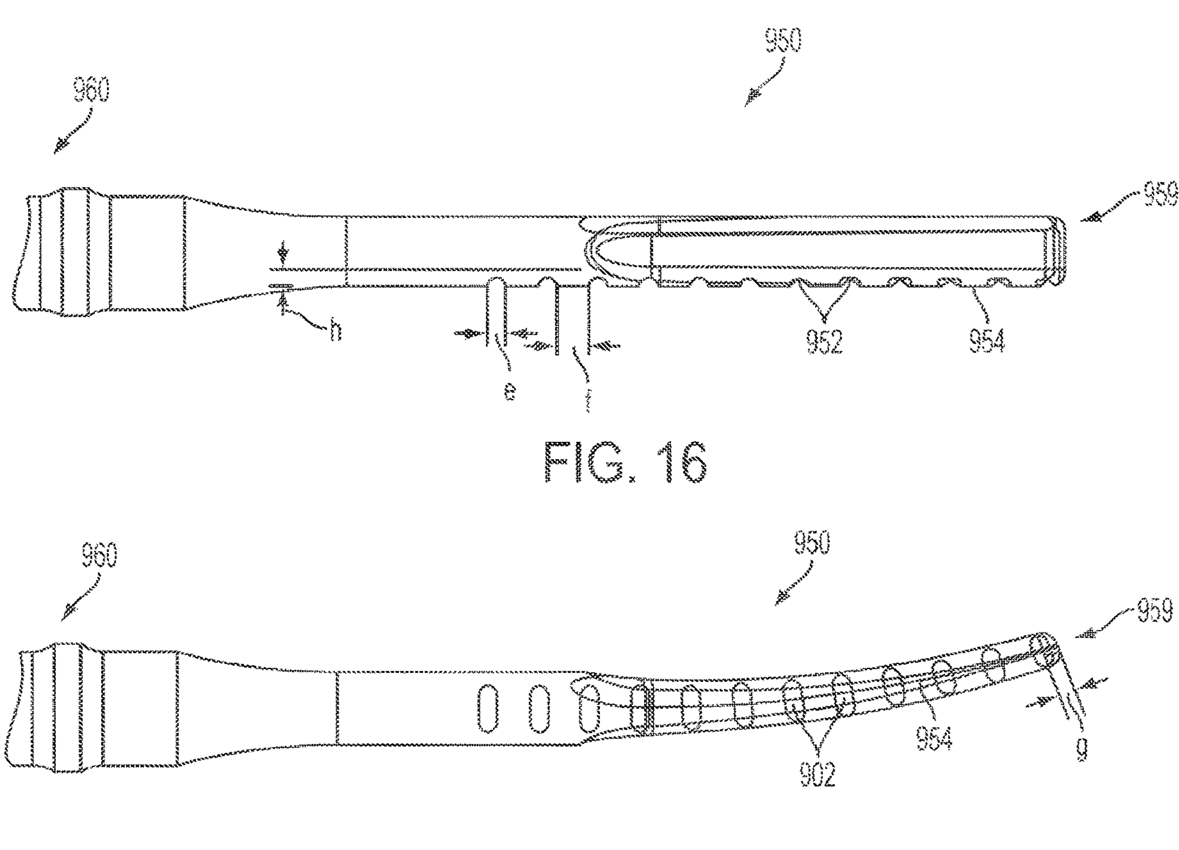
FIG. 16
FIG. 17
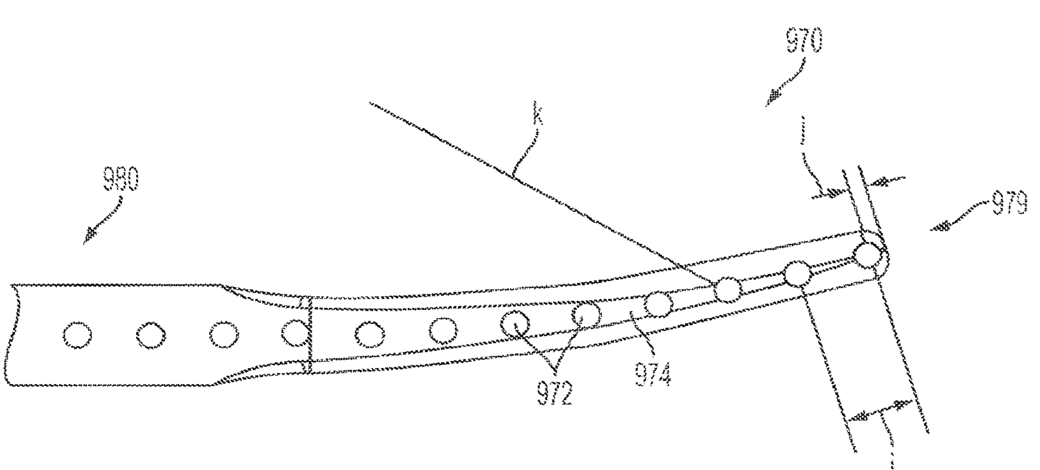
FIG. 18

1304
1300
1304
1306
1310
1302
1308

3110

3200
3204
3124
3202

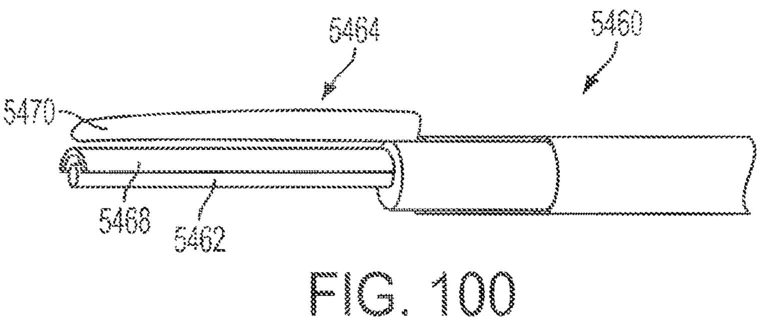
FIG. 100
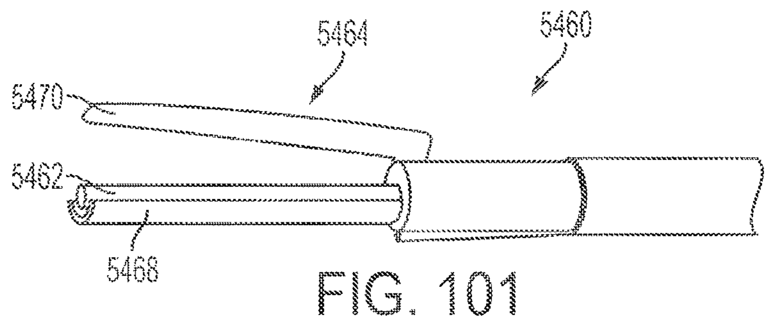
FIG. 101
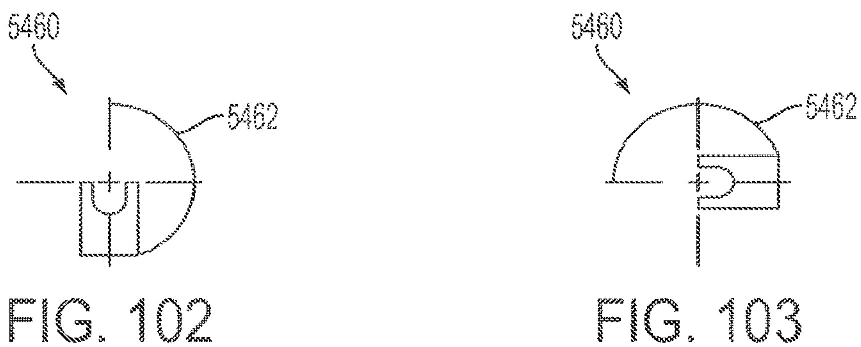
FIG. 102
FIG. 103
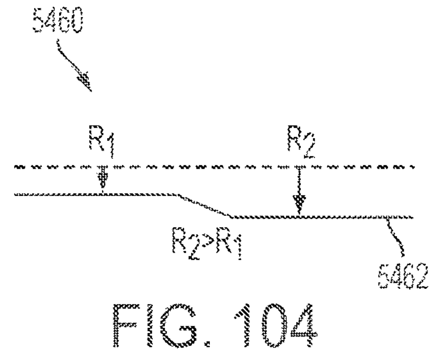
FIG. 104

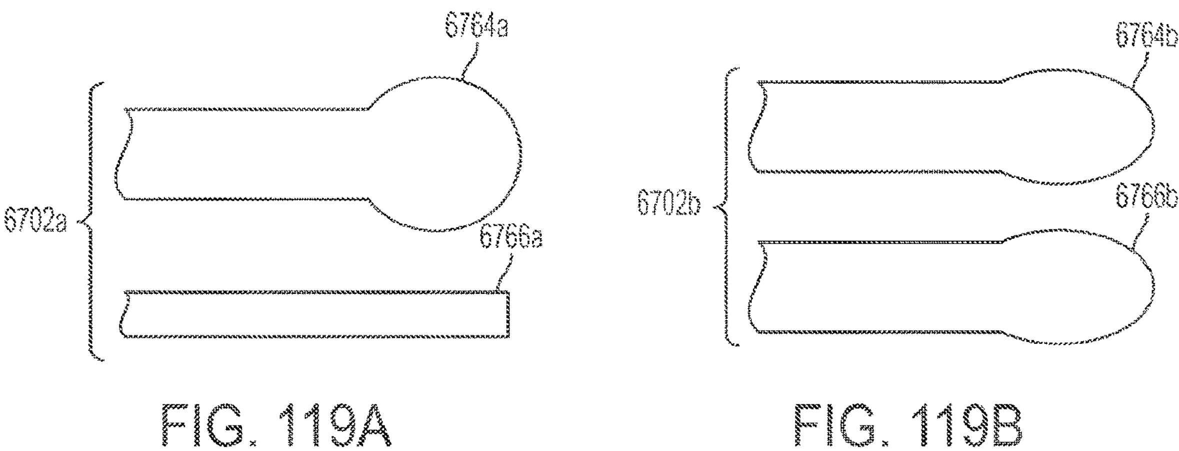
FIG. 119A
FIG. 119B
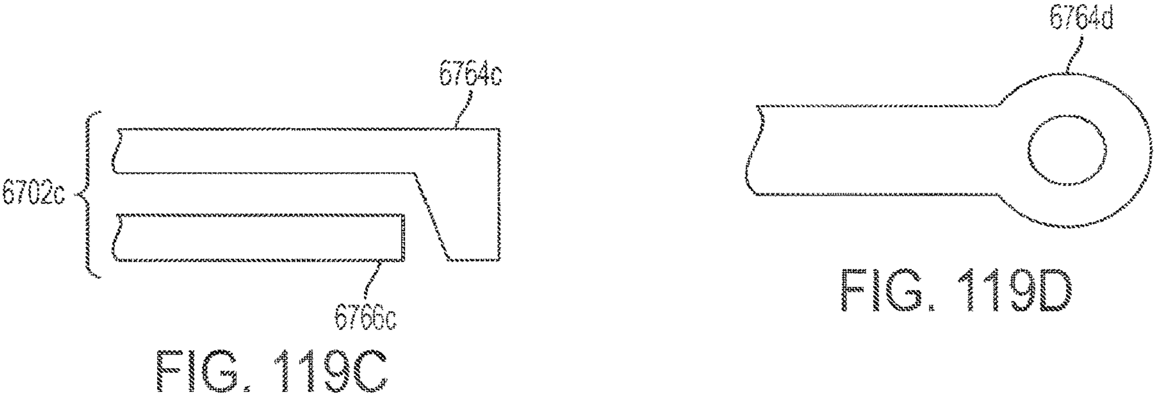
FIG. 119C
FIG. 119D
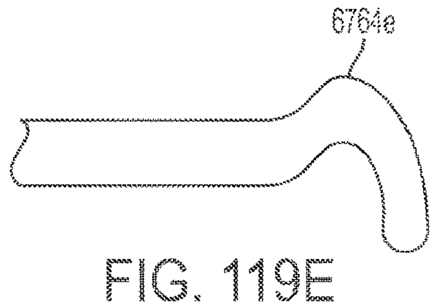
FIG. 119E

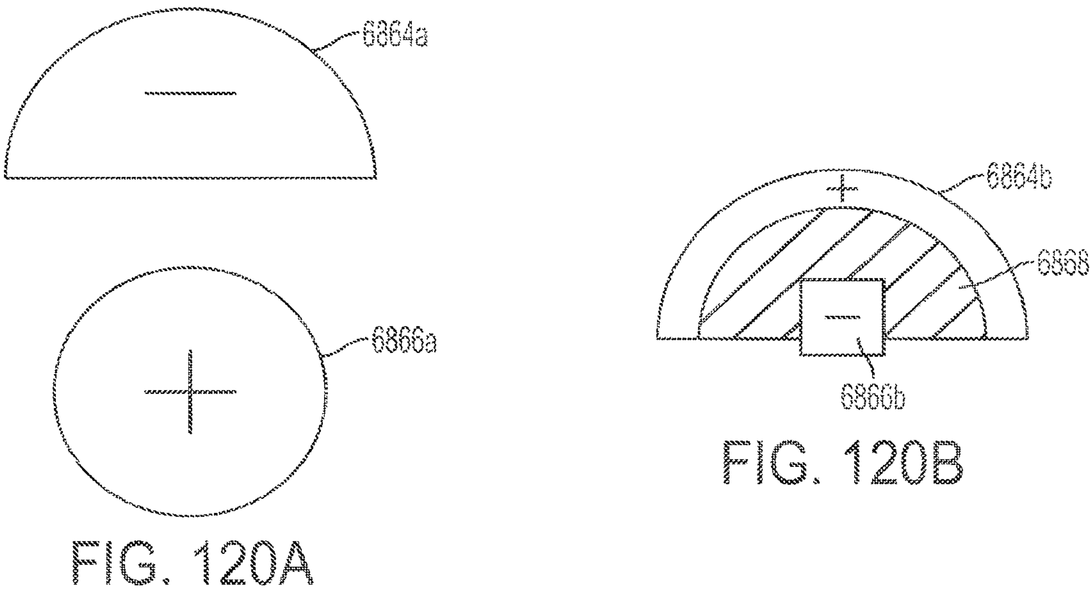
FIG. 120A
FIG. 120B
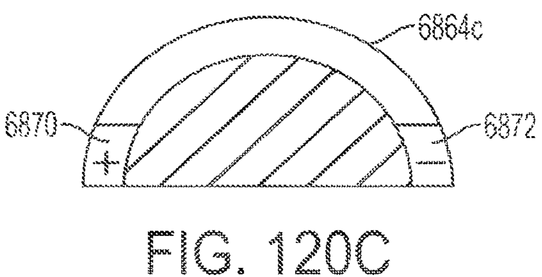
FIG. 120C

ULTRASONIC AND ELECTROSURGICAL DEVICES

CROSS-REFERENCE TO RELATED APPLICATIONS

This application is a continuation application claiming priority under 35 U.S.C. § 120 to U.S. patent application Ser. No. 14/627,792, entitled ULTRASONIC AND ELECTROSURGICAL DEVICES, filed Feb. 20, 2015, now U.S. Patent Application Publication No. 2015/0164538, which is a divisional application claiming priority under 35 U.S.C. § 121 to U.S. patent application Ser. No. 13/843,295, entitled ULTRASONIC AND ELECTROSURGICAL DEVICES, filed Mar. 15, 2013, now U.S. Patent Application Publication No. 2014/0135804, which claims benefit of U.S. Provisional Application No. 61/726,890 filed Nov. 15, 2012 and entitled ULTRASONIC AND ELECTROSURGICAL DEVICES, the disclosure of which are hereby incorporated by reference in their entirety.

INTRODUCTION

The present disclosure is related generally to ultrasonic and electrical surgical devices. More particularly, the present disclosure is related to various blade features for ultrasonic blades to improve tissue grasping, various seals and fluid egress features to prevent build up and accumulation of tissue and other bodily materials encountered during surgery on the distal portion of the tube(s) and the nearby portion of the blade of ultrasonic surgical devices, clamp closure mechanisms for ultrasonic end effectors to provide uniform clamp force, rotation mechanisms for ultrasonic transducers and devices, and combined electrosurgical and ultrasonic devices to provide tissue cutting and spot coagulation.

Ultrasonic surgical devices, such as ultrasonic scalpels, are used in many applications in surgical procedures by virtue of their unique performance characteristics. Depending upon specific device configurations and operational parameters, ultrasonic surgical devices can provide substantially simultaneous transection of tissue and hemostasis by coagulation, desirably minimizing patient trauma. An ultrasonic surgical device comprises a proximally-positioned ultrasonic transducer and an instrument coupled to the ultrasonic transducer having a distally-mounted end effector comprising an ultrasonic blade to cut and seal tissue. The end effector is typically coupled either to a handle and/or a robotic surgical implement via a shaft. The blade is acoustically coupled to the transducer via a waveguide extending through the shaft. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures. Vibrating at high frequencies (e.g., 55,500 times per second), the ultrasonic blade denatures protein in the tissue to form a sticky coagulum. Pressure exerted on tissue by the blade surface in combination with a clamping mechanism collapses blood vessels and allows the coagulum to form a hemostatic seal. A surgeon can control the cutting speed and coagulation by the force applied to the tissue by the end effector, the time over which the force is applied and the selected excursion level of the end effector.

Also used in many surgical applications are electrosurgical devices. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form haemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing adjacent tissues or critical structures. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

SUMMARY

In one embodiment, an ultrasonic surgical instrument comprises a waveguide comprising a proximal end and a distal end, wherein the proximal end is coupled to an ultrasonic transducer; an end effector coupled to the distal end of the waveguide; a tube comprising a lumen, wherein the waveguide is located within the lumen; a clamp arm pivotably connected to the tube; and a tissue accumulation impedance mechanism configured to prevent tissue from accumulating in the lumen.

In another embodiment of the ultrasonic surgical instrument, the tissue accumulation impedance mechanism comprises a boot barrier configured to create a seal between the tube and the end effector.

In another embodiment of the ultrasonic surgical instrument, the boot barrier is sealed to the tube using one or more retention features.

In another embodiment of the ultrasonic surgical instrument, the boot barrier comprises a cavity.

In another embodiment of the ultrasonic surgical instrument, the cavity is rounded to allow fluid to flow out of the cavity.

In another embodiment of the ultrasonic surgical instrument, the boot barrier comprises a plurality of contact points with the blade.

In another embodiment of the ultrasonic surgical instrument, the tissue accumulation impedance mechanism comprises one or more apertures in the tube.

In another embodiment of the ultrasonic surgical instrument, the apertures comprise one or more windows.

In another embodiment of the ultrasonic surgical instrument the apertures comprise one or more holes.

In another embodiment of the ultrasonic surgical instrument, the distal portion comprises a hemispherical cross section.

In another embodiment of the ultrasonic surgical instrument, the tube comprises one or more ribs formed on an inner side of the tube.

In another embodiment of the ultrasonic surgical instrument, the tissue accumulation impedance mechanism comprises a pump configured to provide a positive pressure flow between the blade and the tube, wherein the positive pressure flow prevents tissue ingress into the lumen.

In another embodiment of the ultrasonic surgical instrument, the pump or the outlet of the pump is located distally to a distal-most overmolded seal located within the lumen.

In another embodiment of the ultrasonic surgical instrument the tissue accumulation impedance mechanism comprises a slidable tube disposed within the lumen, the slidable tube slidable from a first position to a second position, wherein in the first position the slidable tube is disposed over the blade, and the second position the blade is exposed.

In one embodiment, an ultrasonic surgical instrument comprises a waveguide comprising a proximal end and a distal end, wherein the proximal end is coupled to an ultrasonic transducer; an end effector coupled to the distal end of the waveguide, the end effector comprising at least one tissue retention feature; a clamp arm operatively coupled to the end effector.

In another embodiment of the ultrasonic surgical instrument, the at least one tissue retention feature comprises one or more indentations/grooves/notches/texture formed in the end effector.

In another embodiment of the ultrasonic surgical instrument, the one or more indentations comprise triangular teeth.

In another embodiment of the ultrasonic surgical instrument, the one or more indentations comprise holes.

In another embodiment of the ultrasonic surgical instrument, the one or more indentations comprise horizontal trenches.

In another embodiment of the ultrasonic surgical instrument, the at least on tissue retention feature comprises one or more projections from the end effector.

In another embodiment of the ultrasonic surgical instrument, the one or more projections comprise triangular teeth.

In another embodiment of the ultrasonic surgical instrument, the one or more projections comprise blocks.

In another embodiment of the ultrasonic surgical instrument, the one or more projections comprise horizontal bumps.

In another embodiment of the ultrasonic surgical instrument, the one or more projections comprise circular bumps.

In another embodiment of the ultrasonic surgical instrument, the at least one tissue retention feature is disposed over an entire length of the blade.

In another embodiment of the ultrasonic surgical instrument, the at least one tissue retention feature is disposed over a discrete section of the blade.

In one embodiment, an ultrasonic surgical instrument comprises a waveguide comprising a proximal end and a distal end, wherein the proximal end is coupled to an ultrasonic transducer; an end effector operatively coupled to the distal end of the waveguide guide; a rotation shroud configured to rotate the waveguide; and a rotation stop mechanism coupled to the rotation shroud prevent rotation of the rotation knob beyond a predetermined rotation.

In another embodiment of the ultrasonic surgical instrument, the shroud comprises at least one channel; at least one boss, the at least one boss located within the at least one channel, wherein the at least one boss has a predetermined lateral movement limit, wherein when the at least one boss reaches the predetermined lateral movement limit, the at least one boss prevents further rotation of the rotation knob.

In another embodiment of the ultrasonic surgical instrument, the rotation stop comprises a gate comprising a first wing and a second wing, wherein the first and second wings are disposed at an angle, wherein the gate is disposed within the shroud and the gate allows a predetermined angle of rotation of the shroud.

In one embodiment, an ultrasonic surgical instrument comprises a waveguide comprising a proximal end and a distal end, wherein the proximal end is coupled to an ultrasonic transducer; an end effector coupled to the distal end of the waveguide; a clamp arm operatively coupled to the end effector; a tube disposed over the waveguide, wherein the tube comprises a counter deflection element, wherein the counter deflection element is configured to allow deflection of the blade, wherein the deflection of the blade counteracts a force placed on the blade by the clamp arm in a clamped position.

In one embodiment, a surgical instrument comprises a waveguide comprising a proximal end and a distal end, wherein the proximal end is coupled to a signal source, the signal source configured to provide an ultrasonic signal and an electrosurgical signal; an end effector coupled to the waveguide; a clamp arm operatively coupled to the end effector; and a sealing button, wherein the sealing button causes the surgical instrument to deliver the electrosurgical signal to the end effector and/or the clamp arm for a first period and the sealing button causes the surgical instrument to deliver the ultrasonic signal to the blade for a second period, wherein the second period is subsequent to the first period.

In another embodiment of the surgical instrument, the sealing button causes the surgical instrument to deliver the ultrasonic signal to the end effector prior to transmitting the electrosurgical signal to the end effector and/or clamp arm.

In another embodiment of the surgical instrument, the sealing button causes the surgical instrument to only deliver the ultrasonic signal to the end effector resulting in haemostatic transection of tissue. A separate spot coagulation button is provided on the handle. When the spot coagulation button is depressed, an electrosurgical signal is provided to either the end effector or the clamp arm or both to effect spot coagulation of tissue.

In another embodiment of the surgical instrument, wherein the electrosurgical signal is a monopolar RF signal.

In another embodiment of the surgical instrument, wherein the electrosurgical signal is a bipolar RF signal.

In one embodiment, a surgical instrument comprises a waveguide comprising a proximal end and a distal end, wherein the proximal end is coupled to an ultrasonic transducer; an end effector coupled to the distal end of the waveguide; a tube disposed over the waveguide; a cam surface formed on or in an outer surface of the tube; and a clamp arm, wherein the clamp arm is operatively coupled to the cam surface.

In another embodiment of the surgical instrument, a pivot pin is located within a hole defined by the end effector, the pivot pin operatively coupled to the clamp arm, wherein the clamp arm pivots about the pivot pin.

In another embodiment of the surgical instrument, the pivot pin is located at the distal most node of the waveguide.

In another embodiment of the surgical instrument, the tube is actuatable and the clamp arm is cammed open and closed against the end effector through relative motion between the tube and the end effector.

In one embodiment, a surgical instrument comprises a waveguide comprising a proximal end and a distal end, wherein the proximal end is coupled to an ultrasonic transducer; an end effector coupled to the distal end of the waveguide, the end effector defining a pin hole; a rigid pin disposed within the pin hole; a clamp arm operatively connected to the outer tube; and a four-bar linkage; wherein the four-bar linkage is operatively coupled to the clamp arm and the rigid pin, wherein the four-bar linkage is actuatable via end effector translation to move the clamp arm to a clamped position.

In another embodiment of the surgical instrument, an outer tube is coupled to the four-bar linkage and the outer-tube actuates the four-bar linkage from a first position to a second position.

In one embodiment, an ultrasonic surgical instrument comprises a waveguide comprising a proximal end and a distal end, wherein the proximal end is coupled to an ultrasonic transducer; an end effector coupled to the distal end of the waveguide, wherein the end effector is partially coated with thermally and electrically insulative material such that the distal end of the end effector comprises one or more exposed sections.

In another embodiment of the ultrasonic surgical instrument end effector, the one or more exposed areas are symmetrical.

In another embodiment of the ultrasonic surgical instrument end effector, the one or more exposed areas are asymmetrical.

In another embodiment of the ultrasonic surgical instrument end effector, the one or more exposed sections are separated by one or more coated sections.

In one embodiment, an ultrasonic surgical instrument comprises a waveguide comprising a proximal end and a distal end, wherein the proximal end is coupled to an ultrasonic transducer; an end effector coupled to the distal end of the waveguide, and a clamp arm is operatively connected to the end effector, wherein the clamp arm is partially coated with thermally and electrically insulative material such that the distal end of the clamp arm comprises one or more exposed sections.

In another embodiment of the ultrasonic surgical instrument clamp arm, the one or more exposed areas are symmetrical.

In another embodiment of the ultrasonic surgical instrument clamp arm, the one or more exposed areas are asymmetrical.

In another embodiment of the ultrasonic surgical instrument clamp arm, the one or more exposed sections are separated by one or more coated sections.

In one embodiment, an ultrasonic surgical instrument comprises a waveguide comprising a proximal end and a distal end, wherein the proximal end is coupled to an ultrasonic transducer; an end effector coupled to the distal end of the waveguide, and a clamp arm is operatively connected to the end effector, wherein the end effector and the clamp arm are partially coated with thermally and electrically insulative material such that the distal end of the end effector and clamp arm comprise one or more exposed sections.

In another embodiment of the ultrasonic surgical instrument, the one or more exposed areas are symmetrical.

In another embodiment of the ultrasonic surgical instrument, the one or more exposed areas are asymmetrical.

In another embodiment of the ultrasonic surgical instrument, the one or more exposed sections are separated by one or more coated sections.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 4 illustrates one embodiment of an ultrasonic blade with protruding block-like grasping features formed on a grasping portion of the blade.

FIG. 5 is a side view of the ultrasonic blade shown in FIG. 4, according to one embodiment.

FIG. 6 illustrates one embodiment of an ultrasonic blade with protruding bump-like or spike-like grasping features formed on a grasping portion of the blade.

FIG. 7A is a side view of the ultrasonic blade shown in FIG. 6, according to one embodiment.

FIG. 7B shows bump-like protrusions, according to one embodiment.

FIG. 7C shows spike-like protrusions, according to one embodiment.

FIG. 8 illustrates one embodiment of an ultrasonic blade with cavity-like grasping features formed on a grasping portion of the blade.

FIG. 9A is a side view of the ultrasonic blade shown in FIG. 8 having cylindrical cavity-like grasping features partially formed into the grasping portion of the blade, according to one embodiment.

FIG. 9B is a side view of the ultrasonic blade shown in FIG. 8 having cylindrical cavity-like grasping features formed through the grasping portion of the blade, according to one embodiment.

FIG. 9C is a side view of the ultrasonic blade shown in FIG. 8 having conical cavity-like grasping features partially formed into the grasping portion of the blade, according to one embodiment.

FIG. 10 illustrates one embodiment of an ultrasonic blade with transverse bump-like grasping features formed on a grasping portion of the blade.

FIG. 11 is a side view of the ultrasonic blade shown in FIG. 10, according to one embodiment.

FIG. 16 is a side view illustrating one embodiment of an ultrasonic blade comprising tooth-like grasping features including horizontal trenches having repeated semicircular grooves formed on a grasping surface of the blade.

FIG. 17 is a top view of the ultrasonic blade shown in FIG. 16, according to one embodiment.

FIG. 18 is a top view illustrating one embodiment of an ultrasonic blade comprising grasping features including cavities formed on a grasping surface of the blade.

FIG. 74A illustrates the gate in a left-biased position such that the rotation knob can be rotated approximately 690 degrees clockwise until a contoured extrusion element on the rotation knob makes contact with the right wing of the gate so that the left wing of the gate prevents motion by reacting statically against the shroud, according to one embodiment.

FIG. 74B illustrates the rotation knob rotated back 360° until it knocks the right wing of the gate into a right-biased position, according to one embodiment.

FIG. 74C illustrates the rotation knob after it knocks the right wing of the gate into a right-biased position, according to one embodiment.

FIG. 76A illustrates the gate in a left-biased position such that the rotation knob comprising a tactile feedback element can be rotated approximately 690 degrees clockwise until a contoured extrusion element on the rotation knob makes contact with the right wing of the gate so that the left wing of the gate prevents motion by reacting statically against the shroud, according to one embodiment.

FIG. 76B illustrates the rotation knob comprising a tactile feedback element rotated back 360° until it knocks the right wing of the gate into a right-biased position, according to one embodiment.

FIG. 76C illustrates the rotation knob comprising a tactile feedback element after it knocks the right wing of the gate into a right-biased position, according to one embodiment.

FIGS. 84-93 illustrate various embodiments of ultrasonic blades partially coated with an electrically insulative material to provide thermal insulation at the tissue contact area to minimize adhesion of tissue to the blade, where the lighter shade regions of the blade represent the coated portions and the darker shaded regions of the blade represent exposed surfaces that enable RF current to flow from the exposed region of the blade, through the tissue, and the movable jaw member. It is conceivable that this feature may be employed on the blade, the clamp arm, or both.

Figure 94:
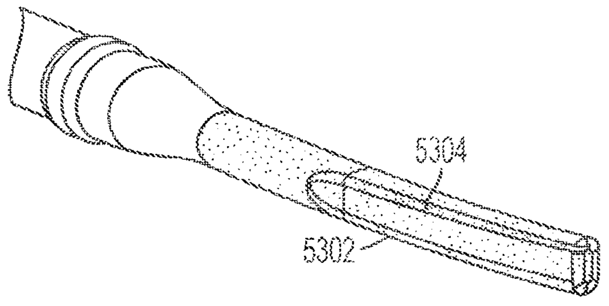
Figure 95:
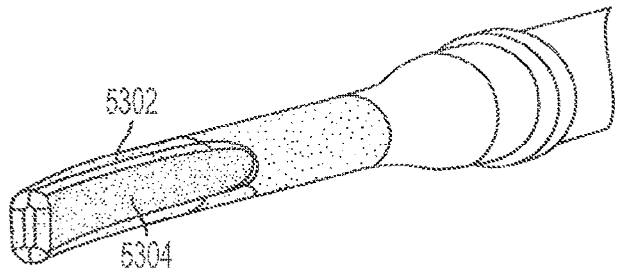

FIGS. 94-95 illustrate embodiments of two ultrasonic blades with non-symmetrical exposed surface, where the blades are coated with an electrically insulative material to provide thermal insulation at the tissue contact area to minimize adhesion of tissue to the blade, where the lighter shade regions of the blade represent the coated portions and the darker shaded regions of the blade represent exposed surfaces that enable RF current to flow from the exposed region of the blade, through the tissue, and the movable jaw member. It is conceivable that this feature may be employed on the blade, the clamp arm, or both.

Figure 96:
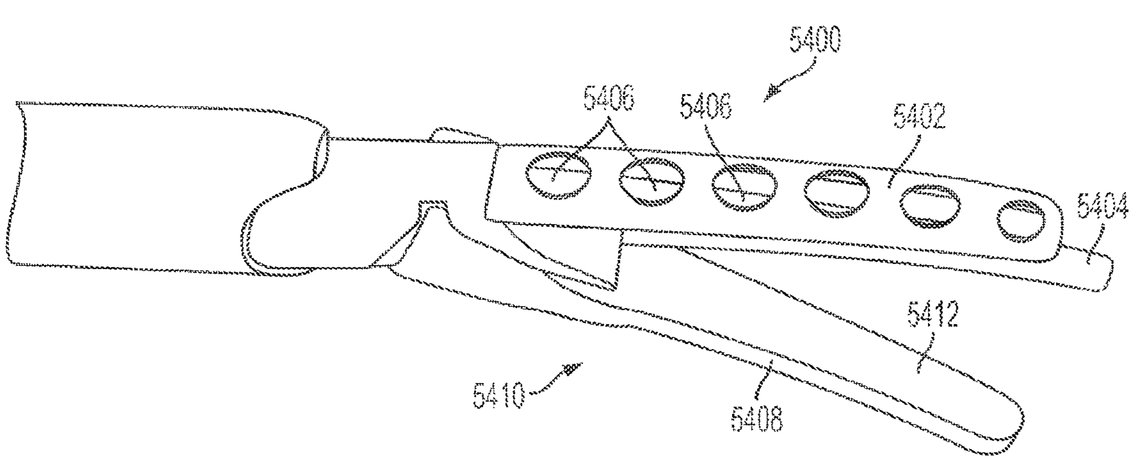

FIG. 96 is a perspective view of one embodiment of an ultrasonic end effector comprising a metal heat shield.

Figure 97:
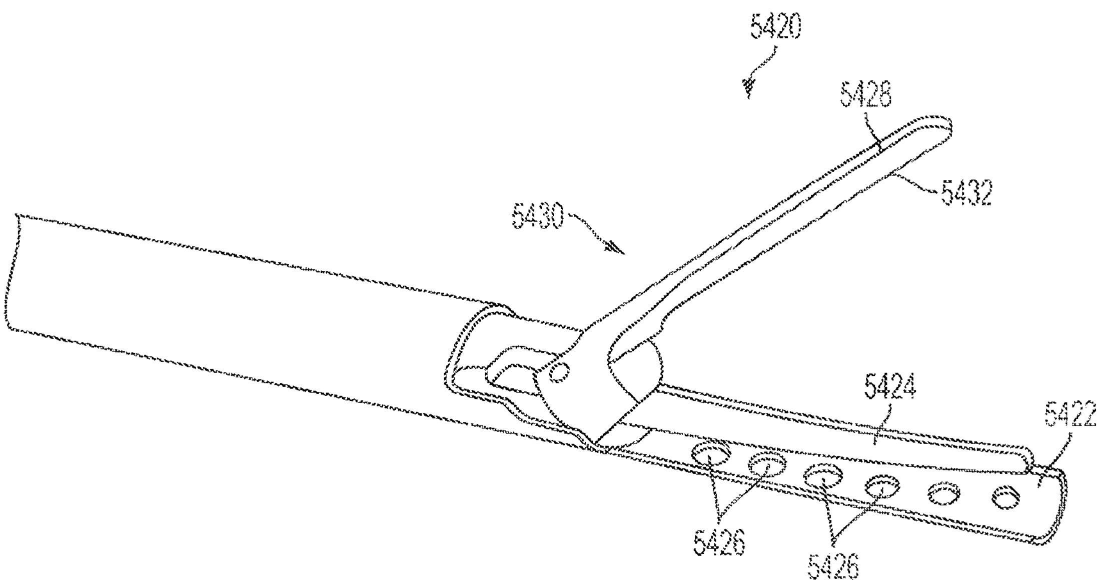

FIG. 97 is a perspective view of another embodiment of an ultrasonic end effector comprising a retractable metal heat shield.

Figure 98:
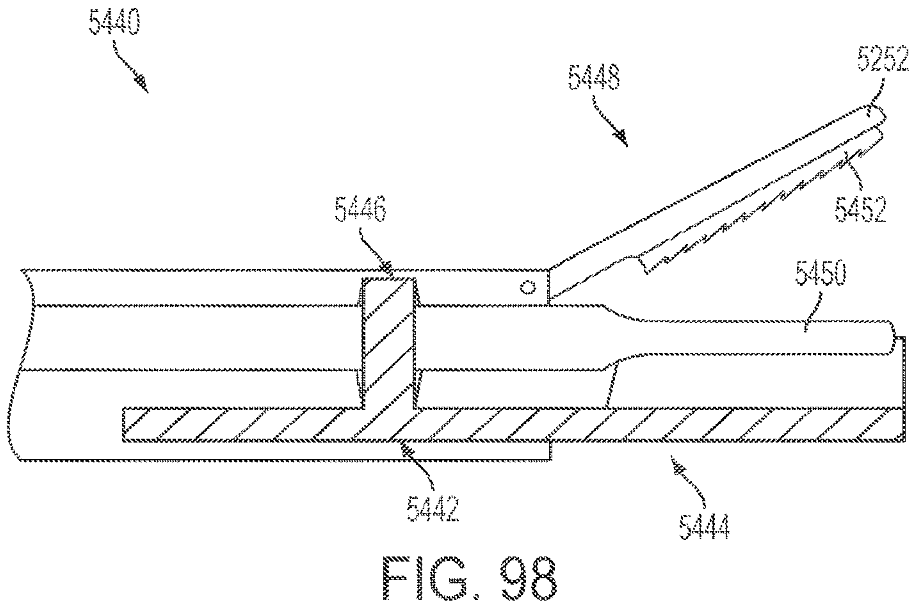

FIG. 98 is a side view of another embodiment of an ultrasonic end effector comprising a heat shield shown in cross-section.

Figure 99:
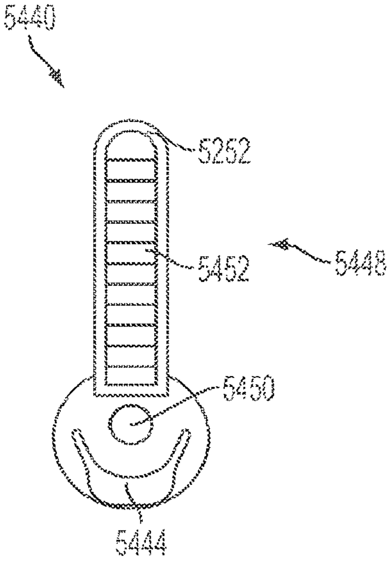

FIG. 99 is a front view of the ultrasonic end effector shown in FIG. 98, according to one embodiment.

FIG. 100 illustrates one embodiment of a clamp arm comprising a movable jaw member shown in a closed position and a dual purpose rotatable heat shield located below the ultrasonic blade.

FIG. 101 illustrates one embodiment of a movable jaw member shown in an open position and a dual purpose rotatable heat shield rotated such that it is interposed between the movable jaw member and the blade.

FIG. 102 illustrates an end view of one embodiment of a dual purpose rotatable heat shield rotated in a first position.

FIG. 103 illustrates an end view of one embodiment of the dual purpose rotatable heat shield rotated in a second position.

FIG. 104 is a top profile view of one embodiment of a heat shield showing a tapered portion of the shield.

Figure 105:
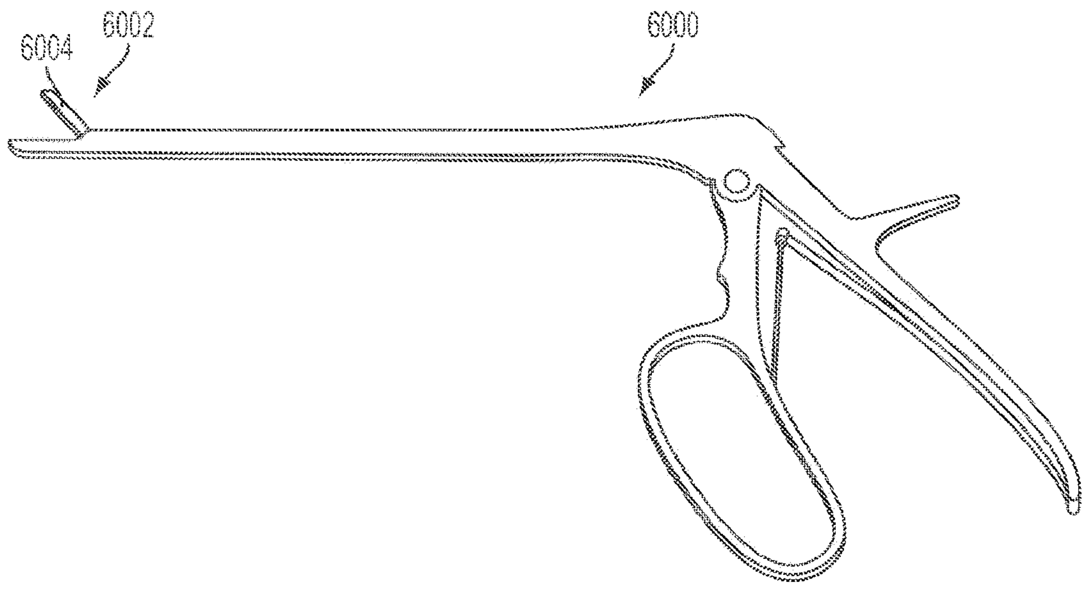

FIG. 105 illustrates a conventional rongeur surgical instrument.

Figure 106:
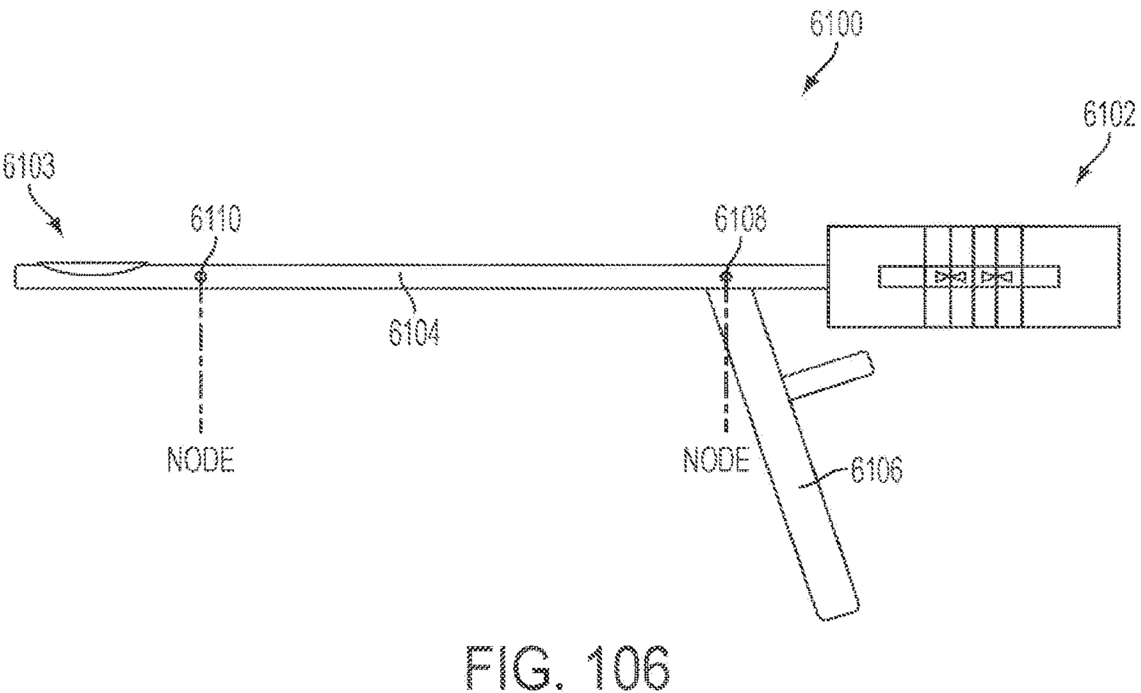

FIG. 106 illustrates one embodiment of an ultrasonic energy driven rongeur device.

Figure 107:
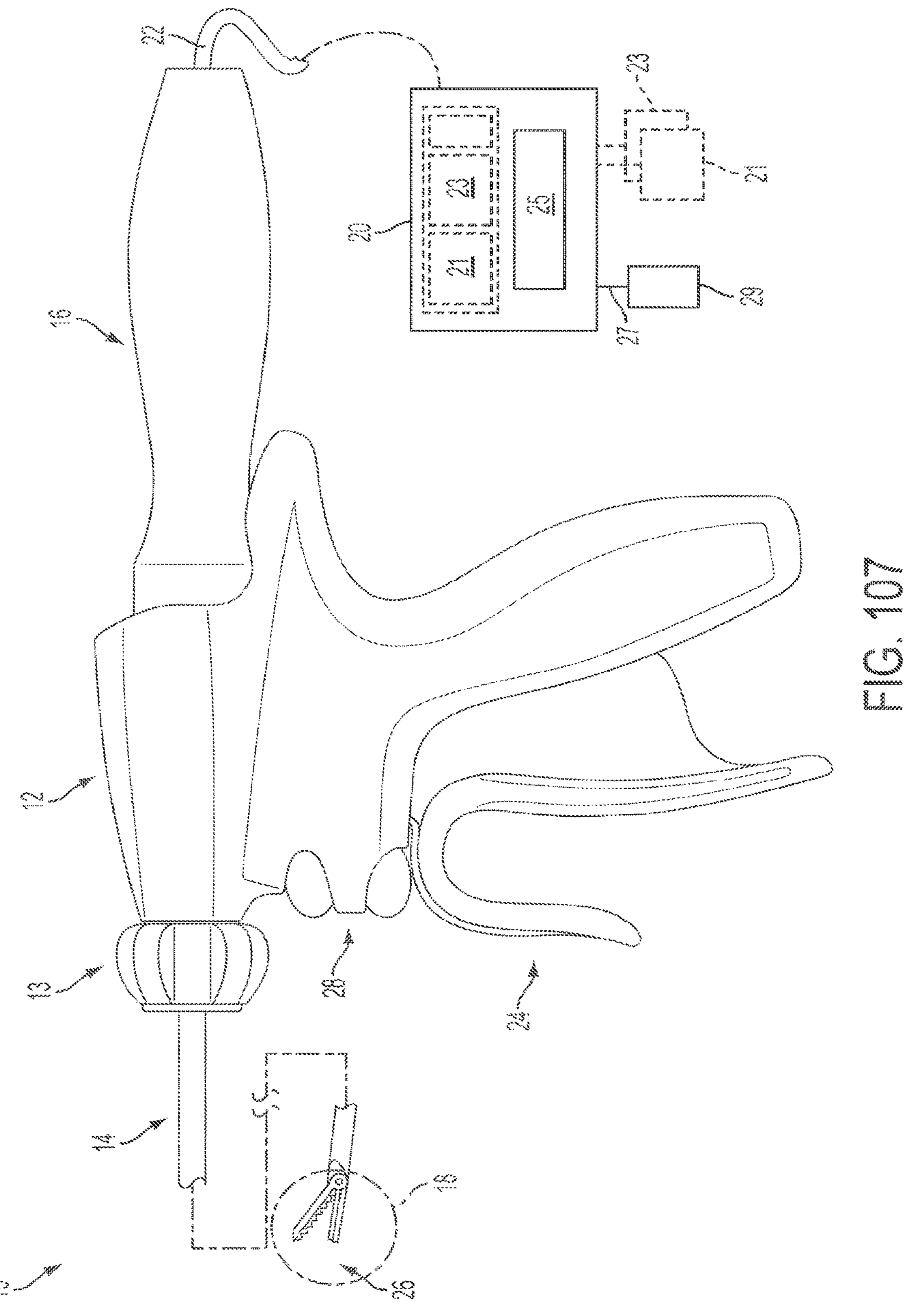

FIG. 107 illustrates one embodiment of a surgical system including a surgical instrument and an ultrasonic generator.

Figure 108:
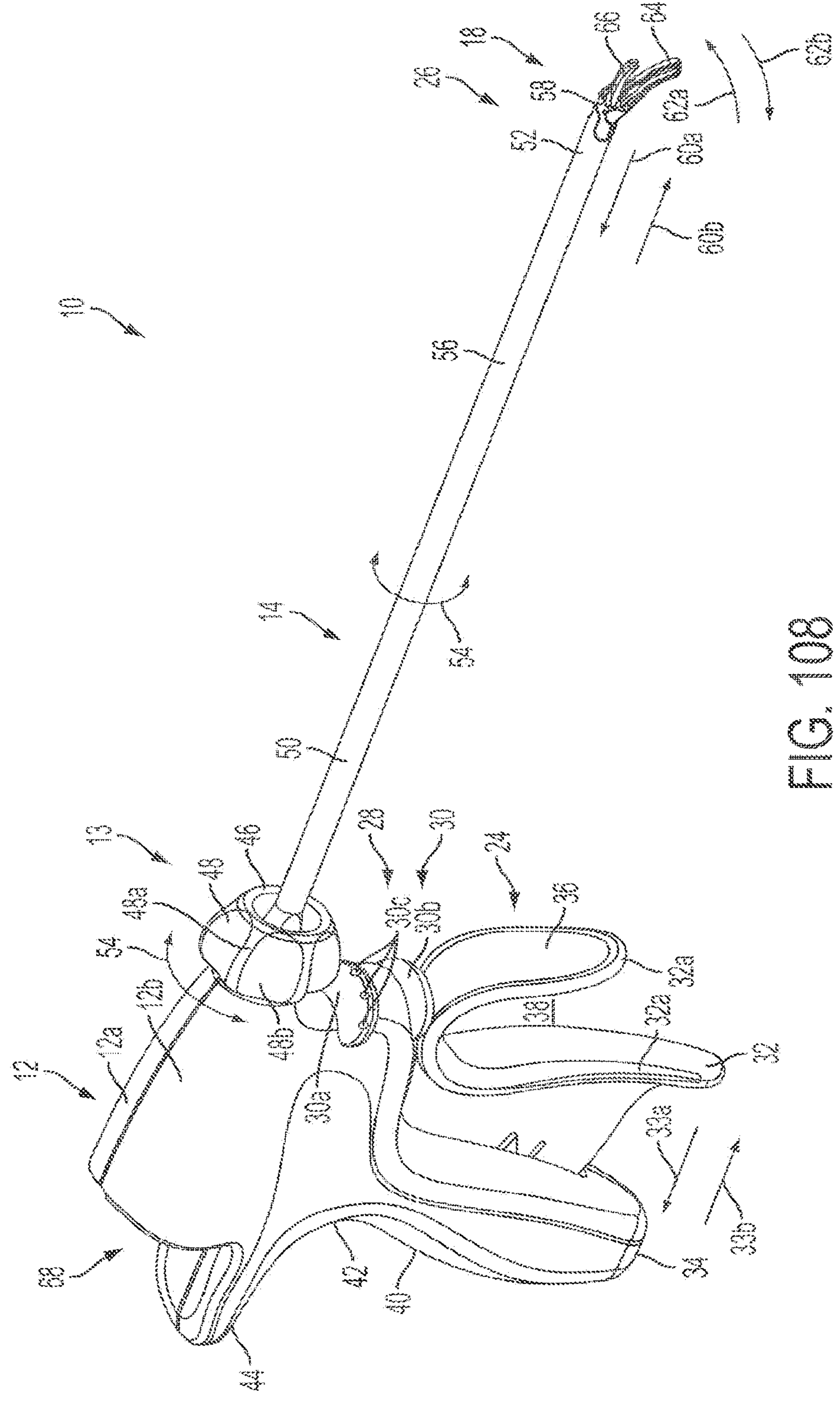

FIG. 108 illustrates one embodiment of the surgical instrument shown in FIG. 107.

Figure 109:
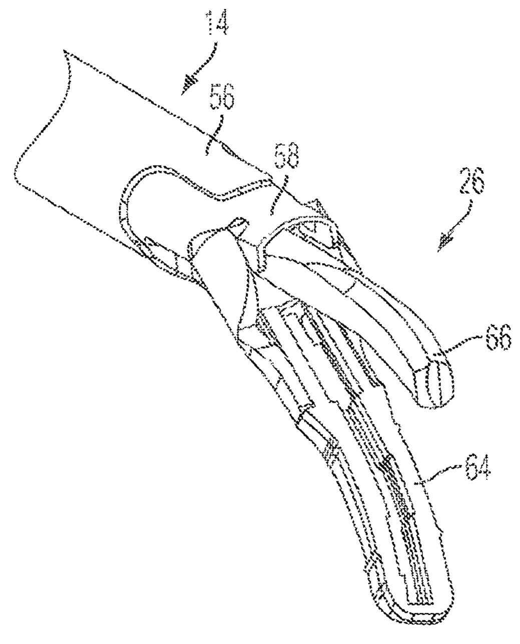

FIG. 109 illustrates one embodiment of an ultrasonic end effector.

Figure 110:
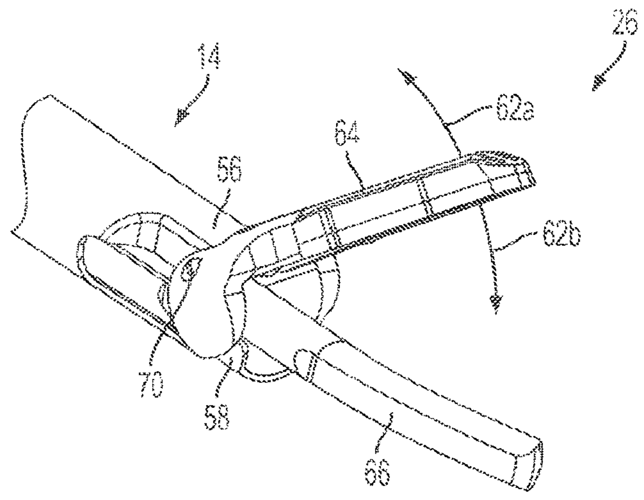

FIG. 110 illustrates another embodiment of an ultrasonic end effector.

Figure 111:
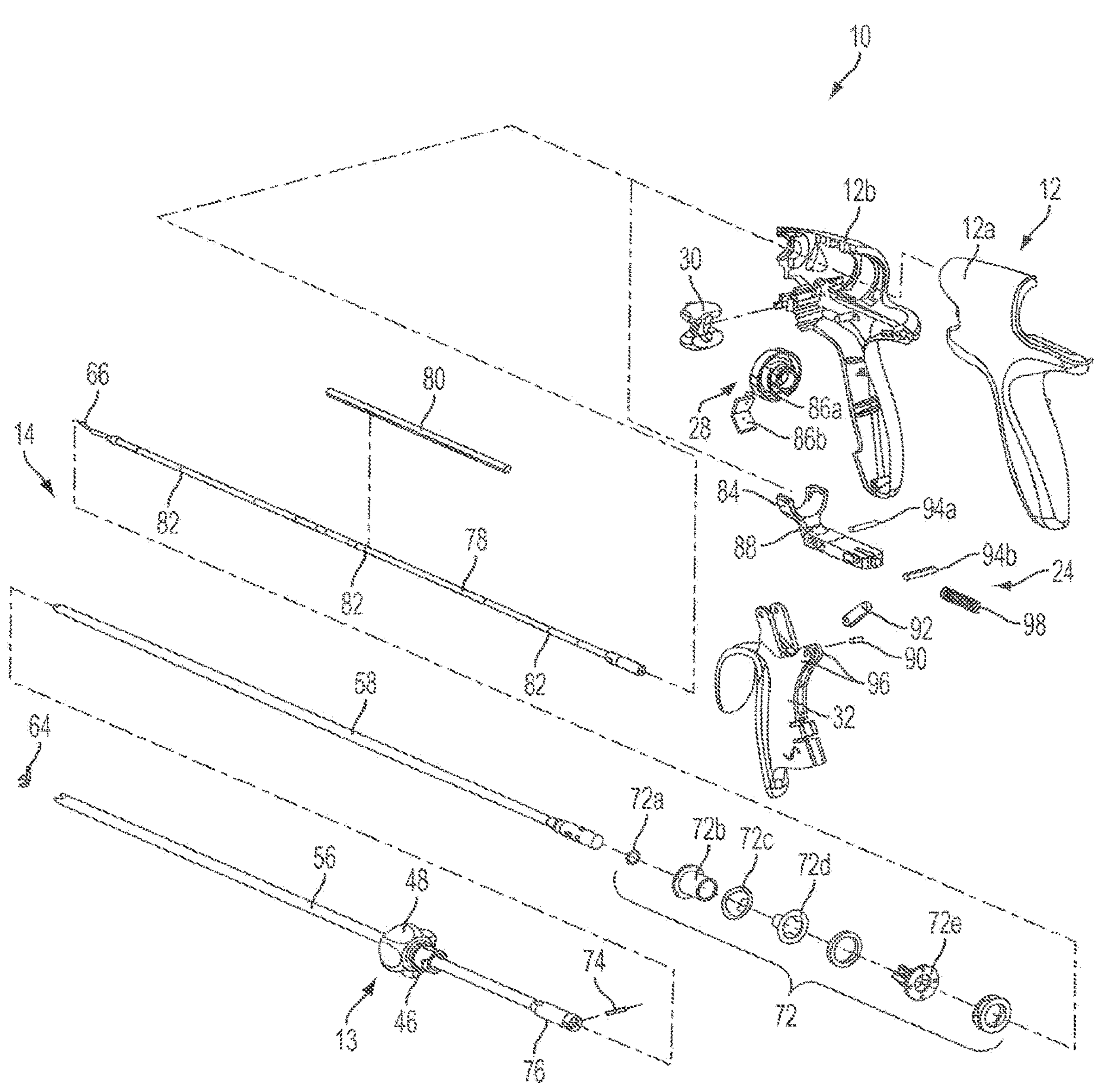

FIG. 111 illustrates an exploded view of one embodiment of the surgical instrument shown in FIG. 107.

Figure 112A:
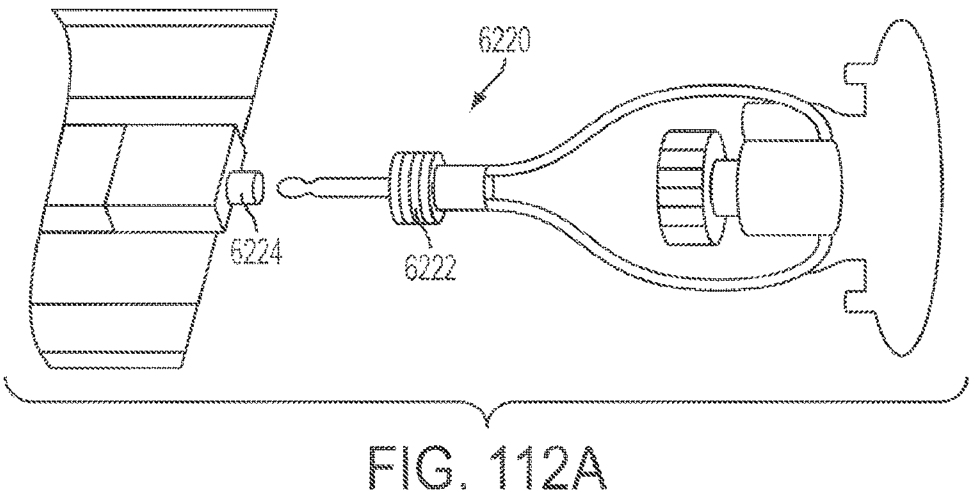
Figure 112B:
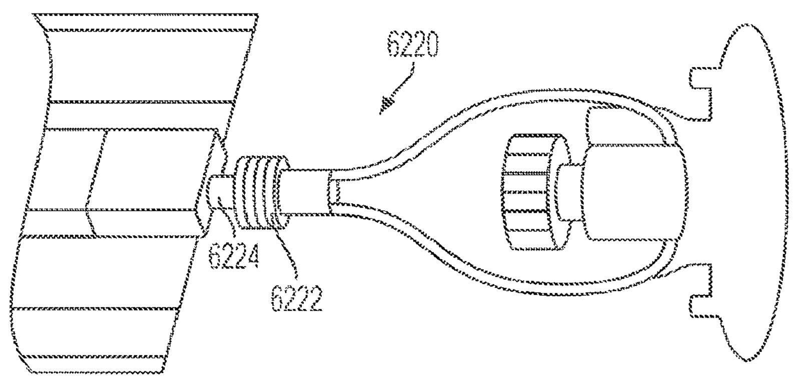
Figure 113A:
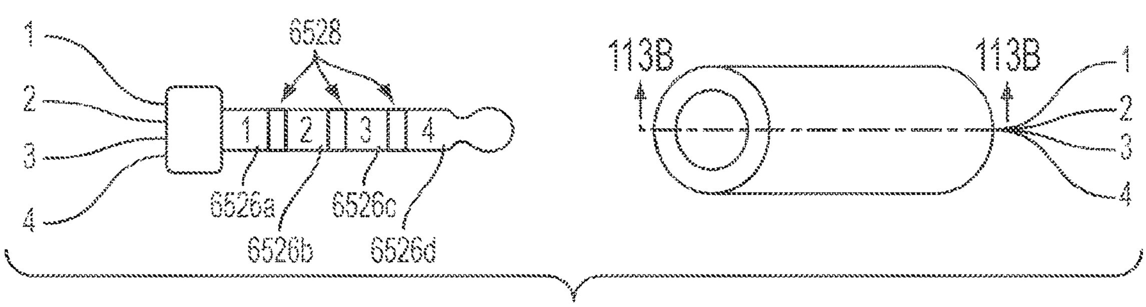
Figure 113B:
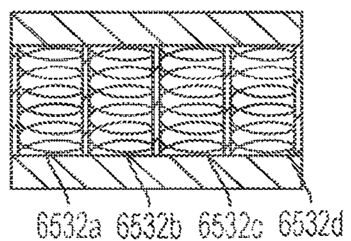
Figure 113C:
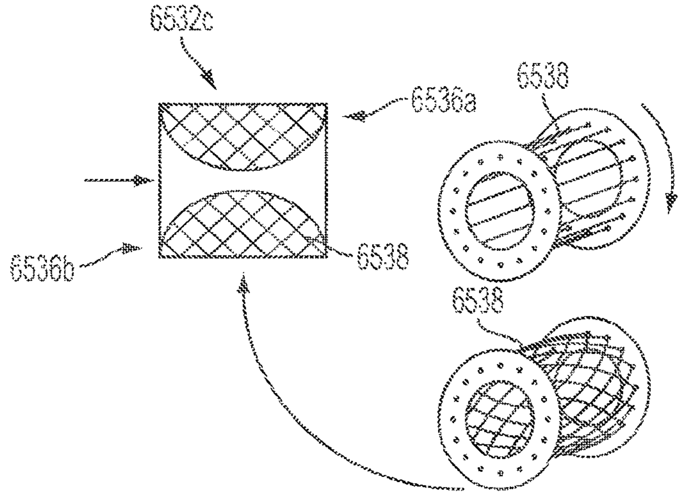

FIGS. 112A and 112B illustrate one embodiment of an unlimited rotation connection for an integrated transducer FIGS. 113A-113C illustrate one embodiment of an unlimited rotation connection for an integrated transducer.

Figure 114A:
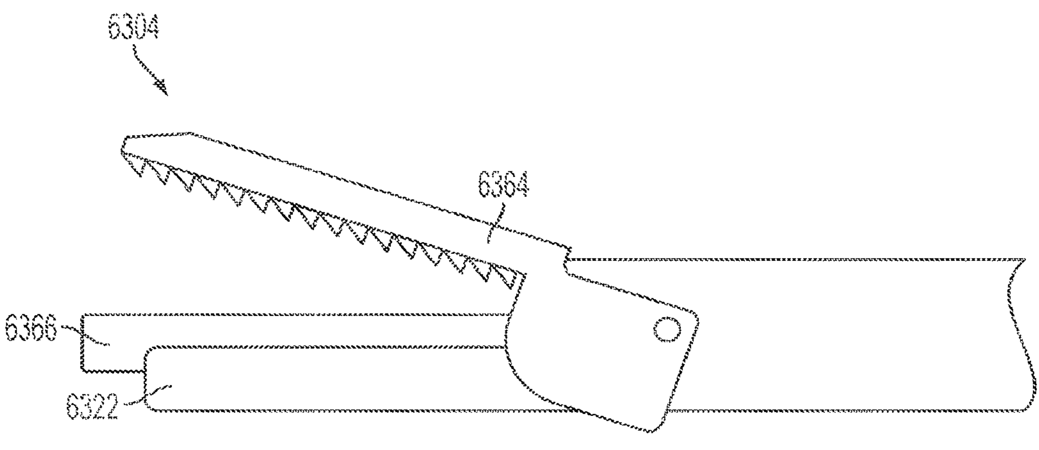
Figure 114B:
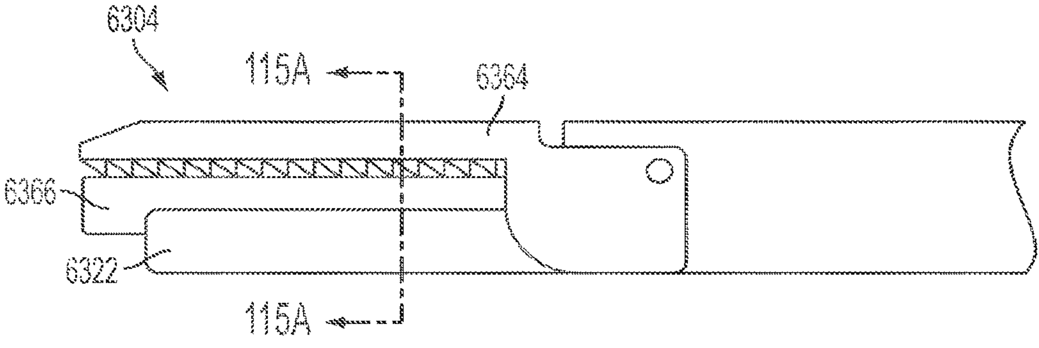

FIGS. 114A and 114B illustrate one embodiment of an integrated RF/ultrasonic surgical end effector.

FIGS. 115A-115I illustrate various electrode arrangements for the integrated RF/ultrasonic surgical end effector of FIGS. 114A and 114B.

Figure 116A:
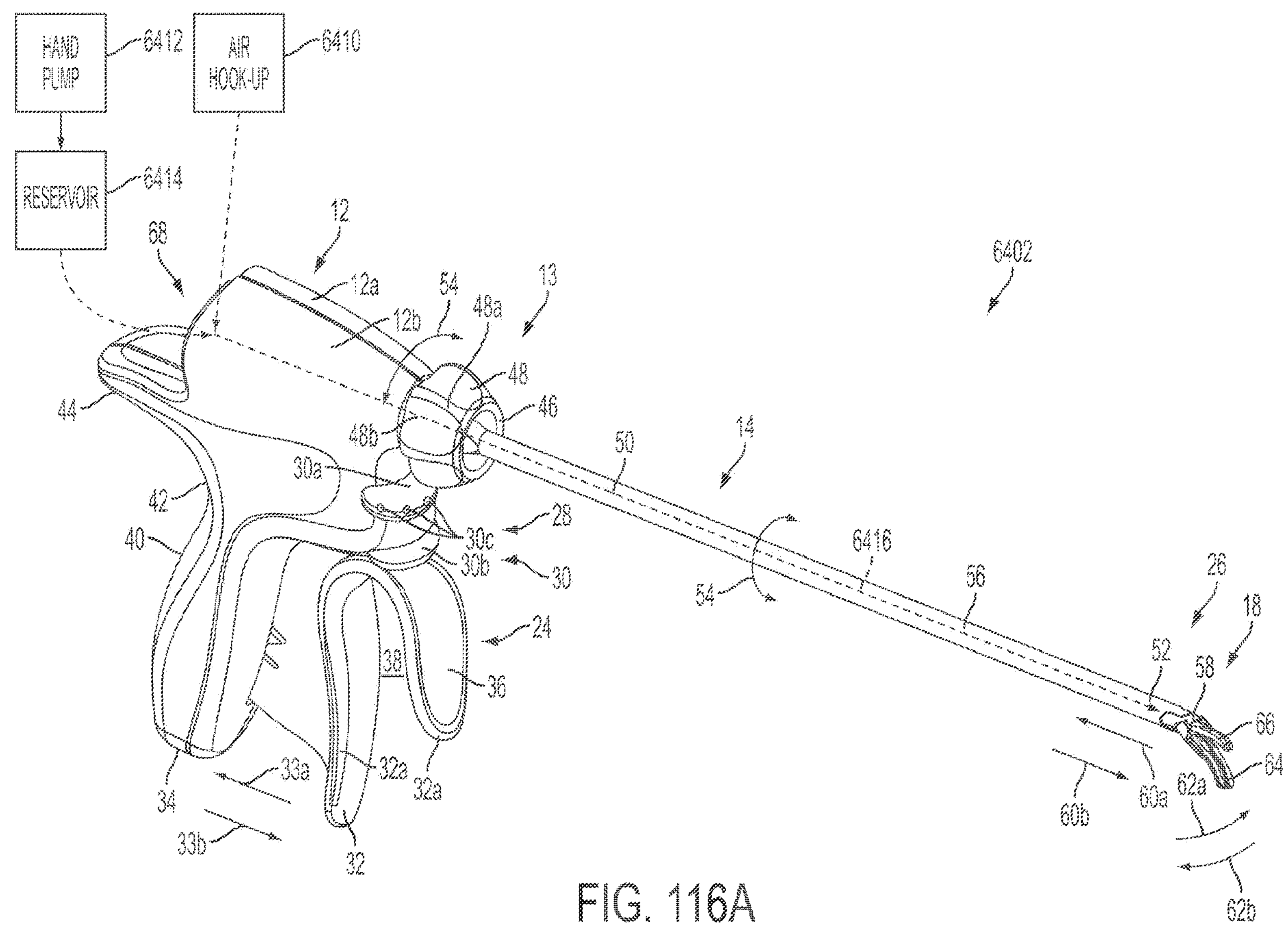

FIG. 116A illustrates one embodiment of an air cooled surgical instrument.

Figure 116B:
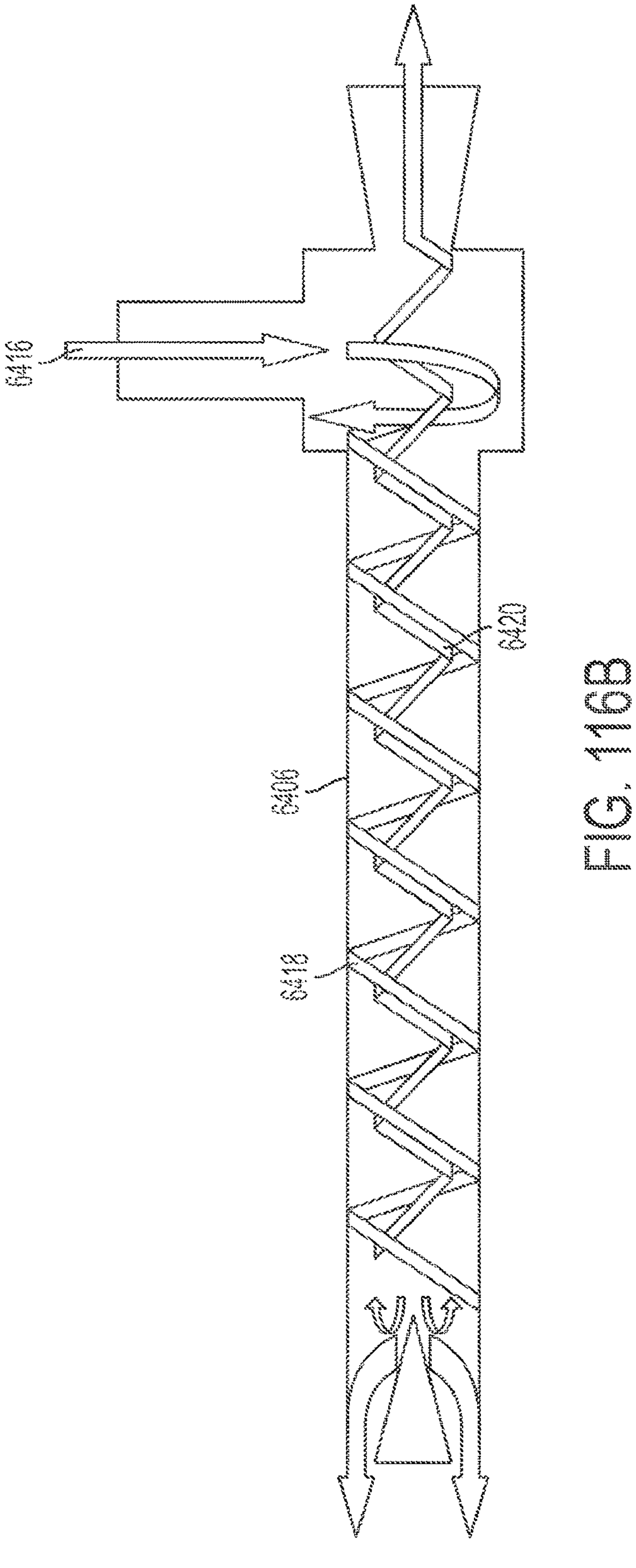

FIG. 116B illustrates one embodiment of a vortex tube.

Figure 117:
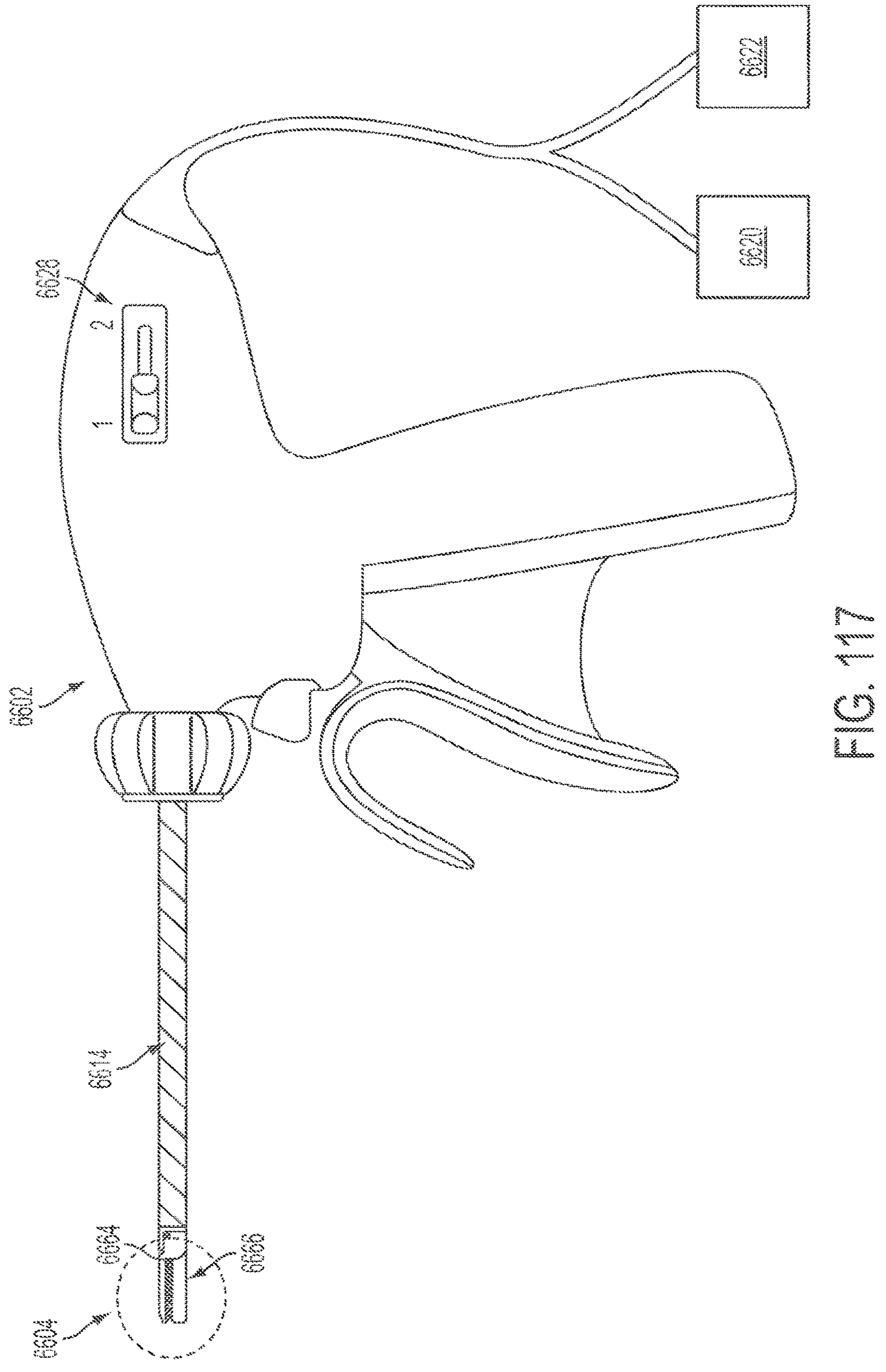

FIG. 117 illustrates one embodiment of an integrated RF/ultrasonic surgical instrument comprising a double pole double throw switch.

Figure 118:
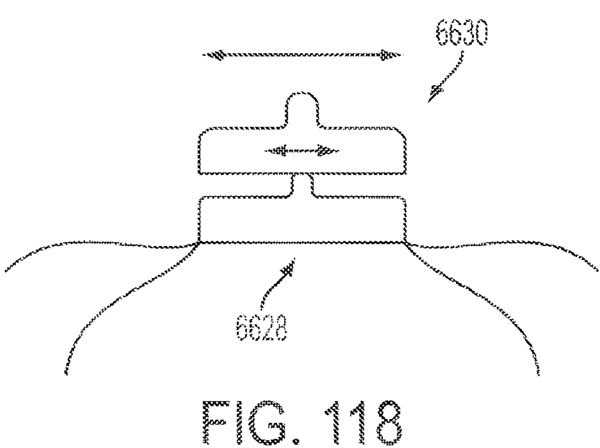

FIG. 118 illustrates one embodiment of a double pole double throw switch.

FIGS. 119A-119E illustrate various embodiments of combination RF/ultrasonic end effectors.

FIGS. 120A-120C illustrate various embodiments of bipolar combination RF/ultrasonic end effectors.

Figure 121A:
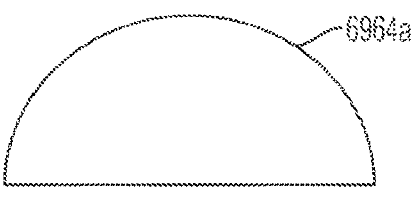
Figure 121B:
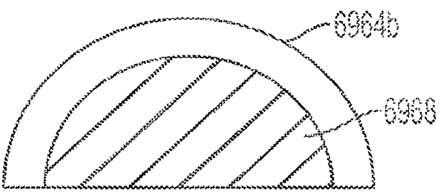
Figure 121C:
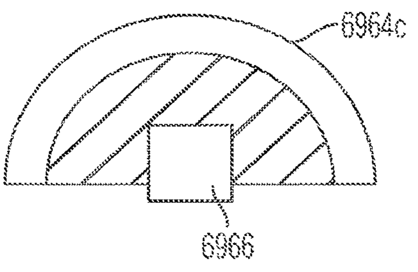

FIGS. 121A-121C illustrate various embodiments of monopolar combination RF/ultrasonic end effectors.

DESCRIPTION

Before explaining the various embodiments of the ultrasonic and electrical surgical devices in detail, it should be noted that the various embodiments disclosed herein are not limited in their application or use to the details of construction and arrangement of parts illustrated in the accompanying drawings and description. Rather, the disclosed embodiments are may be positioned or incorporated in other embodiments, variations and modifications thereof, and may be practiced or carried out in various ways. Accordingly, embodiments of the ultrasonic and electrical surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

In the following description, like reference characters designate like or corresponding parts throughout the several views. Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

In various embodiments, the present disclosure is related to various embodiments of ultrasonic blades comprising various grasping features. Conventional ultrasonic blades lack grasping features. Such grasping features may be desirable on a gripping surface of an ultrasonic blade to provide additional gripping and to prevent tissue milking during grasping and treatment, which in some cases may improve hemostasis. Tissue milking occurs when a tissue section slides, or milks, out of the jaws of a surgical device during treatment. The present disclosure provides various blade modification features to prevent tissue milking, as well as provide better grasping forces.

In various embodiments, the present disclosure is related to various embodiments of devices configured to prevent ingress of surgical matter, e.g., fluid and tissue, in the space between an ultrasonic blade and an inner or outer tube distal of the distal seal. Two main categories of embodiments are described. First, a pressure or energy source attached to the blade-tube subassembly prevents fluid or tissue ingress into the space between the blade and the inner tube. Second, a flexible membrane(s) attached to either the blade or the inner tube prevents fluid or tissue ingress.

In various embodiments, the present disclosure also is related to various embodiments of alternate closure mechanisms for ultrasonic devices. Present ultrasonic devices utilize a tube-in-tube (TnT) closure mechanism to enable closure of the clamp arm, referred to herein as a movable jaw member, against an active length of the ultrasonic blade. The present embodiments of alternate closure mechanisms for ultrasonic devices may yield several advantages. For example, there may be differences among the drag force of actuating the inner tube against the outer tube resulting in variation in device clamp force. Additionally, the pivot location of the clamp arm on the outer tube causes a sharp angular closure, and results in a non-uniform closure profile. Furthermore, present device mechanism may be sensitive to variation in components, as the stackup links the inner and outer tube at the location of the insulated pin, which currently resides near the proximal end of the tube assembly.

In various embodiments, the present disclosure also is related to various embodiments of shaft assembly/transducer rotation limiters to limit the rotation of the shaft and ultrasonic transducer.

In various embodiments, the present disclosure also is related to various embodiments of shaft/ultrasonic transducer rotation systems to provide unlimited continuous rotation of an ultrasonic device. In various embodiments, tactile feedback may be provided to the user before a hard stop is hit.

In various embodiments, the present disclosure also is related to various embodiments of an integrated RF/ultrasonic instrument electrically connected to provide RF spot coagulation energy for pre- or post-ultrasonic treatment of tissues with an ultrasonic/RF generator. The integrated ultrasonic instrument enables the touch up of diffuse bleeding (capillary bleeding, cut site oozing) or pre-treatment of tissue without the need for coupling pressure and improves the coupling pressure needed for ultrasonic instruments to couple the blade to tissue such that friction-based tissue effect is effective. The integrated ultrasonic instrument reduces (1) difficulty in applying enough pressure to generate haemostatic effect in loosely supported (i.e., un-clamped) tissue or (2) coupling pressure that generates too much tissue disruption that, in many cases, makes the diffuse bleeding worse. In one embodiment, a four-lead jack connector is mated with a slidable female mating plug to electrically isolate a secondary RF generator from the ultrasonic transducer when switching between RF energy and ultrasonic energy.

In various embodiments, the present disclosure is also directed to ultrasonic blades comprising heat shields. The heat shields may be fixed, translatable or rotatable. The heat shield also may be used to conduct RF energy to target tissue.

In various embodiments, the present disclosure also is related to coated ultrasonic/RF blades. Ultrasonic blades are coated with an electrically insulative material to provide thermal insulation at the tissue contact area to minimize adhesion of tissue to the blade. Conventional ultrasonic devices utilize one mode of treatment, which limits versatility. For example, conventional ultrasonic devices may be used for blood vessel sealing and transecting tissue. Bipolar or monopolar RF may offer added benefits such as a method for spot coagulation and pretreatment of tissue. Incorporating ultrasonic and RF may provide versatility and increase effectiveness. However, conventional ultrasonic devices utilize coatings to provide reduced friction and thermal insulation at the distal end of the blade. These coatings are electrically insulative, and therefore limit current flow thus decreasing RF effectiveness. Additionally, current density may influence effectiveness. In order to incorporate both modes into one device, a masking or selective coating removal process may be required. Creating an exposed area on the surface of the blade may provide a suitable path for current flow. It is conceivable that the same principles may be applied to the clamping member as well.

General Surgical Instrument Overview

Before launching into a description of various embodiments, the present disclosures turns to the description of FIGS. 107-111, which describes various embodiments of a surgical system in which various embodiments of the ultrasonic and electrical surgical devices described in connection with FIGS. 1-106 may be practiced. Accordingly, FIG. 107 is a right side view of one embodiment of an ultrasonic surgical instrument 10. In the illustrated embodiment, the ultrasonic surgical instrument 10 may be employed in various surgical procedures including laparoscopic, endoscopic or traditional open surgical procedures. In one example embodiment, the ultrasonic surgical instrument 10 comprises a handle assembly 12, an elongated shaft assembly 14, and an ultrasonic transducer 16. The handle assembly 12 comprises a trigger assembly 24, a distal rotation assembly 13, and an activation switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical instrument 10 may be employed in more traditional open surgical procedures and in other embodiments, may be configured for use in laparoscopic or endoscopic procedures.

For the purposes herein, the ultrasonic surgical instrument 10 is described in terms of an laparoscopic instrument; however, it is contemplated that an open and/or endoscopic version of the ultrasonic surgical instrument 10 also may include the same or similar operating components and features as described herein.

In various embodiments, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example embodiments, the generator 20 also comprises an electrosurgery/RF generator module 23 for driving an electrosurgical device (or an electrosurgical embodiment of the ultrasonic surgical instrument 10). In various embodiments, the generator 20 may be formed integrally within the handle assembly 12. In such implementations, a battery would be co-located within the handle assembly 12 to act as the energy source.

In some embodiments, the electrosurgery/RF generator module 23 may be configured to generate a therapeutic and/or a sub-therapeutic energy level. In the example embodiment illustrated in FIG. 107, the generator 20 includes a control system 25 integral with the generator 20, and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level or provide the therapeutic/sub-therapeutic electromagnetic/RF energy. The generator 20 drives or excites the acoustic assembly at any suitable resonant frequency of the acoustic assembly and/or drives the therapeutic/sub-therapeutic electromagnetic/RF energy.

In one embodiment, the electrosurgical/RF generator module 23 may be implemented as an electrosurgery unit (ESU) capable of supplying power sufficient to perform bipolar electrosurgery using RF energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization).

In one embodiment, the electrosurgical/RF generator module 23 may be configured to deliver a sub-therapeutic RF signal to implement a tissue impedance measurement module. In one embodiment, the electrosurgical/RF generator module 23 comprises a bipolar RF generator as described in more detail below. In one embodiment, the electrosurgical/RF generator module 12 may be configured to monitor electrical impedance Z, of tissue T and to control the characteristics of time and power level based on the tissue T by way of a return electrode on provided on a clamp member of the end effector assembly 26. Accordingly, the electrosurgical/RF generator module 23 may be configured for sub-therapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, titled “Electrosurgical Generator for Ultrasonic Surgical Instruments,” the disclosure of which is herein incorporated by reference in its entirety.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting Blade Breakage Using Rate and/or Impedance Information); U.S. Pat. No. 6,662,127 (Method for Detecting Presence of a Blade in an Ultrasonic System); U.S. Pat. No. 6,679,899 (Method for Detecting Transverse Vibrations in an Ultrasonic Hand Piece); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

It will be appreciated that in various embodiments, the generator 20 may be configured to operate in several modes. In one mode, the generator 20 may be configured such that the ultrasonic generator module 21 and the electrosurgical/RF generator module 23 may be operated independently. Alternatively, the ultrasonic generator module 21 may be configured to selectively apply either ultrasonic energy or either therapeutic sub-therapeutic RF energy to the end effector.

For example, the ultrasonic generator module 21 may be activated to apply ultrasonic energy to the end effector assembly 26 and subsequently, either therapeutic sub-therapeutic RF energy may be applied to the end effector assembly 26 by the electrosurgical/RF generator module 23. As previously discussed, the subtherapeutic electrosurgical/RF energy may be applied to tissue clamped between clamp elements of the end effector assembly 26 to measure tissue impedance to control the activation, or modify the activation, of the ultrasonic generator module 21. Tissue impedance feedback from the application of the subtherapeutic energy also may be employed to activate a therapeutic level of the electrosurgical/RF generator module 23 to seal the tissue (e.g., vessel) clamped between clamp elements of the end effector assembly 26.

In another embodiment, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while the ultrasonic blade of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade portion of the end effector assembly 26 is employed for cutting the damaged tissue while the electrosurgical/RF energy is applied to electrode portions of the end effector clamp assembly 26 for sealing the tissue (or vessel). Alternatively, the ultrasonic and the electrosurgical/RF energy can be employed sequentially with a single activation to achieve a desired tissue effect.

When the generator 20 is activated via the triggering mechanism, in one embodiment electrical energy is continuously applied by the generator 20 to a transducer stack or assembly of the acoustic assembly. In another embodiment, electrical energy is intermittently applied (e.g., pulsed) by the generator 20. A phase-locked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a preselected constant level in order to achieve substantially constant excursion at the end effector 18 of the acoustic assembly. In yet another embodiment, a third feedback loop in the control system 25 monitors impedance between electrodes located in the end effector assembly 26. Although FIGS. 107-111 show a manually operated ultrasonic surgical instrument, it will be appreciated that ultrasonic surgical instruments may also be used in robotic applications, for example, as described herein, as well as combinations of manual and robotic applications.

In ultrasonic operation mode, the electrical signal supplied to the acoustic assembly may cause the distal end of the end effector 18 to vibrate longitudinally in the range of, for example, approximately 20 kHz to 250 kHz. According to various embodiments, the blade 22 may vibrate in the range of about 40 kHz to 56 kHz, for example, at about 50.0 kHz. In other embodiments, the blade 22 may vibrate at other frequencies including, for example, about 31 kHz or about 80 kHz. The excursion of the vibrations at the blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

FIG. 108 is a left perspective view of one example embodiment of the ultrasonic surgical instrument 10 showing the handle assembly 12, the distal rotation assembly 13, the elongated shaft assembly 14, and the end effector assembly 26. In the illustrated embodiment the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated shaft assembly 14 is received within the handle assembly 12 and the distal rotation assembly 13. More details relating to the connections between the elongated shaft assembly 14, the handle assembly 12, and the distal rotation assembly 13 are provided in the description of FIG. 98.

In the illustrated embodiment, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33A toward the fixed handle 34 when the user applies a squeezing force against the trigger 32. A spring element 98 (FIG. 111) causes the trigger 32 to pivotally move in direction 33B when the user releases the squeezing force against the trigger 32.

In one example embodiment, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion **32*a* molded over the trigger 32 substrate. The overmolded resilient portion 32*a* is formed to provide a more comfortable contact surface for control of the trigger 32 in outward direction 33B. In one example embodiment, the overmolded resilient portion 32*a* may be provided over a portion of the elongated trigger hook 36. The proximal surface of the elongated trigger hook 32 remains uncoated or coated with a non-resilient substrate to enable the user to easily slide their fingers in and out of the aperture 38**. In another embodiment, the geometry of the trigger forms a fully closed loop which defines an aperture suitably sized to receive one or multiple fingers of the user therethrough. The fully closed loop trigger also may comprise a resilient portion molded over the trigger substrate.

In one example embodiment, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example embodiment, the switch assembly 28 may comprise a toggle switch 30. The toggle switch 30 may be implemented as a single component with a central pivot 304 located within inside the handle assembly 12 to eliminate the possibility of simultaneous activation. In one example embodiment, the toggle switch 30 comprises a first projecting knob **30*a* and a second projecting knob 30*b* to set the power setting of the ultrasonic transducer 16 between a minimum power level (e.g., MIN) and a maximum power level (e.g., MAX). In another embodiment, the rocker switch may pivot between a standard setting and a special setting. The special setting provides one or more special programs to be implemented by the device. The toggle switch 30 rotates about the central pivot as the first projecting knob 30*a* and the second projecting knob 30*b* are actuated. The one or more projecting knobs 30*a*, 30*b* are coupled to one or more arms that move through a small arc and cause electrical contacts to close or open an electric circuit to electrically energize or de-energize the ultrasonic transducer 16 in accordance with the activation of the first or second projecting knobs 30*a*, 30*b*. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30** is activated.

In one example embodiment, the first and second projecting knobs 30*a*, 30*b* are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30*a*, 30*b* may be configured to wrap around the side of the handle assembly 12 to some extent to be more easily accessible by variable finger lengths and to allow greater freedom of access to activation in awkward positions or for shorter fingers.

In the illustrated embodiment, the first projecting knob 30*a* comprises a plurality of tactile elements 30*c*, e.g., textured projections or "bumps" in the illustrated embodiment, to allow the user to differentiate the first projecting knob 30*a* from the second projecting knob 30*b*. It will be appreciated by those skilled in the art that several ergonomic features may be incorporated into the handle assembly 12. Such ergonomic features are described in U.S. Pat. No. 8,623,027 entitled "Ergonomic Surgical Instruments" which is incorporated by reference herein in its entirety.

In one example embodiment, the toggle switch 30 may be operated by the hand of the user. The user may easily access the first and second projecting knobs 30*a*, 30*b* at any point while also avoiding inadvertent or unintentional activation at any time. The toggle switch 30 may readily operated with a finger to control the power to the ultrasonic assembly 16 and/or to the ultrasonic assembly 16. For example, the index finger may be employed to activate the first contact portion 30*a* to turn on the ultrasonic assembly 16 to a maximum (MAX) power level. The index finger may be employed to activate the second contact portion 30*b* to turn on the ultrasonic assembly 16 to a minimum (MIN) power level. In another embodiment, the rocker switch may pivot the instrument 10 between a standard setting and a special setting. The special setting provides one or more special programs to be implemented by the instrument 10. The toggle switch 30 may be operated without the user having to look at the first or second projecting knob 30*a*, 30*b*. For example, the first projecting knob 30*a* or the second projecting knob 30*b* may comprise a texture or projections to tactilely differentiate between the first and second projecting knobs 30*a*, 30*b* without looking.

In other embodiments, the trigger 32 and/or the toggle switch 30 may be employed to actuate the electrosurgical/RF generator module 23 individually or in combination with activation of the ultrasonic generator module 21.

In one example embodiment, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46*a* that is exposed at the distal end. The end cap portion 46*a* of the hub 46 may contact the surface of a trocar during laparoscopic procedures. The hub 46 may be formed of a hard durable plastic such as polycarbonate to alleviate any friction that may occur between the end cap portion 46*a* and the trocar. The rotation knob 48 may comprise "scallops" or flutes formed of raised ribs 48*a* and concave portions 48*b* located between the ribs 48*a* to provide a more precise rotational grip. In one example embodiment, the rotation knob 48 may comprise a plurality of flutes (e.g., three or more flutes). In other embodiments, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example embodiment, the handle assembly 12 is formed from two (2) housing portions or shrouds comprising a first portion 12*a* and a second portion 12*b*. From the perspective of a user viewing the handle assembly 12 from the distal end towards the proximal end, the first portion 12*a* is considered the right portion and the second portion 12*b* is considered the left portion. Each of the first and second portions 12*a*, 12*b* includes a plurality of interfaces 69 (FIG. 111) dimensioned to mechanically align and engage each another to form the handle assembly 12 and enclosing the internal working components thereof. The fixed handle 34, which is integrally associated with the handle assembly 12, takes shape upon the assembly of the first and second portions 12*a* and 12*b* of the handle assembly 12. A plurality of additional interfaces (not shown) may be disposed at various points around the periphery of the first and second portions 12*a* and 12*b* of the handle assembly 12 for ultrasonic welding purposes, e.g., energy direction/deflection points. The first and second portions 12*a* and 12*b* (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example embodiment, the elongated shaft assembly 14 comprises a proximal end 50 adapted to mechanically engage the handle assembly 12 and the distal rotation assembly 13; and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated embodiment, the distal end of the tubular reciprocating tubular actuating member 58 is mechanically engaged to a clamp arm assembly 64, which is pivotable about a pivot point 70, to open and close the clamp arm assembly 64 in response to the actuation and/or release of the trigger 32. For example, in the illustrated embodiment, the clamp arm assembly 64 is movable in direction 62A from an open position to a closed position about a pivot point 70 when the trigger 32 is squeezed in direction 33A. The clamp arm assembly 64 is movable in direction 62B from a closed position to an open position about the pivot point 70 when the trigger 32 is released or outwardly contacted in direction 33B.

In one example embodiment, the end effector assembly 26 is attached at the distal end 52 of the elongated shaft assembly 14 and includes a clamp arm assembly 64 and a blade 66. The jaws of the clamping mechanism of the end effector assembly 26 are formed by clamp arm assembly 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33A moves the clamp arm assembly 64 in direction 62A from an open position, wherein the clamp arm assembly 64 and the blade 66 are disposed in a spaced relation relative to one another, to a clamped or closed position, wherein the clamp arm assembly 64 and the blade 66 cooperate to grasp tissue therebetween. The clamp arm assembly 64 may comprise a clamp pad 69 to engage tissue between the blade 66 and the clamp arm 64. Releasing the trigger 32 in direction 33B moves the clamp arm assembly 64 in direction 62B from a closed relationship, to an open position, wherein the clamp arm assembly 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

In one example embodiment, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33B to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 36 to activate the end effector assembly 26. The shorter span and rotation travel creates a more comfortable grip when closing or squeezing the trigger 32 in direction 33A or when opening the trigger 32 in the outward opening motion in direction 33B lessening the need to extend the fingers further outward. This substantially lessens hand fatigue and strain associated with the outward opening motion of the trigger 32 in direction 33B. The outward opening motion of the trigger may be spring-assisted by spring element 98 (FIG. 111) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user the may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

FIGS. 109-110 illustrate the connection of the elongated shaft assembly 14 relative to the end effector assembly 26. As previously described, in the illustrated embodiment, the end effector assembly 26 comprises a clamp arm assembly 64 and a blade 66 to form the jaws of the clamping mechanism. The blade 66 may be an ultrasonically actuatable blade acoustically coupled to the ultrasonic transducer 16. The trigger 32 is mechanically connected to a drive assembly. Together, the trigger 32 and the drive assembly mechanically cooperate to move the clamp arm assembly 64 to an open position in direction 62A wherein the clamp arm assembly 64 and the blade 66 are disposed in spaced relation relative to one another, to a clamped or closed position in direction 62B wherein the clamp arm assembly 64 and the blade 66 cooperate to grasp tissue therebetween. The clamp arm assembly 64 may comprise a clamp pad 69 to engage tissue between the blade 66 and the clamp arm 64. The distal end of the tubular reciprocating tubular actuating member 58 is mechanically engaged to the end effector assembly 26. In the illustrated embodiment, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated embodiment, the clamp arm assembly 64 is movable from an open position to a closed position in direction 62B about a pivot point 70 when the trigger 32 is squeezed in direction 33A. The clamp arm assembly 64 is movable from a closed position to an open position in direction 62A about the pivot point 70 when the trigger 32 is released or outwardly contacted in direction 33B.

As previously discussed, the clamp arm assembly 64 may comprise electrodes electrically coupled to the electrosurgical/RF generator module 23 to receive therapeutic and/or sub-therapeutic energy, where the electrosurgical/RF energy may be applied to the electrodes either simultaneously or non-simultaneously with the ultrasonic energy being applied to the blade 66. Such energy activations may be applied in any suitable combinations to achieve a desired tissue effect in cooperation with an algorithm or other control logic.

FIG. 111 is an exploded view of the ultrasonic surgical instrument 10 shown in FIG. 108. In the illustrated embodiment, the exploded view shows the internal elements of the handle assembly 12, the handle assembly 12, the distal rotation assembly 13, the switch assembly 28, and the elongated shaft assembly 14. In the illustrated embodiment, the first and second portions 12*a*, 12*b* mate to form the handle assembly 12. The first and second portions 12*a*, 12*b* each comprises a plurality of interfaces 69 dimensioned to mechanically align and engage one another to form the handle assembly 12 and enclose the internal working components of the ultrasonic surgical instrument 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an O-ring 72*a*, a tube collar cap 72*b*, a distal washer 72*c*, a proximal washer 72*d*, and a thread tube collar 72*e*. The reciprocating tubular actuating member 58 is located within a reciprocating yoke 84, which is retained between the first and second portions 12*a*, 12*b* of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical instrument 10. In one example embodiment, a four-link design provides mechanical advantage in a relatively short rotation span, for example.

In one example embodiment, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16 as discussed in more detail below. The ultrasonic transmission waveguide 78 is isolated from the other elements of the elongated shaft assembly 14 by a protective sheath 80 and a plurality of isolation elements 82, such as silicone rings. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86*a*, 86*b* to electrically energize the ultrasonic transducer 16 in accordance with the activation of the first or second projecting knobs 30*a*, 30*b*.

In one example embodiment, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 24 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 enable the assembly to be torqued to a required level. In one example embodiment, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example embodiment, the distal end of the ultrasonic transmission waveguide 78 may be coupled to the proximal end of the blade 66 by an internal threaded connection, preferably at or near an antinode. It is contemplated that the blade 66 may be attached to the ultrasonic transmission waveguide 78 by any suitable means, such as a welded joint or the like. Although the blade 66 may be detachable from the ultrasonic transmission waveguide 78, it is also contemplated that the single element end effector (e.g., the blade 66) and the ultrasonic transmission waveguide 78 may be formed as a single unitary piece.

In one example embodiment, the trigger 32 is coupled to a linkage mechanism to translate the rotational motion of the trigger 32 in directions 33A and 33B to the linear motion of the reciprocating tubular actuating member 58 in corresponding directions 60A and 60B. The trigger 32 comprises a first set of flanges 98 with openings formed therein to receive a first yoke pin 92*a*. The first yoke pin 92*a* is also located through a set of openings formed at the distal end of the yoke 84. The trigger 32 also comprises a second set of flanges 96 to receive a first end 92*a* of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12*a*, 12*b* of the handle assembly 12 to form a trigger pivot point for the trigger 32. A second end 92*b* of the link 92 is received in a slot 384 formed in a proximal end of the yoke 84 and is retained therein by a second yoke pin 94*b*. As the trigger 32 is pivotally rotated about the pivot point 190 formed by the trigger pin 90, the yoke translates horizontally along longitudinal axis "T" in a direction indicated by arrows 60A, 60B.

Ultrasonic Blades with Various Grasping Features

FIGS. 1-11 illustrates various embodiments of ultrasonic blades comprising grasping features. Such grasping features may be included on a gripping surface of an ultrasonic blade to provide additional gripping and prevent tissue milking during grasping and treatment, which in some cases may improve hemostasis. Tissue milking occurs when a tissue section slides, or milks, out of the jaws of a surgical device during treatment. Blade modification features discussed below can prevent tissue milking, as well as provide better grasping forces.

A minimum grasping force for an ultrasonic clamp arm in a medical forceps having a movable jaw member is about 2.25 lb-f when clamped on a dry chamois while the device is inactive. During activation, however, the tissue may milk out of the jaws either proximally or distally. The blade 100 comprising the tooth-like grasping features 102 for an ultrasonic shears device can help prevent tissue milking as well as provide better grasping forces.

Grasping features may take the form of several shapes as described in connection with FIGS. 1-11, for example. The grasping features could be located only on a portion of the blade, such as, for example, the distal tip, the center of the blade, the proximal section, or any portion of the blade. In another embodiment, the grasping features may be located along the entire length or a portion of the blade. In some embodiments, the features illustrated and described with respect to FIGS. 1-11 could be located longitudinally on a portion of the blade, such as, for example, configured along a center line of the blade, the left side of the blade, the right side of the blade, or both the right and left side of the blade. In another embodiment, the grasping features may be configured along the entire width of the blade. Grasping features may include, for example, teeth machined into the blade, teeth protruding from the surface of the blade, protruding blocks, protruding bumps or spikes, holes formed in the blade, or protruding elongated bumps. These and other blade grasping features are described hereinbelow in connection with FIGS. 1-11.

Figure 1:
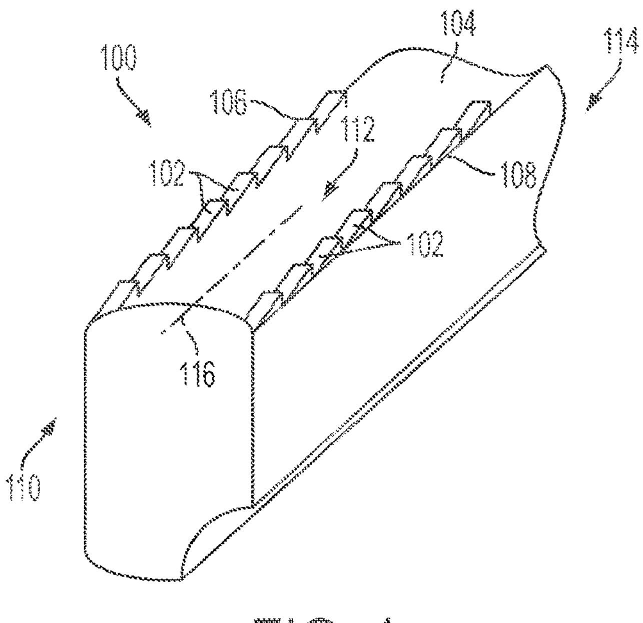
FIG. 1 illustrates one embodiment of an ultrasonic blade with tooth-like grasping features formed on a grasping surface of the blade.

FIG. 1 illustrates one embodiment of an ultrasonic blade 100 with tooth-like grasping features 102 formed on a grasping surface 104 of the blade 100. In the embodiment illustrated in FIG. 1 the tooth-like grasping features 102 are formed along lateral portions 106, 108 of the grasping surface 104 of the blade 100, e.g., the left side of the blade 100 and the right side of the blade 100. In one embodiment, the tooth-like grasping features 102 may be formed along the entire active length or a portion of the blade 100. Elements of the tooth-like grasping features 102 may be uniformly or variable spaced. In other embodiments, the tooth-like grasping features 102 could be located only on a portion of the blade 100, such as, for example, the distal tip 110, the center 112 of the blade 100, the proximal section 114, or any portion of the blade 100. In another embodiment, the tooth-like grasping features 102 may be located along the entire length or a portion of the blade 100. In some embodiments, the tooth-like grasping features 102 could be located longitudinally on a portion of the blade 100, such as, for example, configured along a center line 116 of the blade 100, the left side 108 of the blade 100, the right side 106 of the blade 100, or both the right and left side of the blade 100. In another embodiment, the tooth-like grasping features 102 may be configured along the entire width of the blade 100. The tooth-like grasping features 102 may be configured to trap tissue and prevent disengagement during activation to prevent tissue milking, as well as provide better grasping forces. Accordingly, the tooth-like grasping features 102 formed on the blade 100 improve tissue grasping. The embodiments, however, are not limited in this context.

Figure 2:
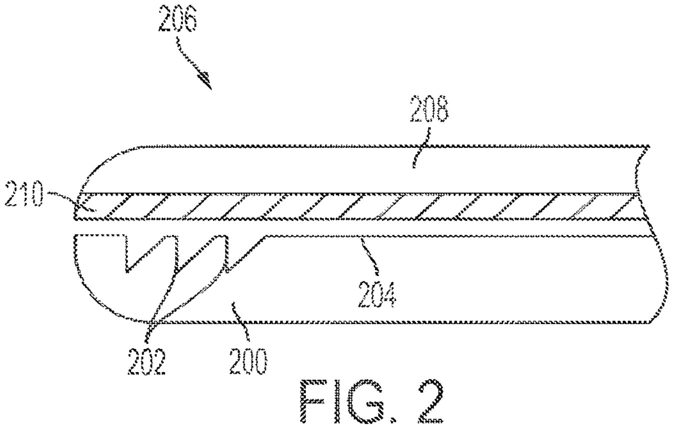
FIG. 2 illustrates one embodiment of the ultrasonic blade with tooth-like grasping features formed on a grasping portion of the blade, where the teeth are machined into the grasping portion of the blade.

FIG. 2 illustrates one embodiment of an ultrasonic blade 200 with tooth-like grasping features 202 formed on a grasping portion 204 of the blade 200 where the teeth are machined into the grasping portion 204 of the blade 200. In the embodiment illustrated in FIG. 2, the blade 200 is part of a medical forceps 206 having a movable jaw member 208, which is commonly referred to as a clamp arm. The movable jaw member 208 comprises a clamp pad 210 to engage tissue between the blade 200 and the movable jaw member 208, e.g., clamp arm. In one embodiment, the tooth-like grasping features 202 may be formed along the entire active length or a portion of the blade 200. Elements of the tooth-like grasping features 202 may be uniformly or variable spaced. Although not shown, the tooth-like grasping features 202 may be formed across the grasping surface 204 of the blade 200, may be formed as multiple rows along the lateral portions of the blade 200 as shown in FIG. 1, or may be formed as a single row along the longitudinal portion of the grasping surface 204 of the blade 200. The tooth-like grasping features 202 may be configured to trap tissue and prevent disengagement during activation to prevent tissue milking, as well as provide better grasping forces. Accordingly, the tooth-like grasping features 202 formed on the blade 200 improve tissue grasping. The embodiments, however, are not limited in this context.

Figure 3:
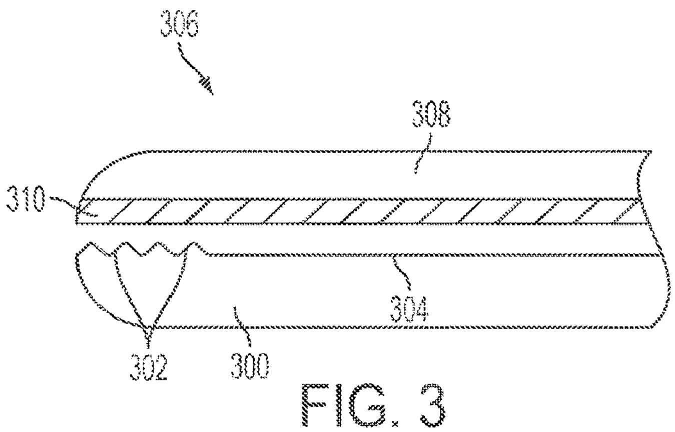
FIG. 3 illustrates one embodiment of the ultrasonic blade with tooth-like grasping features formed on a grasping portion of the blade, where the teeth protrude from the grasping portion of the blade.

FIG. 3 illustrates one embodiment of an ultrasonic blade 300 with tooth-like grasping features 302 formed on a grasping portion 304 of the blade 300, where the teeth 302 protrude from the grasping portion 304 of the blade 300. In the embodiment illustrated in FIG. 3, the blade 300 is part of a medical forceps 306 having a movable jaw member 308, which is commonly referred to as a clamp arm. The movable jaw member 308 comprises a clamp pad 310 to engage tissue between the blade 300 and the movable jaw member 308, e.g., clamp arm. In one embodiment, the tooth-like grasping features 302 may be formed along the entire active length or a portion of the blade 300. Elements of the tooth-like grasping features 302 may be uniformly or variable spaced. Although not shown, the tooth-like grasping features 302 may be formed across the grasping surface 304 of the blade 300, may be formed as multiple rows along the lateral portions of the blade 300 as shown in FIG. 1, or may be formed as a single row along the longitudinal portion of the grasping surface 304 of the blade 300. The tooth-like grasping features 302 may be configured to trap tissue and prevent disengagement during activation to prevent tissue milking, as well as provide better grasping forces. Accordingly, the tooth-like grasping features 302 formed on the blade 300 improve tissue grasping. The embodiments, however, are not limited in this context.

FIG. 4 illustrates one embodiment of an ultrasonic blade 400 with protruding block-like grasping features 402 formed on a grasping 404 portion of the blade 400. FIG. 5 is a side view of the ultrasonic blade shown in FIG. 4. In the embodiment illustrated in FIGS. 4 and 5 the block-like grasping features 402 are formed along lateral portions 406, 408 of the grasping surface 404 of the blade 400. In one embodiment, the block-like grasping features 402 may be formed along the entire active length or a portion of the blade 400. Elements of the block-like grasping features 402 may be uniformly or variable spaced. In other embodiments, the block-like grasping features 402 could be located only on a portion of the blade 400, such as, for example, the distal tip 410, the center 412 of the blade 400, the proximal section 414, or any portion of the blade 400. In another embodiment, the block-like grasping features 402 may be located along the entire length or a portion of the blade 400. In some embodiments, the block-like grasping features 402 could be located longitudinally on a portion of the blade 400, such as, for example, configured along a center line 416 of the blade 400, the left side 408 of the blade 400, the right side 406 of the blade 400, or both the right and left side of the blade 400. In another embodiment, the block-like grasping features 402 may be configured along the entire width of the blade 400. The block-like grasping features 402 may be configured to trap tissue and prevent disengagement during activation to prevent tissue milking, as well as provide better grasping forces. Accordingly, the block-like grasping features 402 formed on the blade 400 improve tissue grasping. The embodiments, however, are not limited in this context.

FIG. 6 illustrates one embodiment of an ultrasonic blade 500 with protruding grasping features 502 formed on a grasping portion 504 of the blade 500. FIG. 7A is a side view of the ultrasonic blade 500 shown in FIG. 6 and FIG. 7B shows the protruding grasping features 502 in the form of bump-like protrusions 510 whereas FIG. 7C shows the protruding grasping features 502 in the form of spike-like protrusions 512. In the embodiment illustrated in FIGS. 6 and 7A the protruding grasping features 502 are formed along lateral portions 506, 508 of the grasping surface 504 of the blade 500. In one embodiment, the grasping features 502 may be formed along the entire active length or a portion of the blade 500. Elements of the grasping features 502 may be uniformly or variable spaced. In other embodiments, the grasping features 502 could be located only on a portion of the blade 500, such as, for example, the distal tip 520, the center 522 of the blade 500, the proximal section 524, or any portion of the blade 500. In another embodiment, the grasping features 502 may be located along the entire length or a portion of the blade 500. In some embodiments, the grasping features 502 could be located longitudinally on a portion of the blade 500, such as, for example, configured along a center line 526 of the blade 500, the left side 508 of the blade 500, the right side 506 of the blade 500, or both the right and left side of the blade 500. In another embodiment, the grasping features 502 may be configured along the entire width of the blade 500. The grasping features 502 may be configured to trap tissue and prevent disengagement during activation to prevent tissue milking, as well as provide better grasping forces. Accordingly, the grasping features 502 formed on the blade 500 improve tissue grasping. The embodiments, however, are not limited in this context.

FIG. 8 illustrates one embodiment of an ultrasonic blade 600 with cavity-like grasping features 602 formed on a grasping portion 604 of the blade 600. FIG. 9A is a side view of an ultrasonic blade 600 having cylindrical cavity-like grasping features 611 partially formed into the grasping portion of the blade 610. FIG. 9B is a side view of an ultrasonic blade 600 having cylindrical cavity-like grasping features 613 formed through a grasping portion of the blade 612. FIG. 9C is a side view of an ultrasonic blade 600 having conical cavity-like grasping features 615 partially formed into the grasping portion of the blade 614. In the embodiment illustrated in FIGS. 8 and 9A-C, the cavity-like grasping features 602 are distributed along portions of the grasping surface 604 of the blade 600. In one embodiment, the grasping features 602 may be formed along the entire active length or a portion of the blade 600. Elements of the grasping features 602 may be uniformly or variable spaced. In other embodiments, the grasping features 602 could be located only on a portion of the blade 600, such as, for example, the distal tip 620, the center 622 of the blade 600, the proximal section 624, or any portion of the blade 600. In another embodiment, the grasping features 602 may be located along the entire length or a portion of the blade 600. In some embodiments, the grasping features 602 could be located longitudinally on a portion of the blade 600, such as, for example, configured along a center line 626 of the blade 600, the left side 608 of the blade 600, the right side 606 of the blade 600, or both the right and left side of the blade 600. In another embodiment, the grasping features 602 may be configured along the entire width of the blade 600. The grasping features 602 may be configured to trap tissue and prevent disengagement during activation to prevent tissue milking, as well as provide better grasping forces. Accordingly, the grasping features 602 formed on the blade 600 improve tissue grasping. The embodiments, however, are not limited in this context.

FIG. 10 illustrates one embodiment of an ultrasonic blade 700 with transverse bump-like grasping features 702 formed on a grasping portion 704 of the blade 700. FIG. 11 is a side view of the ultrasonic blade 700 shown in FIG. 10. In the embodiment illustrated in FIGS. 10 and 11, the transverse bump-like grasping features 702 are distributed transversally along across of the grasping surface 704 of the blade 700. In one embodiment, the transverse bump-like grasping features 702 may be formed along the entire active length or a portion of the blade 700. Elements of the transverse bump-like grasping features 702 may be uniformly or variable spaced. In other embodiments, the transverse bump-like grasping features 702 could be located only on a portion of the blade 700, such as, for example, the distal tip 720, the center 722 of the blade 700, the proximal section 724, or any portion of the blade 700. In another embodiment, the transverse bump-like grasping features 702 may be located along the entire length or a portion of the blade 700. In some embodiments, the transverse bump-like grasping features 702 could be located longitudinally on a portion of the blade 700, such as, for example, configured along a center line 726 of the blade 700, the left side 708 of the blade 700, the right side 706 of the blade 700, or both the right and left side of the blade 700. In another embodiment, the transverse bump-like grasping features 702 may be configured along the entire width of the blade 700. The transverse bump-like grasping features 702 may be configured to trap tissue and prevent disengagement during activation to prevent tissue milking, as well as provide better grasping forces. Accordingly, the transverse bump-like grasping features 702 formed on the blade 700 improve tissue grasping. The embodiments, however, are not limited in this context.

Figures 12, 13:
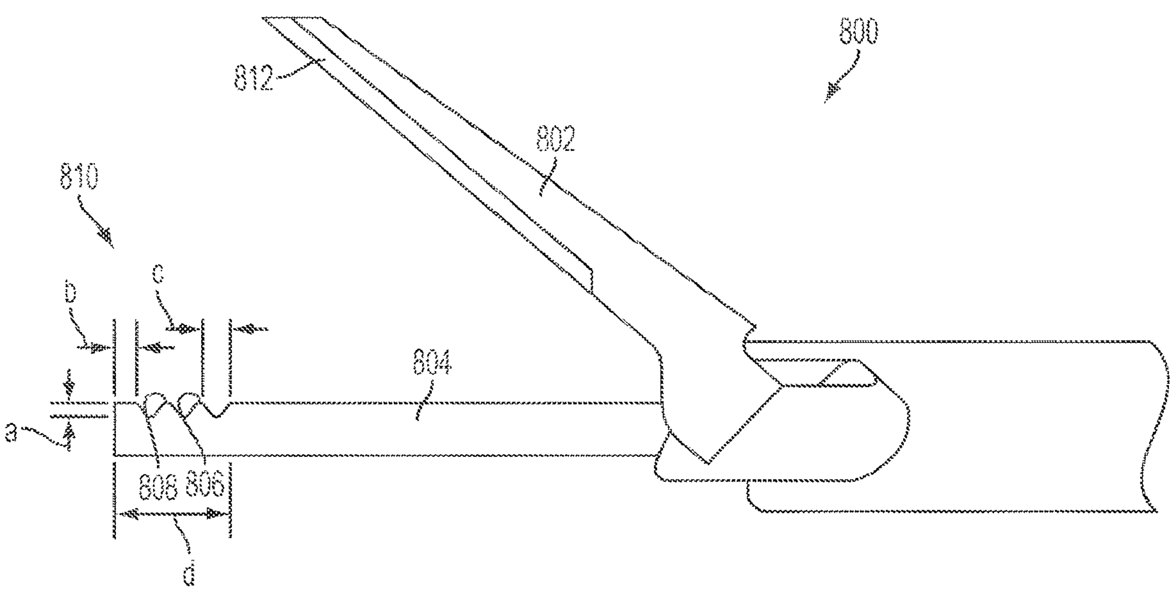
FIG. 12 is a side view of one embodiment of an end effector assembly comprising medical forceps having a movable jaw member and an ultrasonic blade having protrusions in the form of tooth-like grasping features formed on a grasping surface of the blade.
FIG. 13 is a top view of one embodiment of the medical forceps shown in FIG. 12 with the movable jaw member drawn in phantom line to show the ultrasonic blade positioned below the movable jaw member.

FIG. 12 is a side view of one embodiment of an end effector assembly comprising medical forceps 800 having a movable jaw member 802 and an ultrasonic blade 804 having protrusions 806 in the form of tooth-like grasping features formed in the grasping surface 808 of the blade 804. FIG. 13 is a top view of one embodiment of the medical forceps 800 shown in FIG. 12 with the movable jaw member 802 drawn in phantom line to show the ultrasonic blade 804 positioned below the movable jaw member 802.

In one embodiment, the protrusions 806 (e.g., teeth) may be defined by several dimensions. A first dimension “a” represents the height of a protrusion 806 (e.g., tooth). In one embodiment, the dimension “a” may be about 0.12 mm to 0.18 mm. A second dimension “b” represents the width of a protrusion 806 (e.g., tooth). In one embodiment, the dimension “b” may be about 0.2 mm. A third dimension “c” represents the spacing between each protrusion 806. In one embodiment, the dimension “c” is about 0.5 mm. The protrusions 806 may cover, in one embodiment, a distance represented by dimension “d” which can be as little as 2 mm of the blade 804 to provide additional grasping strength. The 2 mm of protrusions 806 may comprise any percentage of the blade 804, such as, for example, 13% of a 15 mm blade. In one embodiment, the height of the protrusion 806 near the distal end 810 of the blade 804 may be approximately 2.3 mm. In one embodiment, the protrusions 806 may comprise about 5% of the total height of the blade 804. In various embodiments, the protrusions 806 may include a pitch of 0.3 mm-1.0 mm, a depth of approximately 0.08 mm-0.8 mm, and an angle of approximately 5-90 degrees. In various embodiments, the protrusions 806 may be in the form of blocks, bumps, spikes, or speed bumps, as previously described. These alternate embodiments of the protrusions 806 would be formed having similar dimensions as the protrusions 806 described in connection with FIGS. 12 and 13 to have a similar affect on tissue, e.g., statistically better tissue grasping forces and preventing tissue milking.

In one embodiment, the protrusions 806 may mate with alternating features formed on the clamp arm 802 or tissue pad 812 portion of the medical forceps 800. In another embodiment, this mating is neither necessary nor required. In one non-mating embodiment, grasping efficiency may be increased by 64% using three features in the form of teeth. The presence of the features does not affect the tissue transection ability of the blade 804. In one embodiment, the blade 804 may comprise protrusions 806 along the entire active length of the blade 804. The protrusions 806 may be configured to trap tissue and prevent disengagement during activation. Various embodiments of protrusions 806 may include blade teeth, horizontal trenches, or cavities, as previously described.

FIGS. 14-18 illustrate various embodiments of ultrasonic blades comprising blade features is to address tissue milking. As previously discussed, tissue milking is defined as the event in which tissue begins to slip out of the jaws of an ultrasonic medical forceps having a movable jaw member and an ultrasonic blade upon device activation. This event increases the difficulty of manipulating tissue in low accessibility conditions. To address this and other issues, the present disclosure provides three embodiments to improve the grasping ability during ultrasonic activation. At least one embodiment of each of the disclosed ultrasonic blades employs repeated features across the active length of the blade. These features are designed to trap tissue and prevent disengagement during activation. Based on the testing, the following embodiments have shown between a 30% and 40% improvement in grasping force during activation over conventional ultrasonic blades. The three embodiments provide ultrasonic blade teeth geometries in the form of blade teeth, horizontal trenches, and holes (e.g., cavities) as described hereinbelow in connection with FIGS. 14-18 to prevent disengagement of tissue from the blade and clamp arm upon ultrasonic activation of the device and to improve tissue grasping ability prior to and during ultrasonic activation. In various embodiments, the ultrasonic blades comprise tissue trapping features to improve grasping ability and prevent tissue disengagement during ultrasonic activation of the blade.

Figure 14:
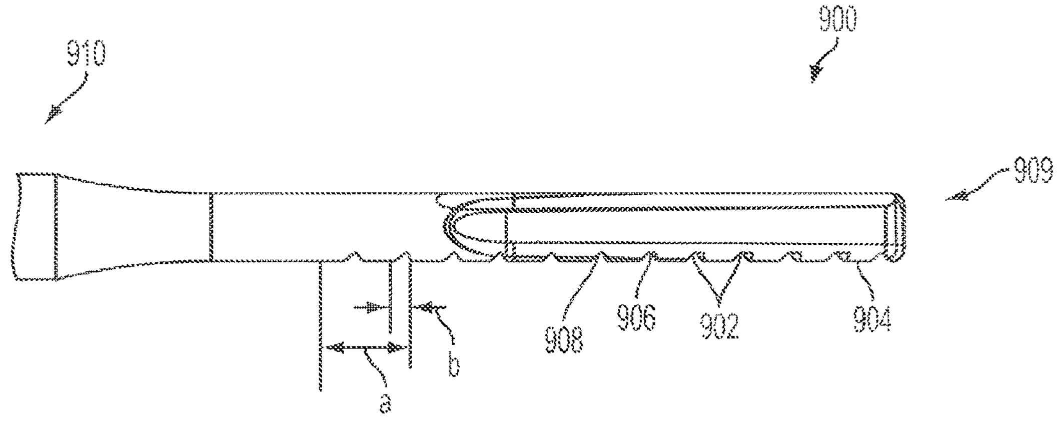
FIG. 14 is a side view illustrating one embodiment of an ultrasonic blade comprising tooth-like grasping features having triangular grooves formed on a grasping surface of the blade.
Figure 15:
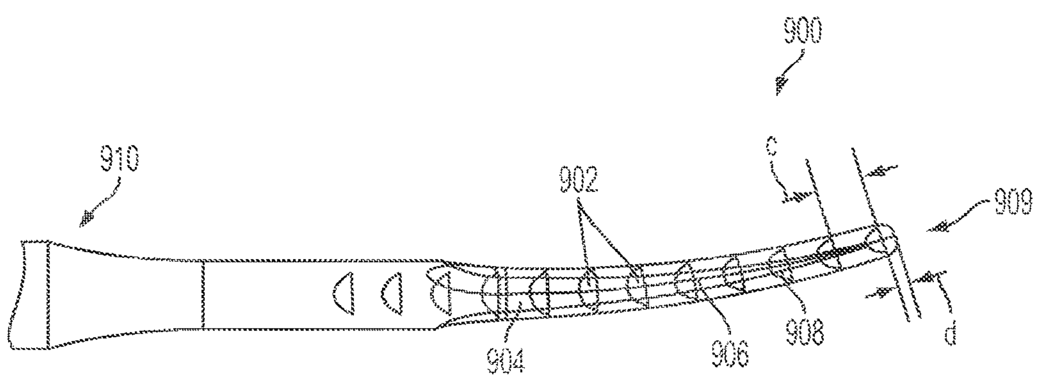
FIG. 15 is a top view of the ultrasonic blade shown in FIG. 14, according to one embodiment.

FIG. 14 is a side view illustrating one embodiment of an ultrasonic blade 900 comprising tooth-like grasping features 902 having triangular grooves formed on a grasping surface 904 of the blade 900. FIG. 15 is a top view of the ultrasonic blade 900 shown in FIG. 14. The blade 900 comprises a proximal end 910 and a distal end 909. The blade 900 comprises tissue trapping features 902 in the form of triangular grooves repeated along a portion of or the entire longitudinal length of the blade 900. A distal side 906 toward the distal end 909 of the blade 900 of each feature 902 may be a surface perpendicular to the longitudinal axis of the blade 900 followed by an angled surface 908 that tapers off in a proximal direction 910. In one embodiment, the features 902 may be characterized by dimensions a, b, c, and d. In one embodiment, dimension "a" represents the heights of the feature 902, which may be approximately 0.010", "b" represents the width of the feature 902, which may be approximately 0.020", "c" represents the distance between the features 902, which may be approximately 0.055", and "d" represents the distance from the most distal feature 902 to the distal 909 tip of the blade 900, which may be approximately 0.015". In one embodiment, the features 902 may be evenly spaced along the longitudinal length of the blade 900. In another embodiment, the triangular grooves grasping features 902 may be unevenly spaced along the longitudinal length of the blade 900. In the illustrated embodiment, the blade 900 comprises 12 evenly spaced triangular grooves grasping features 902 along the longitudinal length of the blade 900.

FIG. 16 is a side view illustrating one embodiment of an ultrasonic blade 950 with tooth-like grasping features 952 including horizontal trenches having repeated semicircular grooves formed on a grasping surface 954 of the blade 950. FIG. 17 is a top view of the ultrasonic blade 950 shown in FIG. 16. The blade 950 comprises a proximal end 960 and a distal end 959. The blade 950 comprises tissue trapping features 952 in the form of horizontal trenches having semicircular grooves repeated along the longitudinal length of the blade 950. In one embodiment, the features 952 may be characterized by dimensions e, f, g, and h. In one embodiment, dimension "e" represents the diameter of the grooves, which may be approximately 0.020", "f' represents the distance between each of the features 952, which may be approximately 0.057", "g" represents the distance from the most distal feature 952 to the distal 909 tip of the blade 950, which may be approximately 0.015", and "h" represents the depth of the grooves which may be approximately 0.005". In one embodiment, the features 952 may be evenly spaced along the longitudinal length of the blade 950. In another embodiment, the semicircular groove grasping features 952 may be unevenly spaced along the longitudinal length of the blade 950. In the illustrated embodiment, the blade 950 comprises 12 evenly spaced semicircular groove grasping features 952 along the longitudinal length of the blade 950.

FIG. 18 is a top view illustrating one embodiment of an ultrasonic blade 970 comprising grasping features 972 including cavities or holes formed on a grasping surface 974 of the blade 970. The blade 970 comprises a proximal end 980 and a distal end 979. The blade 970 comprises tissue trapping features 972 in the form of circular elements repeated along the longitudinal length of the blade 970. In one embodiment, the features 972 may be characterized by dimensions i, j, and k. In one embodiment, dimension "k" represents the diameter of a circular element, which may be approximately 0.020", "i" represents the distance between each of the circular features 972, which may be approximately 0.057", and "j" represents the distance from the most distal feature 972' to the distal 979 tip of the blade 970, which may be approximately 0.015". In one embodiment, the circular features 972 may be evenly spaced along the longitudinal length of the blade 970. In another embodiment, the circular features 972 may be unevenly spaced along the longitudinal length of the blade 970. In the illustrated embodiment, the blade 970 comprises 12 evenly spaced circular grasping features 972 along the longitudinal length of the blade 970.

Ingress Prevention

The present disclosure describes various embodiments of devices to prevent surgical matter, such as fluid or tissue, for example, from entering the space between an ultrasonic blade and an inner tube distal of the blade's distal seal. Two main categories of embodiments are described. First, a pressure or energy source attached to the blade-tube subassembly prevents fluid or tissue ingress into the space between the blade and the inner tube. Second, a flexible membrane(s) attached to either the blade or the inner tube prevents fluid or tissue ingress.

Figure 32:
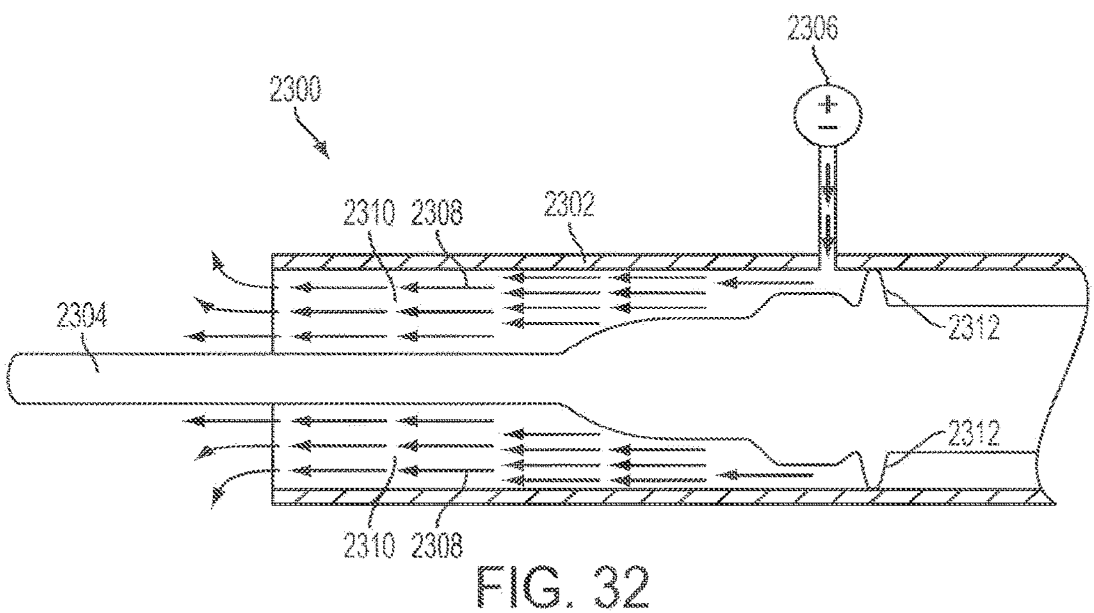
FIG. 32 illustrates one embodiment of a positive pressure fluid flow system to apply a positive pressure fluid flow between an outer tube and an ultrasonic blade at distal end thereof employing a pump or pump outlet located distal of a distal node.

In one embodiment, surgical matter in the form of fluid or tissue, for example, could be prevented from entering the distal inner tube area by the application of a constant pressure of a fluid medium (e.g., air, $CO_2$ or saline solution) in the distal direction. FIG. 32 illustrates one embodiment of a positive pressure fluid flow system 2300 comprising a pump and/or pump outlet 2306 located distal of the distal seal. In the illustrated embodiment, the external pump and/or pump outlet 2306 is fluidically coupled to the device distal of the distal node of an ultrasonic blade 2304. Air or other fluid medium 2308 is pumped into the space 2310 between the blade 2304 and the inner tube 2302, forcing particulates and/or bodily fluids out of that space 2310. As illustrated in FIG. 32, the pump and/or pump outlet 2306 is fluidically coupled to the space 2310 between the tube 2302 and the blade 2304 at a point distal from a distal blade seal 2312, e.g., an O-ring or overmolded seal. Thus, the positive pressure fluid flow 2308 is directed to the distal end of the device to prevent accumulation of surgical matter in the space 2310.

Figure 49:
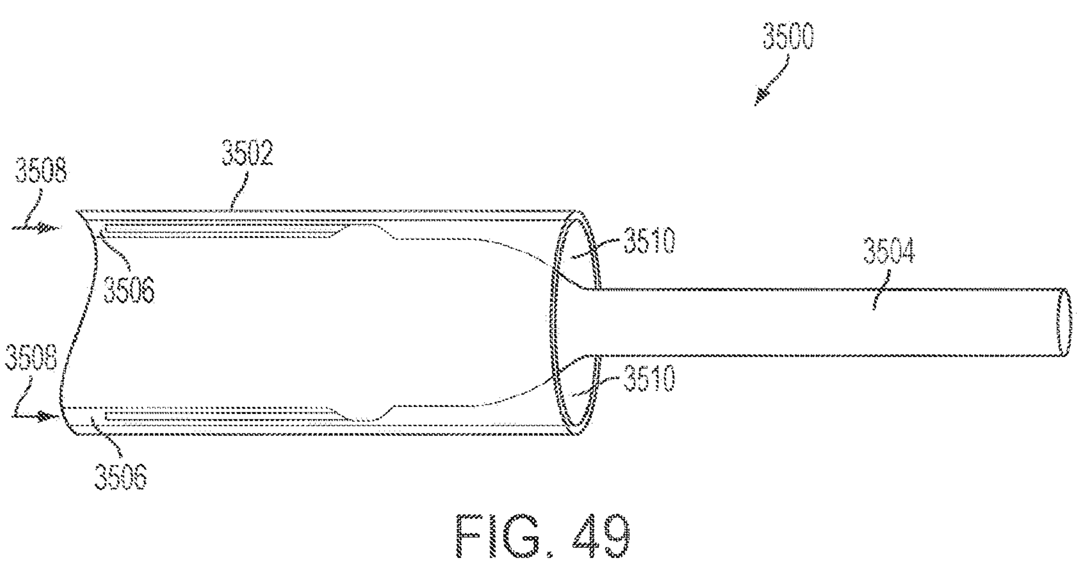
FIG. 49 illustrates one embodiment of a positive fluid pressure system in which air is pumped down the length of the inner tube.

FIG. 49 illustrates one embodiment of a positive fluid pressure system 3500 in which air 3508 is pumped down the length of the inner tube 3502 through space 3506. The air 3508 prevents surgical matter from entering the space 3510 between the ultrasonic blade 3504 and the inner tube 3502. FIG. 49 shows a similar concept to that shown in FIG. 32, but the distal node does not have a seal to the inner tube 3502. Rather, air 3508 is pumped down the full length of the inner tube 3502 to prevent fluid and/or tissue ingress.

Figure 26:
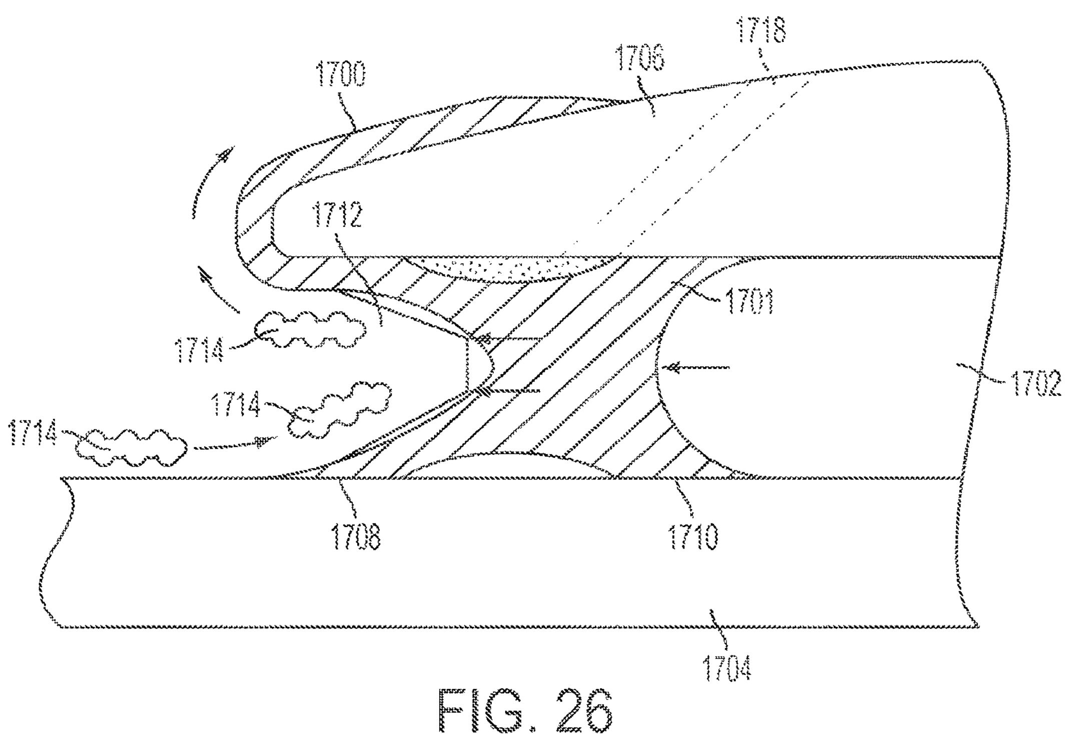
FIG. 26 illustrates one embodiment of a hybrid system comprising a contoured seal comprising a flexible membrane that acts as a pump to force surgical matter out of a distal inner tube area.

FIG. 26 illustrates one embodiment of a hybrid system comprising a contoured seal 1700 comprising a flexible membrane 1701 that acts as a pump to force surgical matter 1714 out of a distal tube 1706 area. The pressurized flexible membrane 1701 blocks tissue ingress by contact. The flexible membrane 1701 is attached to the inner tube 1706 and sealed to the ultrasonic blade 1704. Thus, the relative movement between the blade 1704 and the distal tube 1706 causes the flexible membrane 1701 to act in a pump-like manner to force fluids, tissue, or other surgical matter to flow along the contour of the flexible membrane 1701 and out of the inner tube 1706 area. The contoured seal 1700 seals a space 1702 between a portion of an ultrasonic blade 1704 and a tube 1706. The contoured seal 1700 has two points of contact 1708, 1710 with the ultrasonic blade 1704 to minimize friction and interference and to provide a double seal. A cavity 1712 is defined by the contoured seal 1700 for collecting surgical matter 1714. In an alternative embodiment, a separate duct 1718 may be provided to apply a positive pressure to the flexible membrane of the contoured seal 1700 to expel the surgical matter 1714 from the cavity 1712.

In various other embodiments, a boot barrier (or seal, for example) may be added to an end effector portion of an ultrasonic instrument to prevent the buildup of surgical matter on the end effector. The boot barrier seals the ultrasonic blade to the distal ends of one or more tube(s) near to the proximal end of the tissue effecting portion of the ultrasonic blade. The boot barrier may be made from any suitable materials including compliant, thermally robust material that has a relatively low coefficient of friction in order to minimize the seal load on the blade. Materials suitable for the boot barrier may include, for example, silicone rubber, parylene coated silicon rubber, Tetrafluoroethylene-hexafluoropropylene (FEP), which has similar properties to those of Polytetrafluoroethylene (PTFE) otherwise known in the trade as Teflon, shrink tubing, or any similar material. In another embodiment, the blade may be coated to reduce power draw of the instrument due to inclusion of the boot barrier.

The boot barrier seals to the blade and may provide slight interference to the blade. Where the boot barrier seals to the blade, the boot barrier does not provide vertical reaction for clamping/bending of the blade in order to keep the load on the blade (from the boot) minimized. The boot barrier may seal to the outer diameter of the tube(s), the inner diameter of the tube(s) or both. One or more retention features may be provided on the blade and/or the tube(s) for retaining the boot to the blade and/or the tube(s). In one embodiment, the retention features may also be located on the boot barrier itself.

Generally, the boot barrier prevents build up and accumulation of surgical matter such as, for example, tissue, blood, melted fat, and other related materials encountered during surgery, between the distal portion of the tube(s) and the nearby portion of the blade of the ultrasonic surgery device. This build up and accumulation may result in large and inconsistent mechanical loads on the system resulting in procedure interruptions due to high impedance either causing resonance issues or causing the system to bog down and potentially stop during activation. The tube(s) are needed to protect tissue and users from the ultrasonically active blade and, in the case of shears-type device, to support and/or drive a clamp arm. Ideally, the ultrasonic blade is as active (ultrasonically) as possible in the proximal portion of its tissue effecting length. Solutions that maximize this ultrasonic activity also elongate the portion of the blade between its most distal node and the proximal end its tissue effecting length. The result is a relatively large annular volume that accumulates tissue, blood, fat, etc. with the aforementioned issues.

Figure 19:
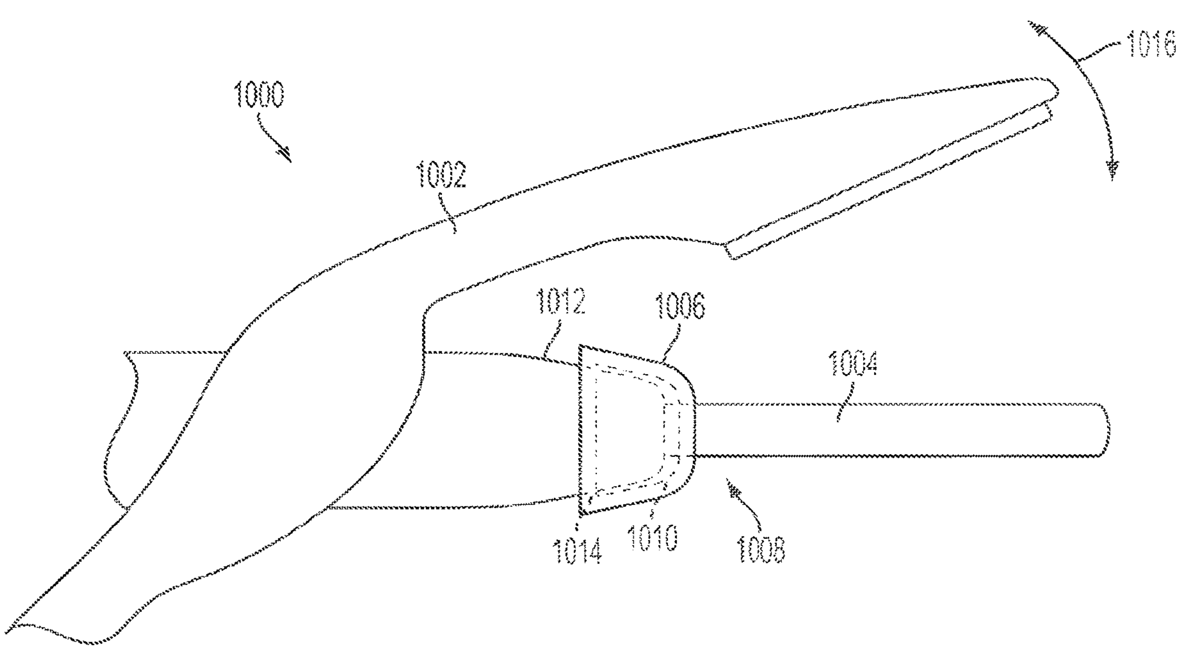
FIG. 19 illustrates one embodiment of an end effector assembly comprising a medical forceps having a movable jaw member and an ultrasonic blade with a flexible seal positioned over a proximal portion of the blade and a distal portion of a tube to seal the blade to an outer diameter of the tube.

FIG. 19 illustrates one embodiment of an end effector assembly 1000 comprising a medical forceps having a movable jaw member 1002 and an ultrasonic blade 1004. The jaw member 1002 is movable in direction 1016. A flexible boot barrier 1006 is positioned over a proximal portion 1008 of the blade 1004 and a distal portion of a tube 1010 to seal the blade 1004 to an outer diameter 1012 of the tube 1010. A retention feature 1014 may be provided on the outer diameter 1012 of the tube 1010 to keep the boot barrier 1006 in place. As previously discussed, the boot barrier 1006 may be made from silicone rubber or other similar materials. In one embodiment, the boot barrier 1006 may be coated with a lubricious material such as parylene, for example, to reduce friction. In an alternative embodiment, the blade 1104 may be coated with similar lubricious materials to reduce friction. Reducing friction between the blade 1004 and the boot barrier 1006 reduces power draw due to the inclusion of the boot barrier 1006.

Figure 20:
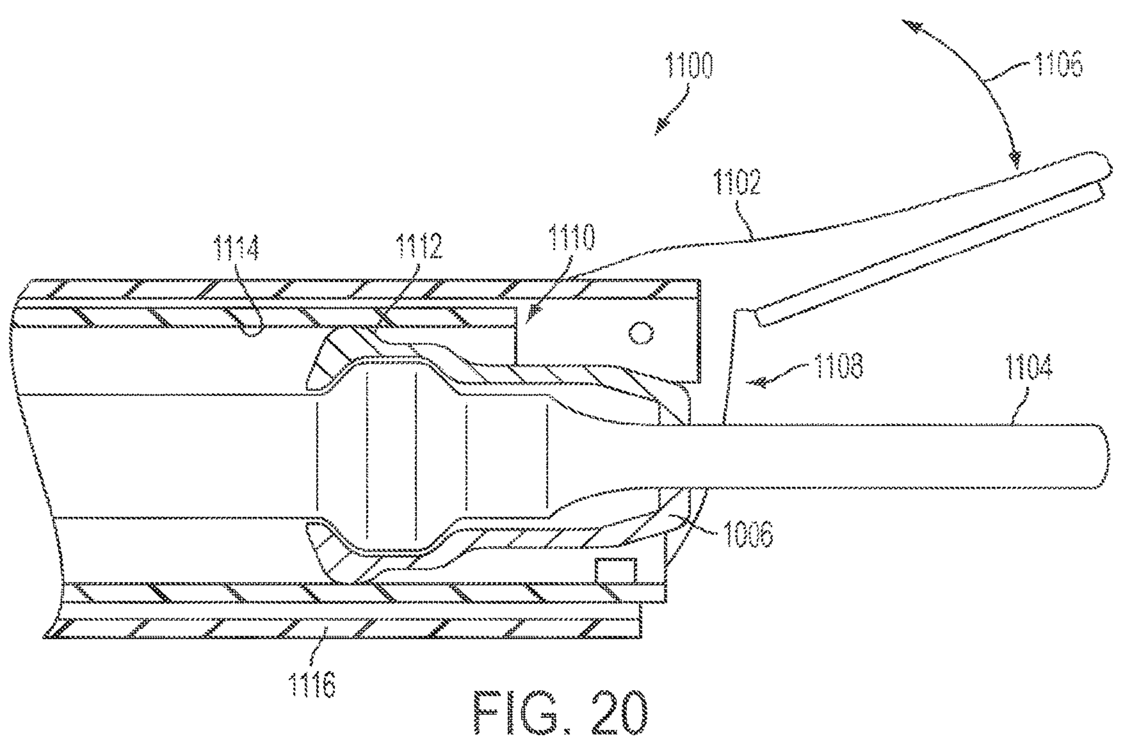
FIG. 20 illustrates one embodiment of an end effector assembly comprising a medical forceps having a movable jaw member and an ultrasonic blade with a flexible seal positioned over a proximal portion of the blade and within a distal portion of a tube to seal the blade to an inner diameter of the tube.

FIG. 20 illustrates one embodiment of an end effector assembly 1100 comprising a medical forceps having a movable jaw member 1102 and an ultrasonic blade 1104. A flexible seal 1106 positioned over a proximal portion 1108 of the blade 1104 and within a distal portion 1110 of an inner tube 1112 to seal the blade 1104 to an inner diameter 1114 of the inner tube 1112. The inner tube 1112 is slidably movable within an outer tube 1116.

Figures 21, 22:
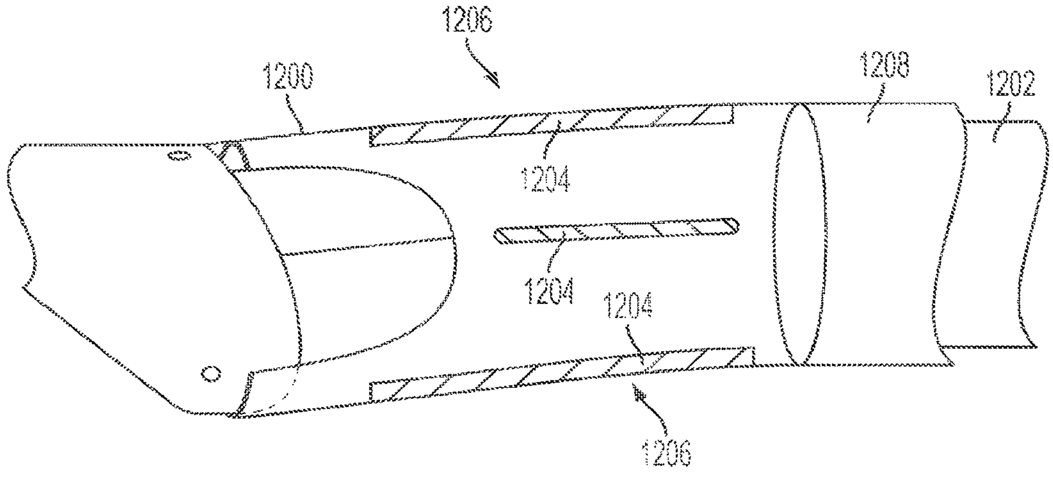
FIG. 21 illustrates one embodiment of a slotted inner tube to conceal a lengthwise portion of an ultrasonic blade where the slots provide fluid egress to discharge surgical matter that may accumulate in a space between the blade and the inner tube.
FIG. 22 illustrates one embodiment of a perforated mutilated inner tube to conceal a lengthwise portion of an ultrasonic blade where the perforations provide fluid egress to discharge surgical matter that may accumulate in a space between the blade and the inner tube.

FIG. 21 illustrates one embodiment of a slotted inner tube 1200 to conceal a lengthwise portion of an ultrasonic blade 1202. Slots 1204 provide fluid/tissue egress to discharge surgical matter that may accumulate in a space 1206 between the blade 1202 and the inner tube 1200. Fluid/tissue egress through the slots 1204 at the distal end of an ultrasonic device prevents the accumulation of surgical matter. In ultrasonic laparoscopic shears, for example, an overmolded silicone distal seal 1208 is provided on or near the distal node of the blade 1202. A boot barrier may be overmolded, positioned just distal to the clamp arm edge, which could prevent tissue pinching, and anchored to the inner tube 1200, or positioned within the inner tube 1200 and non-visible to the user as shown in FIG. 22, for example. In these devices, there is approximately 13 mm length of the blade 1202 that is concealed by the outer tube (not shown) and the inner tube 1200 before the distal seal 1208 is present. Surgical matter, such as fluid, blood, fat, or other tissue, can become lodged in that space between the outer diameter of the blade 1202 and the inner diameter of the inner tube 1200. In other instruments comprising similar shears, the length of exposed blade may increase thus increasing the chance of tissue lodging therein. This could result in increased transection times as the fluid/tissue becomes a heat sink or in relaxed pressure on the blade if the fluid/tissue hardens from applied blade heat. Additionally, if an RF modality is to be added to ultrasonic lap shears technology, tissue and fluid could cause a short circuit if the RF energy is allowed to flow from the blade through tissue that is inside the inner tube, rather than the desired energy path along the active (exposed) length of the blade. Thus a boot or distal tissue ingress prevention method or mechanism is provided as described herein below in connection with FIGS. 21-23 where surgical matter such as fluid or tissue is expelled from between the inner tube 1200 and the blade 1202 by slots 1204, windows, apertures, or perforations formed in the inner tube 1200.

FIG. 22 illustrates one embodiment of a perforated inner tube 1300 to conceal a lengthwise portion of an ultrasonic blade 1302. The inner tube 1300 is perforated with holes 1304 to allow surgical matter such as fluids/tissue to escape. The perforations 1304 provide fluid/tissue egress to discharge surgical matter that may accumulate in a space 1306 between the blade 1302 and the inner tube 1300. In the illustrated embodiment, the inner tube 1300 comprises a 180° half circle and is perforated with holes 1304 to allow fluids/tissue to escape. The tube 1300 is located between the active blade 1302 and the distal most overmold 1310 portion, which is located a distance 1308 from the distal tip of the blade 1302.

Figure 23:
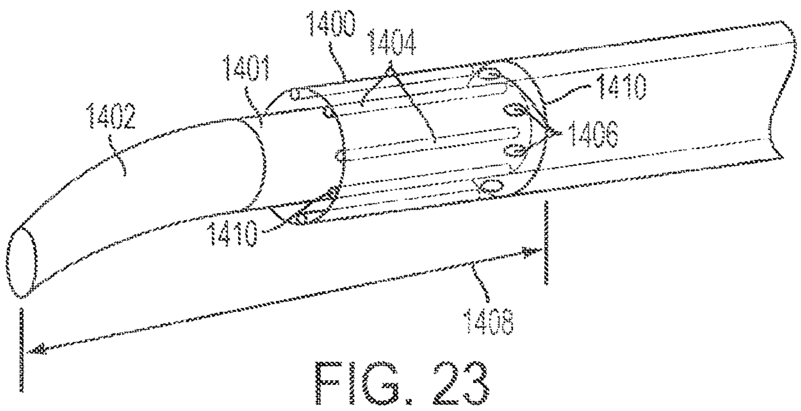
FIG. 23 illustrates one embodiment of a fluid-directing ribbed and perforated inner tube to conceal a lengthwise portion of an ultrasonic blade where the fluid-directing ribs and perforations provide fluid egress to discharge surgical matter that may accumulate in a space between the blade and the inner tube.

FIG. 23 illustrates one embodiment of a fluid-directing ribbed and perforated inner tube 1400 to conceal a lengthwise portion 1401 of an ultrasonic blade 1402. Fluid-directing ribs 1404 perforations 1406 provide fluid egress to discharge surgical matter that may accumulate in a space 1410 between the blade 1402 and the inner tube 1400. The distal most overmold is located at a distance 1408 from the distal tip of the blade 1402. In the illustrated embodiment, the ribs 1404 radiate inward and comprise holes 1406 located between each rib. The ribs 1404 have a clearance with respect to the blade 1402. The spacing of the ribs 1404 is such that only fluids can pass, not solids of appreciable size. The channeling configuration raises fluid velocity and raises likelihood of clearing out of holes 1406.

Figure 24:
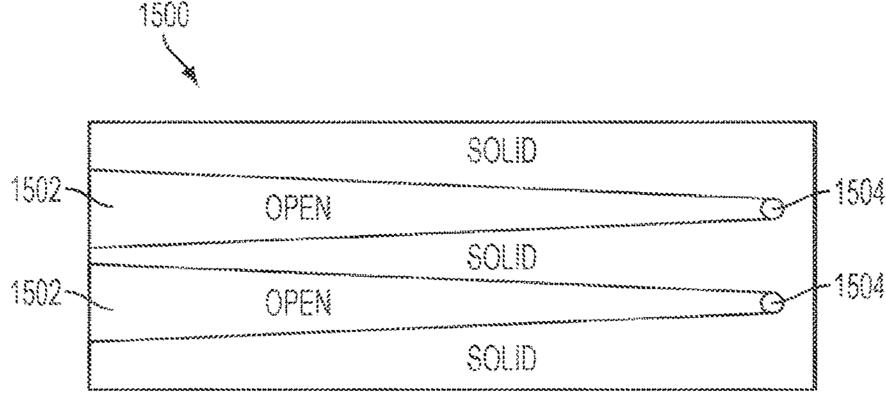
FIG. 24 is one embodiment of a fluid-directing ribbed and perforated inner tube comprising converging ducts

FIG. 24 is one embodiment of a fluid-directing ribbed and perforated inner tube 1500 comprising converging ducts 1502. In one embodiment, the converging ducts 1502 are fluidically coupled to apertures 1504 to provide fluid egress to discharge surgical matter.

Figure 25:
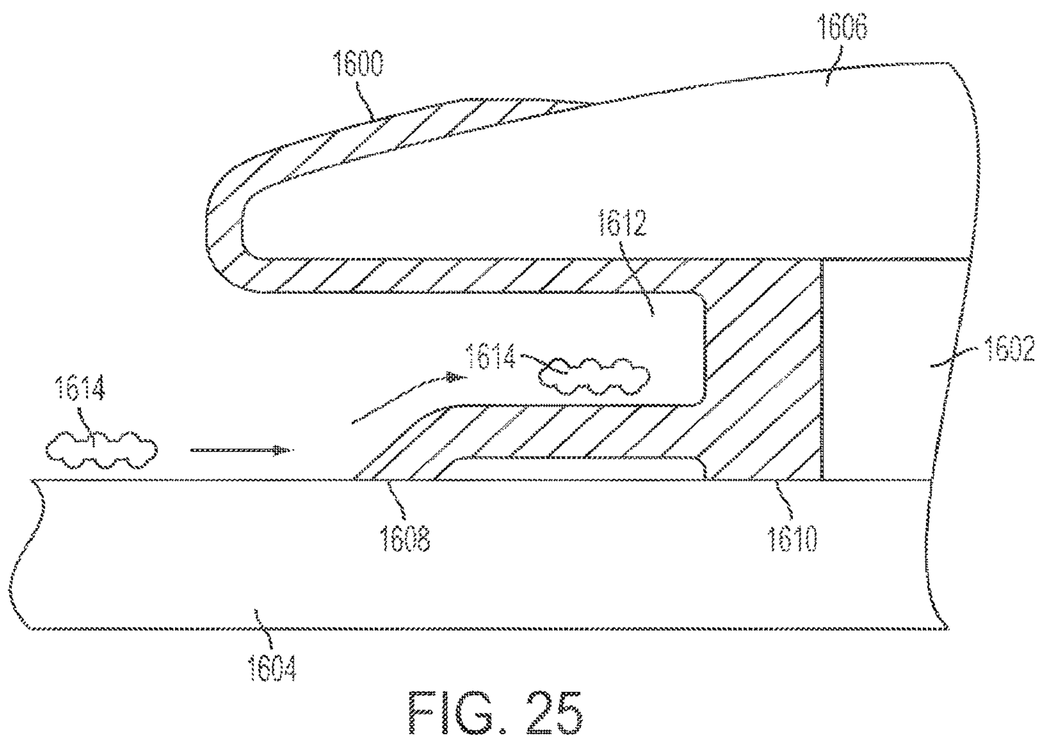
FIG. 25 illustrates one embodiment of a contoured seal to seal a space between a portion of an ultrasonic blade and an outer tube, where the flexible seal having two points of contact and defining a cavity for collecting surgical matter.

FIG. 25 illustrates one embodiment of a contoured seal 1600 to seal a space 1602 between a portion of an ultrasonic blade 1604 distal to the distal seal and a tube 1606. The contoured flexible seal 1600 has two points of contact 1608, 1610 with the ultrasonic blade 1604 to minimize friction and interference and to provide a double seal. A cavity 1612 is defined by the contoured flexible seal 1600 for collecting surgical matter 1614.

Figure 27:
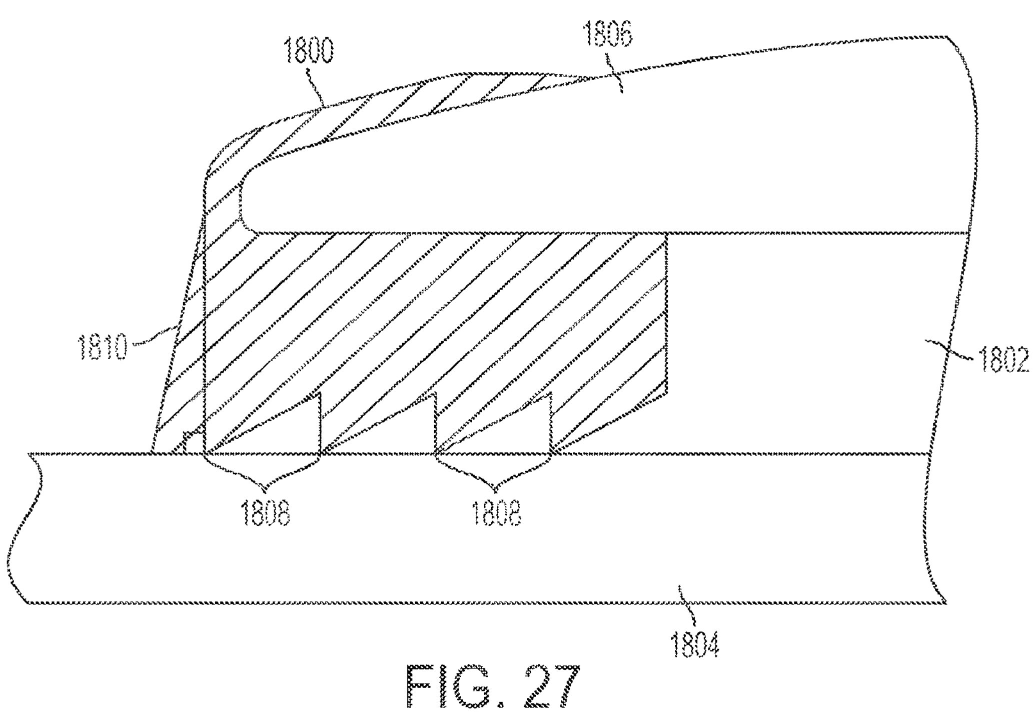
FIG. 27 illustrates one embodiment of a seal to seal a space between a portion of an ultrasonic blade and the tube, the flexible seal multiple points of contact and a low interference point of contact.

FIG. 27 illustrates one embodiment of a seal 1800 to seal a space 1802 between a portion of an ultrasonic blade 1804 distal to the distal seal and a tube 1806. The flexible seal 1800 has multiple points of contact 1808 to provide low interference point of contact between the seal 1800 and the blade 1804. The multiple points of contact 1808 reduce fluid wicking up the shaft of the blade 1804. A nose portion 1810 of the seal 1800 and the multiple points of contact 1808 block surgical matter from entering into the space 1802 between the blade 1804 and the tube 1806.

Figure 28:
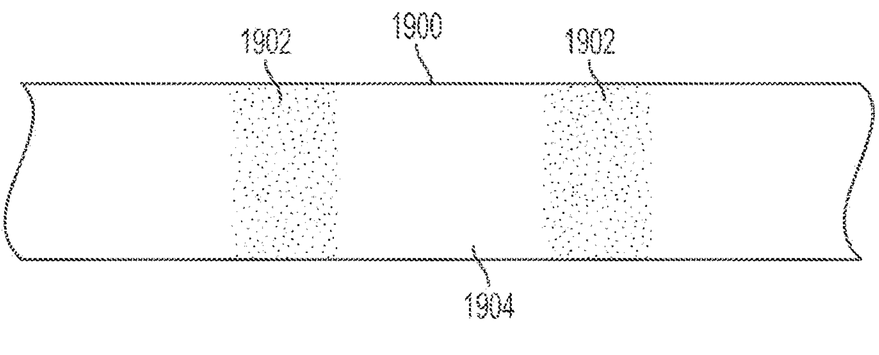
FIG. 28 illustrates etched areas formed on an outer surface of an ultrasonic blade to prevent tissue ingress, according to one embodiment.

FIG. 28 illustrates etched areas 1902 formed on an outer surface 1904 of an ultrasonic blade 1900 to prevent fluid/tissue ingress along the blade due to blade vibration.

Figure 29:
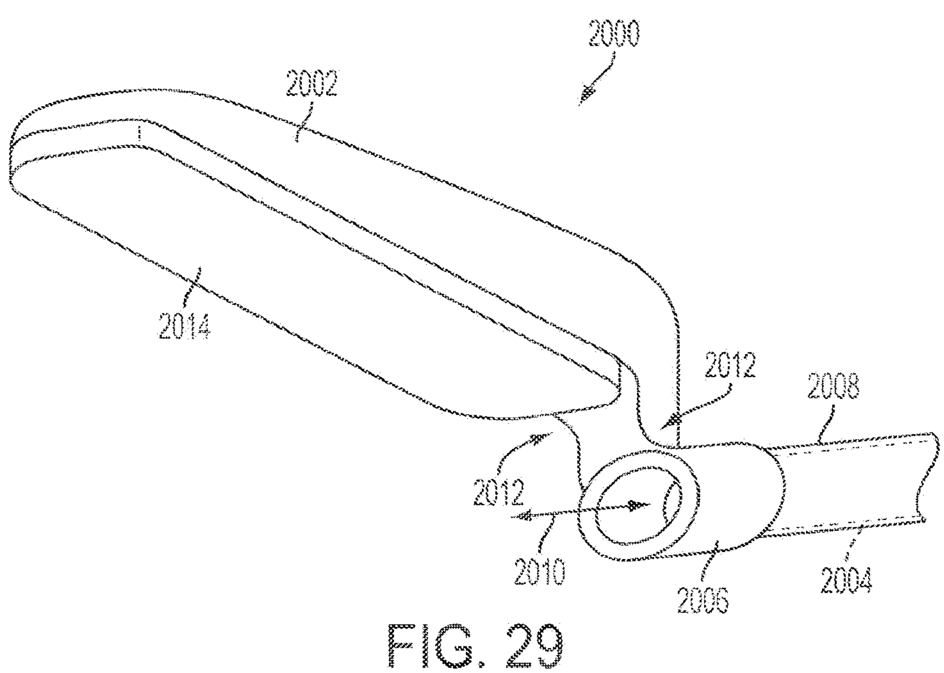
FIG. 29 illustrates one embodiment of an end effector assembly comprising a medical forceps having a movable jaw member and a slidable ultrasonic blade partially retracted within a tube.

FIG. 29 illustrates one embodiment of an end effector assembly 2000 comprising a medical forceps having a movable jaw 2002 member and a slidable ultrasonic blade 2004 partially retracted within a seal 2006. The movable jaw member 2002 comprises a clamp pad 2014 having a living hinge formed by necked down regions 2012 at the interface of the clamp pad 2014 and the seal 2006. The blade 2004 is slidable in direction 2010 and is received within the seal 2006. The seal 2006 is coupled to an inner tube 2008 to seal the blade 2004 to the tube 2008 and prevent fluid/tissue migration proximally.

Figure 30:
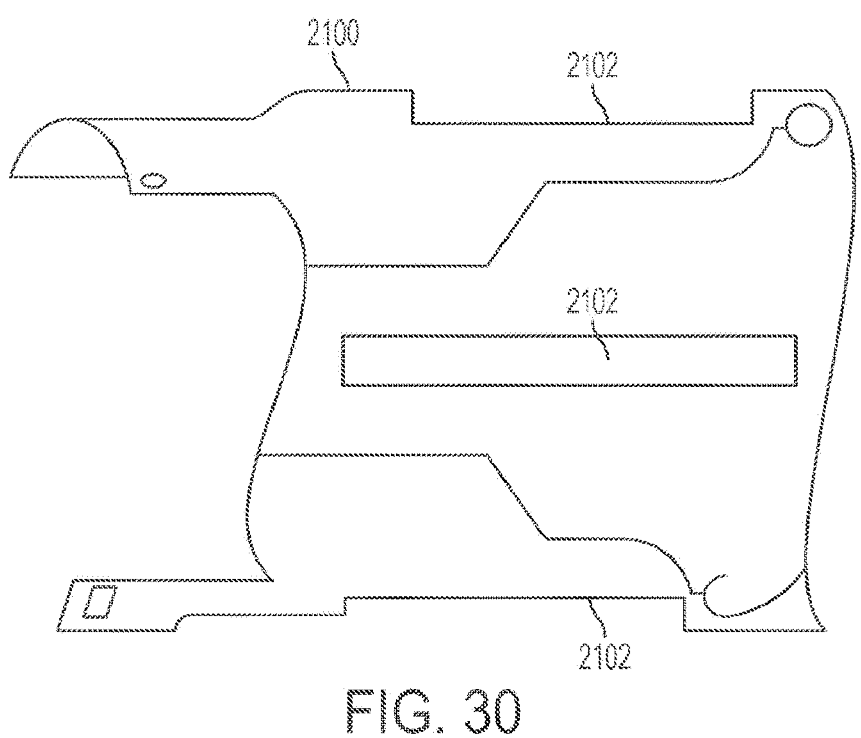
FIG. 30 illustrates one embodiment of an inner tube having machined windows formed therein to allow drainage between the inner and outer tubes.

FIG. 30 illustrates one embodiment of an inner tube 2100 having machined windows 2102 formed therein. The windows 2102 allow drainage between the inner 2100 and an outer tube. This embodiment may be an alternative to the embodiment show in FIG. 21, for example.

Figure 31:
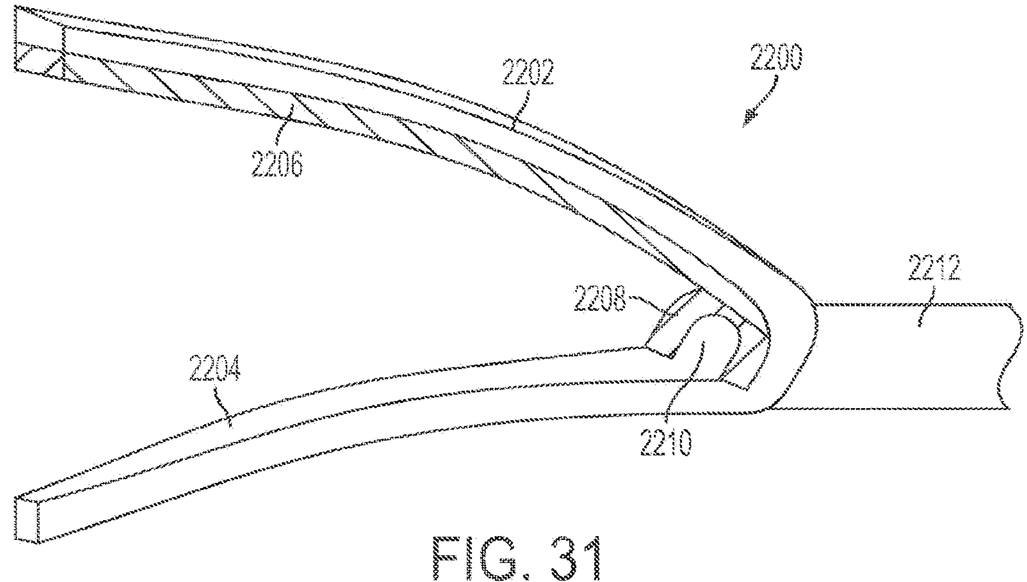
FIG. 31 illustrates one embodiment of an end effector assembly comprising a medical forceps having a movable jaw member and an ultrasonic blade where the movable jaw member includes a pad with a tissue stop to deflect surgical matter where the tissue stop portion is contoured to the movable jaw member to cover an opening of the inner tube.

FIG. 31 illustrates one embodiment of an end effector assembly 2200 comprising a medical forceps having a movable jaw member 2202 and an ultrasonic blade 2204. The movable jaw member 2202 comprises an extended clamp arm pad 2206 that follows the contour of the movable jaw member 2202 (e.g., clamp arm) into the space around the blade 2204 to cover the opening of the inner tube with a tissue stop element 2208. The tissue stop element 2208 deflects surgical matter and prevents it from entering the space between the blade 2204 and the inner tube 2212. The tissue stop element 2208 is contoured to the movable jaw member 2202 to cover an opening 2210 of the inner tube 2212. In one embodiment, the clamp arm pad 2206 is machined with the tissue stop 2208 element to provide minimal interference between the blade 2204 and the tube 2212. The pad 2206 and/or the tissue stop element 2208 may be made of a lubricious material such as Teflon to minimize the load on the blade 2204.

Figure 38:
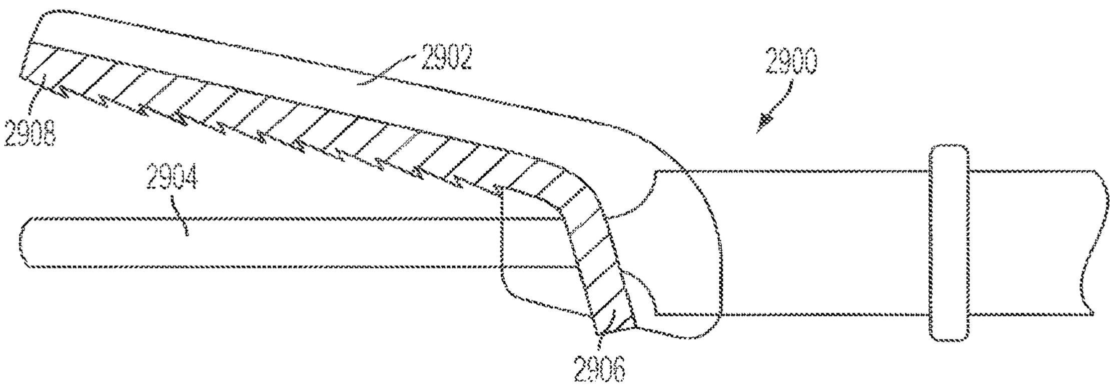
FIG. 38 illustrates one embodiment of an end effector assembly comprising a medical forceps having a movable jaw member and an ultrasonic blade where the movable jaw member comprises a deflector pad to deflect surgical matter.

FIG. 38 illustrates one embodiment of an end effector assembly 2900 comprising a medical forceps having a movable jaw member 2902 and an ultrasonic blade 2904. The movable jaw member 2902 comprises a clamp arm pad 2908 having a deflector pad 2906 to deflect surgical matter.

Figure 39:
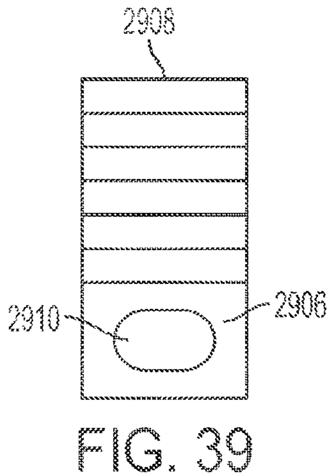
FIG. 39 is a front view of the deflector pad shown in FIG. 38, according to one embodiment.

FIG. 39 is a front view of the clamp arm pad 2908 and deflector pad 2906 shown in FIG. 38. An aperture 2910 is provided in the deflector pad 2906 to receive the ultrasonic blade 2904 therethrough.

Figure 33:
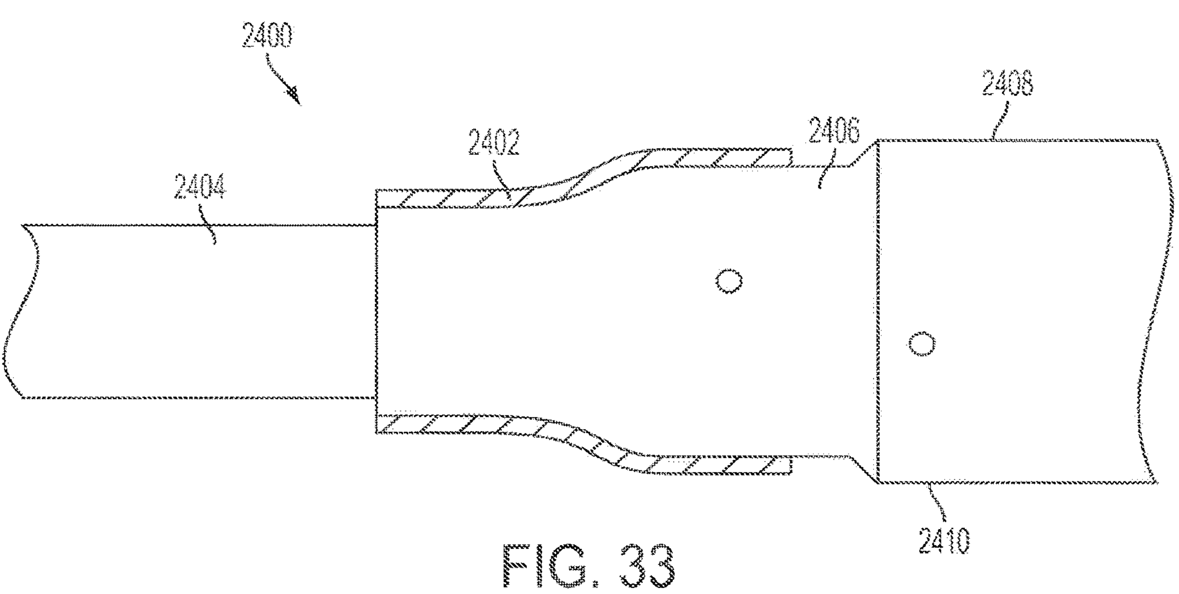
FIG. 33 illustrates a portion of an end effector assembly comprising an ultrasonic blade including one embodiment of a flexible seal to seal the ultrasonic blade to a tube at a distal node, according to one embodiment.

FIG. 33 illustrates a portion of an end effector assembly 2400 comprising an ultrasonic blade 2404 including one embodiment of a boot barrier 2402 to seal the ultrasonic blade 2404 to a tube 2406 distal to the distal node 2410 of the blade. In one embodiment, the boot barrier 2402 seals the blade 2404 to an inner tube 2406 which is disposed within an outer tube 2408. In the embodiment illustrate din FIG. 33, the boot barrier 2402 may be formed of FEP to cover high stress regions of the blade 2404. In the illustrated embodiment, the outer tube 2408 ends at a blade distal node 2410.

Figure 34:
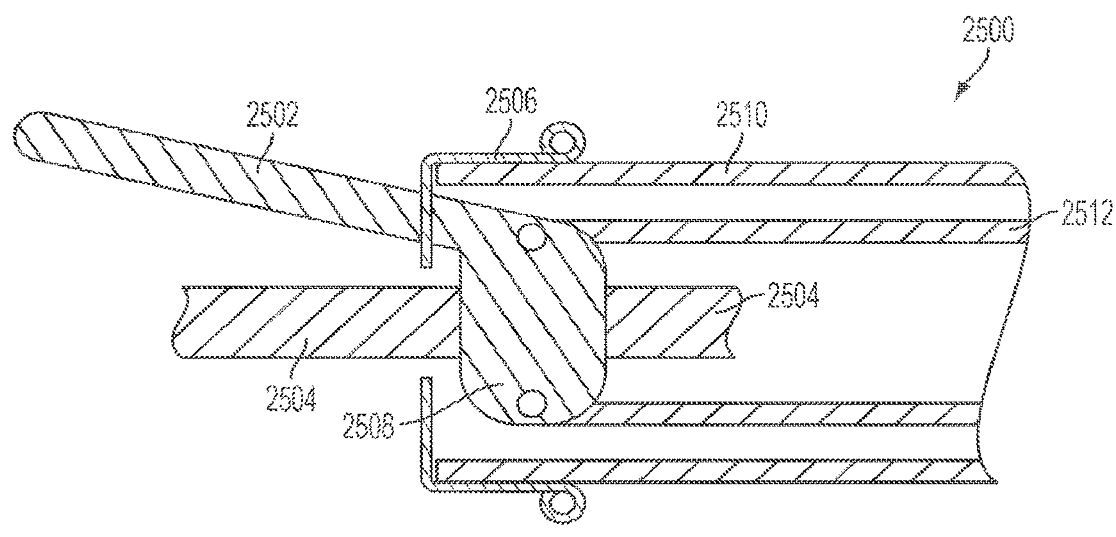
FIG. 34 illustrates one embodiment of an end effector assembly comprising a medical forceps having a movable jaw member and an ultrasonic blade including a flexible seal positioned distal to an edge of the movable jaw member and anchored to a tube to prevent tissue pinching.

FIG. 34 illustrates one embodiment of an end effector assembly 2500 comprising a medical forceps having a movable jaw member 2502 and an ultrasonic blade 2504 including a flexible seal 2506 positioned distal to an edge 2508 of the movable jaw member 2502 and anchored to an outer tube 2510 to prevent tissue pinching. An inner tube 2512 is positioned within the outer tube 2510. The blade 2504 is positioned within the inner tube 2512.

Figure 35:
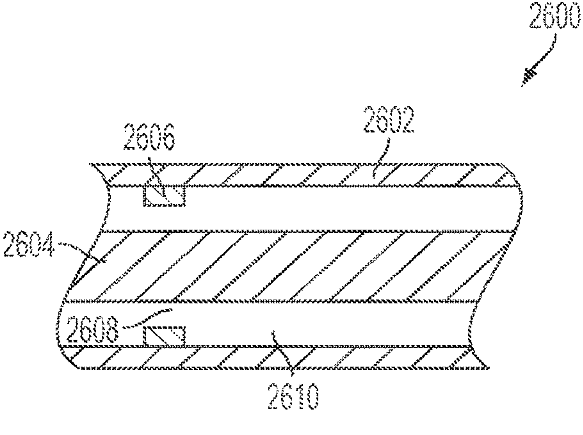
FIG. 35 illustrates one embodiment of a seal positioned within an inner tube and an ultrasonic blade positioned within the inner tube.

FIG. 35 illustrates one embodiment of an end effector assembly 2600 comprising a seal 2606 positioned within an inner tube 2602 and an ultrasonic blade 2604 positioned within the inner tube 2602 such that it is non-visible to the user. The seal 2602 may either be a low friction material to minimize load on the blade 2604 or a small clearance 2608 may be provided between the seal 2606 and the blade 2604 to prevent contact with the blade. The seal 2606 seals the space 2610 defined between the blade 2604 distal to the distal seal and an inner diameter of the inner tube 2602 to prevent the accumulation of surgical matter therein.

Figure 36:
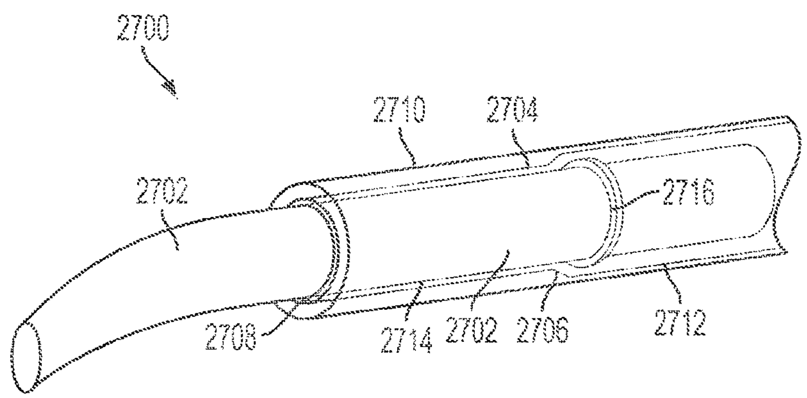
FIG. 36 illustrates one embodiment of a seal mechanism for an ultrasonic blade having a tapered inner tube portion distal to the last seal where the inner tube necks down to a smaller diameter at a distal end defining a reduce entry space for surgical matter.

FIG. 36 illustrates one embodiment of a seal mechanism 2700 for an ultrasonic blade 2702 having a tapered inner tube 2704 portion distal to the blade distal seal 2716 where the inner tube 2704 necks down 2706 to a smaller diameter at a distal end defining a reduced entry space 2708 for surgical matter. A conventional outer tube 2710 is provided over the tapered inner tube 2704. The diameter of the inner tube portion 2712 proximal to the necked down region 2706 is greater than the diameter of the inner tube portion 2714 distal to the necked down region 2706. In one embodiment, the necked down region 2706 coincides with the location just distal to the distal-most overmold 2716. In one embodiment, the inner tube 2704 may be necked down for a portion distal to the distal-most seal, to provide less open space for fluids and solids to enter.

Figure 37:
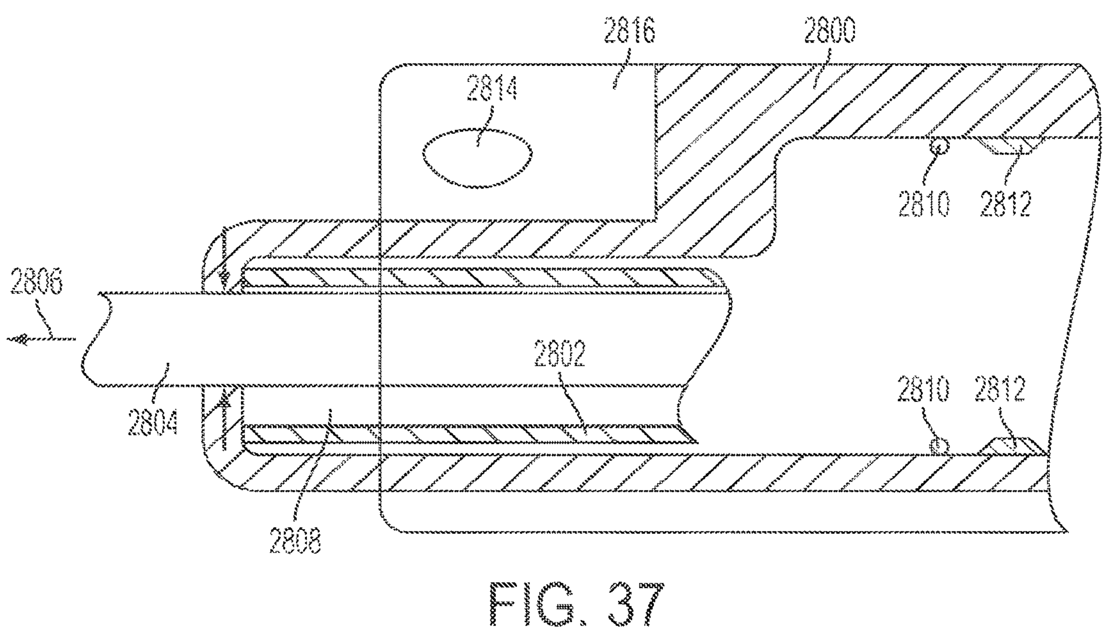
FIG. 37 illustrates one embodiment of an overmolded flexible seal located over an inner tube that an ultrasonic blade punctures through during assembly.

FIG. 37 illustrates one embodiment of an overmolded flexible seal 2800 located over an inner tube 2802 that an ultrasonic blade 2804 punctures through during assembly. As shown, as the blade 2804 is moved distally in direction 2806 during device assembly, the blade 2804 breaks through the overmolded flexible seal 2800 to seal the space 2808 between the blade 2804 and the inner tube 2802. A clamp arm pivot hole 2814 in the outer tube distal clevis 2816 enables a movable jaw member to open and close. An outer tube distal clevis 2816 is located on a distal end of an outer tube. In one embodiment, the clevis 2816 can be welded on the distal end of the outer tube.

Figure 40:
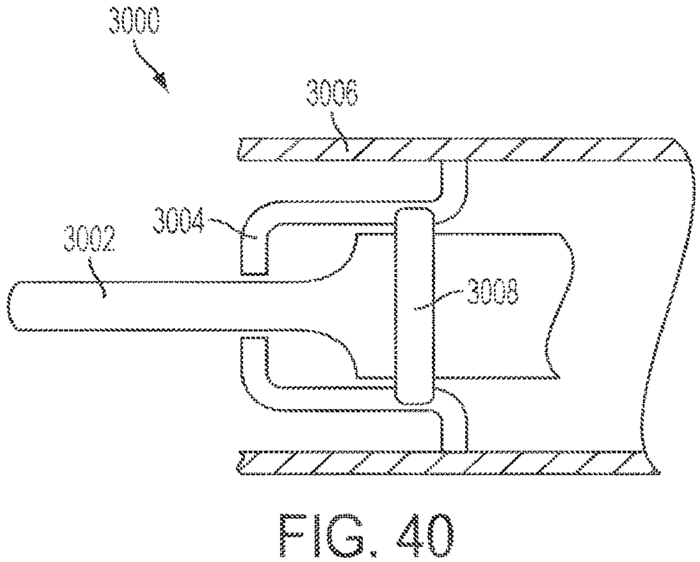
FIG. 40 illustrates one embodiment of a seal system for an ultrasonic blade.

FIG. 40 illustrates one embodiment of a seal system 3000 for an ultrasonic blade 3002. A flexible seal 3004 seals the ultrasonic blade 3002 distal to a distal seal portion 3008. In one embodiment, the flexible seal 3004 seals the blade 3002 to the inner diameter of the inner tube 3006.

Figures 41, 42:
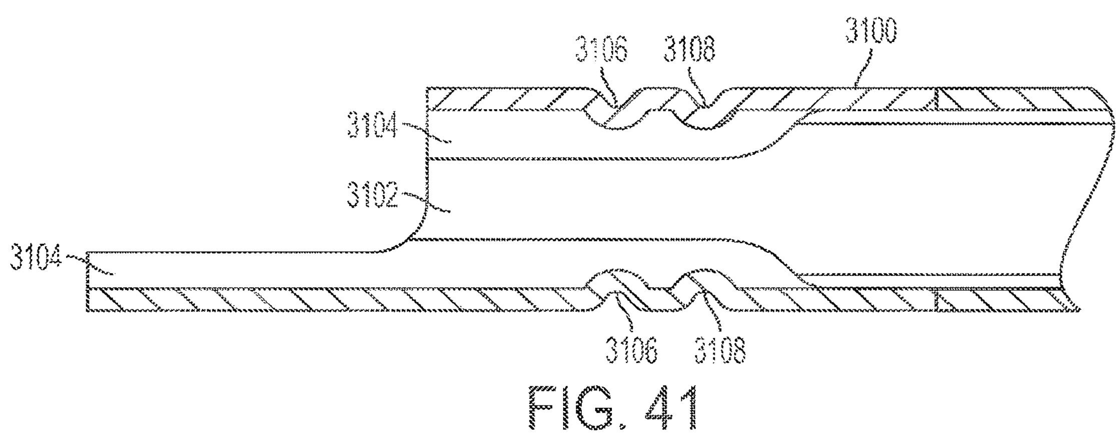
FIG. 41 illustrates one embodiment of a contoured inner tube or component that attaches to an inner tube to provide a circuitous path for fluid.
FIG. 42 illustrates one embodiment of a molded component with compliant arms that serve to block the distal opening of a tube assembly and is attached via the arms going around a pin in the blade at a node location.

FIG. 41 illustrates one embodiment of a contoured inner tube 3102 or component that attaches to an inner tube 3100 to provide a circuitous path 3104 for fluid. An area of the inner tube 3100 comprises a locally swaged pair of grooves 3106, 3108 that may be employed to locate an O-ring that would touch the blade or provide a circuitous path to prevent ingress of fluids during use.

FIG. 42 illustrates one embodiment of a molded component 3110 with compliant arms that serves to block the distal opening of a tube assembly and is attached via arms going around a pin in the blade at a node location.

Figure 43:
FIG. 43 illustrates one embodiment of an overmolded silicone bumper that adheres to the inside of an inner tube.
Figure 43:
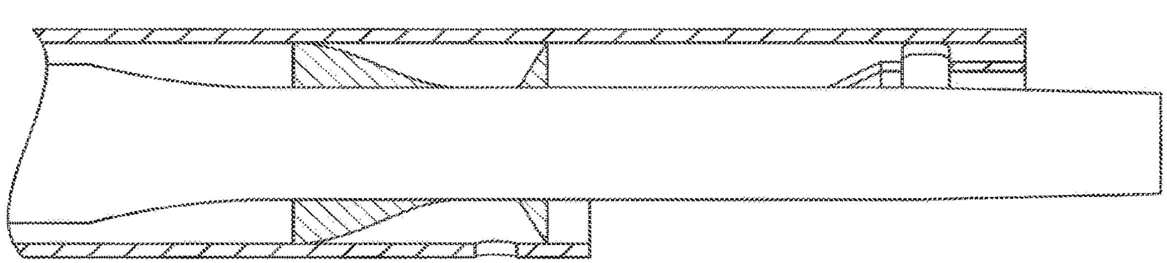
Figure 44:
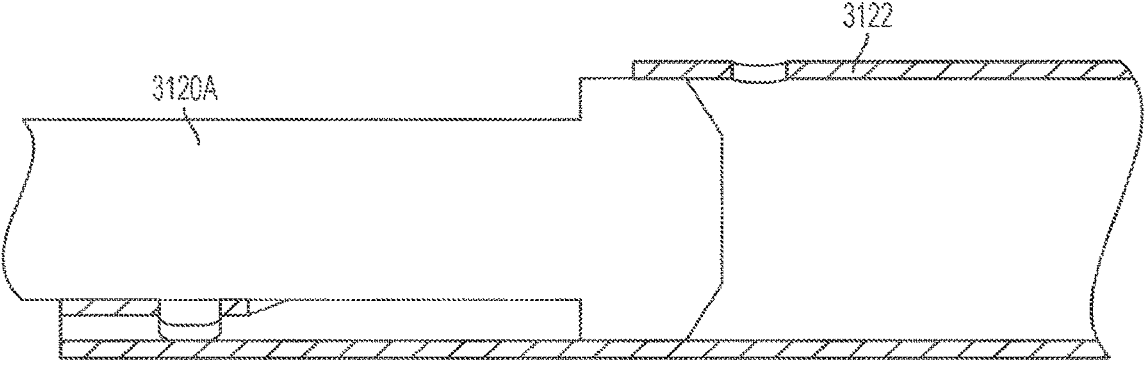
FIGS. 44-47 illustrate one embodiment of how a pair of mandrels can be inserted into an inner tube from both ends to form the overmolded bumper in FIG. 43.
Figure 45:
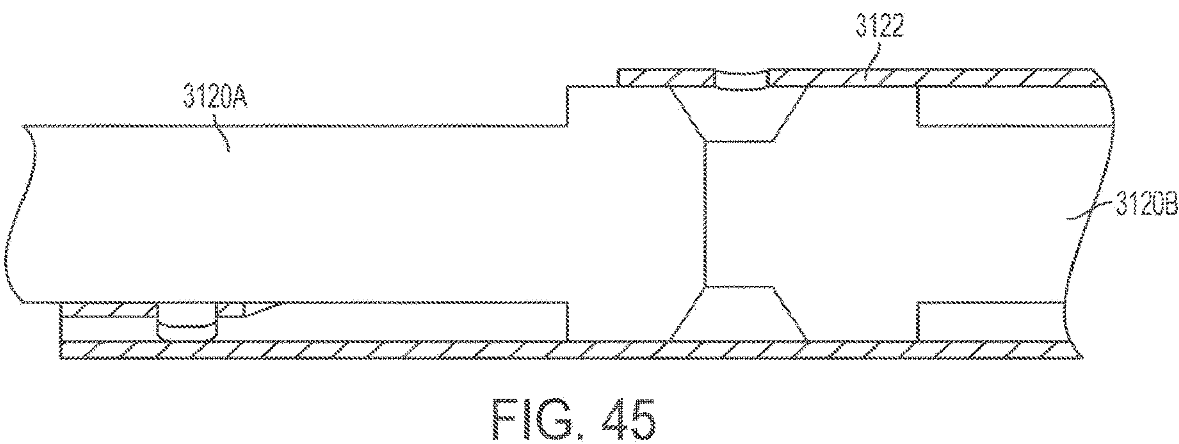
Figure 46:
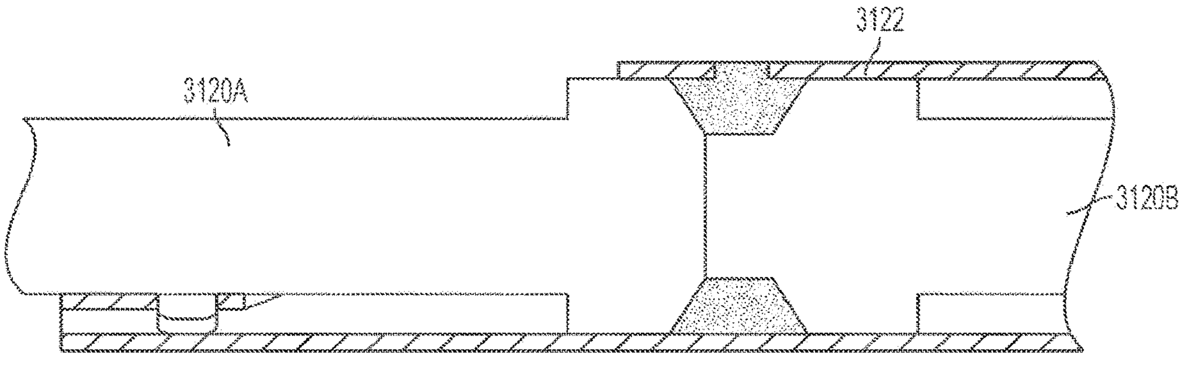

FIG. 43 illustrates one embodiment of an overmolded silicone bumper 3112 that adheres to the inside of an inner tube. The bumper 3112 prevents fluid ingress and does not nominally touch the blade so there is no increase in blade loading during use.

FIGS. 44-47 illustrate one embodiment of how a pair of mandrels 3120A, 3120B can be inserted into an inner 3122 tube from both ends. The mandrels 3120A, 3120B combine to form an overmold channel into which the silicone (or equivalent) bumper 3124 material would be injected. The mandrels would then be removed leaving just the bumper 3124.

Figures 47, 48:
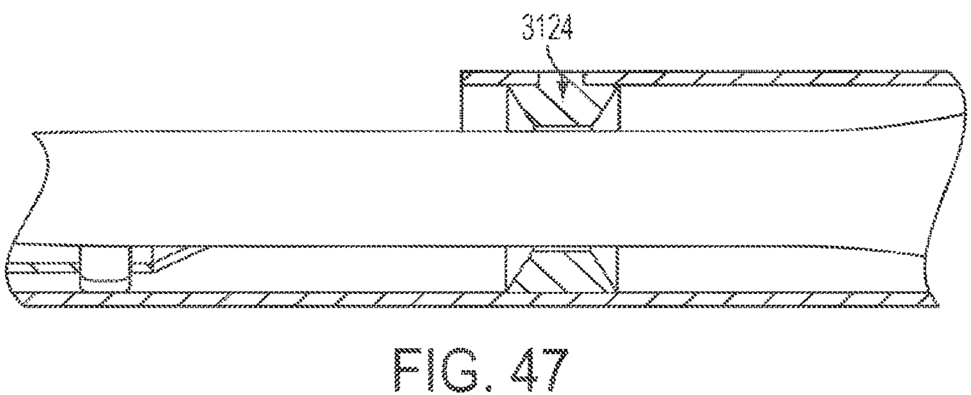
FIG. 48 illustrates one embodiment of an overmolded material affixed to an inner tube that does not seal to the ultrasonic blade.

FIG. 48 illustrates an end view of a seal system 3200 comprising an overmolded bumper 3124 affixed to an inner tube 3202 that does not seal to an ultrasonic blade 3204. In the illustrated embodiment, the seal system 3200 is an end view of the tube assembly shown in FIG. 47 with the molded bumper 3124 in place.

Figure 50:
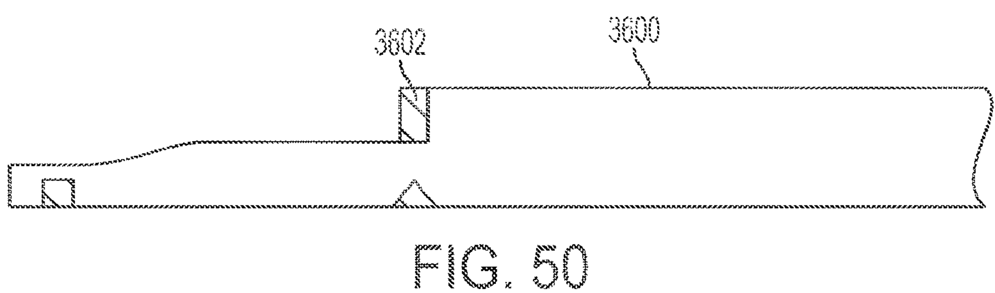
FIG. 50 illustrates one embodiment of an inner tube having a silicone seal attached thereto at minimal interference with ultrasonic blade.

FIG. 50 illustrates one embodiment of an inner tube 3600 comprising having a silicone seal 3602 attached thereto at minimal interference with an ultrasonic blade.

Figure 51:
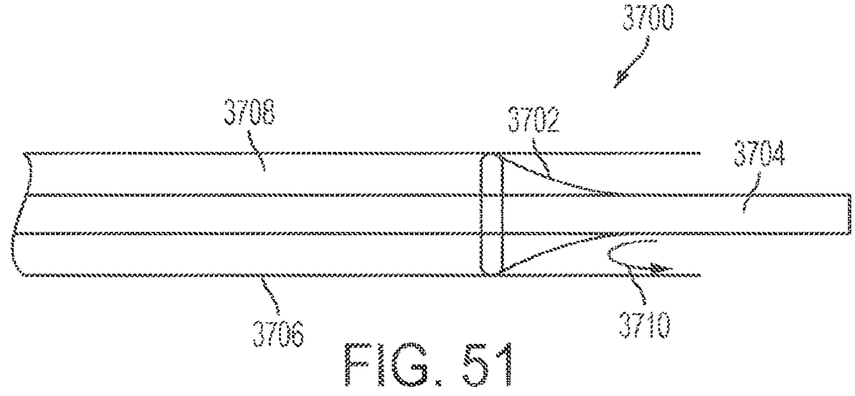
FIG. 51 illustrates one embodiment of seal system for sealing an ultrasonic blade to a tube.

FIG. 51 illustrates one embodiment of seal system 3700 for sealing an ultrasonic blade 3704 to a tube 3706. In the illustrated embodiment, the sealing system 3700 comprises a funnel 3702 to prevent ingress of surgical matter in the space 3708 between the blade 3704 distal to the distal node and the inner tube 3706. The funnel 3702 deflects surgical matter distally 3710.

Figure 52:
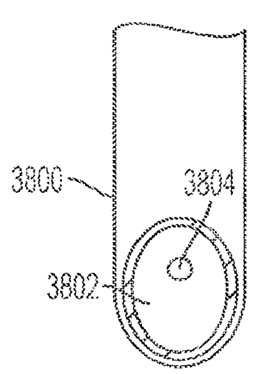
FIG. 52 illustrates one embodiment of a flexible seal located over an inner tube that an ultrasonic blade punctures through during assembly.

FIG. 52 illustrates one embodiment of a flexible seal 3802 located over an inner tube 3800 that an ultrasonic blade punctures through and dilates at location 3804 during assembly.

Figure 53:
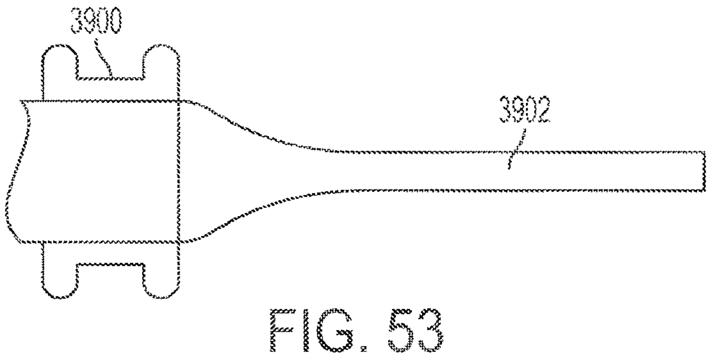
FIG. 53 illustrates one embodiment of an overmolded flexible seal attached to an ultrasonic blade distal of a distal seal.

FIG. 53 illustrates one embodiment of an overmolded flexible seal 3900 attached to an ultrasonic blade 3902 distal of the distal node.

Figure 54:
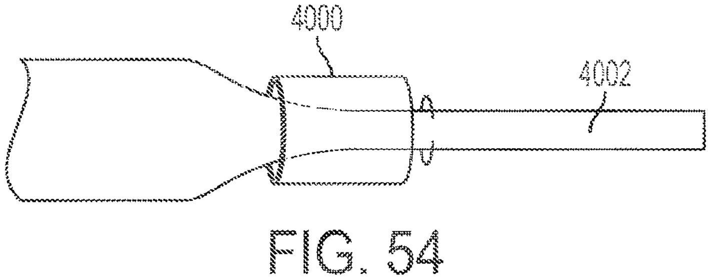
FIG. 54 illustrates one embodiment of an overmolded flexible seal attached to an ultrasonic blade distal of a distal seal.

FIG. 54 illustrates one embodiment of an overmolded flexible seal 4000 attached to an ultrasonic blade 4002 distal of the distal node. In one embodiment, the overmolded flexible seal 4000 is made from an FEP material.

Figure 55:
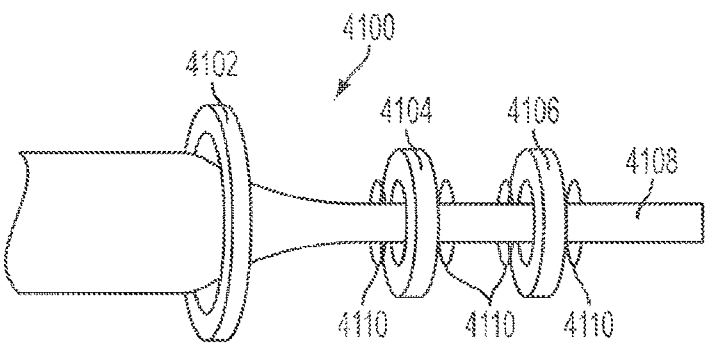
FIG. 55 illustrates one embodiment of a sealing system comprising multiple toroidal seals to seal an ultrasonic blade distal of a distal seal.

FIG. 55 illustrates one embodiment of a sealing system 4100 comprising multiple toroidal seals 4102, 4104, 4106 to seal an ultrasonic blade 4108 distal of the distal node. The toroidal seals 4102, 4104, 4106 are suspended by small overmolded features 4110 that do not interfere with the blade 4108.

Figure 56:
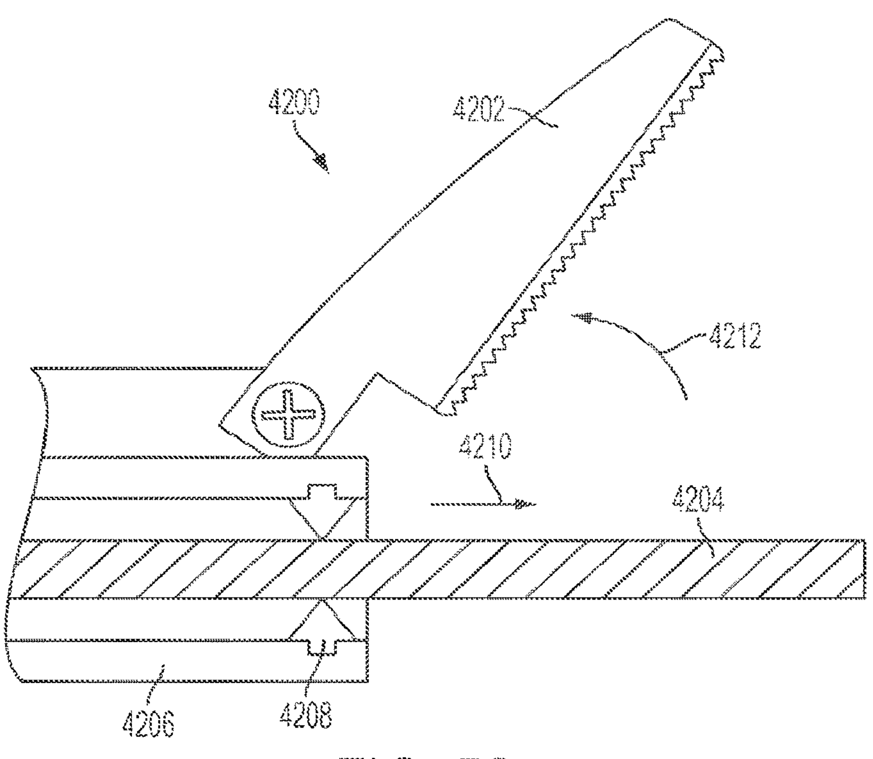
FIG. 56 illustrates one embodiment of an end effector assembly comprising a medical forceps having a movable jaw member in an open position, an ultrasonic blade, and a slidably movable inner tube including a wiping seal.

FIG. 56 illustrates one embodiment of an end effector assembly 4200 comprising a medical forceps having a movable jaw member 4202 in an open position, an ultrasonic blade 4204, and a slidably movable inner tube 4206 including a wiping seal 4208. As illustrated in FIG. 56, the slidably movable inner tube 4206 moves distally in direction 4210 as the jaw member 4212 opens in direction 4212. The wiping seal 4208 surrounds the blade 4204. As the jaw member 4202 opens in direction 4212 the wiping seal 4208 moves distally in direction 4210 along with the inner tube 4206 to wipe surgical matter off the blade 4204.

Figure 57:
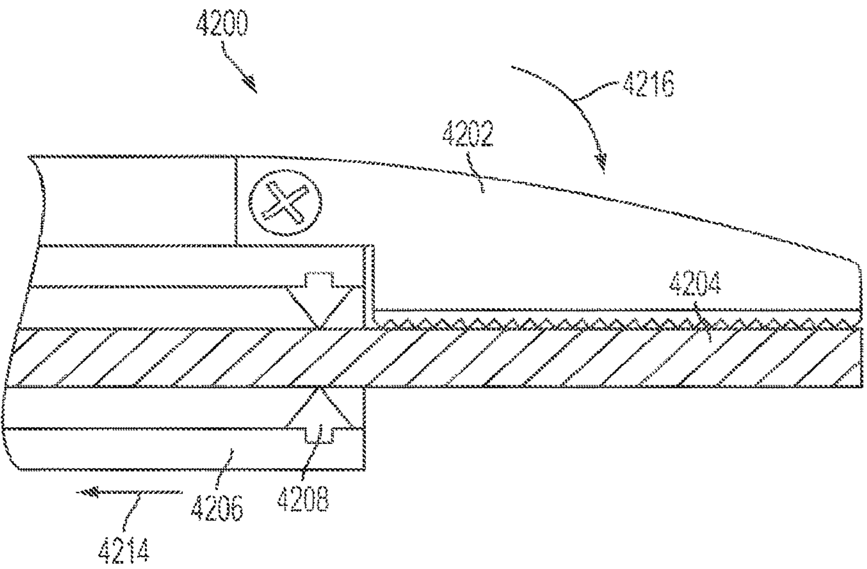
FIG. 57 illustrates one embodiment of the end effector assembly shown in FIG. 56 comprising a medical forceps having a movable jaw member in a closed position.

FIG. 57 illustrates one embodiment of the end effector assembly 4200 shown in FIG. 56 comprising a medical forceps having a movable jaw member 4202 in a closed position. As shown in FIG. 57, as the jaw member 4202 closes in direction 4216, the inner tube 4206 moves proximally in direction 4214 to retract the wiping seal 4208. To wipe the blade 4204 with the wiping seal 4208, the jaw member 4202 is opened as described in connection with FIG. 56.

Figure 58:
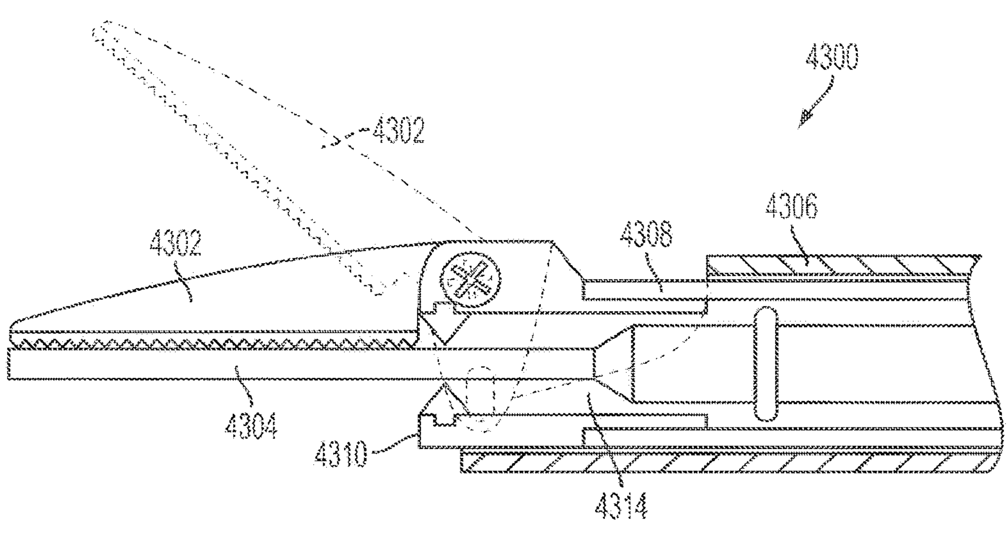
FIG. 58 illustrates one embodiment of an end effector assembly comprising a medical forceps having a movable jaw member in an open position shown in phantom line and a closed position shown in solid line, an ultrasonic blade, a slidably movable outer tube, and a fixed inner tube with a flexible seal located over the blade.

FIG. 58 illustrates one embodiment of an end effector assembly 4300 comprising a medical forceps having a movable jaw member 4302 in a closed position shown in solid line and in an open position shown in phantom line, an ultrasonic blade 4304, a slidably movable outer tube 4306, and a fixed inner tube 4308 with an overmolded flexible seal 4310 located on the inner tube 4308 over the blade 4304.

Figure 59:
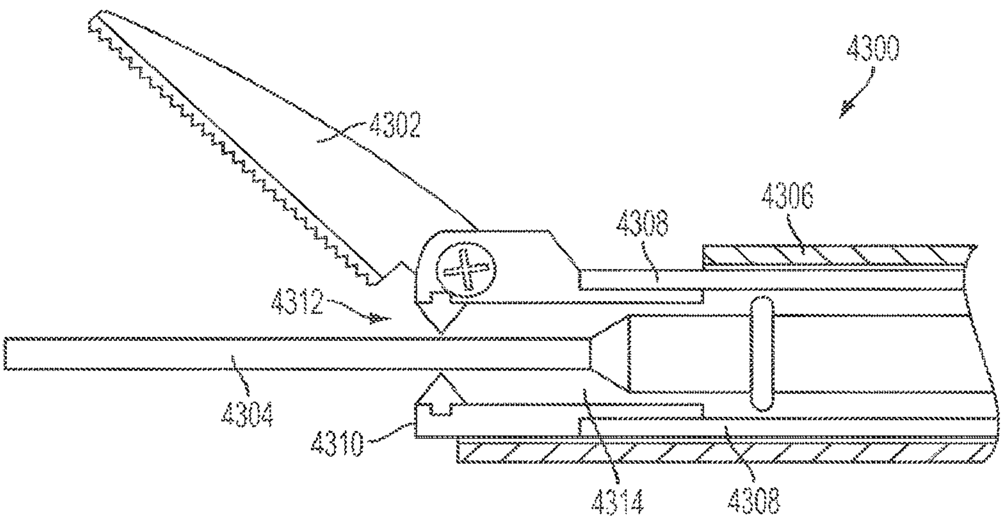
FIG. 59 illustrates one embodiment of an end effector assembly comprising a medical forceps having a movable jaw member in an open position, an ultrasonic blade, a slidably movable outer tube, and a fixed inner tube with a flexible seal overmolded on the inner tube.

FIG. 59 illustrates one embodiment of the end effector assembly 4300 comprising the movable jaw member 4302 in an open position. As shown in FIG. 59, as the jaw member 4202 is opened the overmolded flexible seal 4310 seals the throat 4312 of the device to prevent surgical matter from entering the space 4314 between the blade 4304 and the inner tube 4308.

Alternate Closure Mechanisms for Ultrasonic Devices

Present ultrasonic devices utilize a tube-in-tube (TnT) closure mechanism to enable closure of the clamp arm, referred to herein as a movable jaw member, against an active length of the ultrasonic blade. The following embodiments of alternate closure mechanisms for ultrasonic devices may yield several advantages. For example, there may be differences among the drag force of actuating the inner tube against the outer tube results in variation in device clamp force. Additionally, the pivot location of the clamp arm on the outer tube causes a sharp angular closure, and magnifies the impact to a non-uniform closure profile. Furthermore, the predicate device mechanism may be sensitive to variation in components, as the stackup links the inner and outer tube at the location of the insulated pin, which currently sits near the proximal end of the tube assembly.

One embodiment of an ultrasonic device comprising an alternate closure mechanism is described hereinbelow in connection with FIGS. 60-62. In one embodiment, the ultrasonic device comprises a vibrating blade with a through hole at distal node, an actuator mechanism, an outer tube with cam surfaces at a distal end, and a clamp arm. In another embodiment, the clamp arm is rotatedly fixed to the vibrating blade. In another embodiment, the clamp arm is cammed open and closed (against vibrating blade) through relative motion between the outer tube and vibrating blade. In yet another embodiment, one or more pivots of the clamp arm are positioned at a distal node of the vibrating blade. An illustrative example is discussed hereinbelow.

Figures 60, 61, 62:
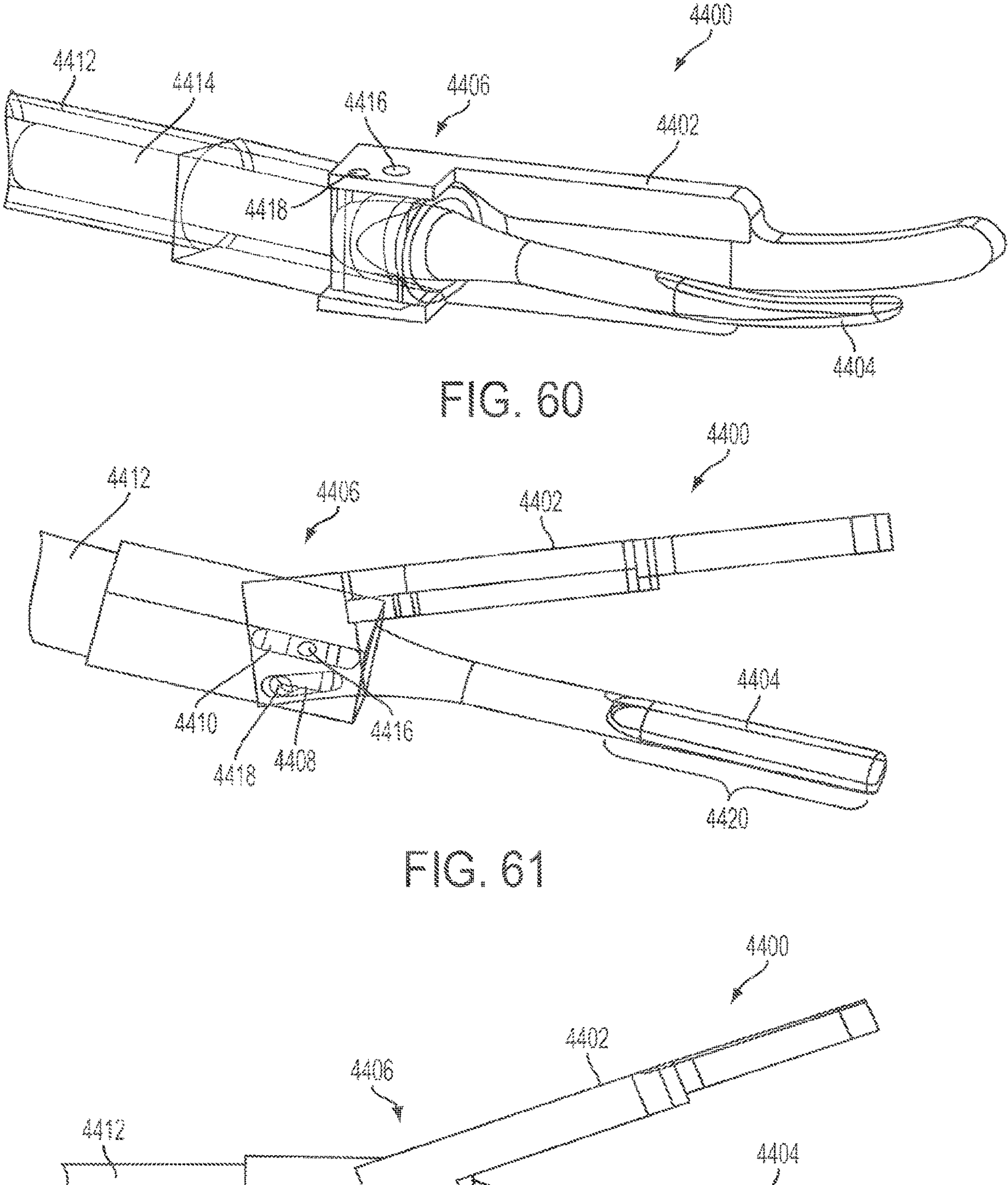
FIG. 60 is a perspective view of one embodiment of an end effector assembly comprising a medical forceps having a movable jaw member and an ultrasonic blade where the movable jaw member is rotatably attached to a distal node.
FIG. 61 is a side view of one embodiment of the end effector assembly shown in FIG. 60 with the movable jaw member in an open position and shown transparent to show outer tube cam slots to rotate the movable jaw member upon relative motion between the blade and the outer tube.
FIG. 62 illustrates one embodiment of the end effector assembly shown in FIG. 60 showing the movable jaw member pivot.

FIG. 60 is a perspective view of one embodiment of an end effector assembly 4400 comprising a medical forceps having a movable jaw member 4402 and an ultrasonic blade 4404 where the movable jaw member is rotatably attached to a distal node 4406. The outer tube 4412 is shown transparent to show the ultrasonic waveguide 4414 located therein. FIG. 61 is a side view of the end effector assembly 4400 shown in FIG. 60 with the movable jaw member 4402 in an open position and shown transparent to show outer tube cam slots 4408, 4410 to rotate the movable jaw member 4402 upon relative motion between the blade 4404 and the outer tube 4412. FIG. 62 illustrates one embodiment of the end effector assembly 4400 showing the movable jaw member 4402 pivot 4416.

With reference now to FIGS. 60-62, in one embodiment, the movable jaw member 4402 (e.g., clamp arm) is rotatably anchored directly to the blade 4404. The anchoring is accomplished through eliminating the inner tube and attaching the movable jaw member 4402 at the most distal node 4406 of the blade 4404 so as not to interfere with the acoustical train of the device. The attachment may be made through the use of a through hole and insulated pin 4416 attached to the movable jaw member 4402, although other attachment means may be used and are contemplated, such as, for example, pins, screws, snap fits, overmolds or the like. Additionally, the outer tube 4412 contains a cam surface, which locates a second pin 4418 attached to the movable jaw member 4402 such that the movable jaw member 4402 rotates about the pivot at pin 4416 in the blade 4404 when there is relative motion between the blade 4404 and the outer tube 4412. Furthermore, additional geometries for the cam surface are contemplated, such as splines, curves, and the like. As shown in the embodiment of FIG. 62, the pivot location at pin 4416 is positioned in a more proximal location than current devices. The benefits of anchoring the movable jaw member 4402 to the blade 4404 at the distal node 4406 allows for a more parallel closure along the active portion 4420 of the blade 4404, ultimately creating a more uniform pressure profile. In one embodiment, the configuration described in connection with FIGS. 60-62 operates at lower temperatures and can eliminate the need for a polyimide clamp arm pad within the movable jaw member 4402. Although not shown in the embodiment of FIG. 62, the outer tube 4412 may extend longitudinally along the axis of the blade, to prevent tissue from contacting the non-active blade 4404 surface Another embodiment of an ultrasonic device comprising an alternate closure mechanism is described in connection with FIGS. 63-67 hereinbelow. The current closure mechanism experiences frictional losses caused by the relative motion of the inner tube against the outer tube and the inner tube against the blade overmolds. These frictional losses can be attributed to decreased tissue feedback experienced by users. In addition, the clamp force and pressure profile associated with tube-in-tube closure may be sensitive to component variation. More consistent sealing and transection ability can be achieved either by tighter tolerances or decreasing the number of components involved in closure. To address these and other issues, in one embodiment the ultrasonic device comprises a vibrating blade with a hole through the distal node, an outer tube, a clamp arm, and a rigid link. In another embodiment, the clamp arm is coupled to the vibrating blade with a rigid link and system of revolute joints. An illustrative example is discussed hereinbelow.

Figure 63:
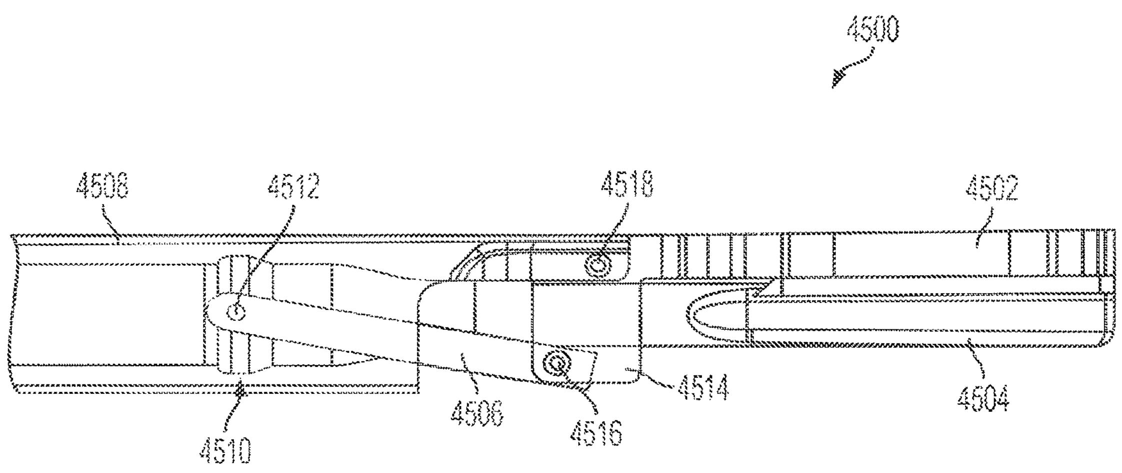
FIG. 63 is a side view of one embodiment of an end effector assembly comprising a medical forceps having a movable jaw member in a closed position and an ultrasonic blade, the end effector assembly comprising a linkage to open and close the movable jaw member by employing relative motion between the outer tube and the blade.
Figure 64:
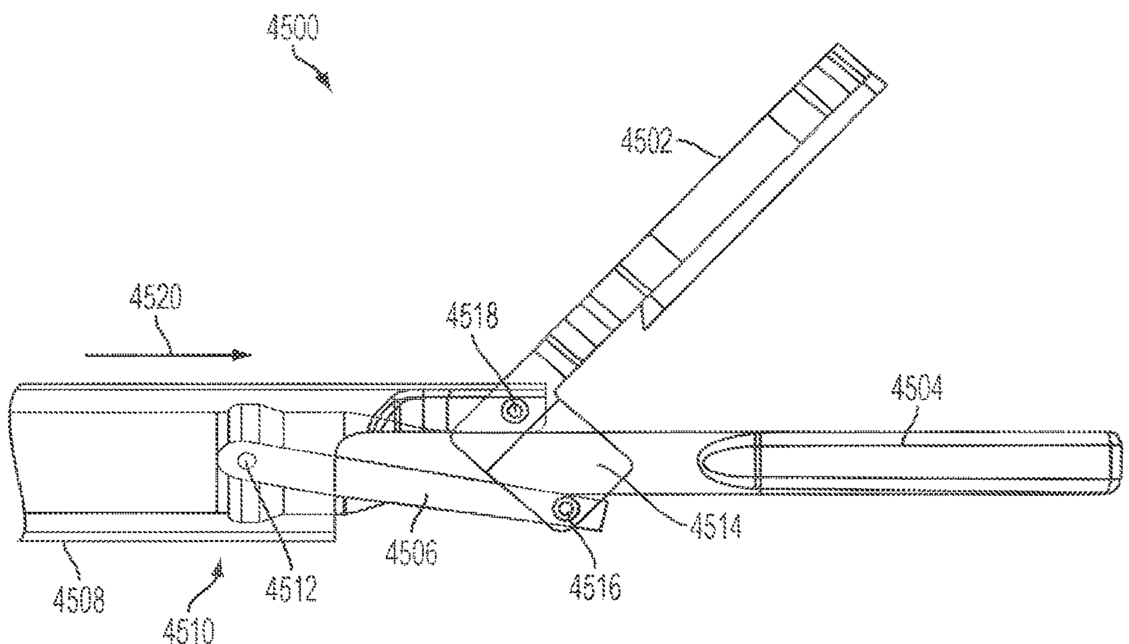
FIG. 64 is a side view of the end effector assembly shown in FIG. 63 with the movable jaw member in an open position, according to one embodiment.
Figure 65:
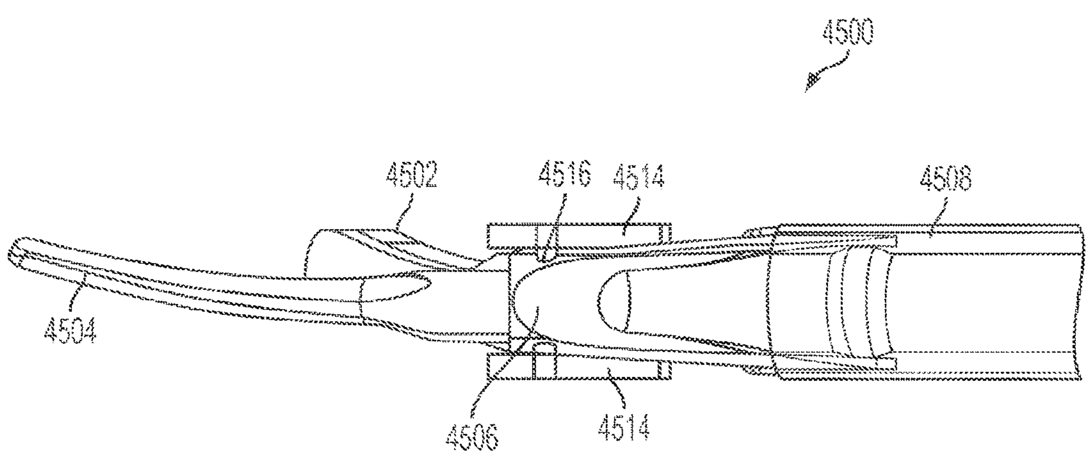
FIG. 65 is a bottom view of the end effector assembly shown in FIG. 63 with the movable jaw member in an open position, according to one embodiment.
Figure 66:
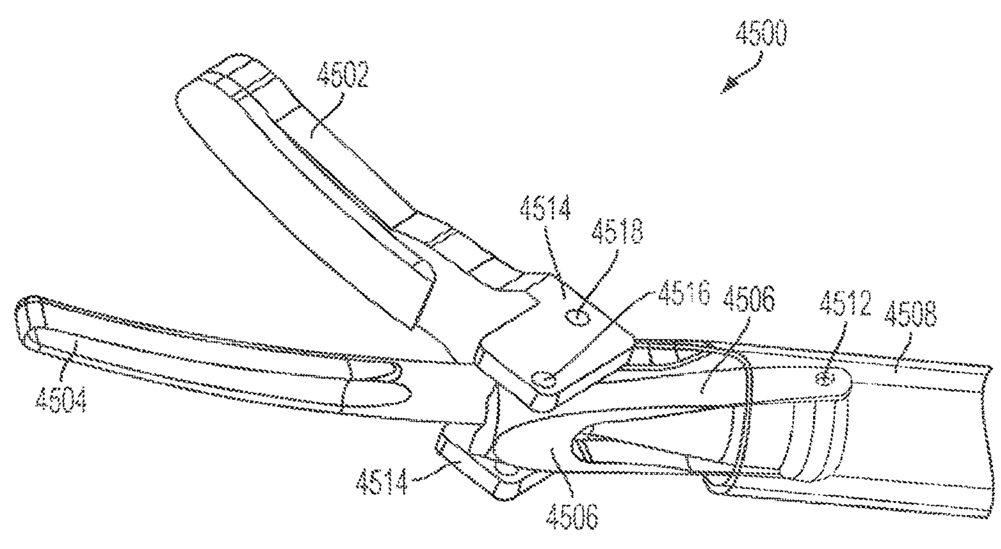
FIG. 66 is a perspective view of the end effector assembly shown in FIG. 63 with the movable jaw member in an open position, according to one embodiment.
Figure 67:
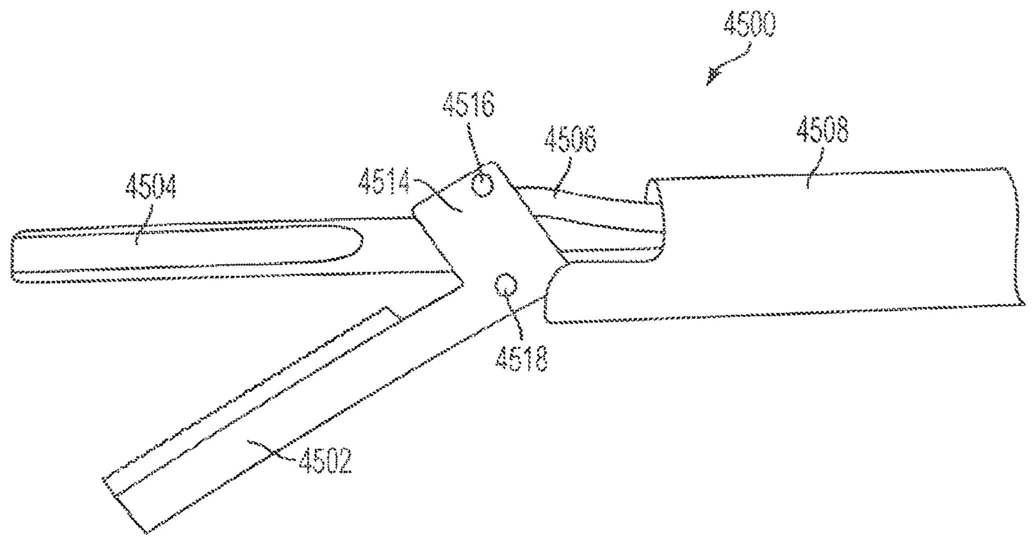
FIG. 67 is a perspective view of the end effector assembly shown in FIG. 63 with the movable jaw member in an open position, according to one embodiment.

FIG. 63 is a side view of one embodiment of an end effector assembly 4500 comprising a medical forceps having a movable jaw member 4502 in a closed position and an ultrasonic blade 4504. The end effector assembly 4500 comprises a linkage 4506 to open and close the movable jaw member 4502 by employing relative motion between the outer tube 4508 and the blade 4504. FIG. 64 is a side view of the end effector assembly 4500 shown in FIG. 63 with the movable jaw member 4502 in an open position. FIG. 65 is a bottom view of the end effector assembly 4500 shown in FIG. 63 with the movable jaw member 4502 in an open position. FIG. 66 is a perspective view of the end effector assembly 4500 shown in FIG. 63 with the movable jaw member 4502 in an open position. FIG. 67 is a perspective view of the end effector assembly 4500 shown in FIG. 63 with the movable jaw member 4502 in an open position.

With reference now to FIGS. 63-67, in one embodiment, the linkage 4506 may be a four bar linkage configured to actuate the movable jaw member 4502 (e.g., clamp arm) by utilizing relative motion between the outer tube 4508 and the blade 4504. The inner tube may be replaced with the rigid link 4506. The link 4506 may be pinned to the blade 4504 through the distal node 4510, although other fastening means are contemplated such as pins, screws, snap fits, and the like. Locating a pin 4512 at the distal node 4510 minimizes interference to the acoustic train of the ultrasonic device. The link 4506 is subsequently pinned to a bottom portion 4514 of the movable jaw member 4502 via pin 4516 and a second pivot of the movable jaw member 4502 is pinned to an end of the outer tube 4508 via pin 4518. Clamping may be achieved by displacing the outer tube 4508 forward relative to the blade 4504 in direction 4520. The link 4506 component ensures that the distance between the distal node 4510 and the lower pivot of the clamp arm remains constant. The presence of the link 4506 forces the movable jaw member 4502 to rotate as the outer tube 4508 is displaced in direction 4520. In one embodiment, the rigid link 4506 may comprise a small stainless steel component formed from progressive stamping, although other materials and manufacturing processes are contemplated, such as metal injection molding (MIM), polymers formed from plastic injection molding, and the like. The use of a rigid link 4506 also allows simplification of a trigger assembly. For example, a trigger assembly for actuating the inner tube may be removed. The use of a four bar linkage 4506 also reduces frictional losses in the tube assembly and results in a decrease in accumulated pressure profile variations.

Yet another embodiment of an ultrasonic device comprising an alternate closure mechanism is described in connection with FIGS. 68-70 hereinbelow. The embodiment illustrated in FIGS. 68-70 addresses issues such as tolerance accumulation between the blade, movable jaw member, inner tube, insulated pin, and rotation knob of existing ultrasonic devices.

Figure 68:
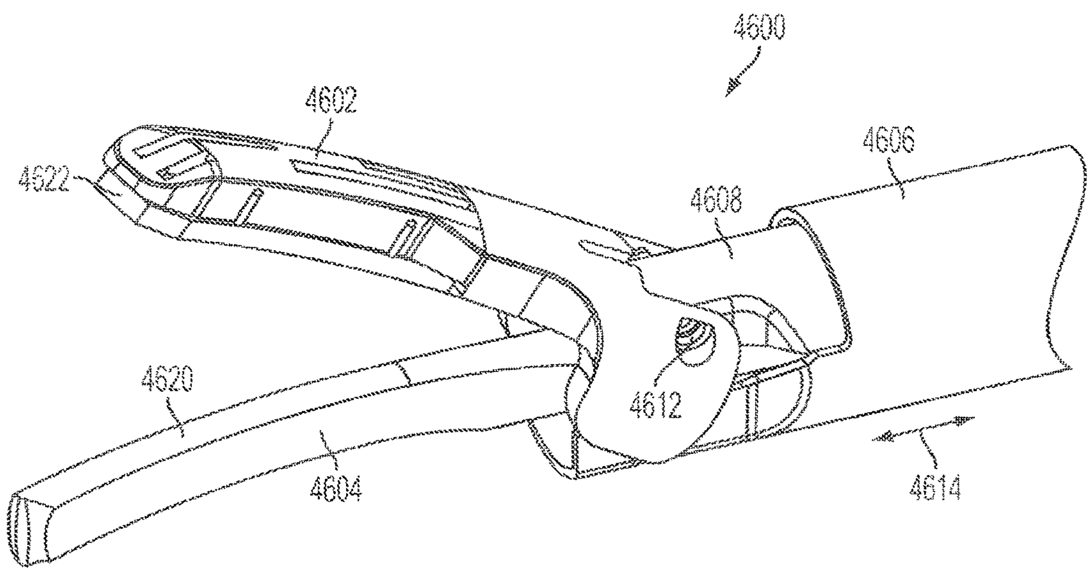
FIG. 68 is a perspective view of one embodiment of an end effector assembly comprising a medical forceps having a movable jaw member and an ultrasonic blade with the movable jaw member shown in an open position, where an outer tube is translated with respect to the blade to open and close the movable jaw member.

FIG. 68 is a perspective view of one embodiment of an end effector assembly 4600 comprising a medical forceps having a movable jaw member 4602 and an ultrasonic blade 4604 with the movable jaw member 4602 shown in an open position. An inner tube 4608 is translated with respect to the blade 4604 to open and close the movable jaw member 4602. FIG. 69 is a perspective view of the inner tube 4608 with the outer tube 4606 removed. The inner tube 4608 is operatively coupled to the end effector assembly 4600 shown in FIG. 68. FIG. 70 is a perspective view of a notch portion 4610 of the inner tube 4608 shown in FIG. 69.

Figure 69:
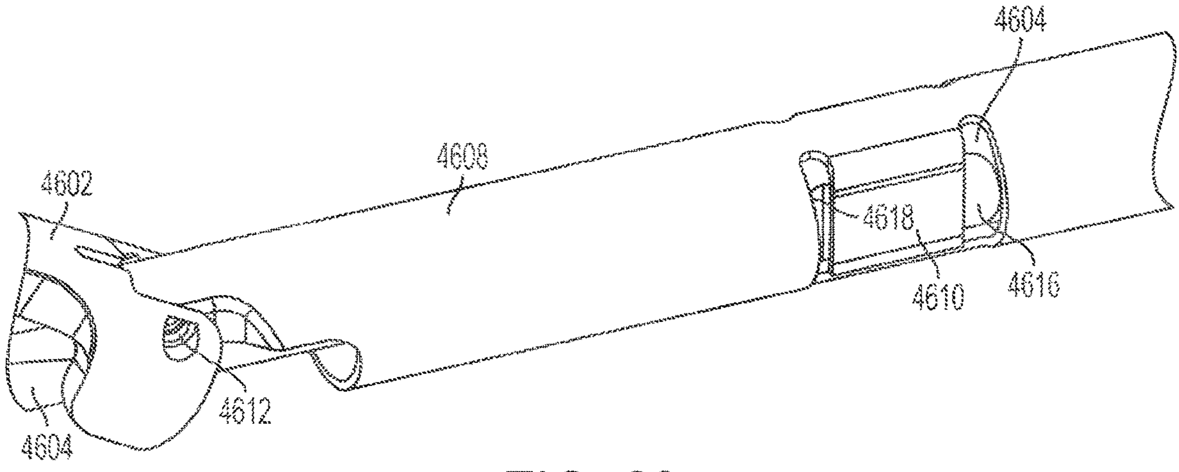
FIG. 69 is a perspective view of the inner tube with the outer tube removed, where the inner tube is operatively coupled to the end effector assembly shown in FIG. 68, according to one embodiment.
Figure 70:
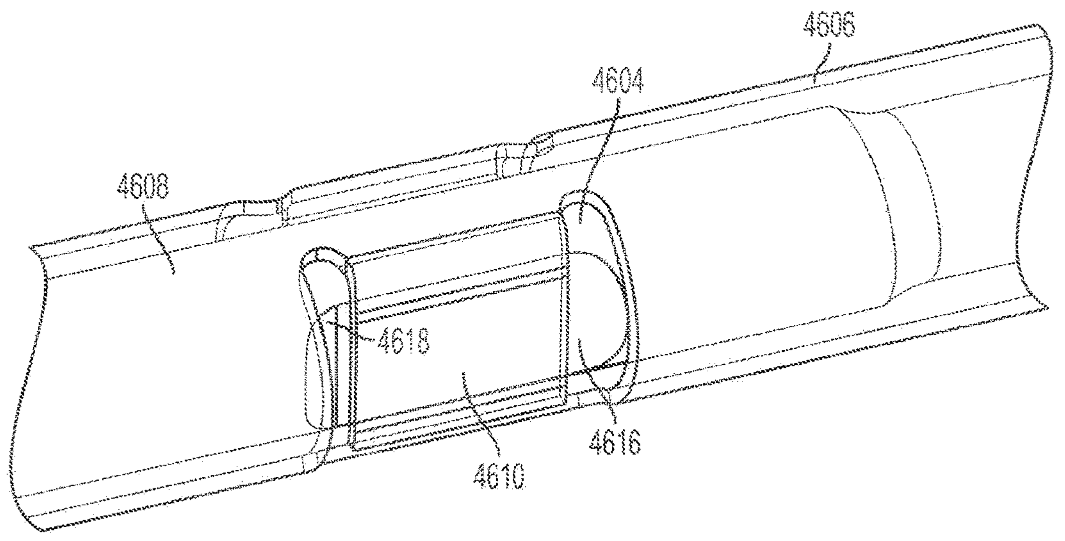
FIG. 70 is a perspective view of a notch portion of the inner tube shown in FIG. 69, according to one embodiment.

With reference now to FIGS. 68-70, in one embodiment, the inner tube 4608 is configured to translate with respect to the blade 4604 to move the movable jaw member 4602 (e.g., clamp arm) and to generate clamp pressure against the blade 4604. In the embodiment illustrated in FIGS. 68-70, the movable jaw member 4602 is attached and pivots at pivot 4612 on the inner tube 4608. The outer tube 4606 translates in direction 4614 to pivot the movable jaw member 4602. The inner tube 4608 has a notched region 4610 as shown in FIGS. 69 and 70, that is squeezed inwardly into notches 4616, 4618 formed in the blade 4604 that would be located at the node location of the blade 4604. In one embodiment, the blade 4604 portion in the notched region 4610 location may be coated with a thin layer of silicone overmold to provide tight relationship between the inner tube 4608 and the blade 4604. such tight relationship provides good movable jaw member 4602 clocking with respect to the blade 4604 cutting surface 4620 (FIG. 68). As shown in FIG. 68, in one embodiment, a clamp arm pad 4622 also may be provided on the inside portion of the movable jaw member 4602.

Figure 71:
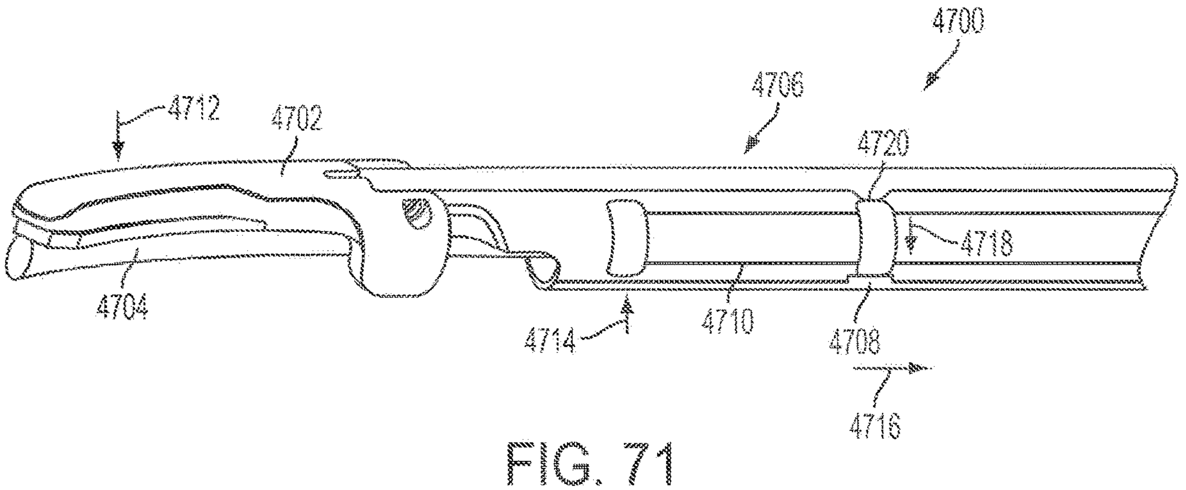
FIG. 71 illustrates one embodiment of an end effector assembly comprising a medical forceps having a movable jaw member in a closed position, an ultrasonic blade, and a shaft assembly configured to counteract deflection of the blade.

FIG. 71 illustrates one embodiment of an end effector assembly 4700 comprising a medical forceps having an end effector with a movable jaw member 4702 in a closed position, an ultrasonic blade 4704, and a shaft assembly 4706 configured to counteract deflection of the blade 4704. A counter deflection element 4720 is provided on an inner tube 4710 at one of the blade nodes 4718 proximal to the distal node 4714 to counteract deflection of the blade 4704 by the movable jaw member 4702. In one embodiment, a downward 4712 deflection of the blade 4704 by the movable jaw member 4702 is counteracted by the downward reaction force of counter deflection element 4720 at the node 4718 proximal to the distal node 4714. In one embodiment, the counter deflection element 4720 may comprise a bulge into the inner lumen to provide downward counter force to the clamping force. In another embodiment, a window 4708 may be cut into the inner tube 4710 to allow a downward force to deflect the blade 4704 without making contact with the opposing wall of the inner tube 4710.

Any of the inner tubes and/or outer tubes disclosed herein may be coated with a polymer used as moisture and dielectric barriers. Among them, parylene C may be selected due to its combination of barrier properties, cost, and other processing advantages. Parylene is the trade name for a variety of chemical vapor deposited poly(p-xylylene), for example. The polymer coating is used to prevent shorting in the shaft from the blade to adjacent metal parts. In one embodiment, the just the inner tube (e.g., actuator) may be coated to prevent it from shorting to the blade which is one "pole" in the combined ultrasonic and bipolar (RF) device, where the other "pole" is the outer tube and the clamp arm. The inner tube insulation provides a more robust and space efficient electrical insulating barrier than an intervening plastic tube, which may be considered an alternative embodiment.

Transducer Support and Limited Rotation with Single Component

In one embodiment, a shaft rotation limiter comprises a single piece which interfaces with a transducer flange by a threaded connection. The rotation limiter provides radial support through a component fixed in the shroud channels. The amount of rotation is limited by the allowed lateral motion of the component in the shroud channels as it is threaded along the transducer. One example of a shaft rotation limiter is described in connection with FIG. 72 hereinbelow.

Figure 72:
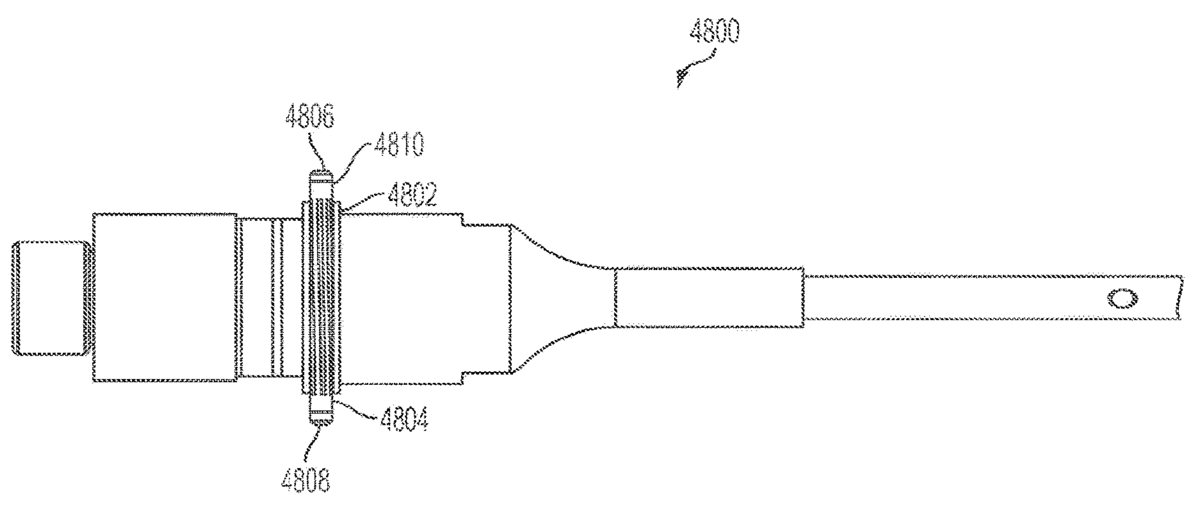
FIG. 72 illustrates one embodiment of an ultrasonic transducer having a modified flange incorporating external threads to allow transducer rotation.

FIG. 72 illustrates one embodiment of an ultrasonic transducer 4800 having a modified flange 4802 incorporating external threads 4804 to allow transducer rotation. In the illustrated embodiment, the transducer flange 4802 is modified to incorporate external threads 4804. The external threads 4804 may mate with a component 4810 having internal threads and at least two protruding bosses 4806, 4808. The protruding bosses 4806, 4808 engage into channels in the device shroud and limit transducer rotation. The shroud illustrated in FIG. 72 is described in further detail in relation to embodiments listed below. The component 4810 with the threaded inner diameter interfaces with the transducer 4800 by threaded connection. Since the component 4810 is limited in transverse travel by the shroud channels, it provides radial support. The component 4810 with the threaded inner diameter translates rotational movement of the transducer 4800 to a lateral motion of the component 4810. Rotation of the blade or transducer 4800 can be provided by a fixed rotation knob. Rotating the knob may cause the internally threaded component 4810 to translate laterally and rotation would be limited when the component 4810 can no longer translate. The lateral movement may be defined by the length of the channel in the shroud or the length of the threaded flange 4802 on the transducer. The shroud allows rotations in excess of 360°. The amount of rotation of the transducer 4800 is limited by the allowed lateral motion of the component 4810 in the shroud channels (not shown).

Limited Rotation of Ultrasonic Device with Rotation >360°

Figure 73:
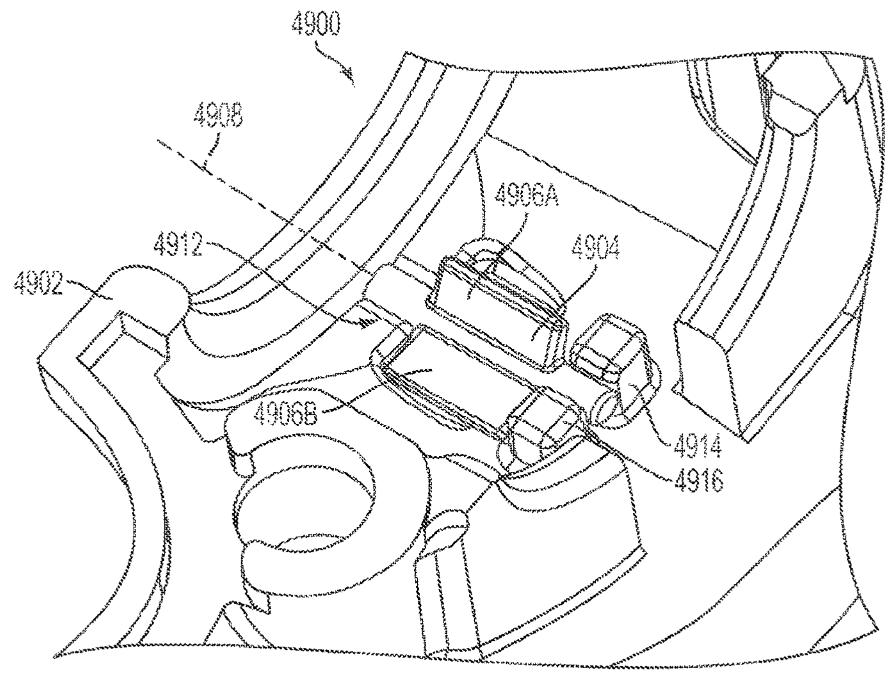
FIG. 73 is a sectional view of one embodiment of an ultrasonic transducer rotation system comprising a shroud and a gate fitted into one-half of the shroud.

FIG. 73 is a sectional view of an ultrasonic transducer rotation system 4900 comprising a shroud 4902 and a gate 4904 fitted into one-half of the shroud 4902. In the illustrated embodiment, the gate 4904 is L-shaped and has two wings 4906A, 4906B (right and left wings, respectively) extending at a fixed angle from a central axis 4908 positioned within a portion of the shroud 4902. One additional component, as well as modifications of a rotation knob and the right-hand or left-hand shroud 4902, allow for approximately 690° of rotation—almost two full rotations. The rotation knob is used by the operator to rotate the shaft and ultrasonic transducer of the device. The additional component is referred to herein as the gate 4904. The gate 4904 is rotationally moveable about axis 4908 within the shroud 4902 to two positions. The rotation knob will have an additional contoured extrusion element that extends to make contact with the gate 4904. Where the gate 4904 is inserted into the shroud 4902 there will be a minimum amount of frictional contact between the shroud 4902 and the gate 4904 to keep the gate 4904 in place while it is not in contact with the rotation knob. The gate 4904 in the shroud 4902 is constrained by a cylindrical hole 4912 and two bosses 4914, 4916 with a slight undercut. The axis 4908 of the gate 4904 that sits in the cylindrical hole 4912 would be constrained in part by features on the rotation knob. The gate 4904 can be made of a rigid metal or a single stamped metal part or injection molded from plastic. The gate 4904 can either snap into place in the shroud 4902 or be ultrasonically welded or heat staked to the shroud 4902 in such a fashion to allow free rotation of the gate 4904 about axis 4908.

Figure 74A:
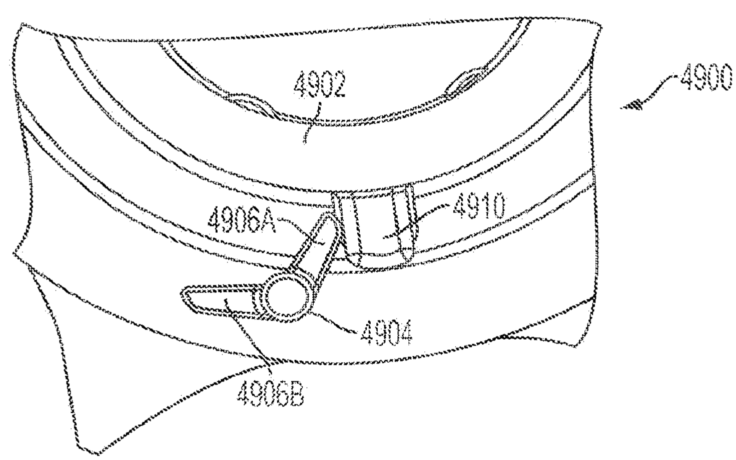
FIGS. 74A-74C illustrate the dynamics of the gate interaction with a rotation knob, according to one embodiment.
Figure 74B:
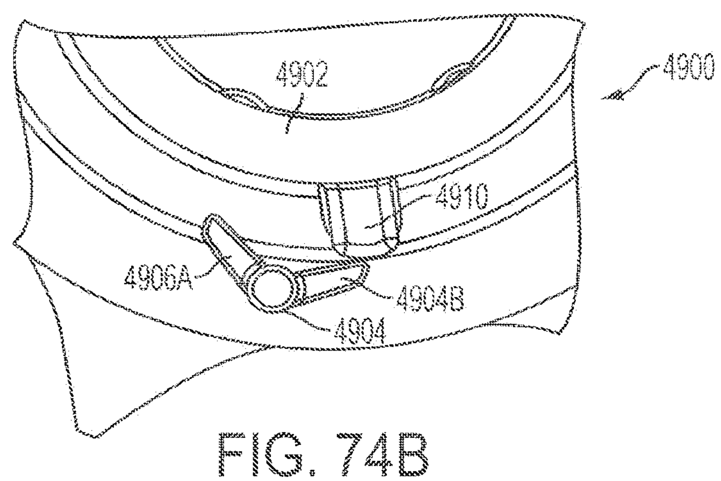
Figure 74C:
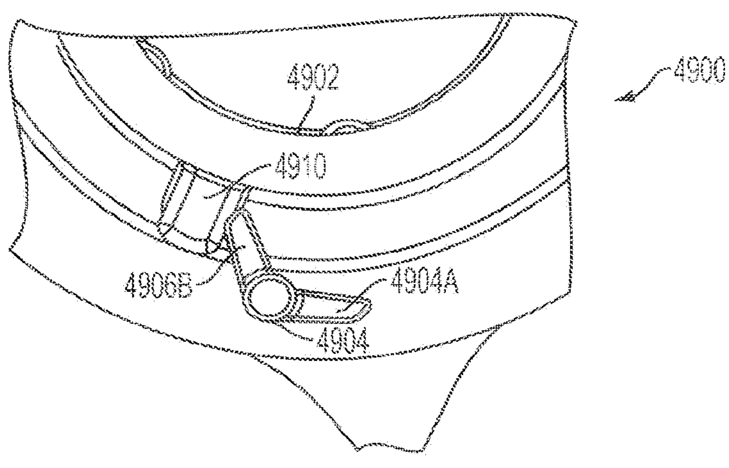

FIGS. 74A-74C illustrate the dynamics of the gate/rotation knob interaction. FIG. 74A illustrates the gate 4904 in a left-biased position such that the rotation knob can be rotated 690° clockwise until a contoured extrusion element 4910 on the rotation knob makes contact with the right wing 4906A of the gate 4904 so that the left wing 4906B of the gate 4904 prevents motion by reacting statically against the shroud 4902. Thus, at the starting point, the rotation knob contoured extrusion element 4910 is contacting the outside of the right wing 4906A of the gate 4904 and is constrained to only move in a counter-clockwise direction.

FIG. 74B illustrates the rotation knob rotated back 360 degrees until it rotates the right wing 4906A of the gate 4904 into a right-biased position. Upon full 360° rotation the rotation knob extrusion 4910 contacts the inside of the right wing 4906A of the gate 4904, rotating the gate 4904 to the right as the knob rotates around.

FIG. 74C illustrates the rotation knob after it rotates the right wing 4906A of the gate 4904 into a right-biased position. Subsequently, the rotation knob can be rotated an additional 330° until the contoured extrusion element 4910 of the rotation knob contacts the left wing 4906B of the gate 4904 and the right wing 4906A of the gate 4904 prevents motion by reacting statically against the shroud 4902. After 690° of rotation the rotation knob contacts the outside of the left wing 4906B of the gate 4904. The right wing 4906A of the gate 4904 is contacting the shroud 4902 and is therefore stopping further rotation of the rotation knob in the counterclockwise direction. This process can be reversed to spin the rotation knob clockwise back to its starting position.

Figure 75:
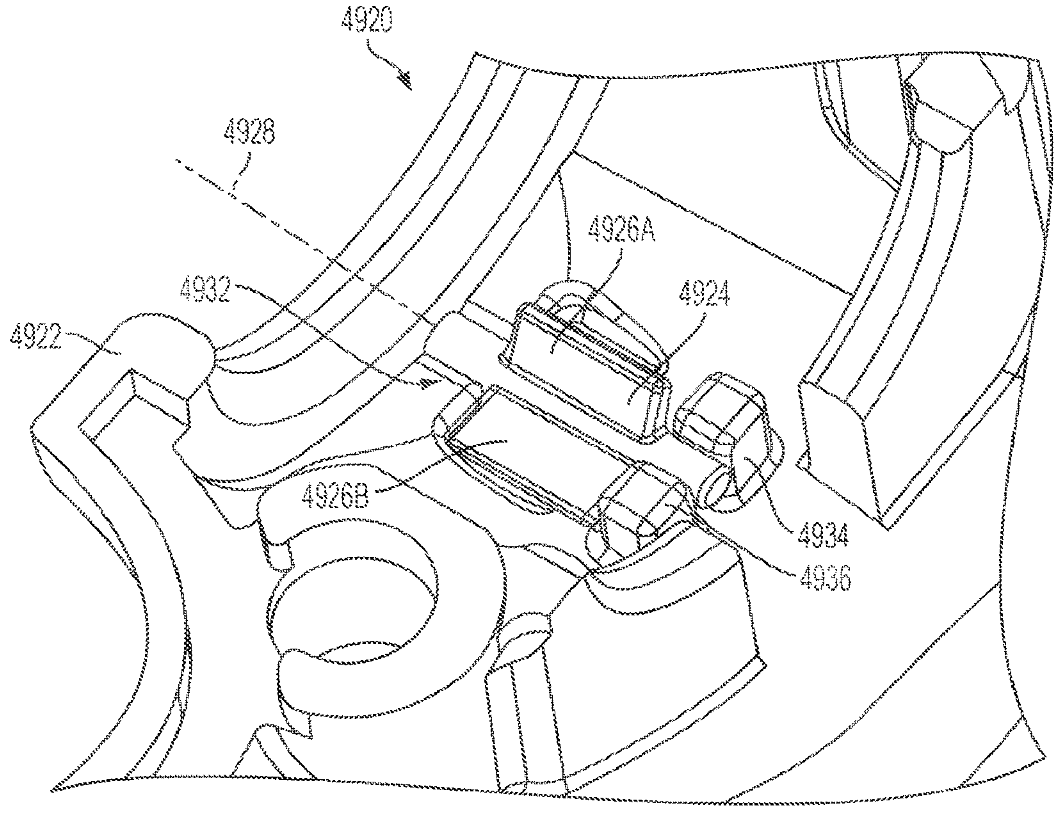
FIG. 75 is a sectional view of one embodiment of an ultrasonic transducer rotation system comprising a shroud and a gate fitted into one-half of the shroud, where the rotation system comprises a tactile feedback element.

FIG. 75 is a sectional view of an ultrasonic transducer rotation system 4920 comprising a shroud 4922 and a gate 4924 fitted into one-half of the shroud 4922, where the rotation system includes a semi-compliant element. In the illustrated embodiment, the gate 4924 is L-shaped and has two wings 4926A, 4926B (right and left wings, respectively) extending at a fixed angle from a central axis 4928 positioned within a portion of the shroud 4922. One additional component, as well as modifications of a rotation knob and the right-hand or left-hand shroud 4922, allow for approximately 690° of rotation—almost two full rotations. The rotation knob is used by the operator to rotate the device shaft and ultrasonic transducer. The additional component is referred to herein as the gate 4924. The gate 4924 is rotationally moveable about axis 4928 within the shroud 4922 to two positions. The rotation knob will have an additional contoured extrusion element that extends to make contact with the gate 4924. Where the gate 4924 is inserted into the shroud 4922 there will be a minimum amount of frictional contact between the shroud 4922 and the gate 4924 to keep the gate 4924 in place while it is not in contact with the rotation knob. The gate 4924 in the shroud 4922 is constrained by a cylindrical hole 4932 and two bosses 4934, 4936 with a slight undercut. The axis 4928 of the gate 4924 that sits in the cylindrical hole 4932 would be constrained in part by features on the rotation knob. The gate 4924 can be made of a rigid metal or injection molded from plastic. The gate 4924 can either snap into place in the shroud 4922 or be ultrasonically welded or heat staked to the shroud 4922 in such a fashion to allow free rotation of gate 4924 about axis 4928.

Unlimited (continuous) rotation of an ultrasonic shear device with an integrated transducer requires the use of additional components that may not be cost-effective. One cost-effective solution is to limit rotation of the shaft of the device, thus allowing for a direct-wired connection between the transducer and the hand activation circuit. A tactile benefit is added to the mechanism that would limit rotation but provide tactile feedback before a hard stop is hit. This tactile feedback element may enable the user to change the way they use the device, either through rotating their wrist to get additional rotation or to choose to rotate the device back to a neutral position to ensure they have enough rotation to accomplish the task they need to perform.

FIGS. 112A and 112B illustrate one embodiment of an unlimited rotation connection for an integrated transducer 6216. An unlimited rotation connection may be provided by the ultrasonic transducer rotation system 6220. The ultrasonic transducer rotation system 6220 may comprise, for example, a male plug 6222 and a female receptacle 6224. The male plug 6222 may be configured to freely rotate within the female receptacle 6224 while maintaining an electrical connection between the ultrasonic transducer 6216 and, for example, power system 6248. For example, in one embodiment, the male plug 6222 and the female receptacle 6224 may comprise a stereo plug and jack. FIG. 112A illustrates the male plug 6222 and the female receptacle 6224 in an uncoupled, or unmated, position. FIG. 112B illustrates the male plug 6222 and the female receptacle 6224 in a coupled, or mated, position. In the mated position, the male plug 6222 is able to freely rotate within the female receptacle while maintaining an electrical connection between the male plug 6222 and the female receptacle 6224.

FIGS. 113A-113C illustrate one embodiment of an unlimited rotation connection 6520. The unlimited rotation connection 6520 comprises a male plug 6522 and a female receptacle 6524. The male plug 6522 may comprise a plurality of electrodes 6526*a-d* coupled to an insulating tube 6528. The male plug 6522 may be coupled to a shaft/transducer assembly and may rotate in unison with the shaft/transducer assembly. In some embodiments, the first and second electrodes 6526*a*-6526*b* may be coupled to the transducer. In some embodiments, the third and fourth electrodes 6526*c*-6526*d* may be coupled to bipolar electrodes located at an end effector. In some embodiments, such as a monopolar electrode arrangement, the fourth electrode 6526*d* may be omitted. The plurality of electrodes 6526 may each be coupled to a wire 6530*a*-6530*d*. The female receptacle 6524 may comprise a plurality of helical contacts 6532*a*-6532*d*. The plurality of helical contacts 6532*a*-6532*d* may be positioned such that each of the helical contacts 6532*a*-6532*d* is electrically coupled to a corresponding electrode 6526*a*-6526*d* on the male plug 6522 when the male plug 6522 is inserted into the female receptacle 6524. FIG. 113B illustrates a cross-sectional view of the female receptacle 6524 take along line B-B. The female receptacle 6524 comprises a individual helical contacts 6532*a*-6532*d* separated by insulators 6534*a*-6534*c*. FIG. 113C illustrates the individual helical contact profile of a helical contact 6532*a*. The helical contact 6532*a* may comprise a first metal plate 6536*a* and a second metal plate 6536*b*. A plurality of twisted wires 6538 may be spirally twisted to assure contact between the male plug 6522 and the metal plates 6536*a*, 6536*b*. In some embodiments, the direction of the spiral may be alternated to provide increased connectivity in all directions of rotation. The twisted wires 6538 may comprise a hyperbolic shape.

The tactile feedback element is added to the limited rotation mechanism shown in FIGS. 73-74C, which includes on the rotation knob an additional contoured extrusion element 4930 that extends to make contact with the gate 4924 (the mechanism that limits rotation). In the embodiment illustrated in FIGS. 75-76C, a contoured extrusion element 4930 (FIGS. 76A-76C) located on the rotation knob can be made of a semi-compliant material. Alternatively, portions of contoured extrusion element 4930 indicated by elements 4938, may be comprised of a semi-compliant material. The semi-compliant material could be made of rubber, medium to high density rubber, silicone, thermoplastic elastomers, springy piece of stainless steel, spring steel, copper, shape memory metals, and the like. Any of these materials can be insert molded or mechanically connected to the rotation knob.

The purpose of the contoured extrusion element 4930 (FIGS. 76A-76C) on the rotation knob is to contact the gate 4924 to provide the motion needed for the gate 4924 to function. Adding compliance to the contoured extrusion element 4930 rotation knob feature enables the user to feel that they are approaching the hard stop a few degrees of rotation before the hard stop is contacted. This feedback may enable the user to change the way they use the device, either through rotating their wrist to get additional rotation or to choose to rotate the device back to a neutral position to ensure they have enough rotation to accomplish the task they need to perform.

Figure 76A:
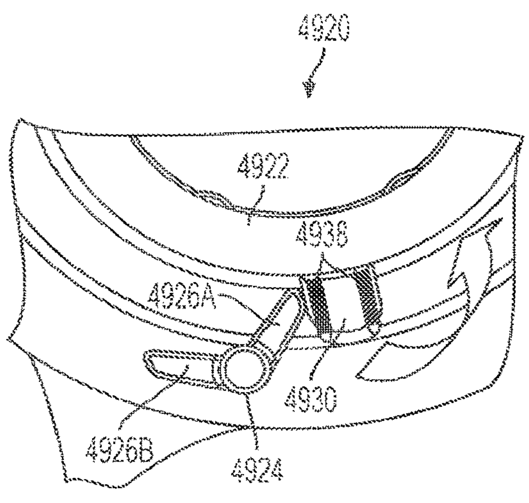
FIGS. 76A-76C illustrate the dynamics of the gate interaction with a rotation knob, where the rotation knob comprises a tactile feedback element, according to one embodiment.
Figure 76B:
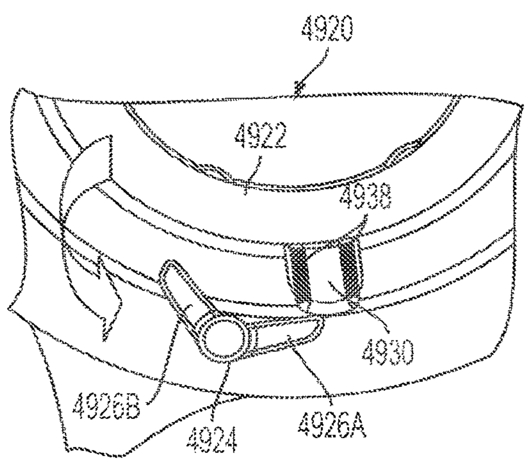
Figure 76C:
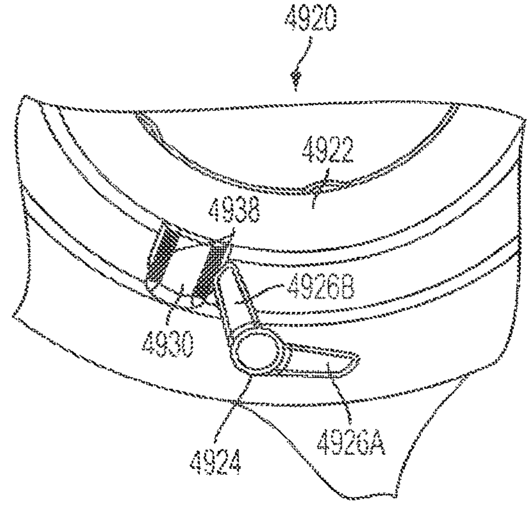

FIGS. 76A-76C illustrate the dynamics of the gate interaction with a rotation knob, where the rotation knob comprises a tactile feedback element. FIG. 76A illustrates the gate 4924 in a left-biased position such that the rotation knob can be rotated 690° clockwise until a contoured extrusion element 4930 on the rotation knob makes contact with the right wing 4906A of the gate 4924 so that the left wing 4926B of the gate 4924 prevents motion by reacting statically against the shroud 4922. Thus, at the starting point, the rotation knob contoured extrusion element 4930 is contacting the outside of the right wing 4926A of the gate 4924 and is constrained to only move in a counter-clockwise direction. A layer of (insert-molded) semi-compliant material 4938 may be located on either side or both sides of the contoured extrusion element 4930. The semi-compliant material 4938 could be made of rubber, medium to high density rubber, silicone, thermoplastic elastomers, springy piece of stainless steel, spring steel, copper, shape memory metals, and the like. Any of these semi-compliant materials 4938 can be insert molded or mechanically connected to the rotation knob.

FIG. 76B illustrates the rotation knob rotated back 360 degrees until it knocks the right wing 4926A of the gate 4924 into a right-biased position. Upon full 360° rotation the contoured extrusion element 4930 of the rotation knob contacts the inside of the right wing 4926A of the gate 4924, rotating the gate 4924 to the right as the knob rotates around. The semi-compliant material 4938 provides tactile feedback to the user.

FIG. 76C illustrates the rotation knob after it rotates the right wing 4926A of the gate 4924 into a right-biased position. Subsequently, the rotation knob can be rotated an additional 330° until the contoured extrusion element 4930 of the rotation knob contacts the left wing 4926B of the gate 4924 and the right wing 4926A of the gate 4924 prevents motion by reacting statically against the shroud 4922. After 690° of rotation the rotation knob contacts the outside of the left wing 4926B of the gate 4924. The right wing 4926A of the gate 4924 is contacting the shroud 4922 and is therefore stopping further rotation of the rotation knob in the counterclockwise direction. This process can be reversed to spin the rotation knob clockwise back to its starting position. The semi-compliant material 4938 provides tactile feedback to the user. The semi-compliant material 4938 tactile feedback element mat enable the user to change the way they use the device, either through rotating their wrist to get additional rotation or to choose to rotate the device back to a neutral position to ensure they have enough rotation to accomplish the task they need to perform.

RF Spot Coagulation with Integrated Ultrasonic/RF Generator

Figure 77:
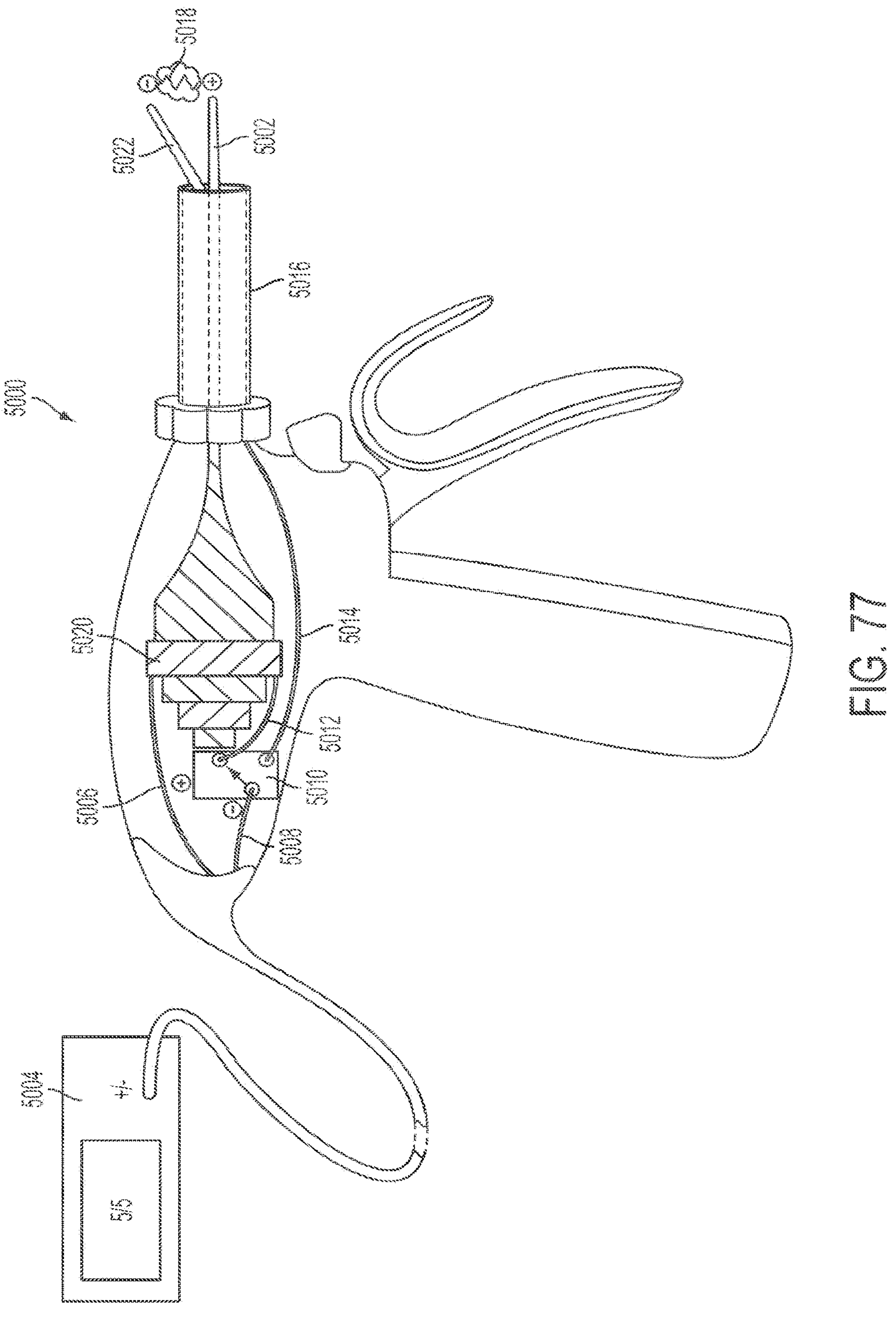
FIG. 77 illustrates one embodiment of an integrated RF/ultrasonic instrument electrically connected such that the ultrasonic blade/horn is electrically connected to a positive lead of an ultrasonic generator coupled to the instrument to provide RF spot coagulation. The clamp arm and tube are connected to the return path.

FIG. 77 illustrates an integrated RF/ultrasonic instrument 5000 electrically connected such that an ultrasonic blade/horn 5002 is electrically connected to a positive lead 5006 of an ultrasonic generator 5004 and is also coupled to an RF generator to provide spot coagulation by applying RF energy to tissue 5018. The integrated RF/ultrasonic instrument 5000 enables the touch up of diffuse bleeding (capillary bleeding, cut site oozing) without the need for ultrasonic coupling pressure. Further, the coupling pressure needed for ultrasonic instruments, to couple the blade to tissue such that friction-based tissue effect is effective, is relatively high which results in (1) difficulty in applying enough pressure to generate hemostatic effect in loosely supported (i.e., unclamped) tissue or (2) coupling pressure that generates too much tissue disruption that, in many cases, makes the diffuse bleeding worse.

In one embodiment, the integrated RF/ultrasonic instrument 5000 is wired such that the horn/blade 5002 is directly connected to the positive lead 5006 of the generator 5004. Conventional ultrasonic devices are wired such that the negative/return lead 5012 is connected to the horn/blade. A switch 5010 is provided to enable two device functionalities (1) ultrasonic and (2) bipolar (RF) to be performed. The first state of the switch 5010 connects the negative/return lead 5008 to the piezoelectric transducer (PZT) stack 5020 such that the generator 5004 drives the PZT stack 5020. The second state of the switch 5010 isolates the PZT stack 5020 and connects the negative/return 5008 to the device tube 5016 and a movable jaw member 5022 (e.g., clamp arm) through an electrical conductor 5014 and allows the generator 5004 signal to be driven through tissue 5018 located between the blade 5002 and the clamp arm 5022. The resistance in the tissue 5018 seals the vessels. Feedback signals also may be provided back to the generator 5004 to adjust signal parameters (e.g., amplitude, frequency, pulsing, modulation, etc.)

In one embodiment, the integrated RF/ultrasonic instrument 5000 may comprise a sealing button, wherein, when pressed, the generator 5004 may produce bipolar RF energy through the handpiece and into the ultrasonic blade 5002 and return through the clamp arm 5022. In one embodiment, the electrical RF current may travel around the outside of the blade 5002 and create a robust bi-polar seal. The duration of the bipolar RF energy may be about one second, after which an algorithm may cause the generator 5004 to switch to the ultrasonic power curve, wherein the blade 5002 would be activated and the cut completed in the middle of two RF seals.

Ultrasonic cutting also may provide some sealing. The application of RF energy provides added confidence that there is an RF seal in place on each side of the blade 5002.

In one embodiment, the RF/ultrasonic device comprises a blade or clamp arm or both with the distal end coated with thermally and electrically insulative material, wherein a distal end of the blade or clamp arm or both may have varying degrees of exposed (uncoated) areas that will be application dependent. In another embodiment, the exposed area on the blade or clamp arm or both may vary depending on application and may be either symmetrical or asymmetrical. In another embodiment, the exposed area on the blade may comprise at least one exposed area/segment separated by at least one coated segment. In one embodiment, a process of masking the blade or clamp arm or both to generate exposed area is provided. Alternatively, coating may be selectively removed to produce the same desired effect. Specific embodiments of such coated blades are described hereinbelow in connection with FIGS. 80-95.

Figure 78:
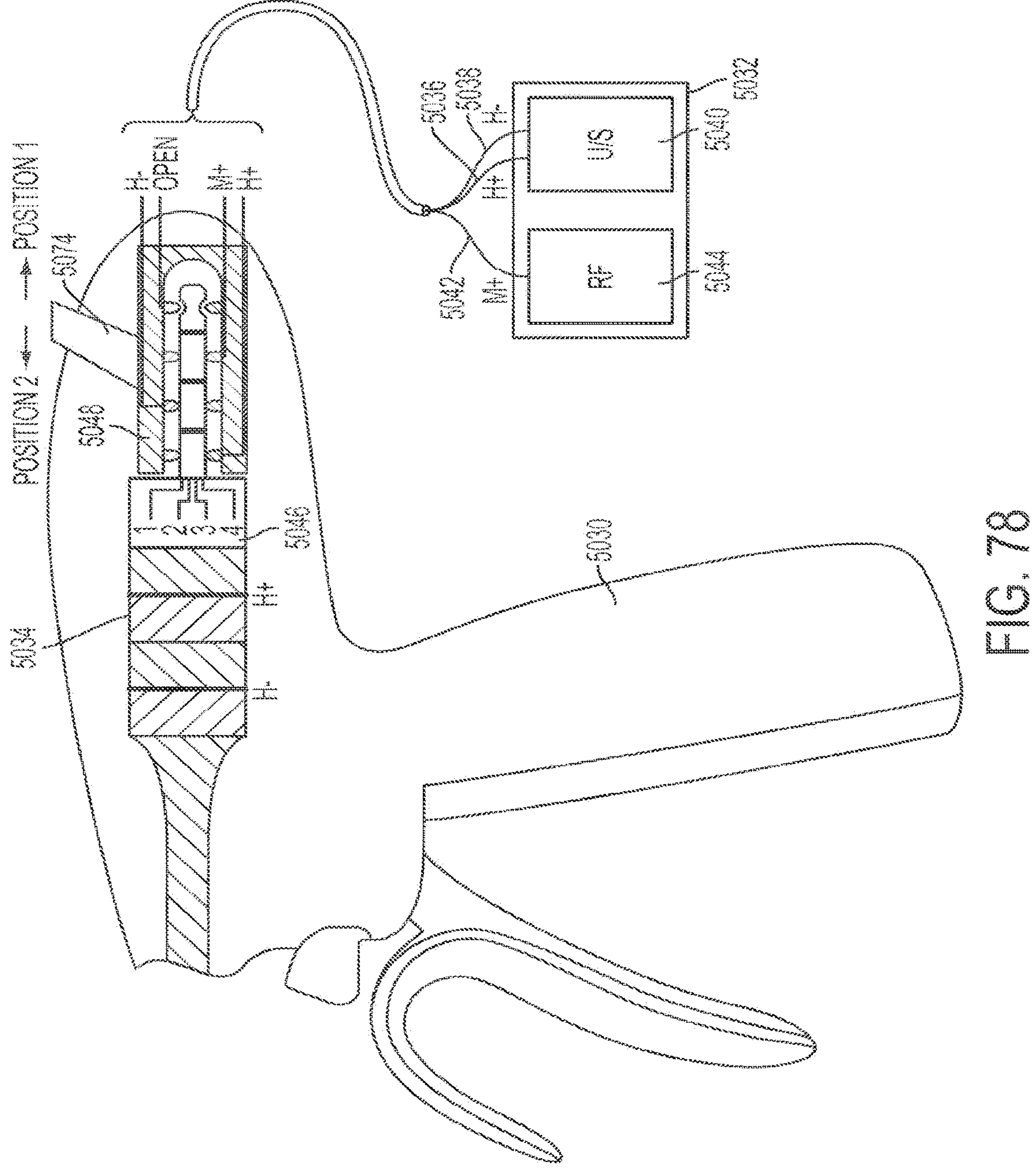
FIG. 78 illustrates one embodiment of an integrated RF/ultrasonic instrument comprising four-lead jack connector mated with a slidable female mating plug electrically connected to a generator.
Figure 79:
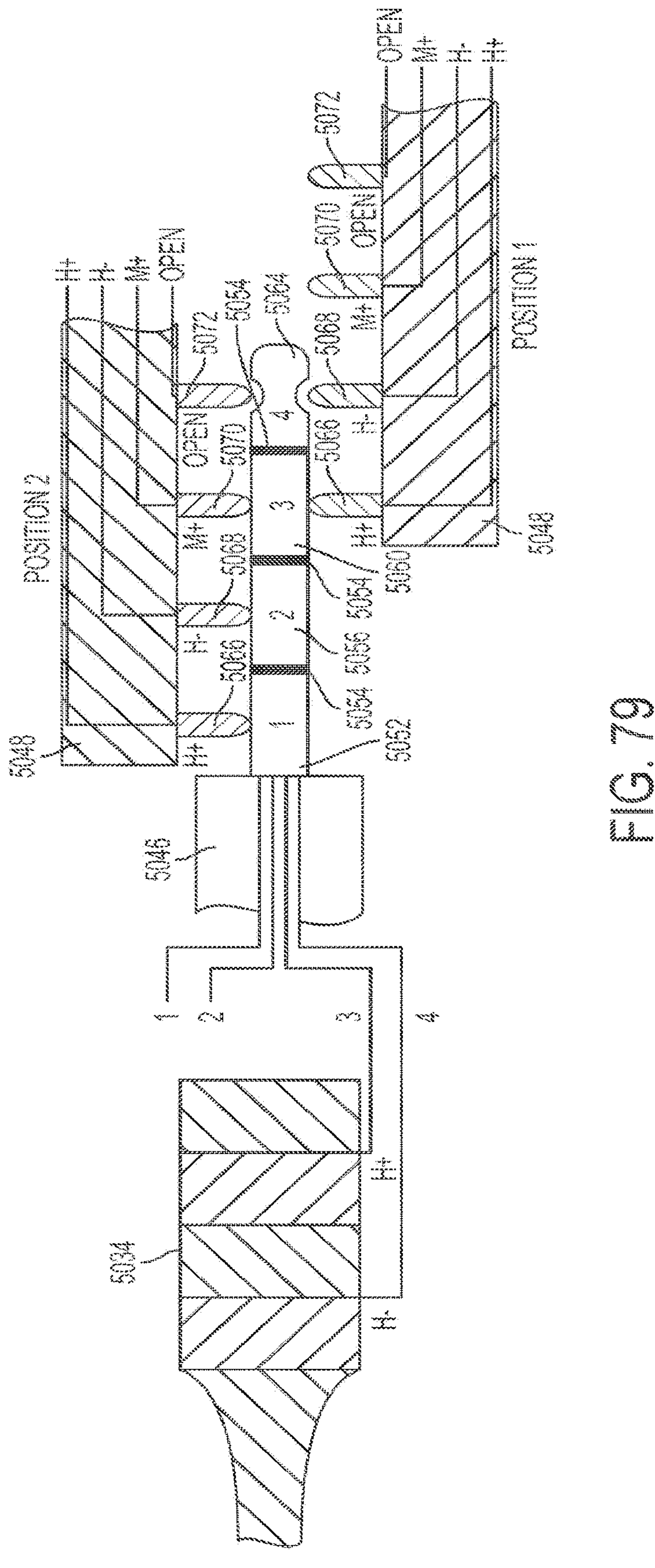
FIG. 79 is a detail view of one embodiment of a four-lead jack connector mated with a slidable female mating plug coupled to an ultrasonic transducer where position 1 provides an ultrasonic signal to the transducer, and where position 2 provides an electrosurgical signal to the device.
Figure 80:
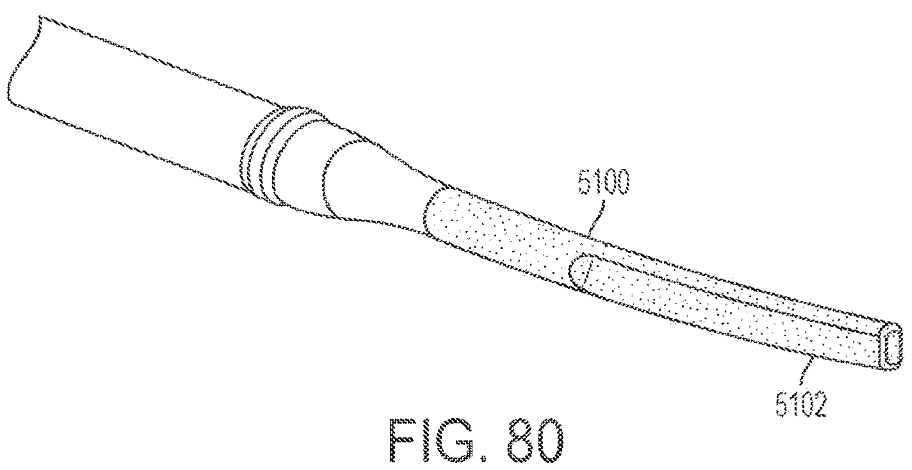
FIGS. 80-83 illustrate various embodiments of ultrasonic blades coated with an electrically insulative material to provide thermal insulation at the tissue contact area to minimize adhesion of tissue to the blade.
Figure 81:
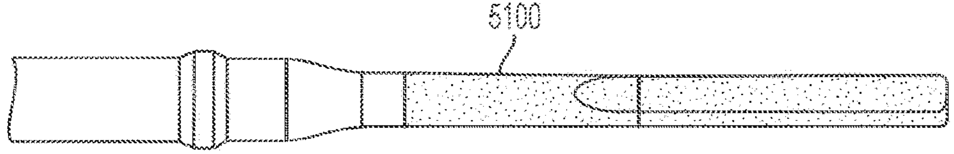
Figure 82:
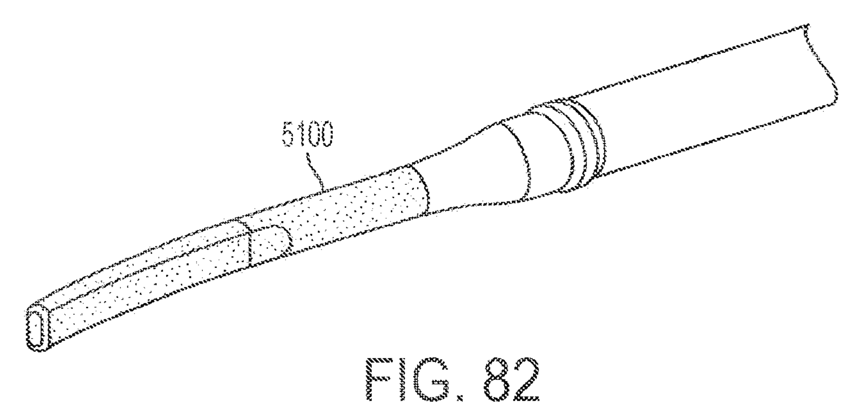
Figure 83:
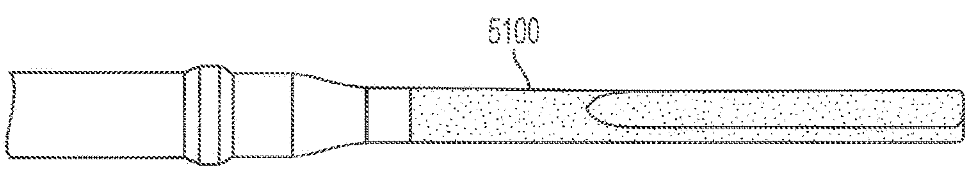
Figure 84:
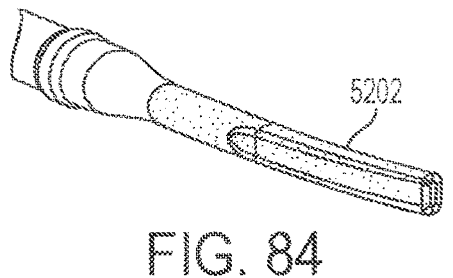
Figure 89:
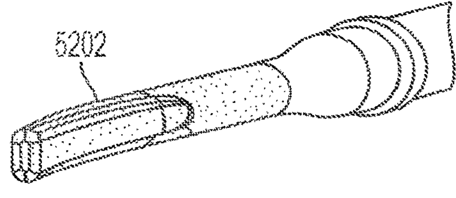
Figure 85:
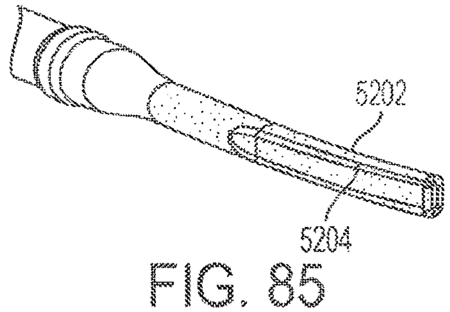
Figure 90:
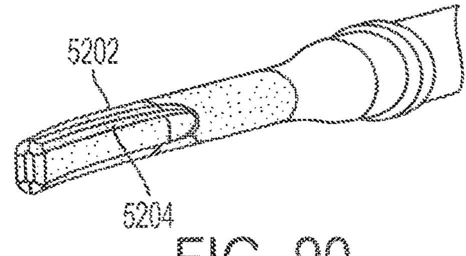
Figure 86:
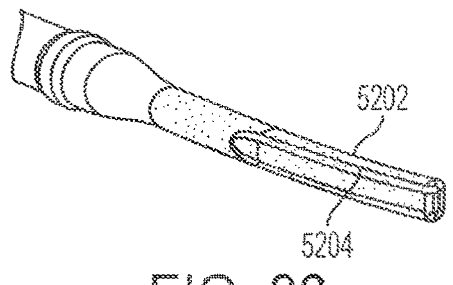
Figure 91:
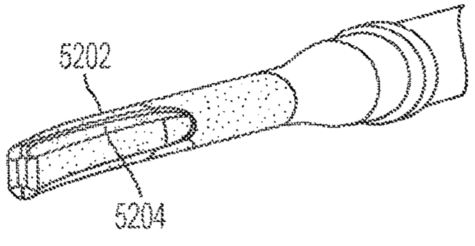
Figure 87:
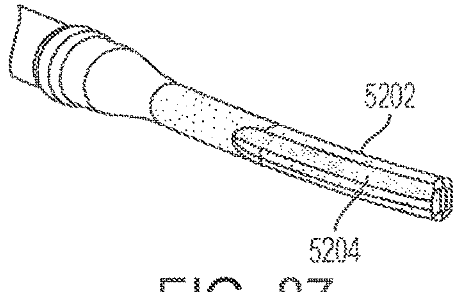
Figure 92:
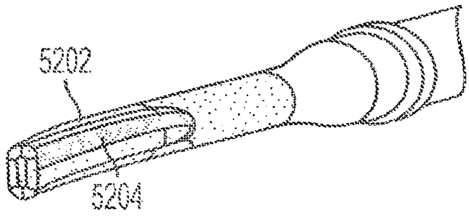
Figure 88:
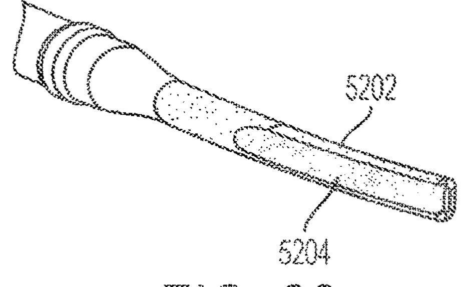
Figure 93:
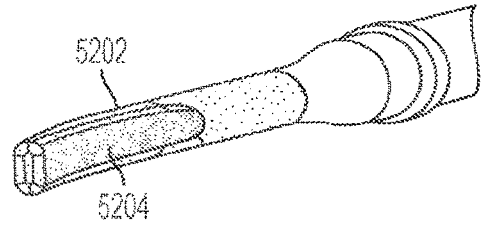

FIG. 78 illustrates one embodiment of an integrated RF/ultrasonic instrument 5030 electrically connected to an energy source such as a generator 5032 comprising four-lead jack connector 5046 is mated with a slidable female mating plug 5048. FIG. 79 is a detail view of the four-lead jack connector 5046 mated with a slidable female mating plug 5048 coupled to an ultrasonic transducer 5034. With reference to FIGS. 78-79, in one embodiment, the generator 5032 may comprise a first ultrasonic energy source such as ultrasonic generator 5040 and a second RF energy source such as an RF generator 5044 either individually or integrated into the same housing. An ultrasonic transducer 5034 is electrically connected to positive and negative leads 5036 (H+), 5038 (H−) of the ultrasonic generator 5040. A monopolar positive lead 5042 (M+) is coupled to the RF generator 5044. A four-lead jack connector 5046 is mated with a slidable female mating plug 5048 to electrically engage either 1) connection of the ultrasonic generator 5040 leads 5036, 5038 to the ultrasonic transducer 5034 or 2) connection of the monopolar RF generator 5044 lead 5042 to the transducer 5034 to prevent connecting both the ultrasonic generator 5040 and the monopolar RF generator 5044 to the transducer 5034 at the same time. In one embodiment, the female connector may be integrated in the device and the four lead jack may be mated to a generator.

A slidable switch 5074 comprises a slidable female connector 5048 configured to receive a rotatable jack connector 5046. The rotatable jack connector 5046 is used for mating with the slidable female connector 5048 for providing an electrical connection between two electrical devices, such as the transducer 5034 and the generator 5032. Referring particularly to FIG. 79, the rotatable jack connector 5046 comprises a tip terminal portion 5064 at a front end thereof, a ground terminal portion 5052 at a rear end thereof and two intermediate terminal portions 5056, 5060 to the tip and ground terminal portions 5064, 5052. The terminal portions 5052, 5056, 5060, 5064 are electrically separated from each other by dielectric insulators 5054. The ground terminal portion 5052 connects with a connecting portion of 5046. Since the structure of the rotatable mating plug 5046 is well known by those skilled in the art, detailed description thereof is omitted here. Conductive terminal portions 1, 2, 3, 4 are electrically connected to terminal portions 5052, 5056, 5060, 5064. Conductive terminal portions 1 and 2 connected to terminal portions 5052, 5056 and are isolated and are not coupled to the transducer 5034. Conductive terminal portions 3 and 4 are electrically connected to terminal portions 5060, 5064 and are electrically connected to the transducer 5034.

In one embodiment, the slidable female connector 5048 is slidable between Position 1 and Position 2. Position 1 may be configured to correspond with ultrasonic mode of operation and Position 2 may be configured to correspond with monopolar mode of operation. In Position 1, the monopolar RF lead 5042 (M+) from the monopolar RF generator 5044 is disconnected physically from the transducer 5034. The slidable female connector 5048 comprises contact portions 5066, 5068, 5070, 5072 configured to electrically engage terminal portions 5052, 5056, 5060, 5064. The slidable female connector 5048 includes an actuator portion 5074 that enables the user to slide the slidable female connector 5048 between multiple positions. As shown in particular in FIG. 79, the slidable female connector 5048 is slidably movable between Position 1 and Position 2, ultrasonic and monopolar RF modes.

Moving the slidable female connector 5048 into Position 1 places the integrated RF/ultrasonic instrument 5030 in ultrasonic mode. In this position, the contact portions 5066, 5068 are electrically engaged with terminal portions 5060, 5064 thereby electrically coupling positive and negative leads 5036 (H+), 5038 (H−) of the ultrasonic generator 5040 to the transducer 5034 through conductive terminal portions 3 and 4. In position 1, the monopolar positive lead 5042 (M+) coupled to the RF generator 5044 is physically disconnected from the transducer 5034.

Moving the slidable female connector 5048 into Position 2 places the integrated RF/ultrasonic instrument 5030 in monopolar RF mode. In this position, the contact portions 5066, 5068 are electrically engaged with terminal portions 5052, 5056 thereby electrically coupling positive and negative leads 5036 (H+), 5038 (H−) of the ultrasonic generator 5040 to isolated conductive terminal portions 1 and 2, effectively disconnecting the ultrasonic generator 5040 from the transducer 5034. In position 2, contact portion 5070 electrically engages terminal portion 5060 thereby electrically coupling the monopolar positive lead 5042 (M+) of the RF generator 5044 to the transducer 5034 through conductive terminal portion 3. Contact portion 5072 electrically engages terminal tip portion 5064, which is electrically isolated, or open.

FIGS. 114A and 114B illustrate one embodiment of an integrated RF/ultrasonic surgical instrument, for example, the integrated RF/ultrasonic surgical instrument 5030, comprising an integrated RF/ultrasonic end effector 6304. The integrated RF/ultrasonic end effector 6304 may be configured to deliver RF energy and/or ultrasonic energy to a tissue section. FIG. 114A illustrates a clamping arm 6364 in an open position. An ultrasonic blade 6366 is positioned such that the clamping arm 6364 and the ultrasonic blade 6366 may clamp tissue therebetween. The ultrasonic blade 6366 is positioned within a heat shield 6322. FIG. 114B illustrates the integrated RF/ultrasonic end effector 6304 in a clamped position.

Figure 115A:
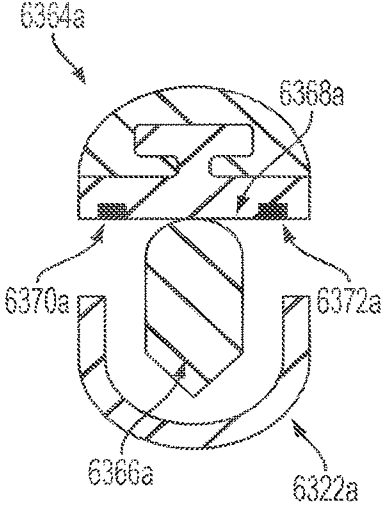
Figure 115B:
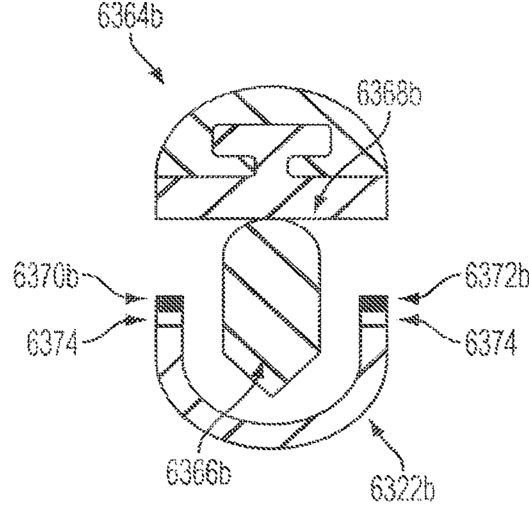
Figure 115C:
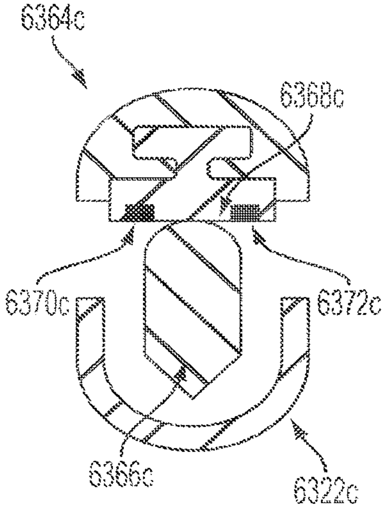
Figure 115D:
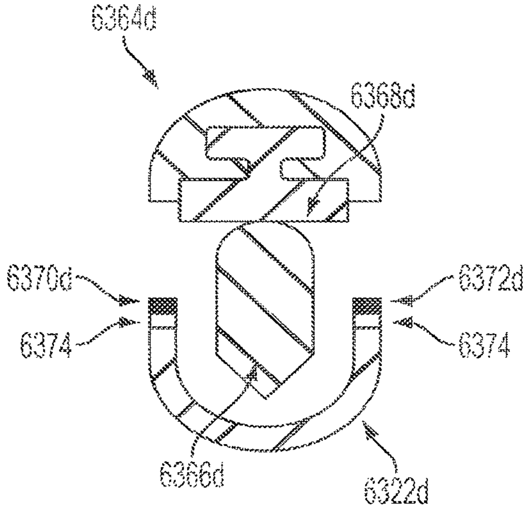
Figure 115E:
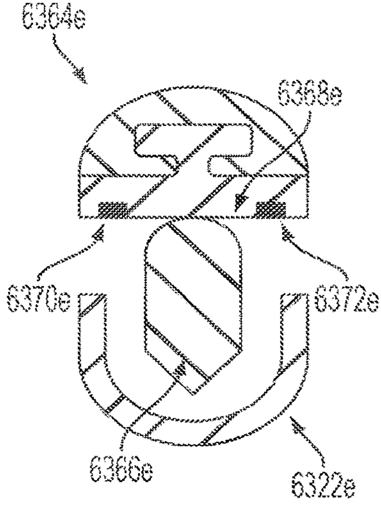
Figure 115F:
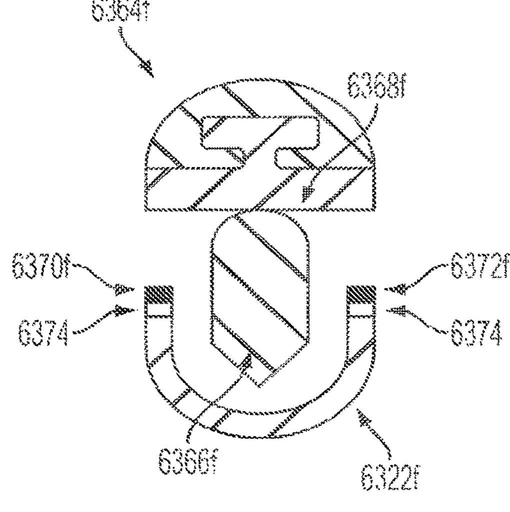

FIGS. 115A-115I illustrate various embodiments of a cross-section of the integrated RF/ultrasonic end effector 6304 taken along line A-A. As can be seen in FIGS. 115A-115I, RF electrodes 6370, 6372 may be located on and/or comprise any suitable portion of the integrated RF/ultrasonic end effector 6304. FIGS. 115A-115F illustrates various embodiments of the integrated RF/ultrasonic end effector 6304 comprising a bipolar electrode arrangement. For example, FIG. 115A illustrates one embodiment of the integrated RF/ultrasonic end effector 6304*a*. Positive electrodes 6370*a*, 6372*a* may be located on the tissue-facing portion of the clamp pad 6368*a*. The clamp arm 6364*a* may comprise a return, or negative, electrode. FIG. 115B illustrates one embodiment of the integrated RF/ultrasonic end effector 6304*b*. The positive electrodes 6370*b*, 6372*b* are located on the heat shield 6322*b*. An insulator 6374 may be located between the positive electrodes 6370*a*, 6370*b* and the heat shield 6322*b* to insulate heat shield 6322*b*. The clamp arm 6364*b* may function as the return electrode. FIG. 115C is similar to FIG. 115A, with the exception that the clamp arm 6364*c* extends laterally beyond the insulting clamp pad 6368*c*. FIG. 115D is similar to FIG. 115B, with the exception that the clamp arm 6364*d* extends laterally beyond the insulating clamp pad 6368*d*. In FIG. 115E, the clamp pad 6368*e* comprises a positive electrode 6370*e* and a negative electrode 6372*e*. In FIG. 115F, the heat shield 6322*f* comprises the positive electrode 6370*f* and the negative electrode 6372*f*.

Figure 115G:
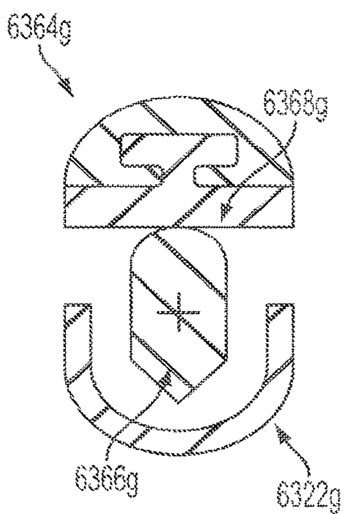
Figure 115H:
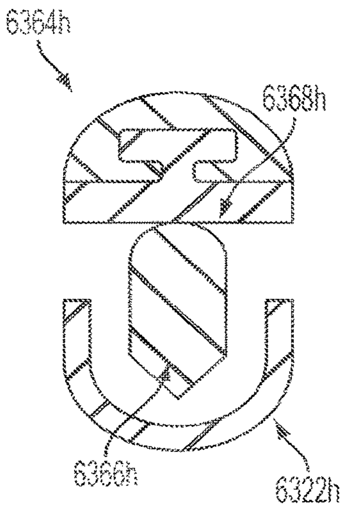
Figure 115I:
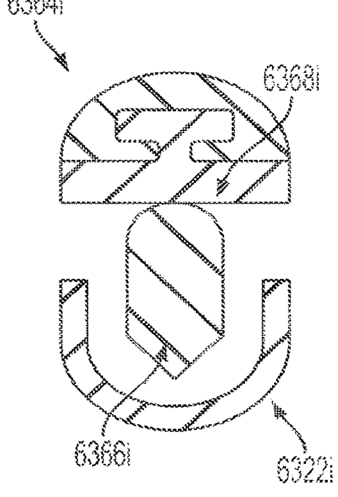

FIGS. 115G-115I illustrate various embodiments of the integrated RF/ultrasonic end effector 6304 comprising a monopolar electrode. In FIG. 115G, the ultrasonic blade 6366*g* comprises a monopolar electrode for delivering RF energy to a tissue section. In FIG. 115H, the clamp arm 6364*h* comprises the monopolar electrode. In FIG. 115I, the heat shield 6322*i* comprises the monopolar electrode.

FIGS. 117-118 illustrate one embodiment of an integrated RF/ultrasonic surgical instrument 6602. The integrated RF/ultrasonic instrument 6602 may comprise an insulated shaft 6614. The shaft 6614 and end effector 6604, including the jaw 6664 and ultrasonic blade 6666, may be energized with monopolar RF energy. The monopolar RF energy may be controlled by a double pole double throw (DPDT) selector switch 6620 located, for example, on the handle 6612 of the integrated RF/ultrasonic instrument 6602. The DPDT selector switch 6628 may switch the integrated RF/ultrasonic instrument 6602 from an ultrasonic generator 6628 to a monopolar RF generator 6622. FIG. 118 illustrates one embodiment of a DPDT selector switch 6628 which may be configured to switch between the ultrasonic generator 6620 and the monopolar RF generator 6622. The DPDT selector switch 6628 may comprise a user toggle 6630.

Coated Ultrasonic/RF Blades

FIGS. 80-83 illustrate various views of an ultrasonic blade 5100 coated with an electrically insulative material 5102 to provide thermal insulation at the tissue contact area to minimize adhesion of tissue to the blade 5100. Conventional ultrasonic devices utilize one mode of treatment, which limits versatility. For example, conventional ultrasonic devices may be used for blood vessel sealing and transecting tissue. Bipolar RF may offer added benefits such as a method for spot coagulation and pretreatment of tissue. Incorporating ultrasonic and RF may provide versatility and increase effectiveness. However, conventional ultrasonic devices utilize coatings to provide insulation at the distal end of the blade. These coatings are electrically insulative, and therefore limit current flow thus decreasing RF effectiveness. Additionally, current density may influence effectiveness. It may be contemplated that the entire waveguide of the blade may be coated with such coating to prevent shorting of the blade to the tube assembly return path. It is also contemplated that a similar coating and masking procedure may be employed in the clamp arm in order to provide a suitable path for current flow. In order to incorporate both energy modes into one device, a masking process for blade tip coating or coating removal process may be required. Creating an exposed area on the surface of the blade may provide a suitable path for current flow.

Accordingly, in one embodiment, an ultrasonic blade 5100 comprises a lubricious coating 5102 having properties similar to Teflon on the distal end of the blade 5100 as shown in FIGS. 80-83. The use of RF as a mode of treatment requires current to flow from the blade 5100, through tissue, and to a movable jaw member generally referred to as a clamp arm. The coating 5102 is used to provide thermal insulation at the contact area and minimize adhesion of tissue to blade 5100. However, the coating 5102 also is electrically insulative, which limits the amount of current flow. A method of masking the blade 5100 or removing coating selectively may be used to create exposed surfaces. In other embodiments, the lubricious coating 5102 provided on the blade 5100 may extend proximally so as to could coat the whole blade 5100, for example. In one embodiment, the blade 5100 may be coated back to the distal node.

FIGS. 84-93 illustrate various ultrasonic blades partially coated with an electrically insulative material to provide thermal and electrical insulation at the tissue contact area to minimize adhesion of tissue to the blade, where the lighter shade regions 5202 of the blade represent the coated portions and the darker shaded regions 5204 of the blade represent exposed surfaces that enable RF current to flow from the exposed region of the blade, through the tissue, and the movable jaw member. The exposed surface is symmetrical. The area on the blade that requires and exposed surface may be application dependent. Therefore, a different percentage of coating/exposed area has been illustrated is FIGS. 84-93. However, the embodiments are not limited to only the illustrated coverage. Although the embodiments shown in connection with FIGS. 84-93 show height-wise variation in electrically insulative blade coating, the lighter shaded regions 5202, it is contemplated within the scope of the present disclosure lengthwise variation in electrically insulative blade coating, the lighter shaded regions 5202, such that a portion of the distal tip of the blade exposed. In one example, the distal ⅓ of the sides of the blade would be exposed.

FIGS. 94-95 illustrate two ultrasonic blades with non-symmetrical exposed surfaces, where the blades are coated with an electrically insulative material to provide thermal insulation at the tissue contact area to minimize adhesion of tissue to the blade, where the lighter shade regions 5302 of the blade represent the coated portions and the darker shaded regions 5304 of the blade represent exposed surfaces that enable RF current to flow from the exposed region of the blade, through the tissue, and the movable jaw member. Current density may impact functionality and may be controlled by providing different surface areas. The surface areas do not have to be symmetrical on each side of the blade tip and may differ depending on performance. In addition, the exposed area may consist of two or more segments that are separated by at least one coated segment (not illustrated). Other coated/exposed geometries are possible as well, such as varying the depth or width of the exposed area along the axis of the blade.

In another embodiment, the blade and/or the tube assembly may be electrically charged to repel surgical matter.

FIGS. 119A-119E illustrate various embodiments of integrated RF/ultrasonic surgical end effectors. The clamp arm may comprise, for example, a circular clamp arm 6764*a*, 6764*b*, a hook clamp arm 6764*c*, a circular clamp arm comprising a cavity 6764*d*, or a curved hook clamp arm 6764*e*. The ultrasonic blade may comprise, for example, a rectangular ultrasonic blade 6766*a*, 6766*c* and/or an elliptical ultrasonic blade 6766*b*. FIGS. 120A-120C illustrate various embodiments of bipolar integrated RF/ultrasonic end effectors. In one embodiment, the clamp arm 6864*a* may comprise first electrode and the ultrasonic blade 6866*a* may comprise a second electrode. The clamp arm 6864*a* or the ultrasonic blade 6866*a* may comprise a return electrode. In some embodiments, the clamp arm 6864*b* may comprise an insulating pad 6868 to separate the clamp arm 6864*b* from the ultrasonic blade 6866*b*. In some embodiments, the clamp arm 6864*c* may comprise both a first electrode 6870 and a second electrode 6872. The first and second electrodes 6870, 6872 may be separated by an insulating portion of the clamp arm 6864*c*.

FIGS. 121A-121C comprise various embodiment of monopolar integrated RF/ultrasonic end effectors. In some embodiments, the entire clamp arm 6964*a* may comprise a monopolar electrode. In some embodiments, the clamp arm 6964*b* may comprise an insulating pad 6968. A portion of the clamp arm 6964*b* may comprise a monopolar electrode. In some embodiments, the clamp arm 6964*c* and an ultrasonic blade 6966 may comprise a single monopolar electrode.

Heat Shielded Ultrasonic Blades

FIG. 96 is a perspective view of one embodiment of an ultrasonic end effector 5400 comprising a metal heat shield 5402. The ultrasonic end effector 5400 comprises a clamp arm 5410. The clamp arm 5410 comprises a movable jaw member 5408 (clamp arm), a tissue pad 5412, an ultrasonic blade 5404, and a heat shield 5402 provided at a distance from the ultrasonic blade 5404. The heat shield 5402 is metal and contains apertures 5406 for air flow which provides cooling to the heat shield 5402 and the ultrasonic blade 5404. The heat shield 5402 is disposed opposite of the movable jaw member 5408.

FIG. 97 is a perspective view of another embodiment of an ultrasonic end effector 5420 comprising a retractable metal heat shield 5422. The ultrasonic end effector 5420 comprises a clamp arm 5430. The clamp arm 5430 comprises a movable jaw member 5428, a tissue pad 5432, an ultrasonic blade 5424, and a heat shield 5422 provided at a distance from the ultrasonic blade 5424. In another embodiment, the metal heat shield 5422 is attachable to the ultrasonic blade 5424 at the distal most node location. The attachment means also acts as a heat sink 5422 to remove heat from the blade 5424. The heat shield 5422 is metal and contains apertures 5426 for air flow which provides cooling to the heat shield 5422 and the ultrasonic blade 5424. The heat shield 5422 is disposed opposite of the movable jaw member 5428.

FIG. 98 is a side view of another embodiment of an ultrasonic end effector 5440 comprising a heat shield 5444 shown in cross-section. The ultrasonic end effector 5440 comprises a clamp arm 5448. The clamp arm 5448 comprises a movable jaw member 5252, an ultrasonic blade 5450, and a heat shield 5444 that also acts as a heat sink 5442. A pad 5452 may be provided on the blade 5450 side of the movable jaw member 5252 to grasp tissue between the pad 5452 and the blade 5450. The attachment of the heat shield 5444/heat sink 5442 is at a node location 5446. FIG. 99 is a front view of the ultrasonic end effector 5440 shown in FIG. 98, according to one embodiment.

FIGS. 100-104 illustrate various views of one embodiment of an ultrasonic end effector 5460 comprising a dual purpose rotatable heat shield 5462. FIG. 100 illustrates one embodiment of a clamp arm 5464 comprising a movable jaw member 5464 shown in a closed position and a dual purpose rotatable heat shield 5462 located below an ultrasonic blade 5468. The ultrasonic end effector 5460 comprises a clamp arm 5464 having a movable jaw member 5470, an ultrasonic blade 5468, and the dual purpose rotatable heat shield 5462. In one embodiment, the clamp arm 5464 comprises a movable jaw member 5470, which is shown in FIG. 100 in a closed position, and the rotatable heat shield 5462 is located below the ultrasonic blade 5468. In this embodiment, the heat shield 5462 is dual purposed and is rotatable about the blade 5468. The blade 5468 in this example is a straight/non-curved configuration. While the heat shield 5468 is disposed opposite of the movable jaw member 5470 (shears type end-effector), it acts as a heat shield 5462. After rotation about the blade 5468, the heat shield 5462 now is disposed between the blade 5468 and the movable jaw member 5470 providing a tissue clamping surface, backed by the blade 5468 providing strength/support for the heat shield 5468. Also, the heat shield 5468 may be configured to provide energy opposite of the energy that may be provided on the movable jaw member 5470 creating a bi-polar energy that may effect tissue.

FIG. 101 illustrates one embodiment of a movable jaw member 5470 shown in an open position and a dual purpose rotatable heat shield 5462 rotated such that it is interposed between the movable jaw member 5470 and the blade 5468.

FIG. 102 illustrates an end view of one embodiment of a dual purpose rotatable heat shield 5462 rotated in a first position. FIG. 103 illustrates an end view of one embodiment of the dual purpose rotatable heat shield 5462 rotated in a second position. With reference now to FIGS. 102-103, the rotatable heat shield 5462 has purposeful alignment that enables a tapered portion of the shield 5642 to come in between the top of the blade 5468 surface and the movable jaw member 5470. This rotation enables "back cutting" if necessary while still allowing normal activation shielding. Additionally an inner contour of the shield 5462 may be configured for contact to "clean" the tip upon rotation if necessary. Further if the shield 5462 is insulated, rotation of the shield 5462 from the stage 1 position into the stage 2 position enables RF energy to be applied for sealing only. Bottom surface of shield could have grip to assist in grasping as well when rotated to position 2.

FIG. 104 is a top profile view of one embodiment of a heat shield 5462 showing a tapered portion of the shield 5462. As shown, in one embodiment the heat shield 5462 includes a tapered portion defined by radius R1 relative to radius R2, where R2>R1.

FIGS. 116A-116B illustrates one embodiment of a cooling system for an ultrasonic surgical instrument. Air 6416 may be forced down an inner tube 6406 of the ultrasonic surgical instrument 6302 and over an ultrasonic end effector 6404. The air movement over the ultrasonic end effector 6304 may cool the ultrasonic end effector 6404. In one embodiment, cold air may be used to increase the cooling of the end effector 6404. Air 6416 may be moved in the direction of shown to cool the ultrasonic end effector 6404 through convection heat transfer from the ultrasonic end effector 6404 to the air. In some embodiments, a hospital air-line 6410 may be coupled to the ultrasonic instrument 6302 to provide compressed air flow through the inner tube 6406. In some embodiments, a hand pump 6412 and a reservoir 6414 may be located in the proximal end of the surgical instrument 6402, such as, for example, in the handle A clinician may operate the hand pump 6412 to generate air pressure within the reservoir 6414. The hand pump 6412 may comprise, for example, a squeeze bulb. The reservoir 6414 and/or the hospital air-line 6410 may be force air over the ultrasonic end effector 6404 with each opening and/or closing of the jaws. In some embodiments, the reservoir 6414 and/or the hospital air-line 6410 may provide a continuous flow of air over the ultrasonic end effector. In some embodiments, the inner tube 6406 may comprise a vortex tub, illustrated in FIG. 116B. The vortex tube may facilitate movement of air 6416 within the inner tube 6406 to travel distally 6418 through the inner tube 6406, over the ultrasonic end effector 6404, and return 6420 to the proximal end of the inner tube 6406 which may be open to release the air. The distal end of the vortex tube may comprise a splitter to split the stream of air 6418 to cool the distal end of the ultrasonic end effector 6404.

Ultrasonic 4-Bar Closure with Application to an Ultrasonic Rongeur

FIG. 105 illustrates a conventional rongeur surgical instrument 6000. Certain orthopedic procedures such as spinal fusion are used to treat degenerative spinal disk disease. One of the most commonly used instruments is the rongeur 6000 as shown in FIG. 105 for the removal of the spinal disk, which is made up of a nucleus and a tough annulus. The rongeur 6000 uses a 4-bar linkage in combination with a clamp arm 6002 comprising a movable jaw member 6004 to take bites of the spinal disk material. Generally speaking, a number of bites (10 to 20) may be taken for complete removal of the spinal disk. The multiple use of the rongeur 6000 can be fatiguing.

Accordingly, FIG. 106 illustrates one embodiment of an ultrasonic energy driven rongeur device 6100. The ultrasonic energy driven rongeur device 6100 comprises an ultrasonic transducer 6102 is added to one member of a 4-bar mechanism. The rongeur device 6100 also comprises two elongate horizontal members. As shown in FIG. 106, only the lower horizontal member 6104 coupled to a handle 6106 is shown. The two elongate horizontal members of the ultrasonic rongeur device 6100 are each attached to one handle 6106 of the ultrasonic rongeur device 6100. The horizontal members are connected with a small link at a distal end 6103, and the forward handle 6106 is the second link. These four members approach parallel-rules. As can be seen in FIG. 106, the bottom horizontal member 6104 is basically a straight rod which does not move. In accordance with one embodiment of the present disclosure, by placing pivots 6108, 6110 of the lower horizontal member 6104 at Nodes, the lower horizontal member 6104 may be considered an ultrasonic waveguide. Accordingly, the rest of the rongeur device 6100 is attached to the lower horizontal arm 6104 at nodes. The proximal end of the lower horizontal member 6104 can be attached to an ultrasonic transducer 6102 to produce ultrasonic displacement at the distal end 6103. The amplitude of the ultrasonic displacement will aid in cutting the tissue and therefore reduce the force required by the surgeon. Not shown here is the need to insert some damping material between the two horizontal members and a sheath on the lower horizontal member 6104 to avoid contact with intervening tissue. Advantages of the ultrasonic driven rongeur device 6100 include, without limitation, a novel closure mechanism for ultrasonic instruments based on a 4-bar linkage, lower force required to take a bite of spinal disk material, reduce surgeon fatigue, and novel instrument architecture for additional applications.

While various details have been set forth in the foregoing description, it will be appreciated that the various aspects of the ultrasonic and electrosurgical devices may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Some or all of the embodiments described herein may generally comprise technologies for ultrasonic and RF treatment of tissue, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

Various aspects of the subject matter described herein are set out in the following numbered clauses:

1. An ultrasonic surgical instrument, comprising: a waveguide comprising a proximal end and a distal end, wherein the proximal end is coupled to an ultrasonic transducer; a tube defining a lumen, wherein the waveguide is located within the lumen; an end effector coupled to the distal end of the waveguide, the end effector comprising an ultrasonic blade and a clamp arm operatively coupled to the end effector; and a tissue accumulation impedance mechanism coupled to the end effector, wherein the tissue accumulation impedance mechanism is configured to prevent tissue from accumulating within the lumen.

2. The surgical instrument of clause 1, wherein the tissue accumulation impedance mechanism comprises a boot barrier configured to create a seal between the tube and the end effector.

3. The surgical instrument of clause 2, wherein the boot barrier is sealed to the tube 4. The surgical instrument of clause 2, wherein the boot is retained by the tube or end effector using one or more retention features.

5. The surgical instrument of clause 2, wherein the boot barrier is sealed to the ultrasonic blade by way of an interference fit between the boot barrier and the ultrasonic blade.

6. The surgical instrument of clause 2, wherein the boot barrier comprises a cavity.

7. The surgical instrument of clause 6, wherein the cavity is rounded to allow fluid to flow out of the cavity.

8. The surgical instrument of clause 2, wherein the boot barrier comprises a plurality of contact points with the blade.

9. The surgical instrument of clause 1, wherein the tissue accumulation impedance mechanism comprises one or more apertures in the tube.

10. The surgical instrument of clause 9, wherein the apertures comprise one or more windows.

11. The surgical instrument of clause 9, wherein the apertures comprises one or more holes.

12. The surgical instrument of clause 1, wherein the tube comprises a distal portion, wherein the distal portion comprises a half-circle cross section.

13. The surgical instrument of clause 1, wherein the tube comprises one or more ribs formed on an inner side of the tube.

14. The surgical instrument of clause 1, wherein the tissue accumulation impedance mechanism comprises a pump configured to provide a positive pressure flow between the blade and the tube, wherein the positive pressure flow prevents tissue ingress into the lumen.

15. The surgical instrument of clause 1, wherein the pump is located distally to a distal-most overmolded seal located within the lumen.

16. The surgical instrument of clause 1, wherein the tissue accumulation impedance mechanism comprises a slidable tube disposed within the lumen, the slidable tube slidable from a first position to a second position, wherein in the first position the slidable tube is disposed over the blade, and wherein in the second position the blade is exposed.

17. An ultrasonic surgical instrument comprising: z waveguide comprising a proximal end and a distal end, wherein the proximal end is coupled to a transducer; an end effector coupled to the distal end of the waveguide, the end effector comprising at least one tissue retention feature; a clamp arm operatively coupled to the end effector.

18. The surgical instrument of clause 17, wherein the at least one tissue retention feature comprises one or more indentations/grooves/notches formed in the end effector.

19. The surgical instrument of clause 18, wherein the one or more indentations comprise triangular teeth.

20. The surgical instrument of clause 18, wherein the one or more indentations comprise holes.

21. The surgical instrument of clause 18, wherein the one or more indentations comprise horizontal trenches.

22. The surgical instrument of clause 17, wherein the at least one tissue retention feature is offset from the tissue dividing crown of the end effector.

23. The surgical instrument of clause 17, wherein the at least on tissue retention feature comprises one or more projections from the end effector.

24. The surgical instrument of clause 23, wherein the one or more projections comprise triangular teeth.

25. The surgical instrument of clause 23, wherein the one or more projections comprise blocks.

26. The surgical instrument of clause 23, wherein the one or more projections comprise horizontal bumps.

27. The surgical instrument of clause 23, wherein the one or more projections comprise circular bumps.

28. The surgical instrument of clause 17, wherein the at least one tissue retention feature is disposed over an entire length of the blade.

29. The surgical instrument of clause 17, wherein the at least one tissue retention feature is disposed over a discrete section of the blade.

30. An ultrasonic surgical instrument, comprising: a waveguide comprising a proximal end and a distal end, wherein the proximal end is coupled to a transducer; an end effector operatively coupled to the distal end of the waveguide guide; a rotation shroud configured to rotate the waveguide; and a rotation stop mechanism coupled to the rotation shroud prevent rotation of the rotation knob beyond a predetermined rotation.

31. The surgical instrument of clause 30, wherein the shroud comprises: at least one channel; and at least one boss, the at least one boss located within the at least one channel, wherein the at least one boss has a predetermined lateral movement limit, wherein when the at least one boss reaches the predetermined lateral movement limit, the at least one boss prevents further rotation of the rotation knob.

32. The surgical instrument of clause 30, wherein the rotation stop comprises: a gate comprising a first wing and a second wing, wherein the first and second wings are disposed at an angle, wherein the gate is disposed within the shroud, and wherein the gate allows a predetermined angle of rotation of the shroud.

33. The surgical instrument of clause 30, wherein the rotation stop comprises a contoured extrusion element.

34. The surgical instrument of clause 33, wherein the contoured extrusion element comprises a tactile feedback element.

35. The surgical instrument of clause 34, wherein the tactile feedback element comprises a semi-compliant material selected from the group consisting of rubber, medium to high density rubber, silicone, thermoplastic elastomer, springy piece of stainless steel, spring steel, copper, shape memory metal, and combinations of any thereof.

36. An ultrasonic surgical instrument, comprising: a waveguide comprising a proximal end and a distal end, wherein the proximal end is coupled to a transducer; an end effector coupled to the distal end of the waveguide; a clamp arm operatively coupled to the end effector; and a tube disposed over the waveguide, wherein the tube comprises a counter deflection element, wherein the counter deflection element is configured to allow deflection of the blade, wherein the deflection of the blade counteracts a force placed on the blade by the clamp arm when in a clamped position.

37. A surgical instrument comprising: a waveguide comprising a proximal end and a distal end, wherein the proximal end is coupled to a signal source, the signal source configured to provide an ultrasonic signal and an electrosurgical signal; an end effector coupled to the waveguide; a clamp arm operatively coupled to the end effector; and a sealing button, wherein the sealing button causes the surgical instrument to deliver the electrosurgical signal to the end effector and the clamp arm for a first period, and wherein the sealing button causes the surgical instrument to deliver the ultrasonic signal to the blade for a second period, wherein the second period is subsequent to the first period.

38. A surgical instrument, comprising: a waveguide comprising a proximal end and a distal end, wherein the proximal end is coupled to a transducer; an end effector coupled to the distal end of the waveguide; a tube disposed over the waveguide; a cam surface formed on an outer surface of the tube; and a clamp arm operatively coupled to the cam surface.

39. The surgical instrument of clause 38, comprising: a pivot pin located within a hole defined by the end effector, the pivot pin operatively coupled to the clamp arm, wherein the clamp arm pivots about the pivot pin.

40. The surgical instrument of clause 39, wherein the pivot pin is located at the distal most node of the waveguide.

41. The surgical instrument of clause 38, wherein the tube is actuatable, and wherein the clamp arm is cammed open and closed against the end effector through relative motion between the tube and the end effector.

42. A surgical instrument, comprising: a waveguide comprising a proximal end and a distal end, wherein the proximal end is coupled to a transducer; an end effector coupled to the distal end of the waveguide, the end effector defining a pin hole; a rigid pin disposed within the pin hole; a clamp arm; and a four-bar linkage; wherein the four-bar linkage is operatively coupled to the clamp arm and the rigid pin, wherein the four-bar linkage is actuatable to move the clamp arm to a clamped position.

43. The surgical instrument of clause 40, comprising: an outer tube, wherein the outer tube is coupled to the four-bar linkage, and wherein the outer-tube actuates the four-bar linkage from a first position to a second position.

44. An ultrasonic surgical instrument, comprising: a waveguide comprising a proximal end and a distal end, wherein the proximal end is coupled to a transducer; and an end effector coupled to the distal end of the waveguide, wherein the end effector is partially coated with thermally and electrically insulative material such that the distal end of the end effector comprises one or more exposed sections.

45. The ultrasonic surgical instrument of clause 44, wherein the one or more exposed areas are symmetrical.

46. The ultrasonic surgical instrument of clause 44, wherein the one or more exposed areas are asymmetrical.

47. The ultrasonic surgical instrument of clause 44, wherein the one or more exposed sections are separated by one or more coated sections.

48. The ultrasonic surgical instrument of clause 44, wherein the waveguide is fully coated with thermally and electrically insulative material.

49. The ultrasonic surgical instrument of clause 44, wherein the waveguide is partially coated with thermally and electrically insulative material.

50. An ultrasonic surgical instrument, comprising: a waveguide comprising a proximal end and a distal end, wherein the proximal end is coupled to a transducer; and an end effector coupled to the distal end of the waveguide, a clamp arm operatively connected to the end effector wherein the clamp arm is partially coated with thermally and electrically insulative material such that the distal end of the clamp arm comprises one or more exposed sections.

51. The ultrasonic surgical instrument of clause 50, wherein the one or more exposed areas are symmetrical.

52. The ultrasonic surgical instrument of clause 50, wherein the one or more exposed areas are asymmetrical.

53. The ultrasonic surgical instrument of clause 50, wherein the one or more exposed sections are separated by one or more coated sections.

54. The ultrasonic surgical instrument of clause 50, wherein the waveguide is fully coated with thermally and electrically insulative material.

55. The ultrasonic surgical instrument of clause 50, wherein the waveguide is fully coated with thermally and electrically insulative material.

56. An ultrasonic surgical instrument, comprising: a waveguide comprising a proximal end and a distal end, wherein the proximal end is coupled to a transducer; and an end effector coupled to the distal end of the waveguide, a clamp arm operatively connected to the end effector wherein the clamp arm and the end effector are partially coated with thermally and electrically insulative material such that the distal end of the end effector and clamp arm comprise one or more exposed sections.

57. The ultrasonic surgical instrument of clause 56, wherein the one or more exposed areas are symmetrical.

58. The ultrasonic surgical instrument of clause 56, wherein the one or more exposed areas are asymmetrical.

59. The ultrasonic surgical instrument of clause 56, wherein the one or more exposed sections are separated by one or more coated sections.

60. The ultrasonic surgical instrument of clause 56, wherein the waveguide is fully coated with thermally and electrically insulative material.

61. The ultrasonic surgical instrument of clause 56, wherein the waveguide is fully coated with thermally and electrically insulative material.

62. An ultrasonic surgical instrument, comprising: ultrasonic end effector comprising an ultrasonic surgical blade and a clamp arm; and a heat shield provided at a predetermined distance from the ultrasonic blade.

63. The ultrasonic instrument of clause 62, wherein the heat shield is rotatable about the ultrasonic blade.

64. The ultrasonic instrument of clause 62, comprising a heat sink.

65. The ultrasonic instrument of clause 62, wherein the heat shield comprises a plurality of apertures.

66. The ultrasonic instrument of clause 62, wherein the heat shield comprises a tapered portion.

67. An integrated radio frequency (RF)/ultrasonic surgical instrument, comprising: an ultrasonic transducer; a jack connector electrically coupled to the ultrasonic transducer; and a slidable female mating plug matable with the jack connector; wherein the slidable female mating plug is slidable in multiple positions to electrically couple the ultrasonic transducer to either an ultrasonic energy source or an RF energy source.

68. The integrated radio frequency (RF)/ultrasonic surgical instrument of clause 67, wherein the jack connector is rotatable with the ultrasonic transducer.

69. The integrated radio frequency (RF)/ultrasonic surgical instrument of clause 67, wherein the jack connector is a four-lead jack connector.

70. The integrated radio frequency (RF)/ultrasonic surgical instrument of clause 67, wherein the slidable female mating plug in slidable between a first position and a second position; wherein in the first position the ultrasonic transducer is electrically coupled to the ultrasonic energy source and is electrically isolated from the RF energy source; and wherein in the second position the ultrasonic transducer is electrically coupled to the RF energy source and is electrically isolated from the ultrasonic energy source.

71. An ultrasonic energy driven rongeur device, comprising: at least one elongate member; a linkage connected to a distal end of the at least one elongate member; an ultrasonic transducer coupled to the at least one elongate member; and a pivot located at an ultrasonic node of the at least one elongate member.

72. The ultrasonic energy driven rongeur device of clause 71, comprising: a second linkage connected to a proximal end of the at least one elongate member; and a second pivot located at a second ultrasonic of the at least one elongate member.

73. The ultrasonic energy driven rongeur device of clause 71, comprising: a second elongate member above the at least one elongate member; and a damping material disposed between the least one elongate member and the second elongate member.

The invention claimed is:

1. A surgical instrument, comprising:

a tube;

a waveguide extending through the tube;

an end effector, comprising:

an ultrasonic blade extending from the waveguide, wherein the ultrasonic blade comprises a vibration node; and a clamp arm pivotable relative to the ultrasonic blade between an open position and a closed position;

a link comprising a first end and a second end;

a first pin coupling a first end of the link to the ultrasonic blade, wherein the first pin extends through the vibration node of the ultrasonic blade;

a second pin coupling the clamp arm to the tube, wherein the clamp arm pivots relative to the ultrasonic blade about a first axis defined by the second pin; and a third pin coupling the second end of the link to the clamp arm, wherein the clamp arm pivots relative to the link about a second axis defined by the third pin, and wherein relative motion between the tube and the ultrasonic blade moves the clamp arm between the open position and the closed position.

2. The surgical instrument of claim 1, wherein the waveguide defines a waveguide axis, and wherein the ultrasonic blade curves away from the waveguide axis.

3. The surgical instrument of claim 1, wherein proximal motion of the tube moves the clamp arm toward the closed position.

4. The surgical instrument of claim 1, wherein the first pin directly couples the first end of the link to the vibration node of the ultrasonic blade.

5. The surgical instrument of claim 1, wherein distal motion of the tube moves the clamp arm toward the closed position.

6. A surgical instrument, comprising:

a tube;

a waveguide extending through the tube;

an end effector, comprising:

an ultrasonic blade extending from the waveguide; and a clamp arm movable relative to the ultrasonic blade between an open position and a closed position;

a link coupled to the clamp arm and the ultrasonic blade, wherein the link comprises a first end and a second end, wherein the link is pivotable relative to the ultrasonic blade about a first pivot axis, and wherein the link is pivotable relative to the clamp arm about a second pivot axis;

a first pin coupling the first end of the link to the ultrasonic blade at the first pivot axis, and wherein the first pin extends through a vibration node of the ultrasonic blade; and a second pin coupling the second end of the link to the clamp arm at the second pivot axis.

7. The surgical instrument of claim 6, wherein:

the first pin pivotably couples the first end of the link to a first lateral side of the ultrasonic blade;

the second pin pivotably couples the second end of the link to a first lateral side of the clamp arm;

the surgical instrument further comprises:

a third pin pivotably coupling the first end of the link to a second lateral side of the ultrasonic blade; and a fourth pin pivotably coupling the second end of the link to a second lateral side of the clamp arm.

8. The surgical instrument of claim 7, wherein the clamp arm is pivotably coupled to the tube at a third pivot axis, wherein relative motion between the tube and the ultrasonic blade moves the clamp arm between the open position and the closed position.

9. The surgical instrument of claim 8, wherein distal motion of the tube moves the clamp arm toward the closed position.

* * * * *